(12) United States Patent
Weiner et al.

(10) Patent No.: US 11,419,925 B2
(45) Date of Patent: Aug. 23, 2022

(54) CANCER VACCINES AND METHODS OF TREATMENT USING THE SAME

(71) Applicants: David B. Weiner, Merion, PA (US); Jian Yan, Wallingford, PA (US); Karuppiah Muthumani, Cherry Hill, NJ (US); Jewell Walters, Philadelphia, PA (US)

(72) Inventors: David B. Weiner, Merion, PA (US); Jian Yan, Wallingford, PA (US); Karuppiah Muthumani, Cherry Hill, NJ (US); Jewell Walters, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 14/775,047

(22) PCT Filed: Mar. 14, 2014

(86) PCT No.: PCT/US2014/029479
§ 371 (c)(1),
(2) Date: Sep. 11, 2015

(87) PCT Pub. No.: WO2014/144885
PCT Pub. Date: Sep. 18, 2014

(65) Prior Publication Data
US 2016/0030536 A1    Feb. 4, 2016

Related U.S. Application Data

(60) Provisional application No. 61/799,952, filed on Mar. 15, 2013.

(51) Int. Cl.
*A61K 39/00* (2006.01)
*A61K 39/395* (2006.01)
*C12N 9/02* (2006.01)

(52) U.S. Cl.
CPC .. *A61K 39/0011* (2013.01); *A61K 39/001144* (2018.08); *A61K 39/001153* (2018.08);
(Continued)

(58) Field of Classification Search
None
See application file for complete search history.

(56) References Cited

U.S. PATENT DOCUMENTS 5,925,729 A * 7/1999 Boon .................. A61P 35/00
530/328
8,637,305 B2   1/2014 Simard et al.
(Continued)

FOREIGN PATENT DOCUMENTS

AU   2013203229 B2 *  7/2015
CN   1612935           5/2005
(Continued)

OTHER PUBLICATIONS

Ha et al., "Enhancing therapeutic vaccination by blocking PD-1-mediated inhibitory signals during chronic infection," The Journal of Experimental Medicine, vol. 205, No. 3: 543-555 (2008).*
(Continued)

*Primary Examiner* — M Franco G Salvoza
(74) *Attorney, Agent, or Firm* — Riverside Law, LLP

(57) ABSTRACT

Disclosed herein are compositions and methods for treating cancer and in particular vaccines that treat and provide protection against tumor growth.

20 Claims, 17 Drawing Sheets

Specification includes a Sequence Listing.

(52) U.S. Cl.
CPC ............. *A61K 39/001156* (2018.08); *A61K 39/001157* (2018.08); *A61K 39/001186* (2018.08); *A61K 39/001188* (2018.08); *A61K 39/001189* (2018.08); *A61K 39/001191* (2018.08); *A61K 39/001192* (2018.08); *A61K 39/001193* (2018.08); *A61K 39/001194* (2018.08); *A61K 39/001195* (2018.08); *A61K 39/3955* (2013.01); *C12N 9/0071* (2013.01); A61K 2039/505 (2013.01); A61K 2039/53 (2013.01); A61K 2039/54 (2013.01); A61K 2039/55522 (2013.01); A61K 2039/55527 (2013.01); A61K 2039/575 (2013.01); C12N 2710/20034 (2013.01); C12N 2730/10111 (2013.01); C12N 2770/24234 (2013.01); C12Y 114/18001 (2013.01)

(56) References Cited

U.S. PATENT DOCUMENTS

| | | | |
|---|---|---|---|
| 2003/0138808 A1 | 7/2003 | Simard et al. | |
| 2003/0215425 A1 | 11/2003 | Simard et al. | |
| 2004/0106128 A1* | 6/2004 | Majumdar | C12N 9/1276 435/6.18 |
| 2004/0132972 A1 | 7/2004 | Kang et al. | |
| 2005/0158332 A1 | 7/2005 | Topalian et al. | |
| 2008/0171711 A1 | 7/2008 | Hoerr et al. | |
| 2008/0311142 A1 | 12/2008 | Yu et al. | |
| 2010/0016687 A1* | 1/2010 | Brauker et al. | C07K 14/005 435/320.1 |
| 2010/0034841 A1 | 2/2010 | Nishimura | |
| 2011/0070290 A1 | 3/2011 | Reed et al. | |
| 2011/0091498 A1 | 4/2011 | Schlom et al. | |
| 2013/0295110 A1* | 11/2013 | Binder | A61K 39/0011 424/142.1 |

FOREIGN PATENT DOCUMENTS

| | | | | |
|---|---|---|---|---|
| CN | 1612935 | A | 5/2005 | |
| EP | 1260229 | A2 | 11/2002 | |
| JP | 2003048853 | | 2/2003 | |
| JP | 2005506045 | | 3/2005 | |
| JP | 2007525492 | | 9/2007 | |
| JP | 2008194046 | | 8/2008 | |
| JP | 2009544333 | | 12/2009 | |
| JP | 2010504356 | | 2/2010 | |
| JP | 2011050395 | | 3/2011 | |
| JP | 2011525375 | | 9/2011 | |
| WO | WO 9621734 | A2 * | 7/1996 | ............ C07K 14/47 |
| WO | WO-9729195 | A2 * | 8/1997 | ......... C07K 14/4748 |
| WO | 9817799 | A1 | 4/1998 | |
| WO | WO 0182963 | A2 * | 11/2001 | ......... A61K 39/0011 |
| WO | 02/068653 | A2 | 9/2002 | |
| WO | WO-02068653 | A2 * | 9/2002 | ......... C07K 14/4748 |
| WO | 03000907 | A2 | 1/2003 | |
| WO | 2003000907 | A2 | 1/2003 | |
| WO | 2004048938 | A2 | 6/2004 | |
| WO | 2005074995 | A2 | 8/2005 | |
| WO | 2008014521 | A2 | 1/2008 | |
| WO | 2008053579 | | 5/2008 | |
| WO | 2008085562 | A2 | 7/2008 | |
| WO | 2010008782 | A1 | 1/2010 | |
| WO | 2010/068680 | A1 | 6/2010 | |
| WO | 2010143010 | A1 | 12/2010 | |
| WO | 2011020119 | A2 | 2/2011 | |
| WO | 2011073901 | A1 | 6/2011 | |
| WO | 2011097640 | A1 | 8/2011 | |
| WO | 2011130566 | A | 10/2011 | |
| WO | 2011160042 | A2 | 12/2011 | |
| WO | 2012065164 | A2 | 5/2012 | |
| WO | WO-2013019603 | A2 * | 2/2013 | ........... A61K 39/145 |
| WO | 2014/091034 | A1 | 6/2014 | |

OTHER PUBLICATIONS

Kraynyak et al., Plasmid-Encoded Interleukin-15 Receptor a Enhances Specific Immune Responses Induced by a DNA Vaccine In Vivo. Hum Gene Ther. 2009. vol. 20(10), pp. 1143-1156. Abstract.
Buonaguro et al. Translating Tumor Antigens into Cancer Vaccines. Clin Vaccine Immunol 2011, vol. 18(1). pp. 23-34. Abstract.
Liao et al., Vaccination with Human Tyrosinase DNA Induces Antibody Responses in Dogs with Advanced Melanoma, Cancer Immunity, 2006, vol. 6, pp. 1-10.
Wolchok et al., Safety and Immunogenicity of Tyrosinase DNA Vaccines in Patients with Melanoma, Molecular Therapy, 2007, 15(11):2044-2050.
Sturm et al., Chromosomal Structure of the HumanTYRP1 and TYRP2 Loci and comparison of the Tyrosinase-Related Protein Gene family, Genomics, 1995, 29:24-34.
Guan et al., 2011, "Anti-tumor Immunity of Gene Vaccine with Nucleofection Technology", Clin Oneal Cancer Res, vol. 8: pp. 92-99.
Qui et al., "Intra-lymph node DNA vaccination as a platform for safe and effective immunotherapy of cancer", AACR 101st Annual Meeting, Washington, DC, Apr. 17-21, 2010. Presentation Abstract.
Miyahara et al., 2005, "Determinati~n of Cellularly Processed HLA-A2402-Restricted Novel en Epitopes Derived from Two Cancer Germ Line Genes. MAGE-A4 and SAGE", Clin Cancer Res, vol. 11(15), pp. 5581-5589.
GenBank Accession No. AAB6031901.1; Tyrosinase [*Homo sapiens*]; Sep. 27, 1993.
GenBank Accession No. AAB59424.1; Ig heavy chain epsilon-1 (V-D-J region) [*Homo sapiens*]; Feb. 11, 2002.
Draghia-Akli Ruxandra et al: "Plasmid-based expression technology using growth hormone releasing hormone: a novel method for physiologically stimulating long-term growth hormone secretion.", Combinatorial Chemistry & High Throughput Screening Mar. 2006, vol. 9, No. 3, Mar. 2006 (Mar. 2006), pp. 181-185, XP009517744, ISSN: 1386-2073.
GenBank Accession No. AAB60319.1; Tyrosinase [*Homo sapiens*]; Sep. 27, 1993. (1 page).
Genbank, Accession No. "AAB59424.1", Ig heavy chain epsilon-1 (V-D-J region)[*Homo sapiens*]), Feb. 11, 2002 (1 page).
Genbank, accession No. "AAH39731.1", Preferentially expressed antigen in melanoma [*Homo sapiens*], Jul. 15, 2006 (2 pages).
International Preliminary Report on Patentability PCT/US2014/029479 (10 pages).
International Search Report and Written Opinion for PCT/US2014/029479 (17 pages).
Liao et al., "Vaccination with human tyrosinase DNA induces antibody responses in dogs with advanced melanoma", Cancer Immunology, 2007, vol. 6, No. 8, p. 1-17.
Liao Jack C F et al., 'Vaccination with human tyrosinase DNA induces antibody responses in dogs with advanced melanoma.', Cancer Immunity 2006, (2006), vol. 6, ISSN 1424-9634.
Qiu Zhiyong et al, "Intra-lymph node DNA vaccination as a platform for safe and effective immunotherapy of cancer", Proceedings of the American Association for Cancer Research Annual Meeting, & 101st Annual Meeting of the American-Association-For-Cancer-Research; Washington, DC, USA; Apr. 17-21, 2010, (Apr. 2010), vol. 51, ISSN 0197-016X, p. 581, XP009150906 (2 pages).
Seleeke Flingai et al: "Synthetic DNA Vaccines: Improved Vaccine Potency by Electroporation and Co-Delivered Genetic Adjuvants", Frontiers in Immunology, vol. 4, Jan. 1, 2013 (Jan. 1, 2013), XP55182442, ISSN: 1664-3224, DOI: 10.3389/fimmu.2013.00354.
Weber et al., "A Phase 1 Study of a Vaccine Targeting Preferentially Expressed Antigen in Melanoma and Prostate-specific Membrane Antigen in Patients With Advanced Solid Tumors", J. Immunother., 2011, 34:556-567.

\* cited by examiner

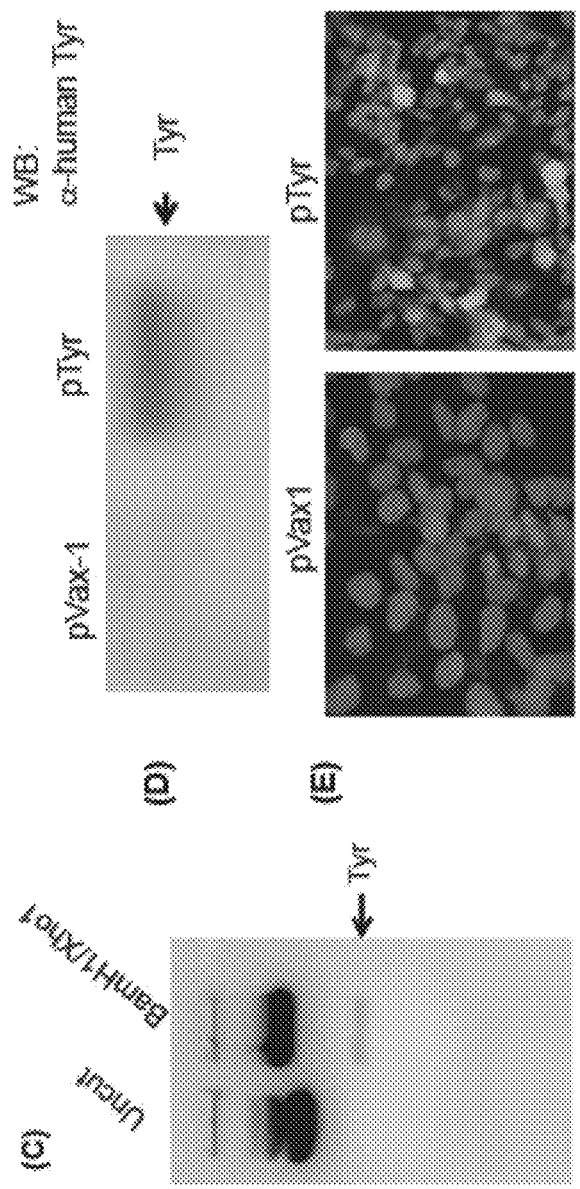
FIG. 1 (con't)

FIG. 8 (con't)

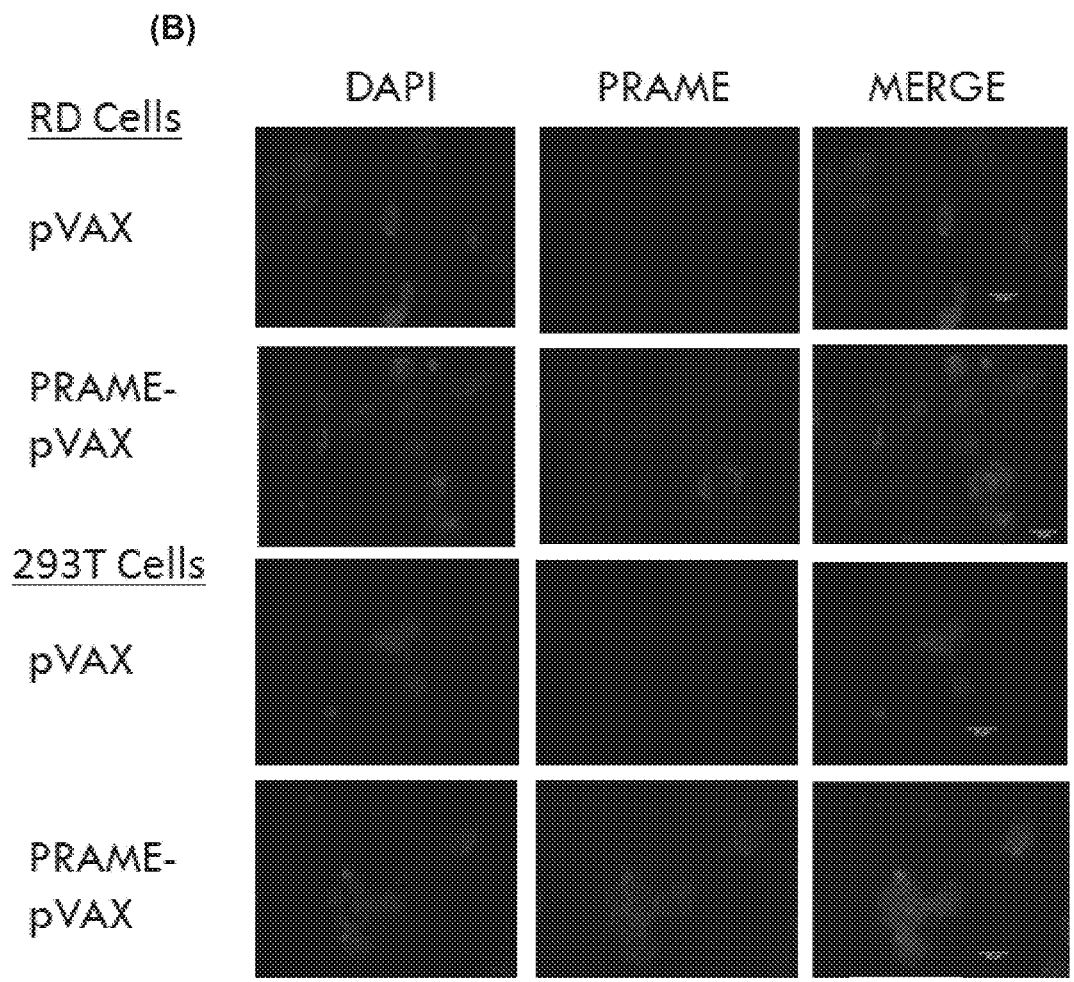
FIG. 10(con't)

FIG. 10(con't)

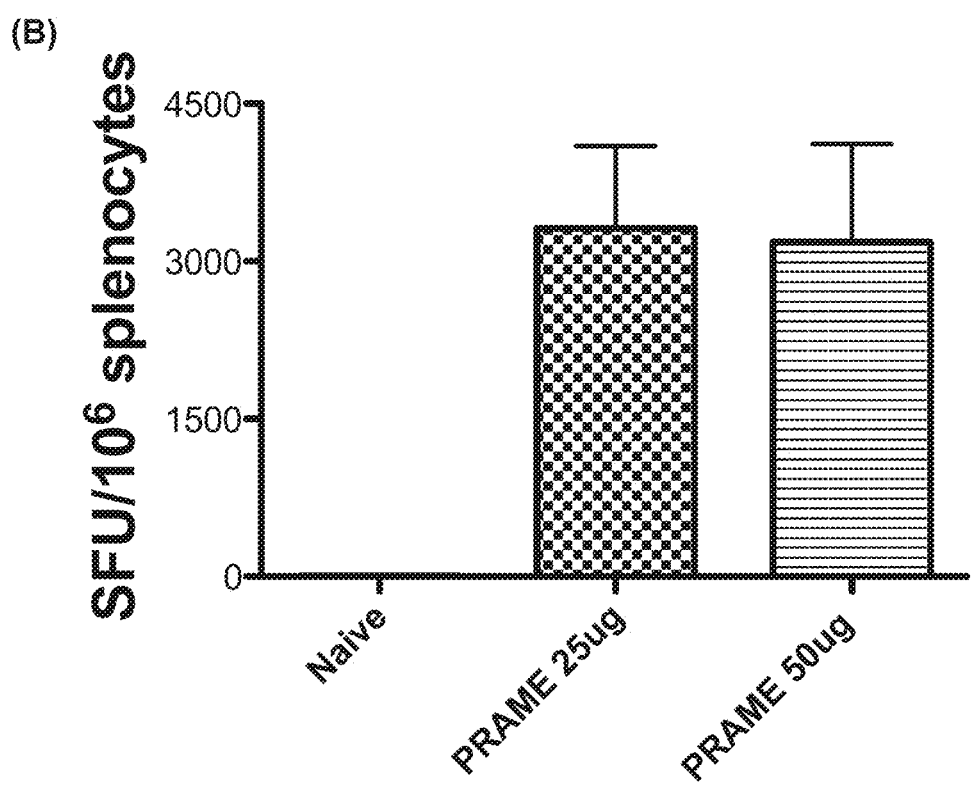
FIG. 11 (con't)

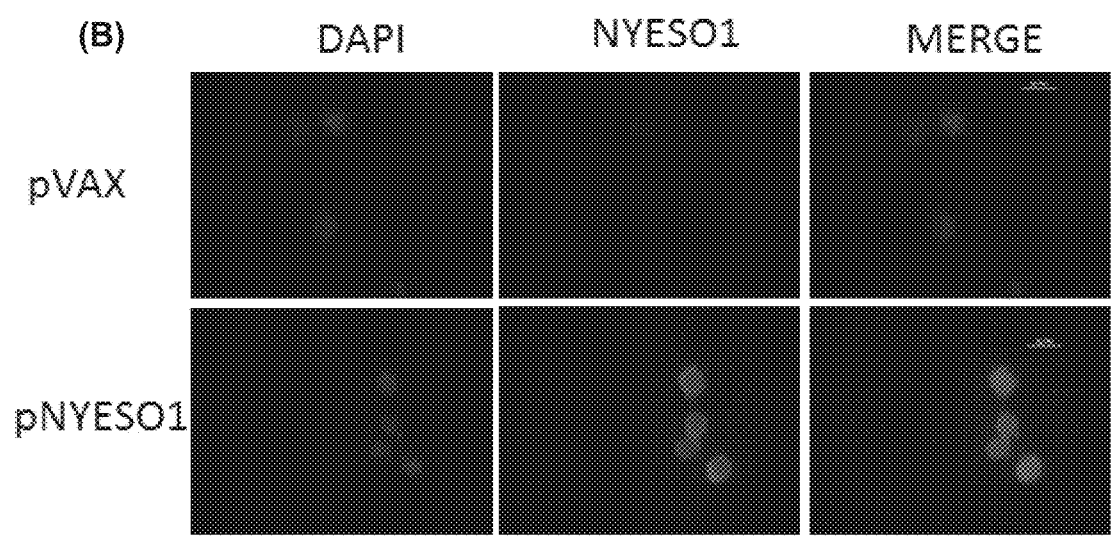
FIG. 12 (con't)

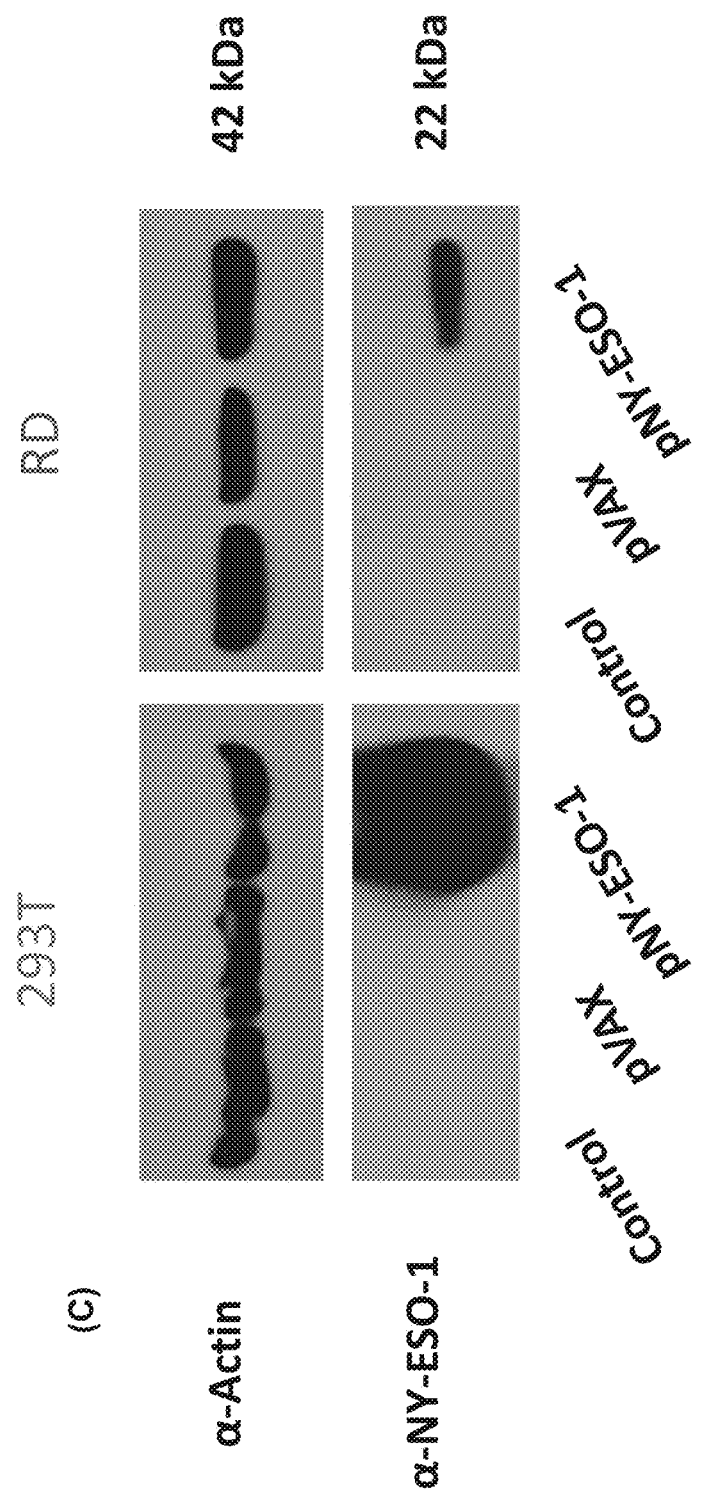
FIG. 12 (con't)

CANCER VACCINES AND METHODS OF TREATMENT USING THE SAME

CROSS-REFERENCE TO RELATED APPLICATIONS

This application is the U.S. national stage application filed under 35 U.S.C. § 371 claiming benefit to International Patent Application No. PCT/US14/029479, filed Mar. 14, 2014, which is entitled to priority under 35 U.S.C. § 119(e) to U.S. Provisional Application No. 61/799,952, filed Mar. 15, 2013, each of which is hereby incorporated by reference in its entirety.

TECHNICAL FIELD

Disclosed herein are compositions and methods for treating cancer and in particular, vaccines that treat and provide protection against tumor growth.

BACKGROUND

Cancer is among the leading causes of death worldwide, and in the United States, is the second most common cause of death, accounting for nearly 1 of every 4 deaths. Cancer arises from a single cell that has transformed from a normal cell into a tumor cell. Such a transformation is often a multistage process, progressing from a pre-cancerous lesion to malignant tumors. Multiple factors contribute this progression, including aging, genetic contributions, and exposure to external agents such as physical carcinogens (e.g., ultraviolet and ionizing radiation), chemical carcinogens (e.g., asbestos, components of tobacco smoke, etc.), and biological carcinogens (e.g., certain viruses, bacteria, and parasites).

Prevention, diagnosis and treatment of cancer may take many different forms. Prevention may include screening for pre-disposing factors (e.g., specific genetic variants), altering behavior (e.g., smoking, diet, and amount of physical activity), and vaccination against viruses (e.g., human papilloma virus hepatitis B virus). Treatment may include chemotherapy, radiation therapy, and surgical removal of a tumor or cancerous tissue. Despite the availability of numerous prevention and treatment methods, such methods often meet with limited success in effectively preventing and/or treating the cancer at hand.

Accordingly, a need exists for the identification and development of compositions and methods for the prevention and/or treatment of cancer to facilitate clinical management of protection against and progression of disease. Furthermore, more effective treatments are required to delay disease progression and/or decrease mortality in subjects suffering from cancer.

SUMMARY OF INVENTION

The present invention is directed to a vaccine comprising one or more nucleic acid or amino acid sequence of cancer antigens that are no longer self-antigens and stimulate an immune response to a particular cancer or tumor associated with a particular cancer. The vaccine can further comprise immune checkpoint inhibitor such as anti-PD-1 and anti-PDL-1 antibodies that prevents the suppression of any component in the immune system such as MHC class presentation, T cell presentation and/or differentiation, B cell presentation and/or differentiation, any cytokine, chemokine or signaling for immune cell proliferation and/or differentiation. The one or more cancer antigens of the vaccine can be a nucleic acid encoding one or more amino acid sequence(s) or amino acid sequence that is selected from the group consisting of: amino acid sequence that is 95% identical or greater to the amino acid sequence of tyrosinase (Tyr); amino acid sequence of tyrosinase-related protein 1 (TYRP1); amino acid sequence that is 95% identical or greater to the amino acid sequence of tyrosinase-related protein 2 (TYRP2); amino acid sequence that is 95% identical or greater to the amino acid sequence of melanoma-associated antigen 4 protein (MAGEA4); amino acid sequence that is 95% identical or greater to the amino acid sequence of growth hormone release hormone (GHRH); amino acid sequence that is 95% identical or greater to the amino acid sequence of MART-1/melan-A antigen (MART-1/Melan-A); amino acid sequence that is 95% identical or greater to the amino acid sequence of cancer testis antigen (NY-ESO-1); amino acid sequence that is 95% identical or greater to the amino acid sequence of cancer testis antigen II (NY-ESO-2); amino acid sequence that is 95% identical or greater to the amino acid sequence of PRAME; amino acid sequence that is 95% identical or greater to the amino acid sequence of WT1; amino acid sequence that is 95% identical or greater to the amino acid sequence of hTERT; or combination thereof. The vaccine can further comprise a nucleic acid encoding one or more antigens selected from the group consisting of: PSA, PSMA, STEAP, PSCA, MAGE A1, gp100, a viral antigen, and combinations thereof.

The present invention is further directed to a method for preventing or treating cancer in a subject in need thereof, the method comprising administering to a subject in need thereof a vaccine comprising a particular number of cancer antigens for treating or preventing a particular cancer. The method may comprise administering to a subject in need thereof a vaccine comprising a CMV cancer antigen to treat or prevent gliobastoma, or administering to a subject in need thereof a vaccine comprising CMV cancer antigen in combination with any one or more of cancer antigens hTERT, NY-ESO-1, MAGE-A1, or WT1 to treat or prevent glioblastoma; administering to a subject in need thereof a vaccine comprising one or more cancer antigens PSA, PSMA, or STEAP to treat or prevent prostate cancer, or administering to a subject in need thereof a vaccine comprising PSA, PSMA, or STEAP in combination with any one or more of cancer antigens hTERT, NY-ESO-1, MAGE-A1 or WT1 to treat or prevent prostate cancer; administering to a subject in need thereof a vaccine comprising one or more cancer antigens tyrosinase, PRAME, or GP-100 to treat or prevent melanoma, or administering to a subject in need thereof a vaccine comprising tyrosinase, PRAME, or GP-100 in combination with any one or more of cancer antigens hTERT, NY-ESO-1, MAGE-A1 or WT1 to treat or prevent melanoma; administering to a subject in need thereof a vaccine comprising one or more cancer antigen HPV 16 E6 or HPV 16 E7 to treat or prevent head and neck cancer, or administering to a subject in need thereof a vaccine comprising HPV 16 E6 or HPV 16 E7 in combination with any one or more of cancer antigens hTERT, NY-ESO-1, MAGE-A1 or WT1 to treat or prevent head and neck cancer; administering to a subject in need thereof a vaccine comprising one or more cancer antigens tyrosinase, PRAME, or GP-100 to treat or prevent melanoma, or administering to a subject in need thereof a vaccine comprising tyrosinase, PRAME, or GP-100 in combination with any one or more of cancer antigens hTERT, NY-ESO-1, MAGE-A1 or WT1 to treat or prevent melanoma; administering to a subject in need thereof a vaccine comprising one or more cancer antigens HPV 6, HPV 11, or HPV 16 to treat or prevent anal cancer, or administering to a subject in need thereof a vaccine comprising HPV 6, HPV 11, or HPV 16 in combination with any one or more of cancer antigens hTERT, NY-ESO-1, MAGE-A1 or WT1 to treat or prevent anal cancer; administering to a subject in need thereof a vaccine comprising one or more cancer antigens HBV core, HBV surface antigen, HCV NS34A, HCV NS5A, HCV NS5B, or HCV NS4B to treat or prevent liver, or administering to a subject in need thereof a vaccine comprising HBV core, HBV surface antigen, HCV NS34A, HCV NS5A, HCV NS5B, or HCV NS4B in combination with any one or more of cancer antigens hTERT, NY-ESO-1, MAGE-A1 or WT1 to treat or prevent liver; administering to a subject in need thereof a vaccine comprising one or more cancer antigens HPV 16 E6/E7 or HPV 18 E6/E7 to treat or prevent cervical cancer, or administering to a subject in need thereof a vaccine comprising HPV 16 E6/E7 or HPV 18 E6/E7 in combination with any one or more of cancer antigens hTERT, NY-ESO-1, MAGE-A1 or WT1 to treat or prevent cervical cancer; or administering to a subject in need thereof a vaccine comprising one or more cancer antigens PRAME, WT-1, or hTERT to treat or prevent blood cancers, or administering to a subject in need thereof a vaccine comprising PRAME, WT-1, or hTERT in combination with any one or more of cancer antigens NY-ESO-1 or MAGE-A1 to treat or prevent blood cancers, wherein the method may further comprise combining the administrative steps of (a)-(i) with an immune checkpoint inhibitor is selected from the group consisting of: anti-PD-1 antibody, anti-PD-L1 antibody, and a combination thereof.

DETAILED DESCRIPTION

Figure 1:
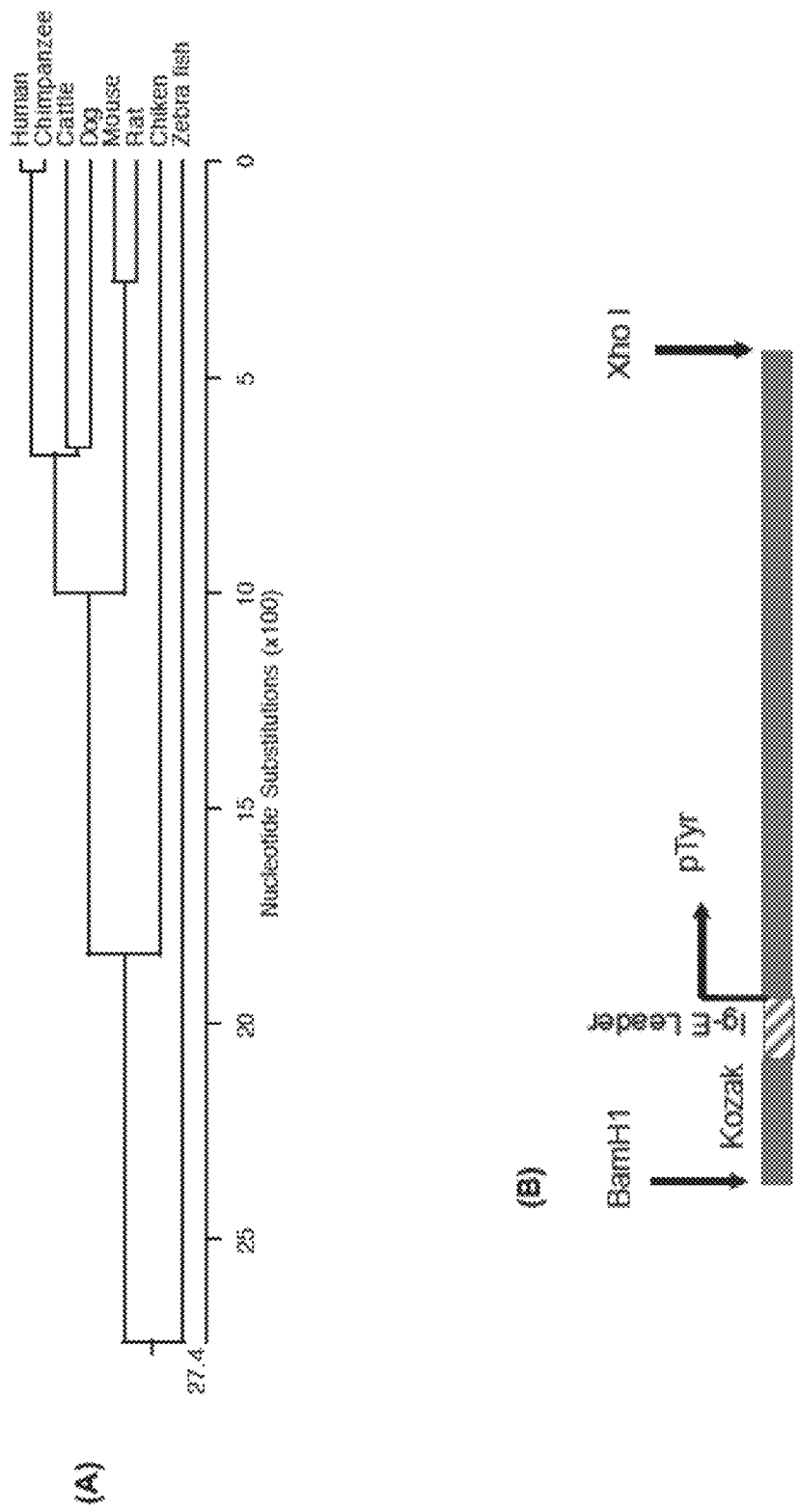
FIGS. 1A-E show construction of pTyr.

The present invention is directed to a vaccine that can be customized for particular cancers and tumors. Antigen consensus sequences have been designed for particular cancer related antigens such as tyrosinase (Tyr), preferentially expressed antigen in melanoma (PRAME), tyrosinase related protein 1 (Tyrp1), cancer testes antigen (NY-ESO-1), hepatitis B virus antigen, and Wilms tumor 1 antigen (WT-1) to be used in the vaccine to allow customized vaccine prevention and treatment of particular cancers. For example, tyrosinase antigen may be used in the vaccine for prevention or treatment of melanomas. The vaccine of the invention can provide any combination of particular cancer antigens for the particular prevention or treatment of the cancer of a subject that is in need of treatment.

One manner for designing the nucleic acid and its' encoded amino acid sequence of the recombinant cancer antigen is by introducing mutations that change particular amino acids in the overall amino acid sequence of the native cancer antigen. The introduction of mutations does not alter the cancer antigen so much that it cannot be universally applied across a mammalian subject, and preferably a human or dog subject, but changes it enough that the resulting amino acid sequence breaks tolerance or is considered a foreign antigen in order to generate an immune response. Another manner may be creating a consensus recombinant cancer antigen that has at least 85% and up to 99% amino acid sequence identity to its' corresponding native cancer antigen; preferably at least 90% and up to 98% sequence identity; more preferably at least 93% and up to 98% sequence identity; or even more preferably at least 95% and up to 98% sequence identity. In some instances the recombinant cancer antigen is 95%, 96%, 97%, 98%, or 99% amino acid sequence identity to its' corresponding native cancer antigen. The native cancer antigen is the antigen normally associated with the particular cancer or cancer tumor. Depending upon the cancer antigen, the consensus sequence of the cancer antigen can be across mammalian species or within subtypes of a species or across viral strains or serotypes. Some cancer antigens do not vary greatly from the wild type amino acid sequence of the cancer antigen. Some cancer antigens have nucleic acid/amino acid sequences that are so divergent across species, that a consensus sequence cannot be generated. In these instances, a recombinant cancer antigen that will break tolerance and generate an immune response is generated that has at least 85% and up to 99% amino acid sequence identity to its' corresponding native cancer antigen; preferably at least 90% and up to 98% sequence identity; more preferably at least 93% and up to 98% sequence identity; or even more preferably at least 95% and up to 98% sequence identity. In some instances the recombinant cancer antigen is 95%, 96%, 97%, 98%, or 99% amino acid sequence identity to its' corresponding native cancer antigen. The aforementioned approaches can be combined so that the final recombinant cancer antigen has a percent similarity to native cancer antigen amino acid sequence as discussed, above.

The recombinant cancer antigen can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune responses. In some embodiments, the induced or elicited cellular immune response can include induction or secretion of interferon-gamma (IFN-γ) and/or tumor necrosis factor alpha (TNF-α). In other embodiments, the induced or elicited immune response can reduce or inhibit one or more immune suppression factors that promote growth of the tumor or cancer expressing the antigen, for example, but not limited to, factors that down regulate MHC presentation, factors that up regulate antigen-specific regulatory T cells (Tregs), PD-L1, FasL, cytokines such as IL-10 and TFG-β, tumor associated macrophages, tumor associated fibroblasts, soluble factors produced by immune suppressor cells, CTLA-4, PD-1, MDSCs, MCP-1, and an immune checkpoint molecule.

The vaccine may be combined further with antibodies to checkpoint inhibitors such as PD-1 and PDL-1 to increase the stimulation of both the cellular and humoral immune responses. Using anti-PD-1 or anti-PDL-1 antibodies prevents PD-1 or PDL-1 from suppressing T-cell and/or B-cell responses. Overall, by designing the cancer antigens to be recognized by the immune system helps to overcome other forms of immune suppression by tumor cells, and these vaccines can be used in combination with suppression or inhibition therapies (such as anti-PD-1 and anti-PDL-1 antibody therapies) to further increase T-cell and/or B-cell responses.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting. The terminology used herein is for the purpose of describing particular embodiments only and is not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

"Adjuvant" as used herein means any molecule added to the DNA plasmid vaccines described herein to enhance the immunogenicity of the antigens encoded by the DNA plasmids and the encoding nucleic acid sequences described hereinafter.

"Antibody" as used herein means an antibody of classes IgG, IgM, IgA, IgD or IgE, or fragments, or derivatives thereof, including Fab, F(ab')2, Fd, and single chain antibodies, diabodies, bispecific antibodies, bifunctional antibodies and derivatives thereof. The antibody can be an antibody isolated from the serum sample of mammal, a polyclonal antibody, affinity purified antibody, or mixtures thereof which exhibits sufficient binding specificity to a desired epitope or a sequence derived therefrom.

"Coding sequence" or "encoding nucleic acid" as used herein means the nucleic acids (RNA or DNA molecule) that comprise a nucleotide sequence which encodes a protein. The coding sequence can further include initiation and termination signals operably linked to regulatory elements including a promoter and polyadenylation signal capable of directing expression in the cells of an individual or mammal to which the nucleic acid is administered.

"Complement" or "complementary" as used herein means a nucleic acid can mean Watson-Crick (e.g., A-T/U and C-G) or Hoogsteen base pairing between nucleotides or nucleotide analogs of nucleic acid molecules.

"Consensus" or "consensus sequence" as used herein means a polypeptide sequence based on analysis of an alignment of multiple sequences for the same gene from different organisms. Nucleic acid sequences that encode a consensus polypeptide sequence can be prepared. Vaccines comprising proteins that comprise consensus sequences and/or nucleic acid molecules that encode such proteins can be used to induce broad immunity against an antigen.

"Electroporation," "electro-permeabilization," or "electro-kinetic enhancement" ("EP") as used interchangeably herein means the use of a transmembrane electric field pulse to induce microscopic pathways (pores) in a bio-membrane; their presence allows biomolecules such as plasmids, oligonucleotides, siRNA, drugs, ions, and water to pass from one side of the cellular membrane to the other.

"Fragment" as used herein with respect to nucleic acid sequences means a nucleic acid sequence or a portion thereof, that encodes a polypeptide capable of eliciting an immune response in a mammal that cross reacts with an antigen disclosed herein. The fragments can be DNA fragments selected from at least one of the various nucleotide sequences that encode protein fragments set forth below. Fragments can comprise at least 10%, at least 20%, at least 30%, at least 40%, at least 50%, at least 60%, at least 70%, at least 80%, at least 90%, or at least 95% of one or more of the nucleic acid sequences set forth below. In some embodiments, fragments can comprise at least 20 nucleotides or more, at least 30 nucleotides or more, at least 40 nucleotides or more, at least 50 nucleotides or more, at least 60 nucleotides or more, at least 70 nucleotides or more, at least 80 nucleotides or more, at least 90 nucleotides or more, at least 100 nucleotides or more, at least 150 nucleotides or more, at least 200 nucleotides or more, at least 250 nucleotides or more, at least 300 nucleotides or more, at least 350 nucleotides or more, at least 400 nucleotides or more, at least 450 nucleotides or more, at least 500 nucleotides or more, at least 550 nucleotides or more, at least 600 nucleotides or more, at least 650 nucleotides or more, at least 700 nucleotides or more, at least 750 nucleotides or more, at least 800 nucleotides or more, at least 850 nucleotides or more, at least 900 nucleotides or more, at least 950 nucleotides or more, or at least 1000 nucleotides or more of at least one of the nucleic acid sequences set forth below.

"Fragment" or "immunogenic fragment" with respect to polypeptide sequences means a polypeptide capable of eliciting an immune response in a mammal that cross reacts with an antigen disclosed herein. The fragments can be polypeptide fragments selected from at least one of the various amino acids sequences below. Fragments of consensus proteins can comprise at least 10%, at least 20%, at least 30%, at least 40%, at least 50%, at least 60%, at least 70%, at least 80%, at least 90% or at least 95% of a consensus protein. In some embodiments, fragments of consensus proteins can comprise at least 20 amino acids or more, at least 30 amino acids or more, at least 40 amino acids or more, at least 50 amino acids or more, at least 60 amino acids or more, at least 70 amino acids or more, at least 80 amino acids or more, at least 90 amino acids or more, at least 100 amino acids or more, at least 110 amino acids or more, at least 120 amino acids or more, at least 130 amino acids or more, at least 140 amino acids or more, at least 150 amino acids or more, at least 160 amino acids or more, at least 170 amino acids or more, at least 180 amino acids or more of a protein sequence disclosed herein.

As used herein, the term "genetic construct" refers to the DNA or RNA molecules that comprise a nucleotide sequence which encodes a protein. The coding sequence includes initiation and termination signals operably linked to regulatory elements including a promoter and polyadenylation signal capable of directing expression in the cells of the individual to whom the nucleic acid molecule is administered. As used herein, the term "expressible form" refers to gene constructs that contain the necessary regulatory elements operable linked to a coding sequence that encodes a protein such that when present in the cell of the individual, the coding sequence will be expressed.

The term "homology," as used herein, refers to a degree of complementarity. There can be partial homology or complete homology (i.e., identity). A partially complementary sequence that at least partially inhibits a completely complementary sequence from hybridizing to a target nucleic acid is referred to using the functional term "substantially homologous." When used in reference to a double-stranded nucleic acid sequence such as a cDNA or genomic clone, the term "substantially homologous," as used herein, refers to a probe that can hybridize to a strand of the double-stranded nucleic acid sequence under conditions of low stringency. When used in reference to a single-stranded nucleic acid sequence, the term "substantially homologous," as used herein, refers to a probe that can hybridize to (i.e., is the complement of) the single-stranded nucleic acid template sequence under conditions of low stringency.

"Identical" or "identity" as used herein in the context of two or more nucleic acids or polypeptide sequences means that the sequences have a specified percentage of residues that are the same over a specified region. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) can be considered equivalent. Identity can be performed manually or by using a computer sequence algorithm such as BLAST or BLAST 2.0.

"Immune response" as used herein means the activation of a host's immune system, e.g., that of a mammal, in response to the introduction of antigen. The immune response can be in the form of a cellular or humoral response, or both.

"Nucleic acid" or "oligonucleotide" or "polynucleotide" as used herein means at least two nucleotides covalently linked together. The depiction of a single strand also defines the sequence of the complementary strand. Thus, a nucleic acid also encompasses the complementary strand of a depicted single strand. Many variants of a nucleic acid can be used for the same purpose as a given nucleic acid. Thus, a nucleic acid also encompasses substantially identical nucleic acids and complements thereof. A single strand provides a probe that can hybridize to a target sequence under stringent hybridization conditions. Thus, a nucleic acid also encompasses a probe that hybridizes under stringent hybridization conditions.

Nucleic acids can be single stranded or double stranded, or can contain portions of both double stranded and single stranded sequence. The nucleic acid can be DNA, both genomic and cDNA, RNA, or a hybrid, where the nucleic acid can contain combinations of deoxyribo- and ribo-nucleotides, and combinations of bases including uracil, adenine, thymine, cytosine, guanine, inosine, xanthine hypoxanthine, isocytosine and isoguanine. Nucleic acids can be obtained by chemical synthesis methods or by recombinant methods.

"Operably linked" as used herein means that expression of a gene is under the control of a promoter with which it is spatially connected. A promoter can be positioned 5' (upstream) or 3' (downstream) of a gene under its control. The distance between the promoter and a gene can be approximately the same as the distance between that promoter and the gene it controls in the gene from which the promoter is derived. As is known in the art, variation in this distance can be accommodated without loss of promoter function.

A "peptide," "protein," or "polypeptide" as used herein can mean a linked sequence of amino acids and can be natural, synthetic, or a modification or combination of natural and synthetic.

"Promoter" as used herein means a synthetic or naturally-derived molecule which is capable of conferring, activating or enhancing expression of a nucleic acid in a cell. A promoter can comprise one or more specific transcriptional regulatory sequences to further enhance expression and/or to alter the spatial expression and/or temporal expression of same. A promoter can also comprise distal enhancer or repressor elements, which can be located as much as several thousand base pairs from the start site of transcription. A promoter can be derived from sources including viral, bacterial, fungal, plants, insects, and animals. A promoter can regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

"Signal peptide" and "leader sequence" are used interchangeably herein and refer to an amino acid sequence that can be linked at the amino terminus of a protein set forth herein. Signal peptides/leader sequences typically direct localization of a protein. Signal peptides/leader sequences used herein preferably facilitate secretion of the protein from the cell in which it is produced. Signal peptides/leader sequences are often cleaved from the remainder of the protein, often referred to as the mature protein, upon secretion from the cell. Signal peptides/leader sequences are linked at the amino terminus (i.e., N terminus) of the protein.

"Stringent hybridization conditions" as used herein means conditions under which a first nucleic acid sequence (e.g., probe) will hybridize to a second nucleic acid sequence (e.g., target), such as in a complex mixture of nucleic acids. Stringent conditions are sequence-dependent and will be different in different circumstances. Stringent conditions can be selected to be about 5-10° C. lower than the thermal melting point (Tm) for the specific sequence at a defined ionic strength pH. The Tm can be the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions can be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions can also be achieved with the addition of destabilizing agents such as formamide. For selective or specific hybridization, a positive signal can be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

"Subject" as used herein can mean a mammal that wants to or is in need of being immunized with the herein described vaccines. The mammal can be a human, chimpanzee, dog, cat, horse, cow, mouse, or rat.

"Substantially complementary" as used herein means that a first sequence is at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 180, 270, 360, 450, 540, or more nucleotides or amino acids, or that the two sequences hybridize under stringent hybridization conditions.

"Substantially identical" as used herein means that a first and second sequence are at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% identical over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 180, 270, 360, 450, 540 or more nucleotides or amino acids, or with respect to nucleic acids, if the first sequence is substantially complementary to the complement of the second sequence.

"Treatment" or "treating" as used herein can mean protecting an animal from a disease through means of preventing, suppressing, repressing, or completely eliminating the disease. Preventing the disease involves administering a vaccine of the present invention to an animal prior to onset of the disease. Suppressing the disease involves administering a vaccine of the present invention to an animal after induction of the disease but before its clinical appearance. Repressing the disease involves administering a vaccine of the present invention to an animal after clinical appearance of the disease.

"Variant" used herein with respect to a nucleic acid means (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

"Variant" with respect to a peptide or polypeptide that differs in amino acid sequence by the insertion, deletion, or conservative substitution of amino acids, but retain at least one biological activity. Variant can also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions can be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

A variant may be a nucleic acid sequence that is substantially identical over the full length of the full gene sequence or a fragment thereof. The nucleic acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof. A variant may be an amino acid sequence that is substantially identical over the full length of the amino acid sequence or fragment thereof. The amino acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof.

"Vector" as used herein means a nucleic acid sequence containing an origin of replication. A vector can be a viral vector, bacteriophage, bacterial artificial chromosome or yeast artificial chromosome. A vector can be a DNA or RNA vector. A vector can be a self-replicating extrachromosomal vector, and preferably, is a DNA plasmid. The vector can contain or include one or more heterologous nucleic acid sequences.

2. Vaccine

The present invention is directed to an anti-cancer vaccine. The vaccine can comprise one or more cancer antigens. The vaccine can prevent tumor growth. The vaccine can reduce tumor growth. The vaccine can prevent metastasis of tumor cells. Depending upon the cancer antigen, the vaccine can be targeted to treat liver cancer, prostate cancer, melanomas, blood cancers, head and neck cancer, glioblastoma, recurrent respiratory papillomatosis, anal cancer, cervical cancer, and brain cancer.

The first step in development of the vaccine is to identify a cancer antigen that is not recognized by the immune system and is a self-antigen. The cancer antigen identified is changed from a self-antigen to a foreign antigen in order to be recognized by the immune system. The redesign of the nucleic acid and amino acid sequence of the recombinant cancer antigen from a self to a foreign antigen breaks tolerance of antigen by the immune system. In order to break tolerance, several redesign measures can be applied to the cancer antigen as described below.

The recombinant cancer antigen of the vaccine is not recognized as self, therefore breaking tolerance. The breaking of tolerance can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune responses. In some embodiments, the induced or elicited cellular immune response can include induction or secretion of interferon-gamma (IFN-γ) and/or tumor necrosis factor alpha (TNF-α). In other embodiments, the induced or elicited immune response can reduce or inhibit one or more immune suppression factors that promote growth of the tumor or cancer expressing the antigen, for example, but not limited to, factors that down regulate MHC presentation, factors that up regulate antigen-specific regulatory T cells (Tregs), PD-L1, FasL, cytokines such as IL-10 and TFG-β, tumor associated macrophages, tumor associated fibroblasts, soluble factors produced by immune suppressor cells, CTLA-4, PD-1, MDSCs, MCP-1, and an immune checkpoint molecule.

In a particular embodiment, the vaccine can mediate clearance or prevent growth of tumor cells by inducing (1) humoral immunity via B cell responses to generate antibodies that block monocyte chemoattractant protein-1 (MCP-1) production, thereby retarding myeloid derived suppressor cells (MDSCs) and suppressing tumor growth; (2) increase cytotoxic T lymphocyte such as $CD8^+$ (CTL) to attack and kill tumor cells; (3) increase T helper cell responses; (4) and increase inflammatory responses via IFN-γ and TFN-α or preferably all of the aforementioned. The vaccine can increase tumor free survival by 30%, 31%, 32%, 33%, 34%, 35%, 36%, 37%, 38%, 39%, 40%, 41%, 42%, 43%, 44%, and 45%. The vaccine can reduce tumor mass by 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, and 60% after immunization. The vaccine can prevent and block increases in monocyte chemoattractant protein 1 (MCP-1), a cytokine secreted by myeloid derived suppressor cells. The vaccine can increase tumor survival by 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, and 60%.

The vaccine can increase a cellular immune response in a subject administered the vaccine by about 50-fold to about 6000-fold, about 50-fold to about 5500-fold, about 50-fold to about 5000-fold, about 50-fold to about 4500-fold, about 100-fold to about 6000-fold, about 150-fold to about 6000-fold, about 200-fold to about 6000-fold, about 250-fold to about 6000-fold, or about 300-fold to about 6000-fold as compared to a cellular immune response in a subject not administered the vaccine. In some embodiments the vaccine can increase the cellular immune response in the subject administered the vaccine by about 50-fold, 100-fold, 150-fold, 200-fold, 250-fold, 300-fold, 350-fold, 400-fold, 450-fold, 500-fold, 550-fold, 600-fold, 650-fold, 700-fold, 750-fold, 800-fold, 850-fold, 900-fold, 950-fold, 1000-fold, 1100-fold, 1200-fold, 1300-fold, 1400-fold, 1500-fold, 1600-fold, 1700-fold, 1800-fold, 1900-fold, 2000-fold, 2100-fold, 2200-fold, 2300-fold, 2400-fold, 2500-fold, 2600-fold, 2700-fold, 2800-fold, 2900-fold, 3000-fold, 3100-fold, 3200-fold, 3300-fold, 3400-fold, 3500-fold, 3600-fold, 3700-fold, 3800-fold, 3900-fold, 4000-fold, 4100-fold, 4200-fold, 4300-fold, 4400-fold, 4500-fold, 4600-fold, 4700-fold, 4800-fold, 4900-fold, 5000-fold, 5100-fold, 5200-fold, 5300-fold, 5400-fold, 5500-fold, 5600-fold, 5700-fold, 5800-fold, 5900-fold, or 6000-fold as compared to the cellular immune response in the subject not administered the vaccine.

The vaccine can increase interferon gamma (IFN-γ) levels in a subject administered the vaccine by about 50-fold to about 6000-fold, about 50-fold to about 5500-fold, about 50-fold to about 5000-fold, about 50-fold to about 4500-fold, about 100-fold to about 6000-fold, about 150-fold to about 6000-fold, about 200-fold to about 6000-fold, about 250-fold to about 6000-fold, or about 300-fold to about 6000-fold as compared to IFN-γ levels in a subject not administered the vaccine. In some embodiments the vaccine can increase IFN-γ levels in the subject administered the vaccine by about 50-fold, 100-fold, 150-fold, 200-fold, 250-fold, 300-fold, 350-fold, 400-fold, 450-fold, 500-fold, 550-fold, 600-fold, 650-fold, 700-fold, 750-fold, 800-fold, 850-fold, 900-fold, 950-fold, 1000-fold, 1100-fold, 1200-fold, 1300-fold, 1400-fold, 1500-fold, 1600-fold, 1700-fold, 1800-fold, 1900-fold, 2000-fold, 2100-fold, 2200-fold, 2300-fold, 2400-fold, 2500-fold, 2600-fold, 2700-fold, 2800-fold, 2900-fold, 3000-fold, 3100-fold, 3200-fold, 3300-fold, 3400-fold, 3500-fold, 3600-fold, 3700-fold, 3800-fold, 3900-fold, 4000-fold, 4100-fold, 4200-fold, 4300-fold, 4400-fold, 4500-fold, 4600-fold, 4700-fold, 4800-fold, 4900-fold, 5000-fold, 5100-fold, 5200-fold, 5300-fold, 5400-fold, 5500-fold, 5600-fold, 5700-fold, 5800-fold, 5900-fold, or 6000-fold as compared to IFN-γ levels in the subject not administered the vaccine.

The vaccine can be a DNA vaccine. DNA vaccines are disclosed in U.S. Pat. Nos. 5,593,972, 5,739,118, 5,817,637, 5,830,876, 5,962,428, 5,981,505, 5,580,859, 5,703,055, and 5,676,594, which are incorporated herein fully by reference. The DNA vaccine can further comprise elements or reagents that inhibit it from integrating into the chromosome.

The vaccine can be an RNA of the one or more cancer antigens. The RNA vaccine can be introduced into the cell.

The vaccine can be an attenuated live vaccine, a vaccine using recombinant vectors to deliver antigen, subunit vaccines, and glycoprotein vaccines, for example, but not limited, the vaccines described in U.S. Pat. Nos. 4,510,245; 4,797,368; 4,722,848; 4,790,987; 4,920,209; 5,017,487; 5,077,044; 5,110,587; 5,112,749; 5,174,993; 5,223,424; 5,225,336; 5,240,703; 5,242,829; 5,294,441; 5,294,548; 5,310,668; 5,387,744; 5,389,368; 5,424,065; 5,451,499; 5,453,364; 5,462,734; 5,470,734; 5,474,935; 5,482,713; 5,591,439; 5,643,579; 5,650,309; 5,698,202; 5,955,088; 6,034,298; 6,042,836; 6,156,319 and 6,589,529, which are each incorporated herein by reference.

The vaccine of the present invention can have features required of effective vaccines such as being safe so that the vaccine itself does not cause illness or death; being protective against illness; inducing neutralizing antibody; inducing protective T cell responses; and providing ease of administration, few side effects, biological stability, and low cost per dose. The vaccine can accomplish some or all of these features by containing the cancer antigen as discussed below.

As described in more detail below, the vaccine can further comprise one or more inhibitors of one or more immune checkpoint molecules (i.e., an immune checkpoint inhibitor). Immune check point molecules are described below in more detail. The immune checkpoint inhibitor is any nucleic acid or protein that prevents the suppression of any component in the immune system such as MHC class presentation, T cell presentation and/or differentiation, B cell presentation and/or differentiation, any cytokine, chemokine or signaling for immune cell proliferation and/or differentiation. As also described below in more detail, the vaccine may be combined further with antibodies to checkpoint inhibitors such as PD-1 and PDL-1 to increase the stimulation of both the cellular and humoral immune responses. Using anti-PD-1 or anti-PDL-1 antibodies prevents PD-1 or PDL-1 from suppressing T-cell and/or B-cell responses.

a. Cancer Antigen

The vaccine can comprise one or more cancer antigens. The cancer antigen can be a nucleic acid sequence, an amino acid sequence, or a combination thereof. The nucleic acid sequence can be DNA, RNA, cDNA, a variant thereof, a fragment thereof, or a combination thereof. The nucleic acid sequence can also include additional sequences that encode linker or tag sequences that are linked to the cancer antigen by a peptide bond. The amino acid sequence can be a protein, a peptide, a variant thereof, a fragment thereof, or a combination thereof. The cancer antigen can be a recombinant cancer antigen.

One manner for designing the nucleic acid and its' encoded amino acid sequence of the recombinant cancer antigen is by introducing mutations that change particular amino acids in the overall amino acid sequence of the native cancer antigen. The introduction of mutations does not alter the cancer antigen so much that it cannot be universally applied across a mammalian subject, and preferably a human or dog subject, but changes it enough that the resulting amino acid sequence breaks tolerance or is considered a foreign antigen in order to generate an immune response. Another manner may be creating a consensus recombinant cancer antigen that has at least 85% and up to 99% amino acid sequence identity to its' corresponding native cancer antigen; preferably at least 90% and up to 98% sequence identity; more preferably at least 93% and up to 98% sequence identity; or even more preferably at least 95% and up to 98% sequence identity. In some instances the recombinant cancer antigen is 95%, 96%, 97%, 98%, or 99% amino acid sequence identity to its' corresponding native cancer antigen. The native cancer antigen is the antigen normally associated with the particular cancer or cancer tumor. Depending upon the cancer antigen, the consensus sequence of the cancer antigen can be across mammalian species or within subtypes of a species or across viral strains or serotypes. Some cancer antigens do not vary greatly from the wild type amino acid sequence of the cancer antigen. Some cancer antigens have nucleic acid/amino acid sequences that are so divergent across species, that a consensus sequence cannot be generated. In these instances, a recombinant cancer antigen that will break tolerance and generate an immune response is generated that has at least 85% and up to 99% amino acid sequence identity to its' corresponding native cancer antigen; preferably at least 90% and up to 98% sequence identity; more preferably at least 93% and up to 98% sequence identity; or even more preferably at least 95% and up to 98% sequence identity. In some instances the recombinant cancer antigen is 95%, 96%, 97%, 98%, or 99% amino acid sequence identity to its' corresponding native cancer antigen. The aforementioned approaches can be combined so that the final recombinant cancer antigen has a percent similarity to native cancer antigen amino acid sequence as discussed, above.

The cancer antigen can be one or more of the following antigens: tyrosinase (Tyr), tyrosinase-related protein 1 (TYRP1), tyrosinase-related protein 2 (TYRP2), melanoma-associated antigen 4 protein (MAGEA4), amino acid sequence of growth hormone release hormone (GHRH), amino acid sequence of MART-1/melan-A antigen (MART-1/Melan-A), cancer testis antigen (NY-ESO-1), cancer testis antigen II (NY-ESO-1), and PRAME. The vaccine can be a DNA vaccine comprising polynucleotide sequences encoding tyrosinase (Tyr), tyrosinase-related protein 1 (TYRP1), tyrosinase-related protein 2 (TYRP2), melanoma-associated antigen 4 protein (MAGEA4), amino acid sequence of growth hormone release hormone (GHRH), amino acid sequence of MART-1/melan-A antigen (MART-1/Melan-A), cancer testis antigen (NY-ESO-1), cancer testis antigen II (NY-ESO-1), PRAME, a viral antigen, or combinations thereof. The viral antigen can be one or more antigens from the following viruses: Hepatitis B Virus (e.g., core protein and surface protein), Hepatitis C Virus (e.g., non-structural protein (NS) 34A (NS34A), NS5A, NS5B, NS4B), and Human Papilloma Virus (HPV) 6, HPV 11, HPV 16, and HPV 18.

(1) Tyrosinase (Tyr)

The vaccine of the present invention can comprise the cancer antigen tyrosinase (Tyr), a fragment thereof, or a variant thereof. Tyrosinase is a copper-containing enzyme having tyrosine hydroxylase and dopa oxidase catalytic activities that can be found in microorganisms and plant and animal tissues. Specifically, tyrosinase catalyzes the production of melanin and other pigments by the oxidation of phenols such as tyrosine. Mutations in the TYR gene result in oculocutaneous albinism in mammals and non-pathological polymorphisms in the TYR gene contribute to variation in skin pigmentation.

Additionally, in cancer or tumors such as melanoma, tyrosinase can become unregulated, resulting in increased melanin synthesis. Accordingly, tyrosinase can be a cancer antigen associated with melanoma. In subjects suffering from melanoma, tyrosinase can be a target of cytotoxic T cell recognition. In some instances, however, the immune response to the cancer or tumor (including melanoma) can be suppressed, leading to a microenvironment that supports tumor formation and/or growth and thus, disease progression.

Immune suppression can be facilitated by myeloid derived suppressor cells (MDSCs), which are a mixed population of immature macrophages, granulocytes, dendritic cells, and myeloid cells. The myeloid cells can be a heterogenous population of myeloid progenitor cells and immature myeloid cells (IMCs). Markers of MDSCs can include expression of Gr-1 and CD11b (i.e., Gr-1$^+$ and CD11b$^+$ cells).

Circulation of MDSCs can increase due to chronic infection and expansion of MDSC populations can be associated with autoimmunity and inflammation. Particularly, MDSC expansion (or presence in the tumor or cancerous tissue) can facilitate tumor growth and escape from immune detection and/or regulation, and thus, MDSCs can affect immune responses to anticancer vaccines.

MDSCs can be regulated by Regulator of G-protein signaling 2 (Rgs2) and Rgs2 can be highly expressed in MDSCs derived from tumors. Rgs2 can also be widely expressed in a variety of cells, for example, myeloid cells. MDSCs derived from tumor bearing mice can function differently from MDSCs derived from non-tumor bearing mice. One such difference can be the up-regulation of the production of the chemokine MCP-1, which is secreted by MDSCs. MCP-1 can promote cell migration by signaling through CCR2, a G-protein coupled receptor (GPCR) found on monocytes, endothelial cells, and T cells. Accordingly, MCP-1 can cause migration of endothelial cells, thereby promoting vascularization. Blocking MCP-1 via neutralizing antibodies can inhibit angiogenesis, and thus, can lead to decreased tumor metastases and increased survival. As such, MCP-1 can be considered an angiogenic factor. Besides secreting MCP-1, MDSCs can secrete growth factors, thereby further contributing to tumor growth.

The Tyr antigen can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune responses. In some embodiments, the induced or elicited cellular immune response can include induction or secretion of interferon-gamma (IFN-γ) and/or tumor necrosis factor alpha (TNF-α). In other embodiments, the induced or elicited immune response can reduce or inhibit one or more immune suppression factors that promote growth of the tumor or cancer expressing the antigen, for example, but not limited to, factors that down regulate MHC presentation, factors that up regulate antigen-specific regulatory T cells (Tregs), PD-L1, FasL, cytokines such as IL-10 and TFG-β, tumor associated macrophages, tumor associated fibroblasts, soluble factors produced by immune suppressor cells, CTLA-4, PD-1, MDSCs, MCP-1, and an immune checkpoint molecule, which is described below in more detail.

As demonstrated herein, the Tyr antigen induces antigen-specific T-cell and high titer antibody responses against cancerous or tumor cells (e.g., melanoma cells). Specifically, the Tyr antigen is an important target for immune mediated clearance by inducing (1) humoral immunity via B cell responses to generate antibodies that block monocyte chemoattractant protein-1 (MCP-1) production, thereby retarding myeloid derived suppressor cells (MDSCs) and suppressing tumor growth; (2) increase cytotoxic T lymphocyte such as CD8$^+$ (CTL) to attack and kill tumor cells; (3) increase T helper cell responses; and (4) increase inflammatory responses via IFN-γ and TFN-α or preferably all of the aforementioned. As such, a protective immune response is provided against tumor formation and tumor growth by vaccines comprising the Tyr antigen (e.g., the consensus Tyr antigen, which is described below in more detail) because these vaccines prevent immune suppression by decreasing the population of MDSCs found within the cancerous or tumor tissue and block vascularization of the cancerous or tumor tissue by reducing production or secretion of MCP-1. Accordingly, any user can design a vaccine of the present invention to include a Tyr antigen to provide broad immunity against tumor formation, metastasis of tumors, and tumor growth.

The Tyr antigen can comprise protein epitopes that make them particularly effective as immunogens against which anti-Tyr immune responses can be induced. The Tyr antigen can comprise the full length translation product, a variant thereof, a fragment thereof or a combination thereof. The Tyr antigen can comprise a consensus protein.

The nucleic acid sequence encoding the consensus Tyr antigen can be optimized with regards to codon usage and corresponding RNA transcripts. The nucleic acid encoding the consensus Tyr antigen can be codon and RNA optimized for expression. In some embodiments, the nucleic acid sequence encoding the consensus Tyr antigen can include a Kozak sequence (e.g., GCC ACC) to increase the efficiency of translation. The nucleic acid encoding the consensus Tyr antigen can include multiple stop codons (e.g., TGA TGA) to increase the efficiency of translation termination.

The nucleic acid encoding the consensus Tyr antigen can also encode an immunoglobulin E (IgE) leader sequence. The nucleic acid encoding the consensus Tyr antigen can further encode the IgE leader sequence such that the amino acid sequence of the IgE leader sequence is linked to the amino acid sequence of the consensus Tyr antigen by a peptide bond. The nucleic encoding the consensus Tyr antigen can also include a nucleotide sequence encoding the IgE leader sequence. In some embodiments, the nucleic acid encoding the consensus Tyr antigen is free of or does not contain a nucleotide sequence encoding the IgE leader sequence.

The consensus Tyr antigen can be the nucleic acid sequence SEQ ID NO:1, which encodes for the amino acid sequence SEQ ID NO:2. SEQ ID NO:1 encodes the consensus Tyr protein linked to an IgE leader sequence. The consensus Tyr protein can be linked to the IgE leader sequence and an HA tag. In other embodiments, the consensus Tyr protein can be free of or not linked to an IgE leader sequence and/or an HA tag.

In some embodiments, the consensus Tyr antigen can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in the SEQ ID NO:1. In other embodiments, the consensus Tyr antigen can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:2. The consensus Tyr antigen can be the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:2.

Some embodiments relate to nucleic acid sequences encoding proteins homologous to the Tyr consensus protein, immunogenic fragment of the Tyr consensus protein, and immunogenic fragments of homologous proteins. Such nucleic acid molecules that encode immunogenic proteins that have up to 95% homology to a consensus sequence, up to 96% homology to a consensus sequence, up to 97% homology to a consensus sequence, up to 98% homology to a consensus sequence and up to 99% can be provided. Likewise, nucleic acid sequences encoding the immunogenic fragments set forth herein and the immunogenic fragments of proteins homologous to the proteins set forth herein are also provided.

Some embodiments relate to nucleic acid molecules that encode immunogenic proteins that have 95% homology to the nucleic acid coding sequences herein. Some embodiments relate to nucleic acid molecules that encode immunogenic proteins that have 96% homology to the nucleic acid coding sequences herein. Some embodiments relate to nucleic acid molecules that encode immunogenic proteins that have 97% homology to the nucleic acid coding sequences herein. Some embodiments relate to nucleic acid molecules that encode immunogenic proteins that have 98% homology to the nucleic acid coding sequences herein. Some embodiments relate to nucleic acid molecules that encode immunogenic proteins that have 99% homology to the nucleic acid coding sequences herein. In some embodiments, the nucleic acid molecules with coding sequences disclosed herein that are homologous to a coding sequence of a consensus protein disclosed herein include sequences encoding an IgE leader sequence linked to the 5' end of the coding sequence encoding the homologous protein sequences disclosed herein.

Some embodiments relate to nucleic acid sequences encoding proteins with a particular percent identity to the full length Tyr consensus protein, immunogenic fragment of the Tyr consensus protein, and immunogenic fragments of proteins having identity to the Tyr consensus protein. Such nucleic acid molecules that encode immunogenic proteins that have up to 80% identity to a full length Tyr consensus sequence, up to 85% identity to a full length consensus sequence, up to 90% identity to a full length Tyr consensus sequence, up to 91% identity to a full length Tyr consensus sequence, up to 92% identity to a full length Tyr consensus sequence, up to 93% identity to a full length Tyr consensus sequence, up to 94% identity to a full length Tyr consensus sequence, up to 95% identity to a full length Tyr consensus sequence, up to 96% identity to a full length Tyr consensus sequence, up to 97% identity to a full length Tyr consensus sequence, up to 98% identity to a full length Tyr consensus sequence, and up to 99% identity to a full length Tyr consensus sequence can be provided. Likewise, nucleic acid sequences encoding the immunogenic fragments set forth herein and the immunogenic fragments of proteins with similar percent identities as indicated above to the Tyr proteins set forth herein are also provided.

In some embodiments, the nucleic acid sequence is free of coding sequence that encodes a leader sequence. In some embodiments, the nucleic acid sequence is free of coding sequence that encodes the IgE leader.

Some embodiments relate to fragments of SEQ ID NO:1. Fragments can be at least 10%, at least 15%, at least 20%, at least 25%, at least 30%, at least 35%, at least 40%, at least 45%, at least 50%, at least 55% at least 60%, at least 65%, at least 70%, at least 75%, at least 80%, at least 85%, at least 90%, at least 95%, at least 96%, at least 97%, at least 98% or at least 99% of SEQ ID NO:1. Fragments can be at least 95%, at least 96%, at least 97%, at least 98%, or at least 99% homologous to fragments of SEQ ID NO:1. Fragments can be at least 80%, at least 85%, at least 90% at least 91%, at least 92%, at least 93%, at least 94%, at least 95%, at least 96%, at least 97%, at least 98%, or at least 99% identical to fragments of SEQ ID NO:1. In some embodiments, fragments include sequences that encode a leader sequence, such as for example, an immunoglobulin leader, such as the IgE leader. In some embodiments, fragments are free of coding sequences that encode a leader sequence. In some embodiments, fragments are free of coding sequences that encode a leader sequence, such as for example, the IgE leader.

Furthermore, the amino acid sequence of the consensus Tyr protein is SEQ ID NO:2. The amino acid sequence of the consensus Tyr protein linked to an IgE leader is SEQ ID NO:2. The amino acid sequence of the consensus Tyr protein linked to the IgE leader may be linked to HA tag.

Some embodiments relate to proteins that are homologous to SEQ ID NO:2. Some embodiments relate to immunogenic proteins that have 95% homology to the consensus protein sequences as set forth in SEQ ID NO:2. Some embodiments relate to immunogenic proteins that have 96% homology to the consensus protein sequences as set forth in SEQ ID NO:2. Some embodiments relate to immunogenic proteins that have 97% homology to the consensus protein sequences as set forth in SEQ ID NO:2. Some embodiments relate to immunogenic proteins that have 98% homology to the consensus protein sequences as set forth in SEQ ID NO:2. Some embodiments relate to immunogenic proteins that have 99% homology to the consensus protein sequences as set forth in SEQ ID NO:2.

Some embodiments relate to proteins that are identical to SEQ ID NO:2. Some embodiments relate to immunogenic proteins that have an amino acid sequence that is 80% identical to the full length consensus amino acid sequences as set forth in SEQ ID NO:2. Some embodiments relate to immunogenic proteins that have an amino acid sequence that is 85% identical to the full length consensus amino acid sequences as set forth in SEQ ID NO:2. Some embodiments relate to immunogenic proteins that have an amino acid sequence that is 90% identical to the full length consensus amino acid sequences as set forth in SEQ ID NO:2. Some embodiments relate to immunogenic proteins that have an amino acid sequence that is 91% identical to the full length consensus amino acid sequences as set forth in SEQ ID NO:2. Some embodiments relate to immunogenic proteins that have an amino acid sequence that is 92% identical to the full length consensus amino acid sequences as set forth in SEQ ID NO:2. Some embodiments relate to immunogenic proteins that have an amino acid sequence that is 93% identical to the full length consensus amino acid sequences as set forth in SEQ ID NO:2. Some embodiments relate to immunogenic proteins that have an amino acid sequence that is 94% identical to the full length consensus amino acid sequences as set forth in SEQ ID NO:2. Some embodiments relate to immunogenic proteins that have an amino acid sequence that is 95% identical to the full length consensus amino acid sequences as set forth in SEQ ID NO:2. Some embodiments relate to immunogenic proteins that have an amino acid sequence that is 96% identical to the full length consensus amino acid sequences as set forth in SEQ ID NO:2. Some embodiments relate to immunogenic proteins that have an amino acid sequence that is 97% identical to the full length consensus amino acid sequences as set forth in SEQ ID NO:2. Some embodiments relate to immunogenic proteins that have an amino acid sequence that is 98% identical to the full length consensus amino acid sequences as set forth in SEQ ID NO:2. Some embodiments relate to immunogenic proteins that have an amino acid sequence that is 99% identical to the full length consensus amino acid sequences as set forth in SEQ ID NO:2.

In some embodiments, the protein is free of a leader sequence. In some embodiments, the protein is free of the IgE leader. Fragments of consensus proteins can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of a consensus protein. Immunogenic fragments of SEQ ID NO:2 can be provided Immunogenic fragments can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of SEQ ID NO:2. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

Immunogenic fragments of proteins with amino acid sequences homologous to immunogenic fragments of SEQ ID NO:2 can be provided. Such immunogenic fragments can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of proteins that are 95% or greater homologous to SEQ ID NO:2. Some embodiments relate to immunogenic fragments that have 96% homology to the immunogenic fragments of consensus protein sequences herein. Some embodiments relate to immunogenic fragments that have 97% homology to the immunogenic fragments of consensus protein sequences herein. Some embodiments relate to immunogenic fragments that have 98% homology to the immunogenic fragments of consensus protein sequences herein. Some embodiments relate to immunogenic fragments that have 99% homology to the immunogenic fragments of consensus protein sequences herein. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

Immunogenic fragments of proteins with amino acid sequences identical to immunogenic fragments of SEQ ID NO:2 can be provided. Such immunogenic fragments can comprise at least 10%, at least 15%, at least 20%, at least 25%, at least 30%, at least 35%, at least 40%, at least 45%, at least 50%, at least 55% at least 60%, at least 65%, at least 70%, at least 75%, at least 80%, at least 85%, at least 90%, at least 95%, at least 96%, at least 97%, at least 98% or at least 99% of proteins that are 80%, 85%, 90%, 91%, 92%, 93%, 94%, 95%, 96%, 97%, 98%, or 99% identical to the amino acid sequences set forth in SEQ ID NO:2. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

As referred to herein with regard to linking a signal peptide or leader sequence to the N terminus of a protein, the signal peptide/leader sequence replaces the N terminal methionine of a protein which is encoded by the start codon of the nucleic acid sequence than encodes the protein without a signal peptide coding sequences.

(2) Tyrosinase-Related Protein 1 (TYRP1)

The vaccine of the present invention can comprise the cancer antigen tyrosinase-related Protein 1 (TYRP1), a fragment thereof, or a variant thereof. TYRP1, encoded by the TYRP1 gene, is a 75 kDa transmembrane glycoprotein and is expressed in both normal and malignant melanocytes and melanoma cells. Like tyrosinase, TYRP1 contains a modified termed M-box that can bind to the microphtalmia transcription factor (MITF), which plays a central role within the melanocyte in activating pigmentation, cell proliferation and differentiation. TYRP1 may help to stabilize tyrosinase and can form a heterodimer, which may prevent the premature death of melanocytes by attenuating tyrosinase-mediated cytotoxicity.

As described above for tyrosinase, tyrosinase-related protein 1 (TYRP-1) can also be involved in the synthesis of melanin and pigmentary machinery of the melanocyte, and can be recognized by the immune system in subjects suffering from melanoma. Accordingly, TYRP-1 can be antigen associated with melanoma.

The TRYP-1 antigen can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune responses. In some embodiments, the induced or elicited cellular immune response can include induction or secretion of interferon-gamma (IFN-γ) and/or tumor necrosis factor alpha (TNF-α). In other embodiments, the induced or elicited immune response can reduce or inhibit one or more immune suppression factors that promote growth of the tumor or cancer expressing the antigen, for example, but not limited to, factors that down regulate MHC presentation, factors that up regulate antigen-specific regulatory T cells (Tregs), PD-L1, FasL, cytokines such as IL-10 and TFG-β, tumor associated macrophages, tumor associated fibroblasts, soluble factors produced by immune suppressor cells, CTLA-4, PD-1, MDSCs, MCP-1, and an immune checkpoint molecule, which is described below in more detail.

The TYRP-1 antigen can comprise protein epitopes that make them particularly effective as immunogens against which anti-TYRP-1 immune responses can be induced. The TYRP-1 antigen can comprise the full length translation product, a variant thereof, a fragment thereof or a combination thereof. The TYRP-1 antigen can comprise a consensus protein.

The nucleic acid sequence encoding the consensus TYRP-1 antigen can be optimized with regards to codon usage and corresponding RNA transcripts. The nucleic acid encoding the consensus TYRP-1 antigen can be codon and RNA optimized for expression. In some embodiments, the nucleic acid sequence encoding the consensus TYRP-1 antigen can include a Kozak sequence (e.g., GCC ACC) to increase the efficiency of translation. The nucleic acid encoding the consensus TYRP-1 antigen can include multiple stop codons (e.g., TGA TGA) to increase the efficiency of translation termination.

The nucleic acid encoding the consensus TYRP-1 antigen can also encode an immunoglobulin E (IgE) leader sequence. The nucleic acid encoding the consensus TYRP-1 antigen can further encode the IgE leader sequence such that the amino acid sequence of the IgE leader sequence is linked to the amino acid sequence of the consensus TYRP-1 antigen by a peptide bond. The nucleic encoding the consensus TYRP-1 antigen can also include a nucleotide sequence encoding the IgE leader sequence. In some embodiments, the nucleic acid encoding the consensus TYRP-1 antigen is free of or does not contain a nucleotide sequence encoding the IgE leader sequence.

The consensus TYRP-1 antigen can be the nucleic acid sequence SEQ ID NO:3, which encodes for the amino acid sequence SEQ ID NO:4. SEQ ID NO:3 encodes the consensus TYRP-1 protein linked to an IgE leader sequence. The consensus TYRP-1 protein can be linked to the IgE leader sequence and an HA tag. In other embodiments, the consensus TYRP-1 protein can be free of or not linked to an IgE leader sequence and/or an HA tag.

In some embodiments, the consensus TYRP-1 antigen can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in the SEQ ID NO:3. In other embodiments, the consensus TYRP-1 antigen can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:4. The consensus TYRP-1 antigen can be the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:4.

Some embodiments relate to nucleic acid sequences encoding proteins homologous to the TYRP-1 consensus protein, immunogenic fragment of the TYRP-1 consensus protein, and immunogenic fragments of homologous proteins. Such nucleic acid molecules that encode immunogenic proteins that have up to 95% homology to a consensus sequence, up to 96% homology to a consensus sequence, up to 97% homology to a consensus sequence, up to 98% homology to a consensus sequence and up to 99% can be provided. Likewise, nucleic acid sequences encoding the immunogenic fragments set forth herein and the immunogenic fragments of proteins homologous to the proteins set forth herein are also provided.

Some embodiments relate to nucleic acid molecules that encode immunogenic proteins that have 95% homology to the nucleic acid coding sequences herein. Some embodiments relate to nucleic acid molecules that encode immunogenic proteins that have 96% homology to the nucleic acid coding sequences herein. Some embodiments relate to nucleic acid molecules that encode immunogenic proteins that have 97% homology to the nucleic acid coding sequences herein. Some embodiments relate to nucleic acid molecules that encode immunogenic proteins that have 98% homology to the nucleic acid coding sequences herein. Some embodiments relate to nucleic acid molecules that encode immunogenic proteins that have 99% homology to the nucleic acid coding sequences herein. In some embodiments, the nucleic acid molecules with coding sequences disclosed herein that are homologous to a coding sequence of a consensus protein disclosed herein include sequences encoding an IgE leader sequence linked to the 5' end of the coding sequence encoding the homologous protein sequences disclosed herein.

Some embodiments relate to nucleic acid sequences encoding proteins with a particular percent identity to the full length TYRP-1 consensus protein, immunogenic fragment of the TYRP-1 consensus protein, and immunogenic fragments of proteins having identity to the TYRP-1 consensus protein. Such nucleic acid molecules that encode immunogenic proteins that have up to 80% identity to a full length TYRP-1 consensus sequence, up to 85% identity to a full length TYRP-1 consensus sequence, up to 90% identity to a full length TYRP-1 consensus sequence, up to 91% identity to a full length TYRP-1 consensus sequence, up to 92% identity to a full length TYRP-1 consensus sequence, up to 93% identity to a full length TYRP-1 consensus sequence, up to 94% identity to a full length TYRP-1 consensus sequence, up to 95% identity to a full length TYRP-1 consensus sequence, up to 96% identity to a full length TYRP-1 consensus sequence, up to 97% identity to a full length TYRP-1 consensus sequence, up to 98% identity to a full length TYRP-1 consensus sequence, and up to 99% identity to a full length TYRP-1 consensus sequence can be provided. Likewise, nucleic acid sequences encoding the immunogenic fragments set forth herein and the immunogenic fragments of proteins with similar percent identities as indicated above to the TYRP-1 proteins set forth herein are also provided.

In some embodiments, the nucleic acid sequence is free of coding sequence that encodes a leader sequence. In some embodiments, the nucleic acid sequence is free of coding sequence that encodes the IgE leader.

Some embodiments relate to fragments of SEQ ID NO:3. Fragments can be at least 10%, at least 15%, at least 20%, at least 25%, at least 30%, at least 35%, at least 40%, at least 45%, at least 50%, at least 55% at least 60%, at least 65%, at least 70%, at least 75%, at least 80%, at least 85%, at least 90%, at least 95%, at least 96%, at least 97%, at least 98% or at least 99% of SEQ ID NO:3. Fragments can be at least 95%, at least 96%, at least 97%, at least 98%, or at least 99% homologous to fragments of SEQ ID NO:3. Fragments can be at least 80%, at least 85%, at least 90% at least 91%, at least 92%, at least 93%, at least 94%, at least 95%, at least 96%, at least 97%, at least 98%, or at least 99% identical to fragments of SEQ ID NO:3. In some embodiments, fragments include sequences that encode a leader sequence, such as for example, an immunoglobulin leader, such as the IgE leader. In some embodiments, fragments are free of coding sequences that encode a leader sequence. In some embodiments, fragments are free of coding sequences that encode a leader sequence, such as for example, the IgE leader.

Furthermore, the amino acid sequence of the consensus TYRP-1 protein is SEQ ID NO:4. The amino acid sequence of the consensus TYRP-1 protein linked to an IgE leader is SEQ ID NO:4. The amino acid sequence of the consensus TYRP-1 protein linked to the IgE leader may be linked to HA tag.

Some embodiments relate to proteins that are homologous to SEQ ID NO:4. Some embodiments relate to immunogenic proteins that have 95% homology to the consensus protein sequences as set forth in SEQ ID NO:4. Some embodiments relate to immunogenic proteins that have 96% homology to the consensus protein sequences as set forth in SEQ ID NO:4. Some embodiments relate to immunogenic proteins that have 97% homology to the consensus protein sequences as set forth in SEQ ID NO:4. Some embodiments relate to immunogenic proteins that have 98% homology to the consensus protein sequences as set forth in SEQ ID NO:4. Some embodiments relate to immunogenic proteins that have 99% homology to the consensus protein sequences as set forth in SEQ ID NO:4.

Some embodiments relate to proteins that are identical to SEQ ID NO:4. Some embodiments relate to immunogenic proteins that have an amino acid sequence that is 80% identical to the full length consensus amino acid sequences as set forth in SEQ ID NO:4. Some embodiments relate to immunogenic proteins that have an amino acid sequence that is 85% identical to the full length consensus amino acid sequences as set forth in SEQ ID NO:4. Some embodiments relate to immunogenic proteins that have an amino acid sequence that is 90% identical to the full length consensus amino acid sequences as set forth in SEQ ID NO:4. Some embodiments relate to immunogenic proteins that have an amino acid sequence that is 91% identical to the full length consensus amino acid sequences as set forth in SEQ ID NO:4. Some embodiments relate to immunogenic proteins that have an amino acid sequence that is 92% identical to the full length consensus amino acid sequences as set forth in SEQ ID NO:4. Some embodiments relate to immunogenic proteins that have an amino acid sequence that is 93% identical to the full length consensus amino acid sequences as set forth in SEQ ID NO:4. Some embodiments relate to immunogenic proteins that have an amino acid sequence that is 94% identical to the full length consensus amino acid sequences as set forth in SEQ ID NO:4. Some embodiments relate to immunogenic proteins that have an amino acid sequence that is 95% identical to the full length consensus amino acid sequences as set forth in SEQ ID NO:4. Some embodiments relate to immunogenic proteins that have an amino acid sequence that is 96% identical to the full length consensus amino acid sequences as set forth in SEQ ID NO:4. Some embodiments relate to immunogenic proteins that have an amino acid sequence that is 97% identical to the full length consensus amino acid sequences as set forth in SEQ ID NO:4. Some embodiments relate to immunogenic proteins that have an amino acid sequence that is 98% identical to the full length consensus amino acid sequences as set forth in SEQ ID NO:4. Some embodiments relate to immunogenic proteins that have an amino acid sequence that is 99% identical to the full length consensus amino acid sequences as set forth in SEQ ID NO:4.

In some embodiments, the protein is free of a leader sequence. In some embodiments, the protein is free of the IgE leader. Fragments of consensus proteins can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of a consensus TYRP-1 protein Immunogenic fragments of SEQ ID NO:4 can be provided Immunogenic fragments can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of SEQ ID NO:4. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

Immunogenic fragments of proteins with amino acid sequences homologous to immunogenic fragments of SEQ ID NO:4 can be provided. Such immunogenic fragments can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of proteins that are 95% or greater homologous to SEQ ID NO:4. Some embodiments relate to immunogenic fragments that have 96% homology to the immunogenic fragments of consensus protein sequences herein. Some embodiments relate to immunogenic fragments that have 97% homology to the immunogenic fragments of consensus protein sequences herein. Some embodiments relate to immunogenic fragments that have 98% homology to the immunogenic fragments of consensus protein sequences herein. Some embodiments relate to immunogenic fragments that have 99% homology to the immunogenic fragments of consensus protein sequences herein. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

Immunogenic fragments of proteins with amino acid sequences identical to immunogenic fragments of SEQ ID NO:4 can be provided. Such immunogenic fragments can comprise at least 10%, at least 15%, at least 20%, at least 25%, at least 30%, at least 35%, at least 40%, at least 45%, at least 50%, at least 55% at least 60%, at least 65%, at least 70%, at least 75%, at least 80%, at least 85%, at least 90%, at least 95%, at least 96%, at least 97%, at least 98% or at least 99% of proteins that are 80%, 85%, 90%, 91%, 92%, 93%, 94%, 95%, 96%, 97%, 98%, or 99% identical to the amino acid sequences set forth in SEQ ID NO:4. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

As referred to herein with regard to linking a signal peptide or leader sequence to the N terminus of a protein, the signal peptide/leader sequence replaces the N terminal methionine of a protein which is encoded by the start codon of the nucleic acid sequence than encodes the protein without a signal peptide coding sequences.

(3) Tyrosinase-Related Protein 2 (TYRP2)

The vaccine of the present invention can comprise the cancer antigen tyrosinase-related Protein 2 (TYRP2; also known as dopachrome tautomerase (DCT)), a fragment thereof, or a variant thereof. TYRP2/DCT, encoded by the TYRP2/DCT gene, is a protein comprised of 519 amino acids and is expressed in both normal and malignant melanocytes and melanoma cells. TYRP2/DCT is a well-characterized melanocyte-specific enzyme that, in conjunction with tyrosinase and TYRP1, functions in the conversion of L-tyrosine to melanin in melanocytes. DCT specifically catalyses the tautomerization of the melanin precursors L-DOPAchrome to 5,6-dihydroindole-2-carboxylic acid (DHICA), which is subsequently oxidized by TYRP1 (as discussed above) to form eumelanin. Studies have shown that TYRP2/DCT may be a mediator of drug resistance in melanoma cells, with specificity for DNA-damaging agents. Since TYRP2/DCT has frequently been reported to be highly expressed in melanomas, this melanocyte-specific enzyme plays an important role contributing to intrinsic resistance phenotype of melanomas to various anticancer DNA-damaging drugs.

As described above for tyrosinase, tyrosinase-related protein 2 (TYRP-2) can also be involved in the synthesis of melanin and recognized by the immune system in subjects suffering from melanoma. Additionally, TYRP-2 can mediate drug resistance in melanoma cells. Accordingly, TYRP-2 can be an antigen associated with melanoma.

The TRYP-2 antigen can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune responses. In some embodiments, the induced or elicited cellular immune response can include induction or secretion of interferon-gamma (IFN-γ) and/or tumor necrosis factor alpha (TNF-α). In other embodiments, the induced or elicited immune response can reduce or inhibit one or more immune suppression factors that promote growth of the tumor or cancer expressing the antigen, for example, but not limited to, factors that down regulate MHC presentation, factors that up regulate antigen-specific regulatory T cells (Tregs), PD-L1, FasL, cytokines such as IL-10 and TFG-β, tumor associated macrophages, tumor associated fibroblasts, soluble factors produced by immune suppressor cells, CTLA-4, PD-1, MDSCs, MCP-1, and an immune checkpoint molecule, which is described below in more detail.

The TYRP2 antigen can comprise protein epitopes that make them particularly effective as immunogens against which anti-TYRP2 immune responses can be induced. The TYRP2 antigen can comprise the full length translation product, a variant thereof, a fragment thereof or a combination thereof. The TYRP2 antigen can comprise a consensus protein.

The nucleic acid sequence encoding the consensus TYRP2 antigen can be optimized with regards to codon usage and corresponding RNA transcripts. The nucleic acid encoding the consensus TYRP2 antigen can be codon and RNA optimized for expression. In some embodiments, the nucleic acid sequence encoding the consensus TYRP2 antigen can include a Kozak sequence (e.g., GCC ACC) to increase the efficiency of translation. The nucleic acid encoding the consensus TYRP2 antigen can include multiple stop codons (e.g., TGA TGA) to increase the efficiency of translation termination.

The nucleic acid encoding the consensus TYRP2 antigen can also encode an immunoglobulin E (IgE) leader sequence. The nucleic acid encoding the consensus TYRP2 antigen can further encode the IgE leader sequence such that the amino acid sequence of the IgE leader sequence is linked to the amino acid sequence of the consensus TYRP2 antigen by a peptide bond. The nucleic encoding the consensus TYRP2 antigen can also include a nucleotide sequence encoding the IgE leader sequence. In some embodiments, the nucleic acid encoding the consensus TYRP2 antigen is free of or does not contain a nucleotide sequence encoding the IgE leader sequence.

The consensus TYRP2 antigen can be the nucleic acid sequence SEQ ID NO:5, which encodes for the amino acid sequence SEQ ID NO:6. SEQ ID NO:5 encodes the consensus TYRP2 protein linked to an IgE leader sequence. The consensus TYRP2 protein can be linked to the IgE leader sequence and an HA tag. In other embodiments, the consensus TYRP2 protein can be free of or not linked to an IgE leader sequence and/or an HA tag.

In some embodiments, the consensus TYRP2 antigen can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in the SEQ ID NO:5. In other embodiments, the consensus TYRP2 antigen can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:6. The consensus TYRP2 antigen can be the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:6.

Some embodiments relate to nucleic acid sequences encoding proteins homologous to the TYRP2 consensus protein, immunogenic fragment of the TYRP2 consensus protein, and immunogenic fragments of homologous proteins. Such nucleic acid molecules that encode immunogenic proteins that have up to 95% homology to a consensus sequence, up to 96% homology to a consensus sequence, up to 97% homology to a consensus sequence, up to 98% homology to a consensus sequence and up to 99% can be provided. Likewise, nucleic acid sequences encoding the immunogenic fragments set forth herein and the immunogenic fragments of proteins homologous to the proteins set forth herein are also provided.

Some embodiments relate to nucleic acid molecules that encode immunogenic proteins that have 95% homology to the nucleic acid coding sequences herein. Some embodiments relate to nucleic acid molecules that encode immunogenic proteins that have 96% homology to the nucleic acid coding sequences herein. Some embodiments relate to nucleic acid molecules that encode immunogenic proteins that have 97% homology to the nucleic acid coding sequences herein. Some embodiments relate to nucleic acid molecules that encode immunogenic proteins that have 98% homology to the nucleic acid coding sequences herein. Some embodiments relate to nucleic acid molecules that encode immunogenic proteins that have 99% homology to the nucleic acid coding sequences herein. In some embodiments, the nucleic acid molecules with coding sequences disclosed herein that are homologous to a coding sequence of a consensus protein disclosed herein include sequences encoding an IgE leader sequence linked to the 5' end of the coding sequence encoding the homologous protein sequences disclosed herein.

Some embodiments relate to nucleic acid sequences encoding proteins with a particular percent identity to the full length TYRP2 consensus protein, immunogenic fragment of the TYRP2 consensus protein, and immunogenic fragments of proteins having identity to the TYRP2 consensus protein. Such nucleic acid molecules that encode immunogenic proteins that have up to 80% identity to a full length TYRP2 consensus sequence, up to 85% identity to a full length consensus sequence, up to 90% identity to a full length TYRP2 consensus sequence, up to 91% identity to a full length TYRP2 consensus sequence, up to 92% identity to a full length TYRP2 consensus sequence, up to 93% identity to a full length TYRP2 consensus sequence, up to 94% identity to a full length TYRP2 consensus sequence, up to 95% identity to a full length TYRP2 consensus sequence, up to 96% identity to a full length TYRP2 consensus sequence, up to 97% identity to a full length TYRP2 consensus sequence, up to 98% identity to a full length TYRP2 consensus sequence, and up to 99% identity to a full length TYRP2 consensus sequence can be provided. Likewise, nucleic acid sequences encoding the immunogenic fragments set forth herein and the immunogenic fragments of proteins with similar percent identities as indicated above to the TYRP2 proteins set forth herein are also provided.

In some embodiments, the nucleic acid sequence is free of coding sequence that encodes a leader sequence. In some embodiments, the nucleic acid sequence is free of coding sequence that encodes the IgE leader.

Some embodiments relate to fragments of SEQ ID NO:5. Fragments can be at least 10%, at least 15%, at least 20%, at least 25%, at least 30%, at least 35%, at least 40%, at least 45%, at least 50%, at least 55% at least 60%, at least 65%, at least 70%, at least 75%, at least 80%, at least 85%, at least 90%, at least 95%, at least 96%, at least 97%, at least 98% or at least 99% of SEQ ID NO:5. Fragments can be at least 95%, at least 96%, at least 97%, at least 98%, or at least 99% homologous to fragments of SEQ ID NO:5. Fragments can be at least 80%, at least 85%, at least 90% at least 91%, at least 92%, at least 93%, at least 94%, at least 95%, at least 96%, at least 97%, at least 98%, or at least 99% identical to fragments of SEQ ID NO:5. In some embodiments, fragments include sequences that encode a leader sequence, such as for example, an immunoglobulin leader, such as the IgE leader. In some embodiments, fragments are free of coding sequences that encode a leader sequence. In some embodiments, fragments are free of coding sequences that encode a leader sequence, such as for example, the IgE leader.

Furthermore, the amino acid sequence of the consensus TYRP2 protein is SEQ ID NO:6. The amino acid sequence of the consensus TYRP2 protein linked to an IgE leader is SEQ ID NO:6. The amino acid sequence of the consensus TYRP2 protein linked to the IgE leader may be linked to HA tag.

Some embodiments relate to proteins that are homologous to SEQ ID NO:2. Some embodiments relate to immunogenic proteins that have 95% homology to the consensus protein sequences as set forth in SEQ ID NO:6. Some embodiments relate to immunogenic proteins that have 96% homology to the consensus protein sequences as set forth in SEQ ID NO:6. Some embodiments relate to immunogenic proteins that have 97% homology to the consensus protein sequences as set forth in SEQ ID NO:6. Some embodiments relate to immunogenic proteins that have 98% homology to the consensus protein sequences as set forth in SEQ ID NO:6. Some embodiments relate to immunogenic proteins that have 99% homology to the consensus protein sequences as set forth in SEQ ID NO:6.

Some embodiments relate to proteins that are identical to SEQ ID NO:6. Some embodiments relate to immunogenic proteins that have an amino acid sequence that is 80% identical to the full length consensus amino acid sequences as set forth in SEQ ID NO:6. Some embodiments relate to immunogenic proteins that have an amino acid sequence that is 85% identical to the full length consensus amino acid sequences as set forth in SEQ ID NO:6. Some embodiments relate to immunogenic proteins that have an amino acid sequence that is 90% identical to the full length consensus amino acid sequences as set forth in SEQ ID NO:6. Some embodiments relate to immunogenic proteins that have an amino acid sequence that is 91% identical to the full length consensus amino acid sequences as set forth in SEQ ID NO:6. Some embodiments relate to immunogenic proteins that have an amino acid sequence that is 92% identical to the full length consensus amino acid sequences as set forth in SEQ ID NO:6. Some embodiments relate to immunogenic proteins that have an amino acid sequence that is 93% identical to the full length consensus amino acid sequences as set forth in SEQ ID NO:6. Some embodiments relate to immunogenic proteins that have an amino acid sequence that is 94% identical to the full length consensus amino acid sequences as set forth in SEQ ID NO:6. Some embodiments relate to immunogenic proteins that have an amino acid sequence that is 95% identical to the full length consensus amino acid sequences as set forth in SEQ ID NO:6. Some embodiments relate to immunogenic proteins that have an amino acid sequence that is 96% identical to the full length consensus amino acid sequences as set forth in SEQ ID NO:6. Some embodiments relate to immunogenic proteins that have an amino acid sequence that is 97% identical to the full length consensus amino acid sequences as set forth in SEQ ID NO:6. Some embodiments relate to immunogenic proteins that have an amino acid sequence that is 98% identical to the full length consensus amino acid sequences as set forth in SEQ ID NO:6. Some embodiments relate to immunogenic proteins that have an amino acid sequence that is 99% identical to the full length consensus amino acid sequences as set forth in SEQ ID NO:6.

In some embodiments, the protein is free of a leader sequence. In some embodiments, the protein is free of the IgE leader. Fragments of consensus proteins can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of a consensus protein. Immunogenic fragments of SEQ ID NO:6 can be provided Immunogenic fragments can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of SEQ ID NO:6. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

Immunogenic fragments of proteins with amino acid sequences homologous to immunogenic fragments of SEQ ID NO:6 can be provided. Such immunogenic fragments can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of proteins that are 95% or greater homologous to SEQ ID NO:6. Some embodiments relate to immunogenic fragments that have 96% homology to the immunogenic fragments of consensus protein sequences herein. Some embodiments relate to immunogenic fragments that have 97% homology to the immunogenic fragments of consensus protein sequences herein. Some embodiments relate to immunogenic fragments that have 98% homology to the immunogenic fragments of consensus protein sequences herein. Some embodiments relate to immunogenic fragments that have 99% homology to the immunogenic fragments of consensus protein sequences herein. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

Immunogenic fragments of proteins with amino acid sequences identical to immunogenic fragments of SEQ ID NO:6 can be provided. Such immunogenic fragments can comprise at least 10%, at least 15%, at least 20%, at least 25%, at least 30%, at least 35%, at least 40%, at least 45%, at least 50%, at least 55% at least 60%, at least 65%, at least 70%, at least 75%, at least 80%, at least 85%, at least 90%, at least 95%, at least 96%, at least 97%, at least 98% or at least 99% of proteins that are 80%, 85%, 90%, 91%, 92%, 93%, 94%, 95%, 96%, 97%, 98%, or 99% identical to the amino acid sequences set forth in SEQ ID NO:6. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

As referred to herein with regard to linking a signal peptide or leader sequence to the N terminus of a protein, the signal peptide/leader sequence replaces the N terminal methionine of a protein which is encoded by the start codon of the nucleic acid sequence than encodes the protein without a signal peptide coding sequences.

(4) Melanoma-Associated Antigen 4 (MAGEA4)

The vaccine of the present invention can comprise the cancer antigen Melanoma-associated Antigen 4 (MAGEA4), a fragment thereof, or a variant thereof. MAGE-A4, encoded by the MAGE-A4 gene, is a protein comprised of 317 amino acids and is expressed in male germ cells and tumor cells of various histological types such as gastrointestinal, esophageal and pulmonary carcinomas. MAGE-A4 binds the oncoprotein, Gankyrin. This MAGE-A4 specific binding is mediated by its C-terminus Studies have shown that exogenous MAGE-A4 can partly inhibit the adhesion-independent growth of Gankyrin-overexpressing cells in vitro and suppress the formation of migrated tumors from these cells in nude mice. This inhibition is dependent upon binding between MAGE-A4 and Gankyrin, suggesting that interactions between Gankyrin and MAGE-A4 inhibit Gankyrin-mediated carcinogenesis. It is likely that MAGE expression in tumor tissue is not a cause, but a result of tumor genesis, and MAGE genes take part in the immune process by targeting early tumor cells for destruction.

Melanoma-associated antigen 4 protein (MAGEA4) can be involved in embryonic development and tumor transformation and/or progression. MAGEA4 is normally expressed in testes and placenta. MAGEA4, however, can be expressed in many different types of tumors, for example, melanoma, head and neck squamous cell carcinoma, lung carcinoma, and breast carcinoma. Accordingly, MAGEA4 can be antigen associated with a variety of tumors.

The MAGEA4 antigen can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune responses. In some embodiments, the induced or elicited cellular immune response can include induction or secretion of interferon-gamma (IFN-γ) and/or tumor necrosis factor alpha (TNF-α). In other embodiments, the induced or elicited immune response can reduce or inhibit one or more immune suppression factors that promote growth of the tumor or cancer expressing the antigen, for example, but not limited to, factors that down regulate MHC presentation, factors that up regulate antigen-specific regulatory T cells (Tregs), PD-L1, FasL, cytokines such as IL-10 and TFG-β, tumor associated macrophages, tumor associated fibroblasts, soluble factors produced by immune suppressor cells, CTLA-4, PD-1, MDSCs, MCP-1, and an immune checkpoint molecule, which is described below in more detail.

The MAGEA4 antigen can comprise protein epitopes that make them particularly effective as immunogens against which anti-MAGEA4 immune responses can be induced. The MAGEA4 antigen can comprise the full length translation product, a variant thereof, a fragment thereof or a combination thereof. The MAGEA4 antigen can comprise a consensus protein.

The nucleic acid sequence encoding the consensus MAGEA4 antigen can be optimized with regards to codon usage and corresponding RNA transcripts. The nucleic acid encoding the consensus MAGEA4 antigen can be codon and RNA optimized for expression. In some embodiments, the nucleic acid sequence encoding the consensus MAGEA4 antigen can include a Kozak sequence (e.g., GCC ACC) to increase the efficiency of translation. The nucleic acid encoding the consensus MAGEA4 antigen can include multiple stop codons (e.g., TGA TGA) to increase the efficiency of translation termination.

The nucleic acid encoding the consensus MAGEA4 antigen can also encode an immunoglobulin E (IgE) leader sequence. The nucleic acid encoding the consensus Tyr antigen can further encode the IgE leader sequence such that the amino acid sequence of the IgE leader sequence is linked to the amino acid sequence of the consensus MAGEA4 antigen by a peptide bond. The nucleic encoding the consensus MAGEA4 antigen can also include a nucleotide sequence encoding the IgE leader sequence. In some embodiments, the nucleic acid encoding the consensus MAGEA4 antigen is free of or does not contain a nucleotide sequence encoding the IgE leader sequence.

The consensus MAGEA4 antigen can be the nucleic acid sequence SEQ ID NO:7, which encodes for the amino acid sequence SEQ ID NO:8. SEQ ID NO:7 encodes the consensus MAGEA4 protein linked to an IgE leader sequence. The consensus MAGEA4 protein can be linked to the IgE leader sequence and an HA tag. In other embodiments, the consensus MAGEA4 protein can be free of or not linked to an IgE leader sequence and/or an HA tag.

In some embodiments, the consensus MAGEA4 antigen can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in the SEQ ID NO:7. In other embodiments, the consensus MAGEA4 antigen can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:8. The consensus MAGEA4 antigen can be the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:8.

Some embodiments relate to nucleic acid sequences encoding proteins homologous to the MAGEA4 consensus protein, immunogenic fragment of the MAGEA4 consensus protein, and immunogenic fragments of homologous proteins. Such nucleic acid molecules that encode immunogenic proteins that have up to 95% homology to a consensus sequence, up to 96% homology to a consensus sequence, up to 97% homology to a consensus sequence, up to 98% homology to a consensus sequence and up to 99% can be provided. Likewise, nucleic acid sequences encoding the immunogenic fragments set forth herein and the immunogenic fragments of proteins homologous to the proteins set forth herein are also provided.

Some embodiments relate to nucleic acid molecules that encode immunogenic proteins that have 95% homology to the nucleic acid coding sequences herein. Some embodiments relate to nucleic acid molecules that encode immunogenic proteins that have 96% homology to the nucleic acid coding sequences herein. Some embodiments relate to nucleic acid molecules that encode immunogenic proteins that have 97% homology to the nucleic acid coding sequences herein. Some embodiments relate to nucleic acid molecules that encode immunogenic proteins that have 98% homology to the nucleic acid coding sequences herein. Some embodiments relate to nucleic acid molecules that encode immunogenic proteins that have 99% homology to the nucleic acid coding sequences herein. In some embodiments, the nucleic acid molecules with coding sequences disclosed herein that are homologous to a coding sequence of a consensus protein disclosed herein include sequences encoding an IgE leader sequence linked to the 5' end of the coding sequence encoding the homologous protein sequences disclosed herein.

Some embodiments relate to nucleic acid sequences encoding proteins with a particular percent identity to the full length MAGEA4 consensus protein, immunogenic fragment of the MAGEA4 consensus protein, and immunogenic fragments of proteins having identity to the MAGEA4 consensus protein. Such nucleic acid molecules that encode immunogenic proteins that have up to 80% identity to a full length MAGEA4 consensus sequence, up to 85% identity to a full length consensus sequence, up to 90% identity to a full length MAGEA4 consensus sequence, up to 91% identity to a full length MAGEA4 consensus sequence, up to 92% identity to a full length MAGEA4 consensus sequence, up to 93% identity to a full length MAGEA4 consensus sequence, up to 94% identity to a full length MAGEA4 consensus sequence, up to 95% identity to a full length MAGEA4 consensus sequence, up to 96% identity to a full length MAGEA4 consensus sequence, up to 97% identity to a full length MAGEA4 consensus sequence, up to 98% identity to a full length MAGEA4 consensus sequence, and up to 99% identity to a full length MAGEA4 consensus sequence can be provided. Likewise, nucleic acid sequences encoding the immunogenic fragments set forth herein and the immunogenic fragments of proteins with similar percent identities as indicated above to the MAGEA4 proteins set forth herein are also provided.

In some embodiments, the nucleic acid sequence is free of coding sequence that encodes a leader sequence. In some embodiments, the nucleic acid sequence is free of coding sequence that encodes the IgE leader.

Some embodiments relate to fragments of SEQ ID NO:7. Fragments can be at least 10%, at least 15%, at least 20%, at least 25%, at least 30%, at least 35%, at least 40%, at least 45%, at least 50%, at least 55% at least 60%, at least 65%, at least 70%, at least 75%, at least 80%, at least 85%, at least 90%, at least 95%, at least 96%, at least 97%, at least 98% or at least 99% of SEQ ID NO:7. Fragments can be at least 95%, at least 96%, at least 97%, at least 98%, or at least 99% homologous to fragments of SEQ ID NO:7. Fragments can be at least 80%, at least 85%, at least 90% at least 91%, at least 92%, at least 93%, at least 94%, at least 95%, at least 96%, at least 97%, at least 98%, or at least 99% identical to fragments of SEQ ID NO:7. In some embodiments, fragments include sequences that encode a leader sequence, such as for example, an immunoglobulin leader, such as the IgE leader. In some embodiments, fragments are free of coding sequences that encode a leader sequence. In some embodiments, fragments are free of coding sequences that encode a leader sequence, such as for example, the IgE leader.

Furthermore, the amino acid sequence of the consensus MAGEA4 protein is SEQ ID NO:8. The amino acid sequence of the consensus MAGEA4 protein linked to an IgE leader is SEQ ID NO:8. The amino acid sequence of the consensus MAGEA4 protein linked to the IgE leader may be linked to HA tag.

Some embodiments relate to proteins that are homologous to SEQ ID NO:8. Some embodiments relate to immunogenic proteins that have 95% homology to the consensus protein sequences as set forth in SEQ ID NO:8. Some embodiments relate to immunogenic proteins that have 96% homology to the consensus protein sequences as set forth in SEQ ID NO:8. Some embodiments relate to immunogenic proteins that have 97% homology to the consensus protein sequences as set forth in SEQ ID NO:8. Some embodiments relate to immunogenic proteins that have 98% homology to the consensus protein sequences as set forth in SEQ ID NO:8. Some embodiments relate to immunogenic proteins that have 99% homology to the consensus protein sequences as set forth in SEQ ID NO:8.

Some embodiments relate to proteins that are identical to SEQ ID NO:8. Some embodiments relate to immunogenic proteins that have an amino acid sequence that is 80% identical to the full length consensus amino acid sequences as set forth in SEQ ID NO:8. Some embodiments relate to immunogenic proteins that have an amino acid sequence that is 85% identical to the full length consensus amino acid sequences as set forth in SEQ ID NO:8. Some embodiments relate to immunogenic proteins that have an amino acid sequence that is 90% identical to the full length consensus amino acid sequences as set forth in SEQ ID NO:8. Some embodiments relate to immunogenic proteins that have an amino acid sequence that is 91% identical to the full length consensus amino acid sequences as set forth in SEQ ID NO:8. Some embodiments relate to immunogenic proteins that have an amino acid sequence that is 92% identical to the full length consensus amino acid sequences as set forth in SEQ ID NO:8. Some embodiments relate to immunogenic proteins that have an amino acid sequence that is 93% identical to the full length consensus amino acid sequences as set forth in SEQ ID NO:8. Some embodiments relate to immunogenic proteins that have an amino acid sequence that is 94% identical to the full length consensus amino acid sequences as set forth in SEQ ID NO:8. Some embodiments relate to immunogenic proteins that have an amino acid sequence that is 95% identical to the full length consensus amino acid sequences as set forth in SEQ ID NO:8. Some embodiments relate to immunogenic proteins that have an amino acid sequence that is 96% identical to the full length consensus amino acid sequences as set forth in SEQ ID NO:8. Some embodiments relate to immunogenic proteins that have an amino acid sequence that is 97% identical to the full length consensus amino acid sequences as set forth in SEQ ID NO:8. Some embodiments relate to immunogenic proteins that have an amino acid sequence that is 98% identical to the full length consensus amino acid sequences as set forth in SEQ ID NO:8. Some embodiments relate to immunogenic proteins that have an amino acid sequence that is 99% identical to the full length consensus amino acid sequences as set forth in SEQ ID NO:8.

In some embodiments, the protein is free of a leader sequence. In some embodiments, the protein is free of the IgE leader. Fragments of consensus proteins can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of a consensus protein. Immunogenic fragments of SEQ ID NO:8 can be provided Immunogenic fragments can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of SEQ ID NO:8. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

Immunogenic fragments of proteins with amino acid sequences homologous to immunogenic fragments of SEQ ID NO:8 can be provided. Such immunogenic fragments can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of proteins that are 95% or greater homologous to SEQ ID NO:8. Some embodiments relate to immunogenic fragments that have 96% homology to the immunogenic fragments of consensus protein sequences herein. Some embodiments relate to immunogenic fragments that have 97% homology to the immunogenic fragments of consensus protein sequences herein. Some embodiments relate to immunogenic fragments that have 98% homology to the immunogenic fragments of consensus protein sequences herein. Some embodiments relate to immunogenic fragments that have 99% homology to the immunogenic fragments of consensus protein sequences herein. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

Immunogenic fragments of proteins with amino acid sequences identical to immunogenic fragments of SEQ ID NO:8 can be provided. Such immunogenic fragments can comprise at least 10%, at least 15%, at least 20%, at least 25%, at least 30%, at least 35%, at least 40%, at least 45%, at least 50%, at least 55% at least 60%, at least 65%, at least 70%, at least 75%, at least 80%, at least 85%, at least 90%, at least 95%, at least 96%, at least 97%, at least 98% or at least 99% of proteins that are 80%, 85% 90% 91% 92% 93% 94% 95%, 96%, 97%, 98%, or 99% identical to the amino acid sequences set forth in SEQ ID NO:8. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

As referred to herein with regard to linking a signal peptide or leader sequence to the N terminus of a protein, the signal peptide/leader sequence replaces the N terminal methionine of a protein which is encoded by the start codon of the nucleic acid sequence than encodes the protein without a signal peptide coding sequences.

(5) Growth Hormone Releasing Hormone (GHRH)

The vaccine of the present invention can comprise the cancer antigen growth hormone releasing hormone (GHRH; also known as growth-hormone-releasing factor (GRF or GHRF) or somatocrinin), a fragment thereof, or a variant thereof. GHRH is a 44 amino acid peptide hormone produced in the arcuate nucleus of the hypothalamus. GHRH is secreted by the hypothalamus and stimulates the release of growth hormone, a regulator of growth, metabolism, and body structure, from the pituitary gland. GHRH also stimulates the product of growth hormone. Antagonists of GHRH can inhibit the growth of a variety of cancers, for example, osteosarcomas, glioblastomas, prostate cancer, renal cancer, pancreatic cancer, colorectal cancer, and breast cancer. Accordingly, GHRH can be an antigen associated with a variety of tumors.

The GHRH antigen can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune responses. In some embodiments, the induced or elicited cellular immune response can include induction or secretion of interferon-gamma (IFN-γ) and/or tumor necrosis factor alpha (TNF-α). In other embodiments, the induced or elicited immune response can reduce or inhibit one or more immune suppression factors that promote growth of the tumor or cancer expressing the antigen, for example, but not limited to, factors that down regulate MHC presentation, factors that up regulate antigen-specific regulatory T cells (Tregs), PD-L1, FasL, cytokines such as IL-10 and TFG-β, tumor associated macrophages, tumor associated fibroblasts, soluble factors produced by immune suppressor cells, CTLA-4, PD-1, MDSCs, MCP-1, and an immune checkpoint molecule, which is described below in more detail.

The GHRH antigen can comprise protein epitopes that make them particularly effective as immunogens against which anti-GHRH immune responses can be induced. The GHRH antigen can comprise the full length translation product, a variant thereof, a fragment thereof or a combination thereof. The GHRH antigen can comprise a consensus protein.

The nucleic acid sequence encoding the consensus GHRH antigen can be optimized with regards to codon usage and corresponding RNA transcripts. The nucleic acid encoding the consensus GHRH antigen can be codon and RNA optimized for expression. In some embodiments, the nucleic acid sequence encoding the consensus GHRH antigen can include a Kozak sequence (e.g., GCC ACC) to increase the efficiency of translation. The nucleic acid encoding the consensus GHRH antigen can include multiple stop codons (e.g., TGA TGA) to increase the efficiency of translation termination.

The nucleic acid encoding the consensus GHRH antigen can also encode an immunoglobulin E (IgE) leader sequence. The nucleic acid encoding the consensus GHRH antigen can further encode the IgE leader sequence such that the amino acid sequence of the IgE leader sequence is linked to the amino acid sequence of the consensus GHRH antigen by a peptide bond. The nucleic encoding the consensus GHRH antigen can also include a nucleotide sequence encoding the IgE leader sequence. In some embodiments, the nucleic acid encoding the consensus GHRH antigen is free of or does not contain a nucleotide sequence encoding the IgE leader sequence.

The consensus GHRH antigen can be the nucleic acid sequence SEQ ID NO:9, which encodes for the amino acid sequence SEQ ID NO:10. SEQ ID NO:9 encodes the consensus GHRH protein linked to an IgE leader sequence. The consensus GHRH protein can be linked to the IgE leader sequence and an HA tag. In other embodiments, the consensus GHRH protein can be free of or not linked to an IgE leader sequence and/or an HA tag.

In some embodiments, the consensus GHRH antigen can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in the SEQ ID NO:9. In other embodiments, the consensus GHRH antigen can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:10. The consensus GHRH antigen can be the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:10.

Some embodiments relate to nucleic acid sequences encoding proteins homologous to the GHRH consensus protein, immunogenic fragment of the GHRH consensus protein, and immunogenic fragments of homologous proteins. Such nucleic acid molecules that encode immunogenic proteins that have up to 95% homology to a consensus sequence, up to 96% homology to a consensus sequence, up to 97% homology to a consensus sequence, up to 98% homology to a consensus sequence and up to 99% can be provided. Likewise, nucleic acid sequences encoding the immunogenic fragments set forth herein and the immunogenic fragments of proteins homologous to the proteins set forth herein are also provided.

Some embodiments relate to nucleic acid molecules that encode immunogenic proteins that have 95% homology to the nucleic acid coding sequences herein. Some embodiments relate to nucleic acid molecules that encode immunogenic proteins that have 96% homology to the nucleic acid coding sequences herein. Some embodiments relate to nucleic acid molecules that encode immunogenic proteins that have 97% homology to the nucleic acid coding sequences herein. Some embodiments relate to nucleic acid molecules that encode immunogenic proteins that have 98% homology to the nucleic acid coding sequences herein. Some embodiments relate to nucleic acid molecules that encode immunogenic proteins that have 99% homology to the nucleic acid coding sequences herein. In some embodiments, the nucleic acid molecules with coding sequences disclosed herein that are homologous to a coding sequence of a consensus protein disclosed herein include sequences encoding an IgE leader sequence linked to the 5' end of the coding sequence encoding the homologous protein sequences disclosed herein.

Some embodiments relate to nucleic acid sequences encoding proteins with a particular percent identity to the full length GHRH consensus protein, immunogenic fragment of the GHRH consensus protein, and immunogenic fragments of proteins having identity to the GHRH consensus protein. Such nucleic acid molecules that encode immunogenic proteins that have up to 80% identity to a full length GHRH consensus sequence, up to 85% identity to a full length consensus sequence, up to 90% identity to a full length GHRH consensus sequence, up to 91% identity to a full length GHRH consensus sequence, up to 92% identity to a full length GHRH consensus sequence, up to 93% identity to a full length GHRH consensus sequence, up to 94% identity to a full length GHRH consensus sequence, up to 95% identity to a full length GHRH consensus sequence, up to 96% identity to a full length GHRH consensus sequence, up to 97% identity to a full length GHRH consensus sequence, up to 98% identity to a full length GHRH consensus sequence, and up to 99% identity to a full length GHRH consensus sequence can be provided. Likewise, nucleic acid sequences encoding the immunogenic fragments set forth herein and the immunogenic fragments of proteins with similar percent identities as indicated above to the GHRH proteins set forth herein are also provided.

In some embodiments, the nucleic acid sequence is free of coding sequence that encodes a leader sequence. In some embodiments, the nucleic acid sequence is free of coding sequence that encodes the IgE leader.

Some embodiments relate to fragments of SEQ ID NO:9. Fragments can be at least 10%, at least 15%, at least 20%, at least 25%, at least 30%, at least 35%, at least 40%, at least 45%, at least 50%, at least 55% at least 60%, at least 65%, at least 70%, at least 75%, at least 80%, at least 85%, at least 90%, at least 95%, at least 96%, at least 97%, at least 98% or at least 99% of SEQ ID NO:9. Fragments can be at least 95%, at least 96%, at least 97%, at least 98%, or at least 99% homologous to fragments of SEQ ID NO:9. Fragments can be at least 80%, at least 85%, at least 90% at least 91%, at least 92%, at least 93%, at least 94%, at least 95%, at least 96%, at least 97%, at least 98%, or at least 99% identical to fragments of SEQ ID NO:9. In some embodiments, fragments include sequences that encode a leader sequence, such as for example, an immunoglobulin leader, such as the IgE leader. In some embodiments, fragments are free of coding sequences that encode a leader sequence. In some embodiments, fragments are free of coding sequences that encode a leader sequence, such as for example, the IgE leader.

Furthermore, the amino acid sequence of the consensus GHRH protein is SEQ ID NO:10. The amino acid sequence of the consensus GHRH protein linked to an IgE leader is SEQ ID NO:10. The amino acid sequence of the consensus GHRH protein linked to the IgE leader may be linked to HA tag.

Some embodiments relate to proteins that are homologous to SEQ ID NO:10. Some embodiments relate to immunogenic proteins that have 95% homology to the consensus protein sequences as set forth in SEQ ID NO:10. Some embodiments relate to immunogenic proteins that have 96% homology to the consensus protein sequences as set forth in SEQ ID NO:10. Some embodiments relate to immunogenic proteins that have 97% homology to the consensus protein sequences as set forth in SEQ ID NO:10. Some embodiments relate to immunogenic proteins that have 98% homology to the consensus protein sequences as set forth in SEQ ID NO:10. Some embodiments relate to immunogenic proteins that have 99% homology to the consensus protein sequences as set forth in SEQ ID NO:10.

Some embodiments relate to proteins that are identical to SEQ ID NO:10. Some embodiments relate to immunogenic proteins that have an amino acid sequence that is 80% identical to the full length consensus amino acid sequences as set forth in SEQ ID NO:10. Some embodiments relate to immunogenic proteins that have an amino acid sequence that is 85% identical to the full length consensus amino acid sequences as set forth in SEQ ID NO:10. Some embodiments relate to immunogenic proteins that have an amino acid sequence that is 90% identical to the full length consensus amino acid sequences as set forth in SEQ ID NO:10. Some embodiments relate to immunogenic proteins that have an amino acid sequence that is 91% identical to the full length consensus amino acid sequences as set forth in SEQ ID NO:10. Some embodiments relate to immunogenic proteins that have an amino acid sequence that is 92% identical to the full length consensus amino acid sequences as set forth in SEQ ID NO:10. Some embodiments relate to immunogenic proteins that have an amino acid sequence that is 93% identical to the full length consensus amino acid sequences as set forth in SEQ ID NO:10. Some embodiments relate to immunogenic proteins that have an amino acid sequence that is 94% identical to the full length consensus amino acid sequences as set forth in SEQ ID NO:10. Some embodiments relate to immunogenic proteins that have an amino acid sequence that is 95% identical to the full length consensus amino acid sequences as set forth in SEQ ID NO:10. Some embodiments relate to immunogenic proteins that have an amino acid sequence that is 96% identical to the full length consensus amino acid sequences as set forth in SEQ ID NO:10. Some embodiments relate to immunogenic proteins that have an amino acid sequence that is 97% identical to the full length consensus amino acid sequences as set forth in SEQ ID NO:10. Some embodiments relate to immunogenic proteins that have an amino acid sequence that is 98% identical to the full length consensus amino acid sequences as set forth in SEQ ID NO:10. Some embodiments relate to immunogenic proteins that have an amino acid sequence that is 99% identical to the full length consensus amino acid sequences as set forth in SEQ ID NO:10.

In some embodiments, the protein is free of a leader sequence. In some embodiments, the protein is free of the IgE leader. Fragments of consensus proteins can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of a consensus protein. Immunogenic fragments of SEQ ID NO:10 can be provided Immunogenic fragments can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of SEQ ID NO:10. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

Immunogenic fragments of proteins with amino acid sequences homologous to immunogenic fragments of SEQ ID NO:10 can be provided. Such immunogenic fragments can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of proteins that are 95% or greater homologous to SEQ ID NO:10. Some embodiments relate to immunogenic fragments that have 96% homology to the immunogenic fragments of consensus protein sequences herein. Some embodiments relate to immunogenic fragments that have 97% homology to the immunogenic fragments of consensus protein sequences herein. Some embodiments relate to immunogenic fragments that have 98% homology to the immunogenic fragments of consensus protein sequences herein. Some embodiments relate to immunogenic fragments that have 99% homology to the immunogenic fragments of consensus protein sequences herein. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

Immunogenic fragments of proteins with amino acid sequences identical to immunogenic fragments of SEQ ID NO:10 can be provided. Such immunogenic fragments can comprise at least 10%, at least 15%, at least 20%, at least 25%, at least 30%, at least 35%, at least 40%, at least 45%, at least 50%, at least 55% at least 60%, at least 65%, at least 70%, at least 75%, at least 80%, at least 85%, at least 90%, at least 95%, at least 96%, at least 97%, at least 98% or at least 99% of proteins that are 80%, 85%, 90%, 91%, 92%, 93%, 94%, 95%, 96%, 97%, 98%, or 99% identical to the amino acid sequences set forth in SEQ ID NO:10. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

As referred to herein with regard to linking a signal peptide or leader sequence to the N terminus of a protein, the signal peptide/leader sequence replaces the N terminal methionine of a protein which is encoded by the start codon of the nucleic acid sequence than encodes the protein without a signal peptide coding sequences.

(6) MART-1/Melan-A

The vaccine of the present invention can comprise the cancer antigen MART-1 (also known as Melan-A), a fragment thereof, or a variant thereof. MART-1, encoded by MLANA gene, is a 118-amino acid protein containing a single transmembrane domain and is expressed in most melanoma cells. MART-1 forms a complex with a structural protein and affects its expression, stability, trafficking and processing which is required for melanosome structure and maturation. Accordingly, MART-1 is indispensable for regulating mammalian pigmentation. Defects in melanosome maturation have been linked to susceptibility to cancer. MART-1 may be expressed in numerous cancers, including, but not limited to, melanomas.

Melan-A, also known as melanoma antigen recognized by T cells (MART-1) is a melanocyte differentiation antigen and can be found in normal skin, retina, and melanocytes. Melan-a can be associated with the endoplasmic reticulum and melanosomes. Melan-A can be recognized by cytotoxic T cells as an antigen on melanoma cells, but can also be associated with other tumors having melanocytic origin or differentiation (i.e., cells have melansomes), for example, clear cell sarcoma and melanotic neurofibroma. Accordingly, Melan-A can be antigen associated with a variety of tumors derived from cells having melanosomes.

The Melan-A antigen can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune responses. In some embodiments, the induced or elicited cellular immune response can include induction or secretion of interferon-gamma (IFN-γ) and/or tumor necrosis factor alpha (TNF-α). In other embodiments, the induced or elicited immune response can reduce or inhibit one or more immune suppression factors that promote growth of the tumor or cancer expressing the antigen, for example, but not limited to, factors that down regulate MHC presentation, factors that up regulate antigen-specific regulatory T cells (Tregs), PD-L1, FasL, cytokines such as IL-10 and TFG-β, tumor associated macrophages, tumor associated fibroblasts, soluble factors produced by immune suppressor cells, CTLA-4, PD-1, MDSCs, MCP-1, and an immune checkpoint molecule, which is described below in more detail.

The Melan-A antigen can comprise protein epitopes that make them particularly effective as immunogens against which anti-Melan-A immune responses can be induced. The Melan-A antigen can comprise the full length translation product, a variant thereof, a fragment thereof or a combination thereof. The Melan-A antigen can comprise a consensus protein.

The nucleic acid sequence encoding the consensus Melan-A antigen can be optimized with regards to codon usage and corresponding RNA transcripts. The nucleic acid encoding the consensus Melan-A antigen can be codon and RNA optimized for expression. In some embodiments, the nucleic acid sequence encoding the consensus Melan-A antigen can include a Kozak sequence (e.g., GCC ACC) to increase the efficiency of translation. The nucleic acid encoding the consensus Melan-A antigen can include multiple stop codons (e.g., TGA TGA) to increase the efficiency of translation termination.

The nucleic acid encoding the consensus Melan-A antigen can also encode an immunoglobulin E (IgE) leader sequence. The nucleic acid encoding the consensus Melan-A antigen can further encode the IgE leader sequence such that the amino acid sequence of the IgE leader sequence is linked to the amino acid sequence of the consensus Melan-A antigen by a peptide bond. The nucleic encoding the consensus Melan-A antigen can also include a nucleotide sequence encoding the IgE leader sequence. In some embodiments, the nucleic acid encoding the consensus Melan-A antigen is free of or does not contain a nucleotide sequence encoding the IgE leader sequence.

The consensus Melan-A antigen can be the nucleic acid sequence SEQ ID NO:11, which encodes for the amino acid sequence SEQ ID NO:12. SEQ ID NO:11 encodes the consensus MELAN-A protein linked to an IgE leader sequence. The consensus Melan-A protein can be linked to the IgE leader sequence and an HA tag. In other embodiments, the consensus Melan-A protein can be free of or not linked to an IgE leader sequence and/or an HA tag.

In some embodiments, the consensus Melan-A antigen can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in the SEQ ID NO:11. In other embodiments, the consensus Melan-A antigen can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:12. The consensus Melan-A antigen can be the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:12.

Some embodiments relate to nucleic acid sequences encoding proteins homologous to the Melan-A consensus protein, immunogenic fragment of the Melan-A consensus protein, and immunogenic fragments of homologous proteins. Such nucleic acid molecules that encode immunogenic proteins that have up to 95% homology to a consensus sequence, up to 96% homology to a consensus sequence, up to 97% homology to a consensus sequence, up to 98% homology to a consensus sequence and up to 99% can be provided. Likewise, nucleic acid sequences encoding the immunogenic fragments set forth herein and the immunogenic fragments of proteins homologous to the proteins set forth herein are also provided.

Some embodiments relate to nucleic acid molecules that encode immunogenic proteins that have 95% homology to the nucleic acid coding sequences herein. Some embodiments relate to nucleic acid molecules that encode immunogenic proteins that have 96% homology to the nucleic acid coding sequences herein. Some embodiments relate to nucleic acid molecules that encode immunogenic proteins that have 97% homology to the nucleic acid coding sequences herein. Some embodiments relate to nucleic acid molecules that encode immunogenic proteins that have 98% homology to the nucleic acid coding sequences herein. Some embodiments relate to nucleic acid molecules that encode immunogenic proteins that have 99% homology to the nucleic acid coding sequences herein. In some embodiments, the nucleic acid molecules with coding sequences disclosed herein that are homologous to a coding sequence of a consensus protein disclosed herein include sequences encoding an IgE leader sequence linked to the 5' end of the coding sequence encoding the homologous protein sequences disclosed herein.

Some embodiments relate to nucleic acid sequences encoding proteins with a particular percent identity to the full length Melan-A consensus protein, immunogenic fragment of the Melan-A consensus protein, and immunogenic fragments of proteins having identity to the Melan-A consensus protein. Such nucleic acid molecules that encode immunogenic proteins that have up to 80% identity to a full length Melan-A consensus sequence, up to 85% identity to a full length Melan-A consensus sequence, up to 90% identity to a full length Melan-A consensus sequence, up to 91% identity to a full length Melan-A consensus sequence, up to 92% identity to a full length Melan-A consensus sequence, up to 93% identity to a full length Melan-A consensus sequence, up to 94% identity to a full length Melan-A consensus sequence, up to 95% identity to a full length Melan-A consensus sequence, up to 96% identity to a full length Melan-A consensus sequence, up to 97% identity to a full length Melan-A consensus sequence, up to 98% identity to a full length Melan-A consensus sequence, and up to 99% identity to a full length Melan-A consensus sequence can be provided. Likewise, nucleic acid sequences encoding the immunogenic fragments set forth herein and the immunogenic fragments of proteins with similar percent identities as indicated above to the Melan-A proteins set forth herein are also provided.

In some embodiments, the nucleic acid sequence is free of coding sequence that encodes a leader sequence. In some embodiments, the nucleic acid sequence is free of coding sequence that encodes the IgE leader.

Some embodiments relate to fragments of SEQ ID NO:11. Fragments can be at least 10%, at least 15%, at least 20%, at least 25%, at least 30%, at least 35%, at least 40%, at least 45%, at least 50%, at least 55% at least 60%, at least 65%, at least 70%, at least 75%, at least 80%, at least 85%, at least 90%, at least 95%, at least 96%, at least 97%, at least 98% or at least 99% of SEQ ID NO:11. Fragments can be at least 95%, at least 96%, at least 97%, at least 98%, or at least 99% homologous to fragments of SEQ ID NO:11. Fragments can be at least 80%, at least 85%, at least 90% at least 91%, at least 92%, at least 93%, at least 94%, at least 95%, at least 96%, at least 97%, at least 98%, or at least 99% identical to fragments of SEQ ID NO:11. In some embodiments, fragments include sequences that encode a leader sequence, such as for example, an immunoglobulin leader, such as the IgE leader. In some embodiments, fragments are free of coding sequences that encode a leader sequence. In some embodiments, fragments are free of coding sequences that encode a leader sequence, such as for example, the IgE leader.

Furthermore, the amino acid sequence of the consensus Melan-A protein is SEQ ID NO:12. The amino acid sequence of the consensus Melan-A protein linked to an IgE leader is SEQ ID NO:12. The amino acid sequence of the consensus Melan-A protein linked to the IgE leader may be linked to HA tag.

Some embodiments relate to proteins that are homologous to SEQ ID NO:12. Some embodiments relate to immunogenic proteins that have 95% homology to the consensus protein sequences as set forth in SEQ ID NO:12. Some embodiments relate to immunogenic proteins that have 96% homology to the consensus protein sequences as set forth in SEQ ID NO:12. Some embodiments relate to immunogenic proteins that have 97% homology to the consensus protein sequences as set forth in SEQ ID NO:12. Some embodiments relate to immunogenic proteins that have 98% homology to the consensus protein sequences as set forth in SEQ ID NO:12. Some embodiments relate to immunogenic proteins that have 99% homology to the consensus protein sequences as set forth in SEQ ID NO:12.

Some embodiments relate to proteins that are identical to SEQ ID NO:12. Some embodiments relate to immunogenic proteins that have an amino acid sequence that is 80% identical to the full length consensus amino acid sequences as set forth in SEQ ID NO:12. Some embodiments relate to immunogenic proteins that have an amino acid sequence that is 85% identical to the full length consensus amino acid sequences as set forth in SEQ ID NO:12. Some embodiments relate to immunogenic proteins that have an amino acid sequence that is 90% identical to the full length consensus amino acid sequences as set forth in SEQ ID NO:12. Some embodiments relate to immunogenic proteins that have an amino acid sequence that is 91% identical to the full length consensus amino acid sequences as set forth in SEQ ID NO:12. Some embodiments relate to immunogenic proteins that have an amino acid sequence that is 92% identical to the full length consensus amino acid sequences as set forth in SEQ ID NO:12. Some embodiments relate to immunogenic proteins that have an amino acid sequence that is 93% identical to the full length consensus amino acid sequences as set forth in SEQ ID NO:12. Some embodiments relate to immunogenic proteins that have an amino acid sequence that is 94% identical to the full length consensus amino acid sequences as set forth in SEQ ID NO:12. Some embodiments relate to immunogenic proteins that have an amino acid sequence that is 95% identical to the full length consensus amino acid sequences as set forth in SEQ ID NO:12. Some embodiments relate to immunogenic proteins that have an amino acid sequence that is 96% identical to the full length consensus amino acid sequences as set forth in SEQ ID NO:12. Some embodiments relate to immunogenic proteins that have an amino acid sequence that is 97% identical to the full length consensus amino acid sequences as set forth in SEQ ID NO:12. Some embodiments relate to immunogenic proteins that have an amino acid sequence that is 98% identical to the full length consensus amino acid sequences as set forth in SEQ ID NO:12. Some embodiments relate to immunogenic proteins that have an amino acid sequence that is 99% identical to the full length consensus amino acid sequences as set forth in SEQ ID NO:12.

In some embodiments, the protein is free of a leader sequence. In some embodiments, the protein is free of the IgE leader. Fragments of consensus proteins can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of a consensus protein. Immunogenic fragments of SEQ ID NO:12 can be provided Immunogenic fragments can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of SEQ ID NO:12. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

Immunogenic fragments of proteins with amino acid sequences homologous to immunogenic fragments of SEQ ID NO:12 can be provided. Such immunogenic fragments can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of proteins that are 95% or greater homologous to SEQ ID NO:12. Some embodiments relate to immunogenic fragments that have 96% homology to the immunogenic fragments of consensus protein sequences herein. Some embodiments relate to immunogenic fragments that have 97% homology to the immunogenic fragments of consensus protein sequences herein. Some embodiments relate to immunogenic fragments that have 98% homology to the immunogenic fragments of consensus protein sequences herein. Some embodiments relate to immunogenic fragments that have 99% homology to the immunogenic fragments of consensus protein sequences herein. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

Immunogenic fragments of proteins with amino acid sequences identical to immunogenic fragments of SEQ ID NO:12 can be provided. Such immunogenic fragments can comprise at least 10%, at least 15%, at least 20%, at least 25%, at least 30%, at least 35%, at least 40%, at least 45%, at least 50%, at least 55% at least 60%, at least 65%, at least 70%, at least 75%, at least 80%, at least 85%, at least 90%, at least 95%, at least 96%, at least 97%, at least 98% or at least 99% of proteins that are 80%, 85%, 90%, 91%, 92%, 93%, 94%, 95%, 96%, 97%, 98%, or 99% identical to the amino acid sequences set forth in SEQ ID NO:12. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

As referred to herein with regard to linking a signal peptide or leader sequence to the N terminus of a protein, the signal peptide/leader sequence replaces the N terminal methionine of a protein which is encoded by the start codon of the nucleic acid sequence than encodes the protein without a signal peptide coding sequences.

(7) NY-ESO-1

The vaccine of the present invention can comprise the cancer antigen New York-esophageal cancer-1 (NY-ESO-1; also called CTAG1), a fragment thereof, or a variant thereof. NY-ESO-1, encoded by the CTAG1B gene, is a 180 amino-acid long protein, with a glycine-rich N-terminal region and an extremely hydrophobic C-terminal region. NY-ESO-1 has restricted expression in normal tissues but frequent occurrence in cancer. NY-ESO-1 may be expressed in numerous cancers including, but not limited to, bladder, colorectal, esophagus, gastric, hepatocarcinoma, head and neck, melanoma, non-small cell lung, ovarian, pancreatic, synovial carcinoma and prostate cancers.

Cancer-testis antigen (NY-ESO-1) can be expressed in the testis and ovary. NY-ESO-1 can be associated with a variety of cancers and can induce humoral immune responses. Subjects suffering from cancer or tumors can develop immunogenicity to NY-ESO-1. Accordingly, NY-ESO-1 can be an antigen associated with a variety of tumors.

The NY-ESO-1 antigen can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune responses. In some embodiments, the induced or elicited cellular immune response can include induction or secretion of interferon-gamma (IFN-γ) and/or tumor necrosis factor alpha (TNF-α). In other embodiments, the induced or elicited immune response can reduce or inhibit one or more immune suppression factors that promote growth of the tumor or cancer expressing the antigen, for example, but not limited to, factors that down regulate MHC presentation, factors that up regulate antigen-specific regulatory T cells (Tregs), PD-L1, FasL, cytokines such as IL-10 and TFG-β, tumor associated macrophages, tumor associated fibroblasts, soluble factors produced by immune suppressor cells, CTLA-4, PD-1, MDSCs, MCP-1, and an immune checkpoint molecule, which is described below in more detail.

The NY-ESO-1 antigen can increase a cellular immune response in a subject administered the NY-ESO-1 antigen by about 50-fold to about 6000-fold, about 50-fold to about 5500-fold, about 50-fold to about 5000-fold, about 50-fold to about 4500-fold, about 100-fold to about 6000-fold, about 150-fold to about 6000-fold, about 200-fold to about 6000-fold, about 250-fold to about 6000-fold, or about 300-fold to about 6000-fold as compared to a cellular immune response in a subject not administered the NY-ESO-1 antigen. In some embodiments the NY-ESO-1 antigen can increase the cellular immune response in the subject administered the NY-ESO-1 antigen by about 50-fold, 100-fold, 150-fold, 200-fold, 250-fold, 300-fold, 350-fold, 400-fold, 450-fold, 500-fold, 550-fold, 600-fold, 650-fold, 700-fold, 750-fold, 800-fold, 850-fold, 900-fold, 950-fold, 1000-fold, 1100-fold, 1200-fold, 1300-fold, 1400-fold, 1500-fold, 1600-fold, 1700-fold, 1800-fold, 1900-fold, 2000-fold, 2100-fold, 2200-fold, 2300-fold, 2400-fold, 2500-fold, 2600-fold, 2700-fold, 2800-fold, 2900-fold, 3000-fold, 3100-fold, 3200-fold, 3300-fold, 3400-fold, 3500-fold, 3600-fold, 3700-fold, 3800-fold, 3900-fold, 4000-fold, 4100-fold, 4200-fold, 4300-fold, 4400-fold, 4500-fold, 4600-fold, 4700-fold, 4800-fold, 4900-fold, 5000-fold, 5100-fold, 5200-fold, 5300-fold, 5400-fold, 5500-fold, 5600-fold, 5700-fold, 5800-fold, 5900-fold, or 6000-fold as compared to the cellular immune response in the subject not administered the NY-ESO-1 antigen.

The NY-ESO-1 antigen can increase interferon gamma (IFN-γ) levels in a subject administered the NY-ESO-1 antigen by about 50-fold to about 6000-fold, about 50-fold to about 5500-fold, about 50-fold to about 5000-fold, about 50-fold to about 4500-fold, about 100-fold to about 6000-fold, about 150-fold to about 6000-fold, about 200-fold to about 6000-fold, about 250-fold to about 6000-fold, or about 300-fold to about 6000-fold as compared to IFN-γ levels in a subject not administered the NY-ESO-1 antigen. In some embodiments, the NY-ESO-1 antigen can increase IFN-γ levels in the subject administered the NY-ESO-1 antigen by about 50-fold, 100-fold, 150-fold, 200-fold, 250-fold, 300-fold, 350-fold, 400-fold, 450-fold, 500-fold, 550-fold, 600-fold, 650-fold, 700-fold, 750-fold, 800-fold, 850-fold, 900-fold, 950-fold, 1000-fold, 1100-fold, 1200-fold, 1300-fold, 1400-fold, 1500-fold, 1600-fold, 1700-fold, 1800-fold, 1900-fold, 2000-fold, 2100-fold, 2200-fold, 2300-fold, 2400-fold, 2500-fold, 2600-fold, 2700-fold, 2800-fold, 2900-fold, 3000-fold, 3100-fold, 3200-fold, 3300-fold, 3400-fold, 3500-fold, 3600-fold, 3700-fold, 3800-fold, 3900-fold, 4000-fold, 4100-fold, 4200-fold, 4300-fold, 4400-fold, 4500-fold, 4600-fold, 4700-fold, 4800-fold, 4900-fold, 5000-fold, 5100-fold, 5200-fold, 5300-fold, 5400-fold, 5500-fold, 5600-fold, 5700-fold, 5800-fold, 5900-fold, or 6000-fold as compared to IFN-γ levels in the subject not administered the NY-ESO-1 antigen.

The NY-ESO-1 antigen can comprise protein epitopes that make them particularly effective as immunogens against which anti-NY-ESO-1 immune responses can be induced. The NY-ESO-1 antigen can comprise the full length translation product, a variant thereof, a fragment thereof or a combination thereof. The NY-ESO-1 antigen can comprise a consensus protein.

The nucleic acid sequence encoding the consensus NY-ESO-1 antigen can be optimized with regards to codon usage and corresponding RNA transcripts. The nucleic acid encoding the consensus NY-ESO-1 antigen can be codon and RNA optimized for expression. In some embodiments, the nucleic acid sequence encoding the consensus NY-ESO-1 antigen can include a Kozak sequence (e.g., GCC ACC) to increase the efficiency of translation. The nucleic acid encoding the consensus NY-ESO-1 antigen can include multiple stop codons (e.g., TGA TGA) to increase the efficiency of translation termination.

The nucleic acid encoding the consensus NY-ESO-1 antigen can also encode an immunoglobulin E (IgE) leader sequence. The nucleic acid encoding the consensus NY-ESO-1 antigen can further encode the IgE leader sequence such that the amino acid sequence of the IgE leader sequence is linked to the amino acid sequence of the consensus NY-ESO-1 antigen by a peptide bond. The nucleic encoding the consensus NY-ESO-1 antigen can also include a nucleotide sequence encoding the IgE leader sequence. In some embodiments, the nucleic acid encoding the consensus NY-ESO-1 antigen is free of or does not contain a nucleotide sequence encoding the IgE leader sequence.

The consensus NY-ESO-1 antigen can be the nucleic acid sequence SEQ ID NO:13, which encodes for the amino acid sequence SEQ ID NO:14. SEQ ID NO:13 encodes the consensus NY-ESO-1 protein linked to an IgE leader sequence. The consensus NY-ESO-1 protein can be linked to the IgE leader sequence and an HA tag. In other embodiments, the consensus NY-ESO-1 protein can be free of or not linked to an IgE leader sequence and/or an HA tag.

In some embodiments, the consensus NY-ESO-1 antigen can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in the SEQ ID NO:13. In other embodiments, the consensus NY-ESO-1 antigen can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:14. The consensus NY-ESO-1 antigen can be the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:14.

Some embodiments relate to nucleic acid sequences encoding proteins homologous to the NY-ESO-1 consensus protein, immunogenic fragment of the NY-ESO-1 consensus protein, and immunogenic fragments of homologous proteins. Such nucleic acid molecules that encode immunogenic proteins that have up to 95% homology to a consensus sequence, up to 96% homology to a consensus sequence, up to 97% homology to a consensus sequence, up to 98% homology to a consensus sequence and up to 99% can be provided. Likewise, nucleic acid sequences encoding the immunogenic fragments set forth herein and the immunogenic fragments of proteins homologous to the proteins set forth herein are also provided.

Some embodiments relate to nucleic acid molecules that encode immunogenic proteins that have 95% homology to the nucleic acid coding sequences herein. Some embodiments relate to nucleic acid molecules that encode immunogenic proteins that have 96% homology to the nucleic acid coding sequences herein. Some embodiments relate to nucleic acid molecules that encode immunogenic proteins that have 97% homology to the nucleic acid coding sequences herein. Some embodiments relate to nucleic acid molecules that encode immunogenic proteins that have 98% homology to the nucleic acid coding sequences herein. Some embodiments relate to nucleic acid molecules that encode immunogenic proteins that have 99% homology to the nucleic acid coding sequences herein. In some embodiments, the nucleic acid molecules with coding sequences disclosed herein that are homologous to a coding sequence of a consensus protein disclosed herein include sequences encoding an IgE leader sequence linked to the 5' end of the coding sequence encoding the homologous protein sequences disclosed herein.

Some embodiments relate to nucleic acid sequences encoding proteins with a particular percent identity to the full length NY-ESO-1 consensus protein, immunogenic fragment of the NY-ESO-1 consensus protein, and immunogenic fragments of proteins having identity to the NY-ESO-1 consensus protein. Such nucleic acid molecules that encode immunogenic proteins that have up to 80% identity to a full length NY-ESO-1 consensus sequence, up to 85% identity to a full length consensus sequence, up to 90% identity to a full length NY-ESO-1 consensus sequence, up to 91% identity to a full length NY-ESO-1 consensus sequence, up to 92% identity to a full length NY-ESO-1 consensus sequence, up to 93% identity to a full length NY-ESO-1 consensus sequence, up to 94% identity to a full length NY-ESO-1 consensus sequence, up to 95% identity to a full length NY-ESO-1 consensus sequence, up to 96% identity to a full length NY-ESO-1 consensus sequence, up to 97% identity to a full length NY-ESO-1 consensus sequence, up to 98% identity to a full length NY-ESO-1 consensus sequence, and up to 99% identity to a full length NY-ESO-1 consensus sequence can be provided. Likewise, nucleic acid sequences encoding the immunogenic fragments set forth herein and the immunogenic fragments of proteins with similar percent identities as indicated above to the NY-ESO-1 proteins set forth herein are also provided.

In some embodiments, the nucleic acid sequence is free of coding sequence that encodes a leader sequence. In some embodiments, the nucleic acid sequence is free of coding sequence that encodes the IgE leader.

Some embodiments relate to fragments of SEQ ID NO:13. Fragments can be at least 10%, at least 15%, at least 20%, at least 25%, at least 30%, at least 35%, at least 40%, at least 45%, at least 50%, at least 55% at least 60%, at least 65%, at least 70%, at least 75%, at least 80%, at least 85%, at least 90%, at least 95%, at least 96%, at least 97%, at least 98% or at least 99% of SEQ ID NO:13. Fragments can be at least 95%, at least 96%, at least 97%, at least 98%, or at least 99% homologous to fragments of SEQ ID NO:13. Fragments can be at least 80%, at least 85%, at least 90% at least 91%, at least 92%, at least 93%, at least 94%, at least 95%, at least 96%, at least 97%, at least 98%, or at least 99% identical to fragments of SEQ ID NO:13. In some embodiments, fragments include sequences that encode a leader sequence, such as for example, an immunoglobulin leader, such as the IgE leader. In some embodiments, fragments are free of coding sequences that encode a leader sequence. In some embodiments, fragments are free of coding sequences that encode a leader sequence, such as for example, the IgE leader.

Furthermore, the amino acid sequence of the consensus NY-ESO-1 protein is SEQ ID NO:14. The amino acid sequence of the consensus NY-ESO-1 protein linked to an IgE leader is SEQ ID NO:14. The amino acid sequence of the consensus NY-ESO-1 protein linked to the IgE leader may be linked to HA tag.

Some embodiments relate to proteins that are homologous to SEQ ID NO:14. Some embodiments relate to immunogenic proteins that have 95% homology to the consensus protein sequences as set forth in SEQ ID NO:14. Some embodiments relate to immunogenic proteins that have 96% homology to the consensus protein sequences as set forth in SEQ ID NO:14. Some embodiments relate to immunogenic proteins that have 97% homology to the consensus protein sequences as set forth in SEQ ID NO:14. Some embodiments relate to immunogenic proteins that have 98% homology to the consensus protein sequences as set forth in SEQ ID NO:14. Some embodiments relate to immunogenic proteins that have 99% homology to the consensus protein sequences as set forth in SEQ ID NO:14.

Some embodiments relate to proteins that are identical to SEQ ID NO:14. Some embodiments relate to immunogenic proteins that have an amino acid sequence that is 80% identical to the full length consensus amino acid sequences as set forth in SEQ ID NO:14. Some embodiments relate to immunogenic proteins that have an amino acid sequence that is 85% identical to the full length consensus amino acid sequences as set forth in SEQ ID NO:14. Some embodiments relate to immunogenic proteins that have an amino acid sequence that is 90% identical to the full length consensus amino acid sequences as set forth in SEQ ID NO:14. Some embodiments relate to immunogenic proteins that have an amino acid sequence that is 91% identical to the full length consensus amino acid sequences as set forth in SEQ ID NO:14. Some embodiments relate to immunogenic proteins that have an amino acid sequence that is 92% identical to the full length consensus amino acid sequences as set forth in SEQ ID NO:14. Some embodiments relate to immunogenic proteins that have an amino acid sequence that is 93% identical to the full length consensus amino acid sequences as set forth in SEQ ID NO:14. Some embodiments relate to immunogenic proteins that have an amino acid sequence that is 94% identical to the full length consensus amino acid sequences as set forth in SEQ ID NO:14. Some embodiments relate to immunogenic proteins that have an amino acid sequence that is 95% identical to the full length consensus amino acid sequences as set forth in SEQ ID NO:14. Some embodiments relate to immunogenic proteins that have an amino acid sequence that is 96% identical to the full length consensus amino acid sequences as set forth in SEQ ID NO:14. Some embodiments relate to immunogenic proteins that have an amino acid sequence that is 97% identical to the full length consensus amino acid sequences as set forth in SEQ ID NO:14. Some embodiments relate to immunogenic proteins that have an amino acid sequence that is 98% identical to the full length consensus amino acid sequences as set forth in SEQ ID NO:14. Some embodiments relate to immunogenic proteins that have an amino acid sequence that is 99% identical to the full length consensus amino acid sequences as set forth in SEQ ID NO:14.

In some embodiments, the protein is free of a leader sequence. In some embodiments, the protein is free of the IgE leader. Fragments of consensus proteins can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of a consensus protein. Immunogenic fragments of SEQ ID NO:14 can be provided Immunogenic fragments can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of SEQ ID NO:14. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

Immunogenic fragments of proteins with amino acid sequences homologous to immunogenic fragments of SEQ ID NO:14 can be provided. Such immunogenic fragments can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of proteins that are 95% or greater homologous to SEQ ID NO:14. Some embodiments relate to immunogenic fragments that have 96% homology to the immunogenic fragments of consensus protein sequences herein. Some embodiments relate to immunogenic fragments that have 97% homology to the immunogenic fragments of consensus protein sequences herein. Some embodiments relate to immunogenic fragments that have 98% homology to the immunogenic fragments of consensus protein sequences herein. Some embodiments relate to immunogenic fragments that have 99% homology to the immunogenic fragments of consensus protein sequences herein. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

Immunogenic fragments of proteins with amino acid sequences identical to immunogenic fragments of SEQ ID NO:14 can be provided. Such immunogenic fragments can comprise at least 10%, at least 15%, at least 20%, at least 25%, at least 30%, at least 35%, at least 40%, at least 45%, at least 50%, at least 55% at least 60%, at least 65%, at least 70%, at least 75%, at least 80%, at least 85%, at least 90%, at least 95%, at least 96%, at least 97%, at least 98% or at least 99% of proteins that are 80%, 85%, 90%, 91%, 92%, 93%, 94%, 95%, 96%, 97%, 98%, or 99% identical to the amino acid sequences set forth in SEQ ID NO:14. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

As referred to herein with regard to linking a signal peptide or leader sequence to the N terminus of a protein, the signal peptide/leader sequence replaces the N terminal methionine of a protein which is encoded by the start codon of the nucleic acid sequence than encodes the protein without a signal peptide coding sequences.

(8) NY-ESO-2

The vaccine of the present invention can comprise the cancer antigen New York-esophageal cancer-2 (NY-ESO-2; also known as cancer/testis antigen 2, ESO2, and LAGE1), a fragment thereof, or a variant thereof. NY-ESO-2 is an autoimmunogenic tumor antigen that belongs to the ESO/LAGE family of cancer-testis antigens. NY-ESO-2 can be expressed in a variety of cancers including melanoma, breast cancer, bladder cancer and prostate cancer and is normally expressed in testis tissue. Additionally, NY-ESO-2 can be observed in 25-50% of tumor samples of melanomas, non-small-cell lung carcinomas, bladder, prostate and head and neck cancers. The gene encoding NY-ESO-2 also contains an alternative open reading frame that encodes the protein named CAMEL, a tumor antigen that is recognized by melanoma-specific cytotoxic T-lymphocytes.

Similar to NY-ESO-1, NY-ESO-2 can be expressed in the testis and ovary. NY-ESO-2 can also be associated with a variety of cancers and immunogenic in subjects suffering from cancer or tumors. Accordingly, NY-ESO-2 can be an antigen associated with numerous tumors.

The NY-ESO-2 antigen can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune responses. In some embodiments, the induced or elicited cellular immune response can include induction or secretion of interferon-gamma (IFN-γ) and/or tumor necrosis factor alpha (TNF-α). In other embodiments, the induced or elicited immune response can reduce or inhibit one or more immune suppression factors that promote growth of the tumor or cancer expressing the antigen, for example, but not limited to, factors that down regulate MHC presentation, factors that up regulate antigen-specific regulatory T cells (Tregs), PD-L1, FasL, cytokines such as IL-10 and TFG-β, tumor associated macrophages, tumor associated fibroblasts, soluble factors produced by immune suppressor cells, CTLA-4, PD-1, MDSCs, MCP-1, and an immune checkpoint molecule, which is described below in more detail.

The NY-ESO-2 antigen can increase a cellular immune response in a subject administered the NY-ESO-2 antigen by about 50-fold to about 6000-fold, about 50-fold to about 5500-fold, about 50-fold to about 5000-fold, about 50-fold to about 4500-fold, about 100-fold to about 6000-fold, about 150-fold to about 6000-fold, about 200-fold to about 6000-fold, about 250-fold to about 6000-fold, or about 300-fold to about 6000-fold as compared to a cellular immune response in a subject not administered the NY-ESO-2 antigen. In some embodiments the NY-ESO-2 antigen can increase the cellular immune response in the subject administered the NY-ESO-2 antigen by about 50-fold, 100-fold, 150-fold, 200-fold, 250-fold, 300-fold, 350-fold, 400-fold, 450-fold, 500-fold, 550-fold, 600-fold, 650-fold, 700-fold, 750-fold, 800-fold, 850-fold, 900-fold, 950-fold, 1000-fold, 1100-fold, 1200-fold, 1300-fold, 1400-fold, 1500-fold, 1600-fold, 1700-fold, 1800-fold, 1900-fold, 2000-fold, 2100-fold, 2200-fold, 2300-fold, 2400-fold, 2500-fold, 2600-fold, 2700-fold, 2800-fold, 2900-fold, 3000-fold, 3100-fold, 3200-fold, 3300-fold, 3400-fold, 3500-fold, 3600-fold, 3700-fold, 3800-fold, 3900-fold, 4000-fold, 4100-fold, 4200-fold, 4300-fold, 4400-fold, 4500-fold, 4600-fold, 4700-fold, 4800-fold, 4900-fold, 5000-fold, 5100-fold, 5200-fold, 5300-fold, 5400-fold, 5500-fold, 5600-fold, 5700-fold, 5800-fold, 5900-fold, or 6000-fold as compared to the cellular immune response in the subject not administered the NY-ESO-2 antigen.

The NY-ESO-2 antigen can increase interferon gamma (IFN-γ) levels in a subject administered the NY-ESO-2 antigen by about 50-fold to about 6000-fold, about 50-fold to about 5500-fold, about 50-fold to about 5000-fold, about 50-fold to about 4500-fold, about 100-fold to about 6000-fold, about 150-fold to about 6000-fold, about 200-fold to about 6000-fold, about 250-fold to about 6000-fold, or about 300-fold to about 6000-fold as compared to IFN-γ levels in a subject not administered the NY-ESO-2 antigen. In some embodiments, the NY-ESO-2 antigen can increase IFN-γ levels in the subject administered the NY-ESO-2 antigen by about 50-fold, 100-fold, 150-fold, 200-fold, 250-fold, 300-fold, 350-fold, 400-fold, 450-fold, 500-fold, 550-fold, 600-fold, 650-fold, 700-fold, 750-fold, 800-fold, 850-fold, 900-fold, 950-fold, 1000-fold, 1100-fold, 1200-fold, 1300-fold, 1400-fold, 1500-fold, 1600-fold, 1700-fold, 1800-fold, 1900-fold, 2000-fold, 2100-fold, 2200-fold, 2300-fold, 2400-fold, 2500-fold, 2600-fold, 2700-fold, 2800-fold, 2900-fold, 3000-fold, 3100-fold, 3200-fold, 3300-fold, 3400-fold, 3500-fold, 3600-fold, 3700-fold, 3800-fold, 3900-fold, 4000-fold, 4100-fold, 4200-fold, 4300-fold, 4400-fold, 4500-fold, 4600-fold, 4700-fold, 4800-fold, 4900-fold, 5000-fold, 5100-fold, 5200-fold, 5300-fold, 5400-fold, 5500-fold, 5600-fold, 5700-fold, 5800-fold, 5900-fold, or 6000-fold as compared to IFN-γ levels in the subject not administered the NY-ESO-2 antigen.

The NY-ESO-2 antigen can comprise protein epitopes that make them particularly effective as immunogens against which anti-NY-ESO-2 immune responses can be induced. The NY-ESO-2 antigen can comprise the full length translation product, a variant thereof, a fragment thereof or a combination thereof. The NY-ESO-2 antigen can comprise a consensus protein.

The nucleic acid sequence encoding the consensus NY-ESO-2 antigen can be optimized with regards to codon usage and corresponding RNA transcripts. The nucleic acid encoding the consensus NY-ESO-2 antigen can be codon and RNA optimized for expression. In some embodiments, the nucleic acid sequence encoding the consensus NY-ESO-2 antigen can include a Kozak sequence (e.g., GCC ACC) to increase the efficiency of translation. The nucleic acid encoding the consensus NY-ESO-2 antigen can include multiple stop codons (e.g., TGA TGA) to increase the efficiency of translation termination.

The nucleic acid encoding the consensus NY-ESO-2 antigen can also encode an immunoglobulin E (IgE) leader sequence. The nucleic acid encoding the consensus NY-ESO-2 antigen can further encode the IgE leader sequence such that the amino acid sequence of the IgE leader sequence is linked to the amino acid sequence of the consensus NY-ESO-2 antigen by a peptide bond. The nucleic encoding the consensus NY-ESO-2 antigen can also include a nucleotide sequence encoding the IgE leader sequence. In some embodiments, the nucleic acid encoding the consensus NY-ESO-2 antigen is free of or does not contain a nucleotide sequence encoding the IgE leader sequence.

The consensus NY-ESO-2 antigen can be the nucleic acid sequence SEQ ID NO:15, which encodes for the amino acid sequence SEQ ID NO:16. SEQ ID NO:1 encodes the consensus NY-ESO-2 protein linked to an IgE leader sequence. The consensus NY-ESO-2 protein can be linked to the IgE leader sequence and an HA tag. In other embodiments, the consensus NY-ESO-2 protein can be free of or not linked to an IgE leader sequence and/or an HA tag.

In some embodiments, the consensus NY-ESO-2 antigen can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in the SEQ ID NO:15. In other embodiments, the consensus NY-ESO-2 antigen can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:16. The consensus NY-ESO-2 antigen can be the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:16.

Some embodiments relate to nucleic acid sequences encoding proteins homologous to the NY-ESO-2 consensus protein, immunogenic fragment of the NY-ESO-2 consensus protein, and immunogenic fragments of homologous proteins. Such nucleic acid molecules that encode immunogenic proteins that have up to 95% homology to a consensus sequence, up to 96% homology to a consensus sequence, up to 97% homology to a consensus sequence, up to 98% homology to a consensus sequence and up to 99% can be provided. Likewise, nucleic acid sequences encoding the immunogenic fragments set forth herein and the immunogenic fragments of proteins homologous to the proteins set forth herein are also provided.

Some embodiments relate to nucleic acid molecules that encode immunogenic proteins that have 95% homology to the nucleic acid coding sequences herein. Some embodiments relate to nucleic acid molecules that encode immunogenic proteins that have 96% homology to the nucleic acid coding sequences herein. Some embodiments relate to nucleic acid molecules that encode immunogenic proteins that have 97% homology to the nucleic acid coding sequences herein. Some embodiments relate to nucleic acid molecules that encode immunogenic proteins that have 98% homology to the nucleic acid coding sequences herein. Some embodiments relate to nucleic acid molecules that encode immunogenic proteins that have 99% homology to the nucleic acid coding sequences herein. In some embodiments, the nucleic acid molecules with coding sequences disclosed herein that are homologous to a coding sequence of a consensus protein disclosed herein include sequences encoding an IgE leader sequence linked to the 5' end of the coding sequence encoding the homologous protein sequences disclosed herein.

Some embodiments relate to nucleic acid sequences encoding proteins with a particular percent identity to the full length NY-ESO-2 consensus protein, immunogenic fragment of the NY-ESO-2 consensus protein, and immunogenic fragments of proteins having identity to the NY-ESO-2 consensus protein. Such nucleic acid molecules that encode immunogenic proteins that have up to 80% identity to a full length NY-ESO-2 consensus sequence, up to 85% identity to a full length consensus sequence, up to 90% identity to a full length NY-ESO-2 consensus sequence, up to 91% identity to a full length NY-ESO-2 consensus sequence, up to 92% identity to a full length NY-ESO-2 consensus sequence, up to 93% identity to a full length NY-ESO-2 consensus sequence, up to 94% identity to a full length NY-ESO-2 consensus sequence, up to 95% identity to a full length NY-ESO-2 consensus sequence, up to 96% identity to a full length NY-ESO-2 consensus sequence, up to 97% identity to a full length NY-ESO-2 consensus sequence, up to 98% identity to a full length NY-ESO-2 consensus sequence, and up to 99% identity to a full length NY-ESO-2 consensus sequence can be provided. Likewise, nucleic acid sequences encoding the immunogenic fragments set forth herein and the immunogenic fragments of proteins with similar percent identities as indicated above to the NY-ESO-2 proteins set forth herein are also provided.

In some embodiments, the nucleic acid sequence is free of coding sequence that encodes a leader sequence. In some embodiments, the nucleic acid sequence is free of coding sequence that encodes the IgE leader.

Some embodiments relate to fragments of SEQ ID NO:15. Fragments can be at least 10%, at least 15%, at least 20%, at least 25%, at least 30%, at least 35%, at least 40%, at least 45%, at least 50%, at least 55% at least 60%, at least 65%, at least 70%, at least 75%, at least 80%, at least 85%, at least 90%, at least 95%, at least 96%, at least 97%, at least 98% or at least 99% of SEQ ID NO:15. Fragments can be at least 95%, at least 96%, at least 97%, at least 98%, or at least 99% homologous to fragments of SEQ ID NO:15. Fragments can be at least 80%, at least 85%, at least 90% at least 91%, at least 92%, at least 93%, at least 94%, at least 95%, at least 96%, at least 97%, at least 98%, or at least 99% identical to fragments of SEQ ID NO:15. In some embodiments, fragments include sequences that encode a leader sequence, such as for example, an immunoglobulin leader, such as the IgE leader. In some embodiments, fragments are free of coding sequences that encode a leader sequence. In some embodiments, fragments are free of coding sequences that encode a leader sequence, such as for example, the IgE leader.

Furthermore, the amino acid sequence of the consensus NY-ESO-2 protein is SEQ ID NO:16. The amino acid sequence of the consensus NY-ESO-2 protein linked to an IgE leader is SEQ ID NO:16. The amino acid sequence of the consensus NY-ESO-2 protein linked to the IgE leader may be linked to HA tag.

Some embodiments relate to proteins that are homologous to SEQ ID NO:16. Some embodiments relate to immunogenic proteins that have 95% homology to the consensus protein sequences as set forth in SEQ ID NO:16. Some embodiments relate to immunogenic proteins that have 96% homology to the consensus protein sequences as set forth in SEQ ID NO:16. Some embodiments relate to immunogenic proteins that have 97% homology to the consensus protein sequences as set forth in SEQ ID NO:16. Some embodiments relate to immunogenic proteins that have 98% homology to the consensus protein sequences as set forth in SEQ ID NO:16. Some embodiments relate to immunogenic proteins that have 99% homology to the consensus protein sequences as set forth in SEQ ID NO:16.

Some embodiments relate to proteins that are identical to SEQ ID NO:16. Some embodiments relate to immunogenic proteins that have an amino acid sequence that is 80% identical to the full length consensus amino acid sequences as set forth in SEQ ID NO:16. Some embodiments relate to immunogenic proteins that have an amino acid sequence that is 85% identical to the full length consensus amino acid sequences as set forth in SEQ ID NO:16. Some embodiments relate to immunogenic proteins that have an amino acid sequence that is 90% identical to the full length consensus amino acid sequences as set forth in SEQ ID NO:16. Some embodiments relate to immunogenic proteins that have an amino acid sequence that is 91% identical to the full length consensus amino acid sequences as set forth in SEQ ID NO:16. Some embodiments relate to immunogenic proteins that have an amino acid sequence that is 92% identical to the full length consensus amino acid sequences as set forth in SEQ ID NO:16. Some embodiments relate to immunogenic proteins that have an amino acid sequence that is 93% identical to the full length consensus amino acid sequences as set forth in SEQ ID NO:16. Some embodiments relate to immunogenic proteins that have an amino acid sequence that is 94% identical to the full length consensus amino acid sequences as set forth in SEQ ID NO:16. Some embodiments relate to immunogenic proteins that have an amino acid sequence that is 95% identical to the full length consensus amino acid sequences as set forth in SEQ ID NO:16. Some embodiments relate to immunogenic proteins that have an amino acid sequence that is 96% identical to the full length consensus amino acid sequences as set forth in SEQ ID NO:16. Some embodiments relate to immunogenic proteins that have an amino acid sequence that is 97% identical to the full length consensus amino acid sequences as set forth in SEQ ID NO:16. Some embodiments relate to immunogenic proteins that have an amino acid sequence that is 98% identical to the full length consensus amino acid sequences as set forth in SEQ ID NO:16. Some embodiments relate to immunogenic proteins that have an amino acid sequence that is 99% identical to the full length consensus amino acid sequences as set forth in SEQ ID NO:16.

In some embodiments, the protein is free of a leader sequence. In some embodiments, the protein is free of the IgE leader. Fragments of consensus proteins can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of a consensus protein. Immunogenic fragments of SEQ ID NO:16 can be provided Immunogenic fragments can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of SEQ ID NO:16. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

Immunogenic fragments of proteins with amino acid sequences homologous to immunogenic fragments of SEQ ID NO:16 can be provided. Such immunogenic fragments can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of proteins that are 95% or greater homologous to SEQ ID NO:16. Some embodiments relate to immunogenic fragments that have 96% homology to the immunogenic fragments of consensus protein sequences herein. Some embodiments relate to immunogenic fragments that have 97% homology to the immunogenic fragments of consensus protein sequences herein. Some embodiments relate to immunogenic fragments that have 98% homology to the immunogenic fragments of consensus protein sequences herein. Some embodiments relate to immunogenic fragments that have 99% homology to the immunogenic fragments of consensus protein sequences herein. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

Immunogenic fragments of proteins with amino acid sequences identical to immunogenic fragments of SEQ ID NO:16 can be provided. Such immunogenic fragments can comprise at least 10%, at least 15%, at least 20%, at least 25%, at least 30%, at least 35%, at least 40%, at least 45%, at least 50%, at least 55% at least 60%, at least 65%, at least 70%, at least 75%, at least 80%, at least 85%, at least 90%, at least 95%, at least 96%, at least 97%, at least 98% or at least 99% of proteins that are 80%, 85%, 90%, 91%, 92%, 93%, 94%, 95%, 96%, 97%, 98%, or 99% identical to the amino acid sequences set forth in SEQ ID NO:16. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

As referred to herein with regard to linking a signal peptide or leader sequence to the N terminus of a protein, the signal peptide/leader sequence replaces the N terminal methionine of a protein which is encoded by the start codon of the nucleic acid sequence than encodes the protein without a signal peptide coding sequences.

(9) PRAME

The vaccine of the present invention can comprise the cancer antigen PRAME, a fragment thereof, or a variant thereof. PRAME, encoded by the PRAME gene, is a protein comprised of 509 amino acids and is expressed in testis, placenta, endometrium, ovary, adrenals, and in tissues derived from melanoma, lung, kidney, and head and neck carcinomas. PRAME is also expressed in adult and pediatric acute leukemias, and multiple myeloma. PRAME contains an immunogenic nonapeptide able to elicit a cytotoxic response when presented by HLA-A24. Studies show that overexpression of PRAME in cultured cells induces a caspace-independent cell death responsible for a slower proliferation rate. Other studies demonstrate that overexpression of PRAME also confers growth or survival advantages by antagonizing retinoic acid receptor (RAR) signaling, and is causally involved in the tumorigenic process. Interference of RAR signaling leads to a loss in regulating cellular proliferation, development and differentiation.

PRAME can have an expression pattern similar to the cancer-testis antigens MAGE, BAGE, and GAGE, namely expression in the testis. PRAME, however, can be expressed in human melanomas and acute leukemias. PRAME can be recognized by cytolytic T lymphocytes. Accordingly, PRAME can be an antigen associated with melanoma and leukemias.

The PRAME antigen can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune responses. In some embodiments, the induced or elicited cellular immune response can include induction or secretion of interferon-gamma (IFN-γ) and/or tumor necrosis factor alpha (TNF-α). In other embodiments, the induced or elicited immune response can reduce or inhibit one or more immune suppression factors that promote growth of the tumor or cancer expressing the antigen, for example, but not limited to, factors that down regulate MHC presentation, factors that up regulate antigen-specific regulatory T cells (Tregs), PD-L1, FasL, cytokines such as IL-10 and TFG-β, tumor associated macrophages, tumor associated fibroblasts, soluble factors produced by immune suppressor cells, CTLA-4, PD-1, MDSCs, MCP-1, and an immune checkpoint molecule, which is described below in more detail.

The PRAME antigen can increase a cellular immune response in a subject administered the PRAME antigen by about 50-fold to about 6000-fold, about 50-fold to about 5500-fold, about 50-fold to about 5000-fold, about 50-fold to about 4500-fold, about 100-fold to about 6000-fold, about 150-fold to about 6000-fold, about 200-fold to about 6000-fold, about 250-fold to about 6000-fold, or about 300-fold to about 6000-fold as compared to a cellular immune response in a subject not administered the PRAME antigen. In some embodiments the PRAME antigen can increase the cellular immune response in the subject administered the PRAME antigen by about 50-fold, 100-fold, 150-fold, 200-fold, 250-fold, 300-fold, 350-fold, 400-fold, 450-fold, 500-fold, 550-fold, 600-fold, 650-fold, 700-fold, 750-fold, 800-fold, 850-fold, 900-fold, 950-fold, 1000-fold, 1100-fold, 1200-fold, 1300-fold, 1400-fold, 1500-fold, 1600-fold, 1700-fold, 1800-fold, 1900-fold, 2000-fold, 2100-fold, 2200-fold, 2300-fold, 2400-fold, 2500-fold, 2600-fold, 2700-fold, 2800-fold, 2900-fold, 3000-fold, 3100-fold, 3200-fold, 3300-fold, 3400-fold, 3500-fold, 3600-fold, 3700-fold, 3800-fold, 3900-fold, 4000-fold, 4100-fold, 4200-fold, 4300-fold, 4400-fold, 4500-fold, 4600-fold, 4700-fold, 4800-fold, 4900-fold, 5000-fold, 5100-fold, 5200-fold, 5300-fold, 5400-fold, 5500-fold, 5600-fold, 5700-fold, 5800-fold, 5900-fold, or 6000-fold as compared to the cellular immune response in the subject not administered the PRAME antigen.

The PRAME antigen can increase interferon gamma (IFN-γ) levels in a subject administered the PRAME antigen by about 50-fold to about 6000-fold, about 50-fold to about 5500-fold, about 50-fold to about 5000-fold, about 50-fold to about 4500-fold, about 100-fold to about 6000-fold, about 150-fold to about 6000-fold, about 200-fold to about 6000-fold, about 250-fold to about 6000-fold, or about 300-fold to about 6000-fold as compared to IFN-7 levels in a subject not administered the PRAME antigen. In some embodiments, the PRAME antigen can increase IFN-γ levels in the subject administered the PRAME antigen by about 50-fold, 100-fold, 150-fold, 200-fold, 250-fold, 300-fold, 350-fold, 400-fold, 450-fold, 500-fold, 550-fold, 600-fold, 650-fold, 700-fold, 750-fold, 800-fold, 850-fold, 900-fold, 950-fold, 1000-fold, 1100-fold, 1200-fold, 1300-fold, 1400-fold, 1500-fold, 1600-fold, 1700-fold, 1800-fold, 1900-fold, 2000-fold, 2100-fold, 2200-fold, 2300-fold, 2400-fold, 2500-fold, 2600-fold, 2700-fold, 2800-fold, 2900-fold, 3000-fold, 3100-fold, 3200-fold, 3300-fold, 3400-fold, 3500-fold, 3600-fold, 3700-fold, 3800-fold, 3900-fold, 4000-fold, 4100-fold, 4200-fold, 4300-fold, 4400-fold, 4500-fold, 4600-fold, 4700-fold, 4800-fold, 4900-fold, 5000-fold, 5100-fold, 5200-fold, 5300-fold, 5400-fold, 5500-fold, 5600-fold, 5700-fold, 5800-fold, 5900-fold, or 6000-fold as compared to IFN-γ levels in the subject not administered the PRAME antigen.

The PRAME antigen can comprise protein epitopes that make them particularly effective as immunogens against which anti-PRAME immune responses can be induced. The PRAME antigen can comprise the full length translation product, a variant thereof, a fragment thereof or a combination thereof. The PRAME antigen can comprise a consensus protein.

The nucleic acid sequence encoding the consensus PRAME antigen can be optimized with regards to codon usage and corresponding RNA transcripts. The nucleic acid encoding the consensus PRAME antigen can be codon and RNA optimized for expression. In some embodiments, the nucleic acid sequence encoding the consensus PRAME antigen can include a Kozak sequence (e.g., GCC ACC) to increase the efficiency of translation. The nucleic acid encoding the consensus PRAME antigen can include multiple stop codons (e.g., TGA TGA) to increase the efficiency of translation termination.

The nucleic acid encoding the consensus PRAME antigen can also encode an immunoglobulin E (IgE) leader sequence. The nucleic acid encoding the consensus PRAME antigen can further encode the IgE leader sequence such that the amino acid sequence of the IgE leader sequence is linked to the amino acid sequence of the consensus PRAME antigen by a peptide bond. The nucleic encoding the consensus PRAME antigen can also include a nucleotide sequence encoding the IgE leader sequence. In some embodiments, the nucleic acid encoding the consensus PRAME antigen is free of or does not contain a nucleotide sequence encoding the IgE leader sequence.

The consensus PRAME antigen can be the nucleic acid sequence SEQ ID NO:17, which encodes for the amino acid sequence SEQ ID NO:18. SEQ ID NO:17 encodes the consensus PRAME protein linked to an IgE leader sequence. The consensus PRAME protein can be linked to the IgE leader sequence and an HA tag. In other embodiments, the consensus PRAME protein can be free of or not linked to an IgE leader sequence and/or an HA tag.

In some embodiments, the consensus PRAME antigen can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in the SEQ ID NO:17. In other embodiments, the consensus PRAME antigen can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:18. The consensus PRAME antigen can be the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:18.

Some embodiments relate to nucleic acid sequences encoding proteins homologous to the PRAME consensus protein, immunogenic fragment of the PRAME consensus protein, and immunogenic fragments of homologous proteins. Such nucleic acid molecules that encode immunogenic proteins that have up to 95% homology to a consensus sequence, up to 96% homology to a consensus sequence, up to 97% homology to a consensus sequence, up to 98% homology to a consensus sequence and up to 99% can be provided. Likewise, nucleic acid sequences encoding the immunogenic fragments set forth herein and the immunogenic fragments of proteins homologous to the proteins set forth herein are also provided.

Some embodiments relate to nucleic acid molecules that encode immunogenic proteins that have 95% homology to the nucleic acid coding sequences herein. Some embodiments relate to nucleic acid molecules that encode immunogenic proteins that have 96% homology to the nucleic acid coding sequences herein. Some embodiments relate to nucleic acid molecules that encode immunogenic proteins that have 97% homology to the nucleic acid coding sequences herein. Some embodiments relate to nucleic acid molecules that encode immunogenic proteins that have 98% homology to the nucleic acid coding sequences herein. Some embodiments relate to nucleic acid molecules that encode immunogenic proteins that have 99% homology to the nucleic acid coding sequences herein. In some embodiments, the nucleic acid molecules with coding sequences disclosed herein that are homologous to a coding sequence of a consensus protein disclosed herein include sequences encoding an IgE leader sequence linked to the 5' end of the coding sequence encoding the homologous protein sequences disclosed herein.

Some embodiments relate to nucleic acid sequences encoding proteins with a particular percent identity to the full length PRAME consensus protein, immunogenic fragment of the PRAME consensus protein, and immunogenic fragments of proteins having identity to the PRAME consensus protein. Such nucleic acid molecules that encode immunogenic proteins that have up to 80% identity to a full length PRAME consensus sequence, up to 85% identity to a full length consensus sequence, up to 90% identity to a full length PRAME consensus sequence, up to 91% identity to a full length PRAME consensus sequence, up to 92% identity to a full length PRAME consensus sequence, up to 93% identity to a full length PRAME consensus sequence, up to 94% identity to a full length PRAME consensus sequence, up to 95% identity to a full length PRAME consensus sequence, up to 96% identity to a full length PRAME consensus sequence, up to 97% identity to a full length PRAME consensus sequence, up to 98% identity to a full length PRAME consensus sequence, and up to 99% identity to a full length PRAME consensus sequence can be provided. Likewise, nucleic acid sequences encoding the immunogenic fragments set forth herein and the immunogenic fragments of proteins with similar percent identities as indicated above to the PRAME proteins set forth herein are also provided.

In some embodiments, the nucleic acid sequence is free of coding sequence that encodes a leader sequence. In some embodiments, the nucleic acid sequence is free of coding sequence that encodes the IgE leader.

Some embodiments relate to fragments of SEQ ID NO:17. Fragments can be at least 10%, at least 15%, at least 20%, at least 25%, at least 30%, at least 35%, at least 40%, at least 45%, at least 50%, at least 55% at least 60%, at least 65%, at least 70%, at least 75%, at least 80%, at least 85%, at least 90%, at least 95%, at least 96%, at least 97%, at least 98% or at least 99% of SEQ ID NO:17. Fragments can be at least 95%, at least 96%, at least 97%, at least 98%, or at least 99% homologous to fragments of SEQ ID NO:17. Fragments can be at least 80%, at least 85%, at least 90% at least 91%, at least 92%, at least 93%, at least 94%, at least 95%, at least 96%, at least 97%, at least 98%, or at least 99% identical to fragments of SEQ ID NO:17. In some embodiments, fragments include sequences that encode a leader sequence, such as for example, an immunoglobulin leader, such as the IgE leader. In some embodiments, fragments are free of coding sequences that encode a leader sequence. In some embodiments, fragments are free of coding sequences that encode a leader sequence, such as for example, the IgE leader.

Furthermore, the amino acid sequence of the consensus PRAME protein is SEQ ID NO:18. The amino acid sequence of the consensus PRAME protein linked to an IgE leader is SEQ ID NO:18. The amino acid sequence of the consensus PRAME protein linked to the IgE leader may be linked to HA tag.

Some embodiments relate to proteins that are homologous to SEQ ID NO:18. Some embodiments relate to immunogenic proteins that have 95% homology to the consensus protein sequences as set forth in SEQ ID NO:18. Some embodiments relate to immunogenic proteins that have 96% homology to the consensus protein sequences as set forth in SEQ ID NO:18. Some embodiments relate to immunogenic proteins that have 97% homology to the consensus protein sequences as set forth in SEQ ID NO:18. Some embodiments relate to immunogenic proteins that have 98% homology to the consensus protein sequences as set forth in SEQ ID NO:18. Some embodiments relate to immunogenic proteins that have 99% homology to the consensus protein sequences as set forth in SEQ ID NO:18.

Some embodiments relate to proteins that are identical to SEQ ID NO:18. Some embodiments relate to immunogenic proteins that have an amino acid sequence that is 80% identical to the full length consensus amino acid sequences as set forth in SEQ ID NO:18. Some embodiments relate to immunogenic proteins that have an amino acid sequence that is 85% identical to the full length consensus amino acid sequences as set forth in SEQ ID NO:18. Some embodiments relate to immunogenic proteins that have an amino acid sequence that is 90% identical to the full length consensus amino acid sequences as set forth in SEQ ID NO:18. Some embodiments relate to immunogenic proteins that have an amino acid sequence that is 91% identical to the full length consensus amino acid sequences as set forth in SEQ ID NO:18. Some embodiments relate to immunogenic proteins that have an amino acid sequence that is 92% identical to the full length consensus amino acid sequences as set forth in SEQ ID NO:18. Some embodiments relate to immunogenic proteins that have an amino acid sequence that is 93% identical to the full length consensus amino acid sequences as set forth in SEQ ID NO:18. Some embodiments relate to immunogenic proteins that have an amino acid sequence that is 94% identical to the full length consensus amino acid sequences as set forth in SEQ ID NO:18. Some embodiments relate to immunogenic proteins that have an amino acid sequence that is 95% identical to the full length consensus amino acid sequences as set forth in SEQ ID NO:18. Some embodiments relate to immunogenic proteins that have an amino acid sequence that is 96% identical to the full length consensus amino acid sequences as set forth in SEQ ID NO:18. Some embodiments relate to immunogenic proteins that have an amino acid sequence that is 97% identical to the full length consensus amino acid sequences as set forth in SEQ ID NO:18. Some embodiments relate to immunogenic proteins that have an amino acid sequence that is 98% identical to the full length consensus amino acid sequences as set forth in SEQ ID NO:18. Some embodiments relate to immunogenic proteins that have an amino acid sequence that is 99% identical to the full length consensus amino acid sequences as set forth in SEQ ID NO:18.

In some embodiments, the protein is free of a leader sequence. In some embodiments, the protein is free of the IgE leader. Fragments of consensus proteins can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of a consensus protein. Immunogenic fragments of SEQ ID NO:18 can be provided Immunogenic fragments can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of SEQ ID NO:18. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

Immunogenic fragments of proteins with amino acid sequences homologous to immunogenic fragments of SEQ ID NO:18 can be provided. Such immunogenic fragments can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of proteins that are 95% or greater homologous to SEQ ID NO:18. Some embodiments relate to immunogenic fragments that have 96% homology to the immunogenic fragments of consensus protein sequences herein. Some embodiments relate to immunogenic fragments that have 97% homology to the immunogenic fragments of consensus protein sequences herein. Some embodiments relate to immunogenic fragments that have 98% homology to the immunogenic fragments of consensus protein sequences herein. Some embodiments relate to immunogenic fragments that have 99% homology to the immunogenic fragments of consensus protein sequences herein. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

Immunogenic fragments of proteins with amino acid sequences identical to immunogenic fragments of SEQ ID NO:18 can be provided. Such immunogenic fragments can comprise at least 10%, at least 15%, at least 20%, at least 25%, at least 30%, at least 35%, at least 40%, at least 45%, at least 50%, at least 55% at least 60%, at least 65%, at least 70%, at least 75%, at least 80%, at least 85%, at least 90%, at least 95%, at least 96%, at least 97%, at least 98% or at least 99% of proteins that are 80%, 85%, 90%, 91%, 92%, 93%, 94%, 95%, 96%, 97%, 98%, or 99% identical to the amino acid sequences set forth in SEQ ID NO:18. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

As referred to herein with regard to linking a signal peptide or leader sequence to the N terminus of a protein, the signal peptide/leader sequence replaces the N terminal methionine of a protein which is encoded by the start codon of the nucleic acid sequence than encodes the protein without a signal peptide coding sequences.

(10) PSA

The vaccine of the present invention can comprise the cancer antigen prostate specific antigen (PSA; also known as gamma-seminoprotein or kallikrein-3 (KLK3)), a fragment thereof, or a variant thereof. PSA is an androgen-regulated serine protease produced by prostate epithelial cells and prostate cancer cells and encoded by the KLK3 gene. PSA is often used as a serum marker for prostate cancer. PSA is a member of the tissue kallikrein family and cleaves semenogelins in seminal coagulum after cleavage of the proenzyme to release the active enzyme, thereby liquefying semen to allow sperm to swim freely. Additionally, PSA enzymatic activity is regulated by zinc concentration, namely high zinc concentrations inhibit enzymatic activity of PSA.

The PSA antigen can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune responses. In some embodiments, the induced or elicited cellular immune response can include induction or secretion of interferon-gamma (IFN-γ) and/or tumor necrosis factor alpha (TNF-α). In other embodiments, the induced or elicited immune response can reduce or inhibit one or more immune suppression factors that promote growth of the tumor or cancer expressing the antigen, for example, but not limited to, factors that down regulate MHC presentation, factors that up regulate antigen-specific regulatory T cells (Tregs), PD-L1, FasL, cytokines such as IL-10 and TFG-β, tumor associated macrophages, tumor associated fibroblasts, soluble factors produced by immune suppressor cells, CTLA-4, PD-1, MDSCs, MCP-1, and an immune checkpoint molecule, which is described below in more detail.

The PSA antigen can comprise protein epitopes that make them particularly effective as immunogens against which anti-PSA immune responses can be induced. The PSMA antigen can comprise the full length translation product, a variant thereof, a fragment thereof or a combination thereof. The PSA antigen can comprise a consensus protein.

The nucleic acid sequence encoding the consensus PSA antigen can be optimized with regards to codon usage and corresponding RNA transcripts. The nucleic acid encoding the consensus PSA antigen can be codon and RNA optimized for expression. In some embodiments, the nucleic acid sequence encoding the consensus PSA antigen can include a Kozak sequence (e.g., GCC ACC) to increase the efficiency of translation. The nucleic acid encoding the consensus PSA antigen can include multiple stop codons (e.g., TGA TGA) to increase the efficiency of translation termination.

The nucleic acid encoding the consensus PSA antigen can also encode an immunoglobulin E (IgE) leader sequence. The nucleic acid encoding the consensus PSA antigen can further encode the IgE leader sequence such that the amino acid sequence of the IgE leader sequence is linked to the amino acid sequence of the consensus PSA P antigen by a peptide bond. The nucleic encoding the consensus PSA antigen can also include a nucleotide sequence encoding the IgE leader sequence. In some embodiments, the nucleic acid encoding the consensus PSA antigen is free of or does not contain a nucleotide sequence encoding the IgE leader sequence.

In some embodiments, the nucleic acid encoding the consensus PSA antigen can be a heterologous nucleic acid sequence and/or contain one or more heterologous nucleic acid sequences.

(11) PSMA

The vaccine of the present invention can comprise the cancer antigen prostate specific membrane antigen (PSMA; also known as Glutamate carboxypeptidase II (GCPII), N-acetyl-L-aspartyl-L-glutamate peptidase I (NAALADase I), and NAAG peptidase), a fragment thereof, or a variant thereof. PSMA is encoded by the folate hydrolase 1 (FOLH1) gene. PSMA is a zinc metalloenzyme found residing in membranes and the extracellular space. PSMA is highly expressed in the human prostate and is upregulated in prostate cancer. PSMA is also found to be overexpressed in other cancers such as solid tumors of the kidney, breast, and colon.

The PSMA antigen can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune responses. In some embodiments, the induced or elicited cellular immune response can include induction or secretion of interferon-gamma (IFN-γ) and/or tumor necrosis factor alpha (TNF-α). In other embodiments, the induced or elicited immune response can reduce or inhibit one or more immune suppression factors that promote growth of the tumor or cancer expressing the antigen, for example, but not limited to, factors that down regulate MHC presentation, factors that up regulate antigen-specific regulatory T cells (Tregs), PD-L1, FasL, cytokines such as IL-10 and TFG-β, tumor associated macrophages, tumor associated fibroblasts, soluble factors produced by immune suppressor cells, CTLA-4, PD-1, MDSCs, MCP-1, and an immune checkpoint molecule, which is described below in more detail.

The PSMA antigen can comprise protein epitopes that make them particularly effective as immunogens against which anti-PSMA immune responses can be induced. The PSMA antigen can comprise the full length translation product, a variant thereof, a fragment thereof or a combination thereof. The PSMA antigen can comprise a consensus protein.

The nucleic acid sequence encoding the consensus PSMA antigen can be optimized with regards to codon usage and corresponding RNA transcripts. The nucleic acid encoding the consensus PSMA antigen can be codon and RNA optimized for expression. In some embodiments, the nucleic acid sequence encoding the consensus PSMA antigen can include a Kozak sequence (e.g., GCC ACC) to increase the efficiency of translation. The nucleic acid encoding the consensus PSMA antigen can include multiple stop codons (e.g., TGA TGA) to increase the efficiency of translation termination.

The nucleic acid encoding the consensus PSMA antigen can also encode an immunoglobulin E (IgE) leader sequence. The nucleic acid encoding the consensus PSMA antigen can further encode the IgE leader sequence such that the amino acid sequence of the IgE leader sequence is linked to the amino acid sequence of the consensus PSMA P antigen by a peptide bond. The nucleic encoding the consensus PSMA antigen can also include a nucleotide sequence encoding the IgE leader sequence. In some embodiments, the nucleic acid encoding the consensus PSMA antigen is free of or does not contain a nucleotide sequence encoding the IgE leader sequence.

In some embodiments, the nucleic acid encoding the consensus PSMA antigen can be a heterologous nucleic acid sequence and/or contain one or more heterologous nucleic acid sequences.

(12) STEAP

The vaccine of the present invention can comprise the cancer antigen six-transmembrane epithelial antigen of the prostate antigen (STEAP), a fragment thereof, or a variant thereof. STEAP is a metalloreductase encoded by the STEAP1 gene. STEAP is largely expressed in prostate tissues and is upregulated in cancer cells. STEAP is predicted to be a six-transmembrane protein and is a cell surface antigen found at cell-cell junctions.

The STEAP antigen can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune responses. In some embodiments, the induced or elicited cellular immune response can include induction or secretion of interferon-gamma (IFN-γ) and/or tumor necrosis factor alpha (TNF-α). In other embodiments, the induced or elicited immune response can reduce or inhibit one or more immune suppression factors that promote growth of the tumor or cancer expressing the antigen, for example, but not limited to, factors that down regulate MHC presentation, factors that up regulate antigen-specific regulatory T cells (Tregs), PD-L1, FasL, cytokines such as IL-10 and TFG-β, tumor associated macrophages, tumor associated fibroblasts, soluble factors produced by immune suppressor cells, CTLA-4, PD-1, MDSCs, MCP-1, and an immune checkpoint molecule, which is described below in more detail.

The STEAP antigen can comprise protein epitopes that make them particularly effective as immunogens against which anti-STEAP immune responses can be induced. The STEAP antigen can comprise the full length translation product, a variant thereof, a fragment thereof or a combination thereof. The STEAP antigen can comprise a consensus protein.

The nucleic acid sequence encoding the consensus STEAP antigen can be optimized with regards to codon usage and corresponding RNA transcripts. The nucleic acid encoding the consensus STEAP antigen can be codon and RNA optimized for expression. In some embodiments, the nucleic acid sequence encoding the consensus STEAP antigen can include a Kozak sequence (e.g., GCC ACC) to increase the efficiency of translation. The nucleic acid encoding the consensus STEAP antigen can include multiple stop codons (e.g., TGA TGA) to increase the efficiency of translation termination.

The nucleic acid encoding the consensus STEAP antigen can also encode an immunoglobulin E (IgE) leader sequence. The nucleic acid encoding the consensus STEAP antigen can further encode the IgE leader sequence such that the amino acid sequence of the IgE leader sequence is linked to the amino acid sequence of the consensus STEAP antigen by a peptide bond. The nucleic encoding the consensus STEAP antigen can also include a nucleotide sequence encoding the IgE leader sequence. In some embodiments, the nucleic acid encoding the consensus STEAP antigen is free of or does not contain a nucleotide sequence encoding the IgE leader sequence.

In some embodiments, the nucleic acid encoding the consensus STEAP antigen can be a heterologous nucleic acid sequence and/or contain one or more heterologous nucleic acid sequences.

(13) PSCA

The vaccine of the present invention can comprise the cancer antigen prostate specific stem cell antigen (PSCA), a fragment thereof, or a variant thereof. PSCA is a glycosylphosphatidylinositol (GPI)-anchored cell surface protein and is encoded by an androgen-responsive gene. PSCA is a member of the Thy-1/Ly-6 family of GPI-anchored cell surface antigens. PSCA is upregulated in many cancers including prostate, bladder, and pancreatic cancers.

The PSCA antigen can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune responses. In some embodiments, the induced or elicited cellular immune response can include induction or secretion of interferon-gamma (IFN-γ) and/or tumor necrosis factor alpha (TNF-α). In other embodiments, the induced or elicited immune response can reduce or inhibit one or more immune suppression factors that promote growth of the tumor or cancer expressing the antigen, for example, but not limited to, factors that down regulate MHC presentation, factors that up regulate antigen-specific regulatory T cells (Tregs), PD-L1, FasL, cytokines such as IL-10 and TFG-β, tumor associated macrophages, tumor associated fibroblasts, soluble factors produced by immune suppressor cells, CTLA-4, PD-1, MDSCs, MCP-1, and an immune checkpoint molecule, which is described below in more detail.

The PSCA antigen can comprise protein epitopes that make them particularly effective as immunogens against which anti-PSCA immune responses can be induced. The PSCA antigen can comprise the full length translation product, a variant thereof, a fragment thereof or a combination thereof. The PSCA antigen can comprise a consensus protein.

The nucleic acid sequence encoding the consensus PSCA antigen can be optimized with regards to codon usage and corresponding RNA transcripts. The nucleic acid encoding the consensus PSCA antigen can be codon and RNA optimized for expression. In some embodiments, the nucleic acid sequence encoding the consensus PSCA antigen can include a Kozak sequence (e.g., GCC ACC) to increase the efficiency of translation. The nucleic acid encoding the consensus PSCA antigen can include multiple stop codons (e.g., TGA TGA) to increase the efficiency of translation termination.

The nucleic acid encoding the consensus PSCA antigen can also encode an immunoglobulin E (IgE) leader sequence. The nucleic acid encoding the consensus PSCA antigen can further encode the IgE leader sequence such that the amino acid sequence of the IgE leader sequence is linked to the amino acid sequence of the consensus PSCA antigen by a peptide bond. The nucleic encoding the consensus PSCA antigen can also include a nucleotide sequence encoding the IgE leader sequence. In some embodiments, the nucleic acid encoding the consensus PSCA antigen is free of or does not contain a nucleotide sequence encoding the IgE leader sequence.

In some embodiments, the nucleic acid encoding the consensus PSCA antigen can be a heterologous nucleic acid sequence and/or contain one or more heterologous nucleic acid sequences.

(14) hTERT

The vaccine of the present invention can comprise the cancer antigen hTERT, a fragment thereof, or a variant thereof hTERT is a human telomerase reverse transcriptase that synthesizes a TTAGGG tag on the end of telomeres to prevent cell death due to chromosomal shortening. Hyperproliferative cells can have abnormally high expression of hTERT. Abnormal expression of hTERT can also occur in hyperproliferative cells infected with HCV and HPV. Thus, immunotherapy for both HPV and HCV may be enhanced by targeting cells that express hTERT at abnormal levels. HPV and HCV antigens are discussed below in more detail. The hTERT cancer antigen can further be defined by U.S. patent application Ser. No. 14/139,660, filed Dec. 23, 2013, which is incorporated by reference in its' entirety.

Additionally, hTERT expression in dendritic cells transfected with hTERT genes can induce CD8+ cytotoxic T cells and elicit CD4+ T cells in an antigen-specific fashion. Therefore, use of hTERT expression within antigen presenting cells (APCs) to delay senescence and sustain their capacity to present the antigen of choice can be used in immunotherapeutic methods such as in the methods described herein.

The hTERT antigen can be associated with or expressed by any number of cancers including, but not limited to, melanoma, prostate cancer, liver cancer, cervical cancer, recurrent respiratory papillomatosis (RRP), anal cancer, head and neck cancer, and blood cancers. Accordingly, the vaccine, when including the hTERT antigen described herein, can be used for treating subjects suffering from any number of cancers including, but not limited to, melanoma, prostate cancer, liver cancer, cervical cancer, recurrent respiratory papillomatosis (RRP), anal cancer, head and neck cancer, and blood cancers.

The nTERT antigen can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune responses. In some embodiments, the induced or elicited cellular immune response can include induction or secretion of interferon-gamma (IFN-γ) and/or tumor necrosis factor alpha (TNF-α). In other embodiments, the induced or elicited immune response can reduce or inhibit one or more immune suppression factors that promote growth of the tumor or cancer expressing the antigen, for example, but not limited to, factors that down regulate MHC presentation, factors that up regulate antigen-specific regulatory T cells (Tregs), PD-L1, FasL, cytokines such as IL-10 and TFG-β, tumor associated macrophages, tumor associated fibroblasts, soluble factors produced by immune suppressor cells, CTLA-4, PD-1, MDSCs, MCP-1, and an immune checkpoint molecule, which is described below in more detail.

The hTERT antigen can comprise protein epitopes that make them particularly effective as immunogens against which anti-hTERT immune responses can be induced. The hTERT antigen can comprise the full length translation product, a variant thereof, a fragment thereof or a combination thereof. The hTERT antigen can comprise a consensus protein.

The nucleic acid sequence encoding the hTERT antigen or consensus hTERT antigen can be optimized with regards to codon usage and corresponding RNA transcripts. The nucleic acid encoding the hTERT antigen or consensus hTERT antigen can be codon and RNA optimized for expression. In some embodiments, the nucleic acid sequence encoding the hTERT antigen or consensus hTERT antigen can include a Kozak sequence (e.g., GCC ACC) to increase the efficiency of translation. The nucleic acid encoding the hTERT antigen or consensus hTERT antigen can include multiple stop codons (e.g., TGA TGA) to increase the efficiency of translation termination.

The nucleic acid encoding the hTERT antigen or consensus hTERT antigen can also encode an immunoglobulin E (IgE) leader sequence. The nucleic acid encoding the hTERT antigen or consensus hTERT antigen can further encode the IgE leader sequence such that the amino acid sequence of the IgE leader sequence is linked to the amino acid sequence of the hTERT antigen or consensus hTERT antigen by a peptide bond, respectively. The nucleic encoding the hTERT antigen or consensus hTERT antigen can also include a nucleotide sequence encoding the IgE leader sequence. In some embodiments, the nucleic acid encoding the hTERT antigen or consensus HTERT antigen is free of or does not contain a nucleotide sequence encoding the IgE leader sequence.

In some embodiments, the nucleic acid encoding the hTERT antigen or consensus hTERT antigen can be a heterologous nucleic acid sequence and/or contain one or more heterologous nucleic acid sequences. The nucleic acid encoding the hTERT antigen or consensus hTERT antigen can be mutated relative to the wild-type hTERT antigen such that one or more amino acids or residues in the amino acid sequence of the hTERT antigen or consensus hTERT antigen, respectively, is replaced or substituted with another amino acid or residue. The nucleic acid encoding the hTERT antigen or consensus hTERT antigen can be mutated relative to the wild-type hTERT antigen such that one or more residues in the amino acid sequence of the hTERT antigen or consensus hTERT antigen, respectively, are replaced or substituted with another residue, thereby causing the immune system to no longer be tolerant of hTERT in the mammal administered the nucleic acid encoding the hTERT antigen or consensus hTERT antigen, the hTERT antigen or consensus hTERT antigen, or combinations thereof. The nucleic acid encoding hTERT antigen or consensus hTERT antigen can be mutated relative to the wild-type hTERT antigen such that arginine 589, aspartate 1005, or both arginine 589 and aspartate 1005 in the amino acid sequence of the hTERT antigen or consensus hTERT antigen is replaced or substituted by a tyrosine residue.

The hTERT antigen can be the nucleic acid sequence SEQ ID NO:23, which encodes for the amino acid sequence SEQ ID NO:24. SEQ ID NO:23 encodes the hTERT protein linked to an IgE leader sequence. The hTERT protein can be linked to the IgE leader sequence and an HA tag. In other embodiments, the hTERT protein can be free of or not linked to an IgE leader sequence and/or an HA tag.

In some embodiments, the hTERT antigen can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in the SEQ ID NO:23. In other embodiments, the hTERT antigen can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:24. The hTERT antigen can be the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:24.

Some embodiments relate to nucleic acid sequences encoding proteins homologous to the hTERT protein, immunogenic fragment of the hTERT protein, and immunogenic fragments of homologous proteins. Such nucleic acid molecules that encode immunogenic proteins that have up to 95% homology to a sequence, up to 96% homology to a sequence, up to 97% homology to a sequence, up to 98% homology to a sequence and up to 99% can be provided. Likewise, nucleic acid sequences encoding the immunogenic fragments set forth herein and the immunogenic fragments of proteins homologous to the proteins set forth herein are also provided.

Some embodiments relate to nucleic acid molecules that encode immunogenic proteins that have 95% homology to the nucleic acid coding sequences herein. Some embodiments relate to nucleic acid molecules that encode immunogenic proteins that have 96% homology to the nucleic acid coding sequences herein. Some embodiments relate to nucleic acid molecules that encode immunogenic proteins that have 97% homology to the nucleic acid coding sequences herein. Some embodiments relate to nucleic acid molecules that encode immunogenic proteins that have 98% homology to the nucleic acid coding sequences herein. Some embodiments relate to nucleic acid molecules that encode immunogenic proteins that have 99% homology to the nucleic acid coding sequences herein. In some embodiments, the nucleic acid molecules with coding sequences disclosed herein that are homologous to a coding sequence of a consensus protein disclosed herein include sequences encoding an IgE leader sequence linked to the 5' end of the coding sequence encoding the homologous protein sequences disclosed herein.

Some embodiments relate to nucleic acid sequences encoding proteins with a particular percent identity to the full length hTERT protein, immunogenic fragment of the hTERT protein, and immunogenic fragments of proteins having identity to the hTERT protein. Such nucleic acid molecules that encode immunogenic proteins that have up to 80% identity to a full length hTERT sequence, up to 85% identity to a full length sequence, up to 90% identity to a full length hTERT sequence, up to 91% identity to a full length hTERT sequence, up to 92% identity to a full length hTERT sequence, up to 93% identity to a full length hTERT sequence, up to 94% identity to a full length hTERT sequence, up to 95% identity to a full length hTERT sequence, up to 96% identity to a full length hTERT sequence, up to 97% identity to a full length hTERT sequence, up to 98% identity to a full length hTERT sequence, and up to 99% identity to a full length hTERT sequence can be provided. Likewise, nucleic acid sequences encoding the immunogenic fragments set forth herein and the immunogenic fragments of proteins with similar percent identities as indicated above to the HTERT proteins set forth herein are also provided.

In some embodiments, the nucleic acid sequence is free of coding sequence that encodes a leader sequence. In some embodiments, the nucleic acid sequence is free of coding sequence that encodes the IgE leader.

Some embodiments relate to fragments of SEQ ID NO:23. Fragments can be at least 10%, at least 15%, at least 20%, at least 25%, at least 30%, at least 35%, at least 40%, at least 45%, at least 50%, at least 55% at least 60%, at least 65%, at least 70%, at least 75%, at least 80%, at least 85%, at least 90%, at least 95%, at least 96%, at least 97%, at least 98% or at least 99% of SEQ ID NO:23. Fragments can be at least 95%, at least 96%, at least 97%, at least 98%, or at least 99% homologous to fragments of SEQ ID NO:23. Fragments can be at least 80%, at least 85%, at least 90% at least 91%, at least 92%, at least 93%, at least 94%, at least 95%, at least 96%, at least 97%, at least 98%, or at least 99% identical to fragments of SEQ ID NO:23. In some embodiments, fragments include sequences that encode a leader sequence, such as for example, an immunoglobulin leader, such as the IgE leader. In some embodiments, fragments are free of coding sequences that encode a leader sequence. In some embodiments, fragments are free of coding sequences that encode a leader sequence, such as for example, the IgE leader.

Furthermore, the amino acid sequence of the hTERT protein is SEQ ID NO:24. The amino acid sequence of the hTERT protein linked to an IgE leader is SEQ ID NO:24. The amino acid sequence of the hTERT protein linked to the IgE leader may be linked to HA tag.

Some embodiments relate to proteins that are homologous to SEQ ID NO:24. Some embodiments relate to immunogenic proteins that have 95% homology to the protein sequences as set forth in SEQ ID NO:24. Some embodiments relate to immunogenic proteins that have 96% homology to the protein sequences as set forth in SEQ ID NO:24. Some embodiments relate to immunogenic proteins that have 97% homology to the protein sequences as set forth in SEQ ID NO:24. Some embodiments relate to immunogenic proteins that have 98% homology to the protein sequences as set forth in SEQ ID NO:24. Some embodiments relate to immunogenic proteins that have 99% homology to the protein sequences as set forth in SEQ ID NO:24.

Some embodiments relate to proteins that are identical to SEQ ID NO:24. Some embodiments relate to immunogenic proteins that have an amino acid sequence that is 80% identical to the full length amino acid sequences as set forth in SEQ ID NO:24. Some embodiments relate to immunogenic proteins that have an amino acid sequence that is 85% identical to the full length amino acid sequences as set forth in SEQ ID NO:24. Some embodiments relate to immunogenic proteins that have an amino acid sequence that is 90% identical to the full length amino acid sequences as set forth in SEQ ID NO:24. Some embodiments relate to immunogenic proteins that have an amino acid sequence that is 91% identical to the full length amino acid sequences as set forth in SEQ ID NO:24. Some embodiments relate to immunogenic proteins that have an amino acid sequence that is 92% identical to the full length amino acid sequences as set forth in SEQ ID NO:24. Some embodiments relate to immunogenic proteins that have an amino acid sequence that is 93% identical to the full length amino acid sequences as set forth in SEQ ID NO:24. Some embodiments relate to immunogenic proteins that have an amino acid sequence that is 94% identical to the full length amino acid sequences as set forth in SEQ ID NO:24. Some embodiments relate to immunogenic proteins that have an amino acid sequence that is 95% identical to the full length amino acid sequences as set forth in SEQ ID NO:24. Some embodiments relate to immunogenic proteins that have an amino acid sequence that is 96% identical to the full length amino acid sequences as set forth in SEQ ID NO:24. Some embodiments relate to immunogenic proteins that have an amino acid sequence that is 97% identical to the full length amino acid sequences as set forth in SEQ ID NO:24. Some embodiments relate to immunogenic proteins that have an amino acid sequence that is 98% identical to the full length amino acid sequences as set forth in SEQ ID NO:24. Some embodiments relate to immunogenic proteins that have an amino acid sequence that is 99% identical to the full length amino acid sequences as set forth in SEQ ID NO:24.

In some embodiments, the protein is free of a leader sequence. In some embodiments, the protein is free of the IgE leader. Fragments of proteins can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of a protein. Immunogenic fragments of SEQ ID NO:24 can be provided. Immunogenic fragments can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of SEQ ID NO:24. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

Immunogenic fragments of proteins with amino acid sequences homologous to immunogenic fragments of SEQ ID NO:24 can be provided. Such immunogenic fragments can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of proteins that are 95% or greater homologous to SEQ ID NO:18. Some embodiments relate to immunogenic fragments that have 96% homology to the immunogenic fragments of protein sequences herein. Some embodiments relate to immunogenic fragments that have 97% homology to the immunogenic fragments of protein sequences herein. Some embodiments relate to immunogenic fragments that have 98% homology to the immunogenic fragments of protein sequences herein. Some embodiments relate to immunogenic fragments that have 99% homology to the immunogenic fragments of protein sequences herein. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

Immunogenic fragments of proteins with amino acid sequences identical to immunogenic fragments of SEQ ID NO:24 can be provided. Such immunogenic fragments can comprise at least 10%, at least 15%, at least 20%, at least 25%, at least 30%, at least 35%, at least 40%, at least 45%, at least 50%, at least 55% at least 60%, at least 65%, at least 70%, at least 75%, at least 80%, at least 85%, at least 90%, at least 95%, at least 96%, at least 97%, at least 98% or at least 99% of proteins that are 80%, 85%, 90%, 91%, 92%, 93%, 94%, 95%, 96%, 97%, 98%, or 99% identical to the amino acid sequences set forth in SEQ ID NO:24. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

As referred to herein with regard to linking a signal peptide or leader sequence to the N terminus of a protein, the signal peptide/leader sequence replaces the N terminal methionine of a protein which is encoded by the start codon of the nucleic acid sequence than encodes the protein without a signal peptide coding sequences.

Fragments of SEQ ID NO:23 may comprise 30 or more nucleotides, including preferably sequences that encode an immunodominant epitope. In some embodiments, fragments of SEQ ID NO:23 may comprise 45 or more nucleotides, including preferably sequences that encode an immunodominant epitope. In some embodiments, fragments of SEQ ID NO:23 may comprise 60 or more nucleotides, including preferably sequences that encode an immunodominant epitope. In some embodiments, fragments of SEQ ID NO:23 may comprise 75 or more nucleotides, including preferably sequences that encode an immunodominant epitope. In some embodiments, fragments of SEQ ID NO:23 may comprise 90 or more nucleotides, including preferably sequences that encode an immunodominant epitope. In some embodiments, fragments of SEQ ID NO:23 may comprise 120 or more nucleotides, including preferably sequences that encode an immunodominant epitope. In some embodiments, fragments of SEQ ID NO:23 may comprise 150 or more nucleotides, including preferably sequences that encode an immunodominant epitope. In some embodiments, fragments of SEQ ID NO:23 may comprise 180 or more nucleotides, including preferably sequences that encode an immunodominant epitope. In some embodiments, fragments of SEQ ID NO:23 may comprise 210 or more nucleotides, including preferably sequences that encode an immunodominant epitope. In some embodiments, fragments of SEQ ID NO:23 may comprise 240 or more nucleotides, including preferably sequences that encode an immunodominant epitope. In some embodiments, fragments of SEQ ID NO:23 may comprise 270 or more nucleotides, including preferably sequences that encode an immunodominant epitope. In some embodiments, fragments of SEQ ID NO:23 may comprise 300 or more nucleotides, including preferably sequences that encode an immunodominant epitope. In some embodiments, fragments of SEQ ID NO:23 may comprise 360 or more nucleotides, including preferably sequences that encode an immunodominant epitope. In some embodiments, fragments of SEQ ID NO:23 may comprise 420 or more nucleotides, including preferably sequences that encode an immunodominant epitope. In some embodiments, fragments of SEQ ID NO:23 may comprise 480 or more nucleotides, including preferably sequences that encode an immunodominant epitope. In some embodiments, fragments of SEQ ID NO:23 may comprise 540 or more nucleotides, including preferably sequences that encode an immunodominant epitope. In some embodiments, fragments of SEQ ID NO:23 may comprise 600 or more nucleotides, including preferably sequences that encode an immunodominant epitope. In some embodiments, fragments of SEQ ID NO:23 may comprise 300 or more nucleotides, including preferably sequences that encode an immunodominant epitope. In some embodiments, fragments of SEQ ID NO:23 may comprise 660 or more nucleotides, including preferably sequences that encode an immunodominant epitope. In some embodiments, fragments of SEQ ID NO:23 may comprise 720 or more nucleotides, including preferably sequences that encode an immunodominant epitope. In some embodiments, fragments of SEQ ID NO:23 may comprise 780 or more nucleotides, including preferably sequences that encode an immunodominant epitope. In some embodiments, fragments of SEQ ID NO:23 may comprise 840 or more nucleotides, including preferably sequences that encode an immunodominant epitope. In some embodiments, fragments of SEQ ID NO:23 may comprise 900 or more nucleotides, including preferably sequences that encode an immunodominant epitope. In some embodiments, fragments of SEQ ID NO:23 may comprise 960 or more nucleotides, including preferably sequences that encode an immunodominant epitope. In some embodiments, fragments of SEQ ID NO:23 may comprise 1020 or more nucleotides, including preferably sequences that encode an immunodominant epitope. In some embodiments, fragments of SEQ ID NO:23 may comprise 1080 or more nucleotides, including preferably sequences that encode an immunodominant epitope. In some embodiments, fragments of SEQ ID NO:23 may comprise 1140 or more nucleotides, including preferably sequences that encode an immunodominant epitope. In some embodiments, fragments of SEQ ID NO:23 may comprise 1200 or more nucleotides, including preferably sequences that encode an immunodominant epitope. In some embodiments, fragments of SEQ ID NO:23 may comprise 1260 or more nucleotides, including preferably sequences that encode an immunodominant epitope. In some embodiments, fragments of SEQ ID NO:23 may comprise 1320 or more nucleotides, including preferably sequences that encode an immunodominant epitope. In some embodiments, fragments of SEQ ID NO:23 may comprise 1380 or more nucleotides, including preferably sequences that encode an immunodominant epitope. In some embodiments, fragments of SEQ ID NO:23 may comprise 1440 or more nucleotides, including preferably sequences that encode an immunodominant epitope. In some embodiments, fragments of SEQ ID NO:23 may comprise 1500 or more nucleotides, including preferably sequences that encode an immunodominant epitope. In some embodiments, fragments of SEQ ID NO:23 may comprise 1560 or more nucleotides, including preferably sequences that encode an immunodominant epitope. In some embodiments, fragments of SEQ ID NO:23 may comprise 1620 or more nucleotides, including preferably sequences that encode an immunodominant epitope. In some embodiments, fragments of SEQ ID NO:23 may comprise 1680 or more nucleotides, including preferably sequences that encode an immunodominant epitope. In some embodiments, fragments of SEQ ID NO:23 may comprise 1740 or more nucleotides, including preferably sequences that encode an immunodominant epitope. In some embodiments, fragments of SEQ ID NO:23 may comprise 1800 or more nucleotides, including preferably sequences that encode an immunodominant epitope. In some embodiments, fragments of SEQ ID NO:23 may comprise 1860 or more nucleotides, including preferably sequences that encode an immunodominant epitope. In some embodiments, fragments of SEQ ID NO:23 may comprise 1920 or more nucleotides, including preferably sequences that encode an immunodominant epitope. In some embodiments, fragments of SEQ ID NO:34 may comprise 1980 or more nucleotides, including preferably sequences that encode an immunodominant epitope. In some embodiments, fragments of SEQ ID NO:23 may comprise 2040 or more nucleotides, including preferably sequences that encode an immunodominant epitope. In some embodiments, fragments of SEQ ID NO:23 may comprise 2100 or more nucleotides, including preferably sequences that encode an immunodominant epitope. In some embodiments, fragments of SEQ ID NO:23 may comprise 2160 or more nucleotides, including preferably sequences that encode an immunodominant epitope. In some embodiments, fragments of SEQ ID NO:23 may comprise 2220 or more nucleotides, including preferably sequences that encode an immunodominant epitope. In some embodiments, fragments of SEQ ID NO:23 may comprise 2280 or more nucleotides, including preferably sequences that encode an immunodominant epitope. In some embodiments, fragments of SEQ ID NO:23 may comprise 2340 or more nucleotides, including preferably sequences that encode an immunodominant epitope. In some embodiments, fragments of SEQ ID NO:23 may comprise 2400 or more nucleotides, including preferably sequences that encode an immunodominant epitope. In some embodiments, fragments of SEQ ID NO:23 may comprise 2460 or more nucleotides, including preferably sequences that encode an immunodominant epitope. In some embodiments, fragments of SEQ ID NO:23 may comprise 2520 or more nucleotides, including preferably sequences that encode an immunodominant epitope. In some embodiments, fragments of SEQ ID NO:23 may comprise 2580 or more nucleotides, including preferably sequences that encode an immunodominant epitope. In some embodiments, fragments of SEQ ID NO:23 may comprise 2640 or more nucleotides, including preferably sequences that encode an immunodominant epitope. In some embodiments, fragments of SEQ ID NO:23 may comprise 2700 or more nucleotides, including preferably sequences that encode an immunodominant epitope. In some embodiments, fragments of SEQ ID NO:23 may comprise 2760 or more nucleotides, including preferably sequences that encode an immunodominant epitope. In some embodiments, fragments of SEQ ID NO:23 may comprise 2820 or more nucleotides, including preferably sequences that encode an immunodominant epitope. In some embodiments, fragments of SEQ ID NO:23 may comprise 2880 or more nucleotides, including preferably sequences that encode an immunodominant epitope. In some embodiments, fragments of SEQ ID NO:23 may comprise 2940 or more nucleotides, including preferably sequences that encode an immunodominant epitope. In some embodiments, fragments of SEQ ID NO:23 may comprise 3000 or more nucleotides, including preferably sequences that encode an immunodominant epitope. In some embodiments, fragments of SEQ ID NO:23 may comprise 3060 or more nucleotides, including preferably sequences that encode an immunodominant epitope. In some embodiments, fragments of SEQ ID NO:23 may comprise 3120 or more nucleotides, including preferably sequences that encode an immunodominant epitope. In some embodiments, fragments of SEQ ID NO:23 may comprise 3180 or more nucleotides, including preferably sequences that encode an immunodominant epitope. In some embodiments, fragments of SEQ ID NO:23 may comprise 3240 or more nucleotides, including preferably sequences that encode an immunodominant epitope. In some embodiments, fragments of SEQ ID NO:23 may comprise 3300 or more nucleotides, including preferably sequences that encode an immunodominant epitope. In some embodiments, fragments of SEQ ID NO:23 may comprise 3360 or more nucleotides, including preferably sequences that encode an immunodominant epitope. In some embodiments, fragments of SEQ ID NO:23 may comprise 3420 or more nucleotides, including preferably sequences that encode an immunodominant epitope. In some embodiments, fragments of SEQ ID NO:23 may comprise 3480 or more nucleotides, including preferably sequences that encode an immunodominant epitope. In some embodiments, fragments of SEQ ID NO:23 may comprise coding sequences for the IgE leader sequences. In some embodiments, fragments of SEQ ID NO:23 do not comprise coding sequences for the IgE leader sequences.

Fragments may comprise fewer than 60 nucleotides, in some embodiments fewer than 75 nucleotides, in some embodiments fewer than 90 nucleotides, in some embodiments fewer than 120 nucleotides, in some embodiments fewer than 150 nucleotides, in some embodiments fewer than 180 nucleotides, in some embodiments fewer than 210 nucleotides, in some embodiments fewer than 240 nucleotides, in some embodiments fewer than 270 nucleotides, in some embodiments fewer than 300 nucleotides, in some embodiments fewer than 360 nucleotides, in some embodiments fewer than 420 nucleotides, in some embodiments fewer than 480 nucleotides, in some embodiments fewer than 540 nucleotides, in some embodiments fewer than 600 nucleotides, in some embodiments fewer than 660 nucleotides, in some embodiments fewer than 720 nucleotides, in some embodiments fewer than 780 nucleotides, in some embodiments fewer than 840 nucleotides, in some embodiments fewer than 900 nucleotides, in some embodiments fewer than 960 nucleotides, in some embodiments fewer than 1020 nucleotides, in some embodiments fewer than 1080 nucleotides, in some embodiments fewer than 1140 nucleotides, in some embodiments fewer than 1200 nucleotides, in some embodiments fewer than 1260 nucleotides, in some embodiments fewer than 1320 nucleotides, in some embodiments fewer than 1380 nucleotides, in some embodiments fewer than 1440 nucleotides, in some embodiments fewer than 1500 nucleotides, in some embodiments fewer than 1560 nucleotides, in some embodiments fewer than 1620 nucleotides, in some embodiments fewer than 1680 nucleotides, in some embodiments fewer than 1740 nucleotides, in some embodiments fewer than 1800 nucleotides, in some embodiments fewer than 1860 nucleotides, in some embodiments fewer than 1920 nucleotides, in some embodiments fewer than 1980 nucleotides, in some embodiments fewer than 2040 nucleotides, in some embodiments fewer than 2100 nucleotides, in some embodiments fewer than 2160 nucleotides, in some embodiments fewer than 2220 nucleotides, in some embodiments fewer than 2280 nucleotides, in some embodiments fewer than 2340 nucleotides, in some embodiments fewer than 2400 nucleotides, in some embodiments fewer than 2460 nucleotides, in some embodiments fewer than 2520 nucleotides, in some embodiments fewer than 2580 nucleotides, in some embodiments fewer than 2640 nucleotides, in some embodiments fewer than 2700 nucleotides, in some embodiments fewer than 2760 nucleotides, in some embodiments fewer than 2820 nucleotides, in some embodiments fewer than 2860 nucleotides, in some embodiments fewer than 2940 nucleotides, in some embodiments fewer than 3000 nucleotides, in some embodiments fewer than 3060 nucleotides, in some embodiments fewer than 3120 nucleotides, in some embodiments fewer than 3180 nucleotides, in some embodiments fewer than 3240 nucleotides, in some embodiments fewer than 3300 nucleotides, in some embodiments fewer than 3360 nucleotides, in some embodiments fewer than 3420 nucleotides, in some embodiments fewer than 3480 nucleotides, and in some embodiments fewer than 3510 nucleotides.

Fragments of SEQ ID NO:24 may comprise 15 or more amino acids, including preferably sequences that encode an immunodominant epitope. In some embodiments, fragments of SEQ ID NO:24 may comprise 18 or more amino acids, including preferably sequences that encode an immunodominant epitope. In some embodiments, fragments of SEQ ID NO:24 may comprise 21 or more amino acids, including preferably sequences that encode an immunodominant epitope. In some embodiments, fragments of SEQ ID NO:24 may comprise 24 or more amino acids, including preferably sequences that encode an immunodominant epitope. In some embodiments, fragments of SEQ ID NO:24 may comprise 30 or more amino acids, including preferably sequences that encode an immunodominant epitope. In some embodiments, fragments of SEQ ID NO:24 may comprise 36 or more amino acids, including preferably sequences that encode an immunodominant epitope. In some embodiments, fragments of SEQ ID NO:24 may comprise 42 or more amino acids, including preferably sequences that encode an immunodominant epitope. In some embodiments, fragments of SEQ ID NO:24 may comprise 48 or more amino acids, including preferably sequences that encode an immunodominant epitope. In some embodiments, fragments of SEQ ID NO:24 may comprise 54 or more amino acids, including preferably sequences that encode an immunodominant epitope. In some embodiments, fragments of SEQ ID NO:24 may comprise 60 or more amino acids, including preferably sequences that encode an immunodominant epitope. In some embodiments, fragments of SEQ ID NO:24 may comprise 66 or more amino acids, including preferably sequences that encode an immunodominant epitope. In some embodiments, fragments of SEQ ID NO:24 may comprise 72 or more amino acids, including preferably sequences that encode an immunodominant epitope. In some embodiments, fragments of SEQ ID NO:24 may comprise 90 or more amino acids, including preferably sequences that encode an immunodominant epitope. In some embodiments, fragments of SEQ ID NO:24 may comprise 120 or more amino acids, including preferably sequences that encode an immunodominant epitope. In some embodiments, fragments of SEQ ID NO:24 may comprise 150 or more amino acids, including preferably sequences that encode an immunodominant epitope. In some embodiments, fragments of SEQ ID NO:24 may comprise 180 or more amino acids, including preferably sequences that encode an immunodominant epitope. In some embodiments, fragments of SEQ ID NO:24 may comprise 210 or more amino acids, including preferably sequences that encode an immunodominant epitope. In some embodiments, fragments of SEQ ID NO:24 may comprise 240 or more amino acids, including preferably sequences that encode an immunodominant epitope. In some embodiments, fragments of SEQ ID NO:24 may comprise 270 or more amino acids, including preferably sequences that encode an immunodominant epitope. In some embodiments, fragments of SEQ ID NO:24 may comprise 300 or more amino acids, including preferably sequences that encode an immunodominant epitope. In some embodiments, fragments of SEQ ID NO:24 may comprise 330 or more amino acids, including preferably sequences that encode an immunodominant epitope. In some embodiments, fragments of SEQ ID NO:24 may comprise 360 or more amino acids, including preferably sequences that encode an immunodominant epitope. In some embodiments, fragments of SEQ ID NO:24 may comprise 390 or more amino acids, including preferably sequences that encode an immunodominant epitope. In some embodiments, fragments of SEQ ID NO:24 may comprise 420 or more amino acids, including preferably sequences that encode an immunodominant epitope. In some embodiments, fragments of SEQ ID NO:24 may comprise 450 or more amino acids, including preferably sequences that encode an immunodominant epitope. In some embodiments, fragments of SEQ ID NO:24 may comprise 480 or more amino acids, including preferably sequences that encode an immunodominant epitope. In some embodiments, fragments of SEQ ID NO:24 may comprise 510 or more amino acids, including preferably sequences that encode an immunodominant epitope. In some embodiments, fragments of SEQ ID NO:24 may comprise 540 or more amino acids, including preferably sequences that encode an immunodominant epitope. In some embodiments, fragments of SEQ ID NO:24 may comprise 570 or more amino acids, including preferably sequences that encode an immunodominant epitope. In some embodiments, fragments of SEQ ID NO:24 may comprise 600 or more amino acids, including preferably sequences that encode an immunodominant epitope. In some embodiments, fragments of SEQ ID NO:24 may comprise 630 or more amino acids, including preferably sequences that encode an immunodominant epitope. In some embodiments, fragments of SEQ ID NO:24 may comprise 660 or more amino acids, including preferably sequences that encode an immunodominant epitope. In some embodiments, fragments of SEQ ID NO:24 may comprise 690 or more amino acids, including preferably sequences that encode an immunodominant epitope. In some embodiments, fragments of SEQ ID NO:24 may comprise 720 or more amino acids, including preferably sequences that encode an immunodominant epitope. In some embodiments, fragments of SEQ ID NO:24 may comprise 750 or more amino acids, including preferably sequences that encode an immunodominant epitope. In some embodiments, fragments of SEQ ID NO:24 may comprise 780 or more amino acids, including preferably sequences that encode an immunodominant epitope. In some embodiments, fragments of SEQ ID NO:24 may comprise 810 or more amino acids, including preferably sequences that encode an immunodominant epitope. In some embodiments, fragments of SEQ ID NO:24 may comprise 840 or more amino acids, including preferably sequences that encode an immunodominant epitope. In some embodiments, fragments of SEQ ID NO:24 may comprise 870 or more amino acids, including preferably sequences that encode an immunodominant epitope. In some embodiments, fragments of SEQ ID NO:24 may comprise 900 or more amino acids, including preferably sequences that encode an immunodominant epitope. In some embodiments, fragments of SEQ ID NO:24 may comprise 930 or more amino acids, including preferably sequences that encode an immunodominant epitope. In some embodiments, fragments of SEQ ID NO:24 may comprise 960 or more amino acids, including preferably sequences that encode an immunodominant epitope. In some embodiments, fragments of SEQ ID NO:24 may comprise 990 or more amino acids, including preferably sequences that encode an immunodominant epitope. In some embodiments, fragments of SEQ ID NO:24 may comprise 1020 or more amino acids, including preferably sequences that encode an immunodominant epitope. In some embodiments, fragments of SEQ ID NO:24 may comprise 1050 or more amino acids, including preferably sequences that encode an immunodominant epitope. In some embodiments, fragments of SEQ ID NO:24 may comprise 1080 or more amino acids, including preferably sequences that encode an immunodominant epitope. In some embodiments, fragments of SEQ ID NO:24 may comprise 1110 or more amino acids, including preferably sequences that encode an immunodominant epitope. In some embodiments, fragments of SEQ ID NO:24 may comprise 1140 or more amino acids, including preferably sequences that encode an immunodominant epitope. In some embodiments, fragments of SEQ ID NO:24 may comprise 1170 or more amino acids, including preferably sequences that encode an immunodominant epitope. In some embodiments, fragments of SEQ ID NO:24 may comprise 1200 or more amino acids, including preferably sequences that encode an immunodominant epitope. In some embodiments, fragments of SEQ ID NO:24 may comprise 1230 or more amino acids, including preferably sequences that encode an immunodominant epitope. In some embodiments, fragments of SEQ ID NO:24 may comprise 1260 or more amino acids, including preferably sequences that encode an immunodominant epitope. In some embodiments, fragments of SEQ ID NO:24 may comprise 1290 or more amino acids, including preferably sequences that encode an immunodominant epitope. In some embodiments, fragments of SEQ ID NO:24 may comprise 1320 or more amino acids, including preferably sequences that encode an immunodominant epitope. In some embodiments, fragments of SEQ ID NO:24 may comprise 1350 or more amino acids, including preferably sequences that encode an immunodominant epitope. In some embodiments, fragments of SEQ ID NO:24 may comprise 1380 or more amino acids, including preferably sequences that encode an immunodominant epitope. In some embodiments, fragments of SEQ ID NO:24 may comprise 1410 or more amino acids, including preferably sequences that encode an immunodominant epitope. In some embodiments, fragments of SEQ ID NO:24 may comprise 1440 or more amino acids, including preferably sequences that encode an immunodominant epitope. In some embodiments, fragments of SEQ ID NO:24 may comprise 1470 or more amino acids, including preferably sequences that encode an immunodominant epitope. In some embodiments, fragments of SEQ ID NO:24 may comprise 1500 or more amino acids, including preferably sequences that encode an immunodominant epitope. In some embodiments, fragments of SEQ ID NO:24 may comprise coding sequences for the IgE leader sequences. In some embodiments, fragments of SEQ ID NO:24 do not comprise coding sequences for the IgE leader sequences.

Fragments may comprise fewer than 24 amino acids, in some embodiments fewer than 30 amino acids, in some embodiments fewer than 36 amino acids, in some embodiments fewer than 42 amino acids, in some embodiments fewer than 48 amino acids, in some embodiments fewer than 54 amino acids, in some embodiments fewer than 60 amino acids, in some embodiments fewer than 72 amino acids, in some embodiments fewer than 90 amino acids, in some embodiments fewer than 120 amino acids, in some embodiments fewer than 150 amino acids, in some embodiments fewer than 180 amino acids, in some embodiments fewer than 210 amino acids in some embodiments fewer than 240 amino acids, in some embodiments fewer than 260 amino acids, in some embodiments fewer than 290 amino acids, in some embodiments fewer than 320 amino acids, in some embodiments fewer than 350 amino acids, in some embodiments fewer than 380 amino acids, in some embodiments fewer than 410 amino acids in some embodiments fewer than 440 amino acids, in some embodiments fewer than 470 amino acids in some embodiments fewer than 500 amino acids, in some embodiments fewer than 530 amino acids in some embodiments fewer than 560 amino acids, in some embodiments fewer than 590 amino acids, in some embodiments fewer than 620 amino acids, in some embodiments fewer than 650 amino acids, in some embodiments fewer than 680 amino acids, in some embodiments fewer than 710 amino acids, in some embodiments fewer than 740 amino acids, in some embodiments fewer than 770 amino acids, in some embodiments fewer than 800 amino acids, in some embodiments fewer than 830 amino acids, in some embodiments fewer than 860 amino acids, in some embodiments fewer than 890 amino acids, in some embodiments fewer than 920 amino acids, in some embodiments fewer than 950 amino acids, in some embodiments fewer than 980 amino acids, in some embodiments fewer than 1010 amino acids, in some embodiments fewer than 1040 amino acids, in some embodiments fewer than 1070 amino acids, in some embodiments fewer than 1200 amino acids, in some embodiments fewer than 1230 amino acids, in some embodiments fewer than 1260 amino acids, in some embodiments fewer than 1290 amino acids, in some embodiments fewer than 1320 amino acids, in some embodiments fewer than 1350 amino acids, in some embodiments fewer than 1380 amino acids, in some embodiments fewer than 1410 amino acids, in some embodiments fewer than 1440 amino acids, in some embodiments fewer than 1470 amino acids, and in some embodiments fewer than 1500 amino acids.

(15) MAGE A1

The vaccine of the present invention can comprise the cancer antigen melanoma-associated antigen 1 (MAGE A1), a fragment thereof, or a variant thereof. MAGE A1, encoded by the MAGEA1 gene, is a 280-amino acid protein, and has been found only to be expressed by tumor cells and germ cells. MAGE A1 relies on DNA methylation for its repression in normal somatic tissues. These genes become activated in many types of tumors in the course of the genome-wide demethylation process, which often accompanies tumorgenesis. Specifically, during neoplastic transformation, these genes are activated, expressed, and may become antigenic targets that are recognized and attacked by the immune system. Therefore, MAGE genes take part in the immune process by targeting some early tumor cells for immune destruction. MAGE A1 may be expressed in numerous cancers, including, but not limited to, melanomas, lung carcenomas and esophageal squamous-cell carcinomas.

The MAGE A1 antigen can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune responses. In some embodiments, the induced or elicited cellular immune response can include induction or secretion of interferon-gamma (IFN-γ) and/or tumor necrosis factor alpha (TNF-α). In other embodiments, the induced or elicited immune response can reduce or inhibit one or more immune suppression factors that promote growth of the tumor or cancer expressing the antigen, for example, but not limited to, factors that down regulate MHC presentation, factors that up regulate antigen-specific regulatory T cells (Tregs), PD-L1, FasL, cytokines such as IL-10 and TFG-β, tumor associated macrophages, tumor associated fibroblasts, soluble factors produced by immune suppressor cells, CTLA-4, PD-1, MDSCs, MCP-1, and an immune checkpoint molecule, which is described below in more detail.

(16) WT1

The vaccine of the present invention can comprise the cancer antigen Wilm's tumor 1 (WT1), a fragment thereof, or a variant thereof. WT1 is a transcription factor containing at the N-terminus, a proline/glutamine-rich DNA-binding domain and at the C-terminus, four zinc finger motifs. WT1 plays a role in the normal development of the urogenital system and interacts with numerous factors, for example, p53, a known tumor suppressor and the serine protease HtrA2, which cleaves WT1 at multiple sites after treatment with a cytotoxic drug.

Mutation of WT1 can lead to tumor or cancer formation, for example, Wilm's tumor or tumors expressing WT1. Wilm's tumor often forms in one or both kidneys before metastasizing to other tissues, for example, but not limited to, liver tissue, urinary tract system tissue, lymph tissue, and lung tissue. Accordingly, Wilm's tumor can be considered a metastatic tumor. Wilm's tumor usually occurs in younger children (e.g., less than 5 years old) and in both sporadic and hereditary forms. The WT1 cancer antigen can further be defined by PCT/US13/75141, filed Dec. 23, 2013, which are hereby incorporated by reference in its' entirety.

The WT-1 antigen can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune responses. In some embodiments, the induced or elicited cellular immune response can include induction or secretion of interferon-gamma (IFN-γ) and/or tumor necrosis factor alpha (TNF-α). In other embodiments, the induced or elicited immune response can reduce or inhibit one or more immune suppression factors that promote growth of the tumor or cancer expressing the antigen, for example, but not limited to, factors that down regulate MHC presentation, factors that up regulate antigen-specific regulatory T cells (Tregs), PD-L1, FasL, cytokines such as IL-10 and TFG-β, tumor associated macrophages, tumor associated fibroblasts, soluble factors produced by immune suppressor cells, CTLA-4, PD-1, MDSCs, MCP-1, and an immune checkpoint molecule, which is described below in more detail.

Accordingly, the vaccine can be used for treating subjects suffering from Wilm's tumor. The vaccine can be used for treating subjects suffering from any number of cancers including, but not limited to, melanoma, prostate cancer, liver cancer, cervical cancer, recurrent respiratory papillomatosis (RRP), anal cancer, head and neck cancer, and blood cancers. The vaccine can also be used for treating subjects with cancers or tumors that express WT1 for preventing development of such tumors in subjects. The WT1 antigen can differ from the native, "normal" WT1 gene, and thus, provide therapy or prophylaxis against an WT1 antigen-expressing tumor. Accordingly, WT1 antigen sequences that differ from the native WT1 gene (i.e., mutated WT1 genes or sequences) are provided herein.

Transcripts of the native WT1 gene are processed into a variety of mRNAs, and the resulting proteins are not all of equal value for inducing an immune response. The mutated WT1 genes described herein avoid alternative processing, producing one full-length transcript and resulting in stronger induction of effector T and B cell responses. The first mutated WT1 sequence is referred to as CON WT1 with modified Zinc Fingers or ConWT1-L. SEQ ID NO: 19 is a nucleic acid sequence encoding the WT1 antigen CON WT1 with modified Zinc Fingers. SEQ ID NO:20 is the amino acid sequence of WT1 antigen CON WT1 with modified Zinc Fingers. The second mutated WT1 sequence is referred to as CON WT1 without Zinc Fingers or ConWT1-S. SEQ ID NO:21 is a nucleic acid sequence encoding the WT1 antigen CON WT1 without Zinc Fingers. SEQ ID NO:22 is the amino acid sequence of WT1 antigen CON WT1 without modified Zinc Fingers.

The WT1 antigen can be a consensus antigen (or immunogen) sequence derived from two or more species. The WT1 antigen can comprise a consensus sequence and/or modification(s) for improved expression. Modification can include codon optimization, RNA optimization, additional of a kozak sequence (e.g., GCC ACC) for increased translation initiation and/or the addition of an immunoglobulin leader sequence to increase the immunogenicity of the WT1 antigen. The WT1 antigen can comprise a signal peptide such as an immunoglobulin signal peptide, for example, but not limited to, an immunoglobulin E (IgE) or immunoglobulin G (IgG) signal peptide. In some embodiments, the WT1 consensus antigen can comprise a hemagglutinin (HA) tag. The WT1 consensus antigen can be designed to elicit stronger and broader cellular and/or humoral immune responses than a corresponding codon optimized WT1 antigen.

The WT1 consensus antigen can comprise one or more mutations in one or more zinc fingers, thereby eliciting stronger and broader cellular and/or humoral immune responses than a corresponding codon optimized WT1 antigen. The one or more mutations can be a substitution of one or more of the amino acids that coordinate the zinc ion in the one or more zinc fingers. The one or more amino acids that coordinate the zinc ion can be a CCHH motif. Accordingly, in some embodiments, the one or more mutations can replace 1, 2, 3, or all 4 amino acids of CCHH motif.

In other embodiments, the one or more mutations are such that residues 312, 317, 342, and 347 of SEQ ID NO:20 are any residue other than cysteine (C) and residues 330, 334, 360, and 364 of SEQ ID NO:20 are any residue other than histidine (H). In particular, the one or more mutations are such that residues 312, 317, 330, 334, 342, 347, 360, and 364 of SEQ ID NO:20 are glycine (G).

In other embodiments, one or more of the zinc fingers can be removed from the WT1 consensus antigen. One, two, three, or all four of the zinc fingers can be removed from the WT1 consensus antigen.

The WT1 consensus antigen can be the nucleic acid SEQ ID NO:19, which encodes SEQ ID NO:20. In some embodiments, the WT1 consensus antigen can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, or 99% identity over an entire length of the nucleic acid sequence set forth in SEQ ID NO:19. In other embodiments, the WT1 consensus antigen can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, or 99% identity over an entire length of the amino acid sequence set forth in SEQ ID NO:20.

In still other embodiments, the WT1 consensus antigen can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, or 99% identity over an entire length of the amino acid sequence set forth in SEQ ID NO:20, provided that residues 312, 317, 342, and 347 of SEQ ID NO:20 are any residue other than cysteine (C) and residues 330, 334, 360, and 364 of SEQ ID NO:20 are any residue other than histidine (H). In other embodiments, the WT1 consensus antigen can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, or 99% identity over an entire length of the amino acid sequence set forth in SEQ ID NO:20, provided that residues 312, 317, 330, 334, 342, 347, 360, and 364 of SEQ ID NO:20 are glycine (G).

The WT1 consensus antigen can be the amino acid sequence SEQ ID NO:20. In some embodiments, the WT1 consensus antigen can be the amino acid sequence having at least about 80%, 81%, 82%, 83%, 84%, 85%, 86%, 87%, 88%, 89%, 90%, 91%, 92%, 93%, 94%, 95%, 96%, 97%, 98%, or 99% identity over an entire length of the amino acid sequence set forth in SEQ ID NO:20. The WT1 consensus antigen can be the amino acid sequence having at least about 80%, 81%, 82%, 83%, 84%, 85%, 86%, 87%, 88%, 89%, 90%, 91%, 92%, 93%, 94%, 95%, 96%, 97%, 98%, or 99% identity over an entire length of the amino acid sequence set forth in SEQ ID NO:20, provided that residues 312, 317, 342, and 347 of SEQ ID NO:20 are any residue other than cysteine (C) and residues 330, 334, 360, and 364 of SEQ ID NO:20 are any residue other than histidine (H). In some embodiments, the WT1 consensus antigen can be the amino acid sequence having at least about 80%, 81%, 82%, 83%, 84%, 85%, 86%, 87%, 88%, 89%, 90%, 91%, 92%, 93%, 94%, 95%, 96%, 97%, 98%, or 99% identity over an entire length of the amino acid sequence set forth in SEQ ID NO:20, provided that residues 312, 317, 330, 334, 342, 347, 360, and 364 of SEQ ID NO:20 are glycine (G).

The WT1 consensus antigen can be the nucleic acid SEQ ID NO:21, which encodes SEQ ID NO:22. In some embodiments, the WT1 consensus antigen can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, or 99% identity over an entire length of the nucleic acid sequence set forth in SEQ ID NO:21. In other embodiments, the WT1 consensus antigen can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, or 99% identity over an entire length of the amino acid sequence set forth in SEQ ID NO:22.

The WT1 consensus antigen can be the amino acid sequence SEQ ID NO:22. In some embodiments, the WT1 consensus antigen can be the amino acid sequence having at least about 80%, 81%, 82%, 83%, 84%, 85%, 86%, 87%, 88%, 89%, 90%, 91%, 92%, 93%, 94%, 95%, 96%, 97%, 98%, or 99% identity over an entire length of the amino acid sequence set forth in SEQ ID NO:22.

Immunogenic fragments of SEQ ID NO:20 and SEQ ID NO:22 can be provided. Immunogenic fragments can comprise at least 60%, at least 65%, at least 70%, at least 75%, at least 80%, at least 85%, at least 90%, at least 95%, at least 96%, at least 97%, at least 98%, or at least 99% of SEQ ID NO:20 and/or SEQ ID NO:22. In some embodiments, immunogenic fragments can comprise at least 60%, at least 65%, at least 70%, at least 75%, at least 80%, at least 85%, at least 90%, at least 95%, at least 96%, at least 97%, at least 98%, or at least 99% of SEQ ID NO:20, provided that if residues 312, 317, 342, and 347 of SEQ ID NO:20 are present in the immunogenic fragment, then these residues are any residue other than cysteine (C), and provided that if residues 330, 334, 360, and 364 of SEQ ID NO:20 are present in the immunogenic fragment, then these residues are any residue other than histidine (H). In other embodiments, immunogenic fragments can comprise at least 60%, at least 65%, at least 70%, at least 75%, at least 80%, at least 85%, at least 90%, at least 95%, at least 96%, at least 97%, at least 98%, or at least 99% of SEQ ID NO:20, provided that if residues 312, 317, 330, 334, 342, 347, 360, and 364 of SEQ ID NO:20 are present in the immunogenic fragment, then these residues are glycine (G).

In some embodiments, immunogenic fragments include a leader sequence, for example, an immunoglobulin leader sequence, such as the immunoglobulin E (IgE) leader sequence. In some embodiments, immunogenic fragments are free of a leader sequence.

Immunogenic fragments of proteins with amino acid sequences having identity to immunogenic fragments of SEQ ID NO:20 and 22 can be provided. Such fragments can comprise at least 60%, at least 65%, at least 70%, at least 75%, at least 80%, at least 85%, at least 90%, at least 95%, at least 96%, at least 97%, at least 98%, or at least 99% of proteins having 95% or greater identity to SEQ ID NO:20 and/or SEQ ID NO:22. Some embodiments relate to immunogenic fragments that have 96% or greater identity to the immunogenic fragments of WT1 protein sequences herein. Some embodiments relate to immunogenic fragments that have 97% or greater identity to the immunogenic fragments of WT1 protein sequences herein. Some embodiments relate to immunogenic fragments that have 98% or greater identity to the immunogenic fragments of WT1 protein sequences herein. Some embodiments relate to immunogenic fragments that have 99% or greater identity to the immunogenic fragments of WT1 protein sequences herein. In some embodiments, immunogenic fragments include a leader sequence, for example, an immunoglobulin leader sequence such as the IgE leader sequence. In some embodiments, the immunogenic fragments are free of a leader sequence.

Some embodiments relate to immunogenic fragments of SEQ ID NO:19 and SEQ ID NO:21 Immunogenic fragments can comprise at least 60%, at least 65%, at least 70%, at least 75%, at least 80%, at least 85%, at least 90%, at least 95%, at least 96%, at least 97%, at least 98%, or at least 99% of SEQ ID NO:19 and/or SEQ ID NO:21. In some embodiments, immunogenic fragments include sequences that encode a leader sequence, for example, an immunoglobulin leader sequence such as the IgE leader sequence. In some embodiments, immunogenic fragments are free of coding sequences that encode a leader sequence.

Immunogenic fragments of nucleic acids with nucleotide sequences having identity to immunogenic fragments of SEQ ID NO:19 and SEQ ID NO:21 can be provided. Such fragments can comprise at least 60%, at least 65%, at least 70%, at least 75%, at least 75%, at least 80%, at least 85%, at least 90%, at least 95%, at least 96%, at least 97%, at least 98%, or at least 99% of nucleic acids having 95% or greater identity to SEQ ID NO:19 and/or SEQ ID NO:21. Some embodiments relate to immunogenic fragments that have 96% or greater identity to the immunogenic fragments of WT1 nucleic acid sequences herein. Some embodiments relate to immunogenic fragments that have 97% or greater identity to the immunogenic fragments of WT1 nucleic acid sequences herein. Some embodiments relate to immuno-genic fragments that have 98% or greater identity to the immunogenic fragments of WT1 nucleic acid sequences herein. Some embodiments relate to immunogenic fragments that have 99% or greater identity to the immunogenic fragments of WT1 nucleic sequences herein. In some embodiments, immunogenic fragments include sequences that encode a leader sequence, for example, an immunoglobulin leader sequence such as the IgE leader sequence. In some embodiments, immunogenic fragments are free of coding sequences that encode a leader sequence.

(17) gp100

The vaccine of the present invention can comprise the cancer antigen glycoprotein 100 (gp100; also known as Trp2 and premelanosome protein (PMEL)), a fragment thereof, or a variant thereof gp100 is encoded by the PMEL gene. It is a 70 kDa type 1 transmembrane glycoprotein, comprised of 661 amino acids that plays a central role in the biogenesis of melanosomes as it is involved in the maturation of melanosomes from stage I to II. gp100 drives the formation of striations from within multivesicular bodies and is directly involved in the biogenesis of premelanosomes. gp100 is enriched in premelanosomes relative to mature melanosomes, but overexpressed by proliferating neonatal melanocytes and during tumor growth. The gp100 protein includes a variety of immunogenic epitopes that are recognized by cytotoxic T lymphocytes from peripheral blood of melanoma patients and from tumor infiltrating lymphocytes.

The gp100 antigen can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune responses. In some embodiments, the induced or elicited cellular immune response can include induction or secretion of interferon-gamma (IFN-γ) and/or tumor necrosis factor alpha (TNF-α). In other embodiments, the induced or elicited immune response can reduce or inhibit one or more immune suppression factors that promote growth of the tumor or cancer expressing the antigen, for example, but not limited to, factors that down regulate MHC presentation, factors that up regulate antigen-specific regulatory T cells (Tregs), PD-L1, FasL, cytokines such as IL-10 and TFG-β, tumor associated macrophages, tumor associated fibroblasts, soluble factors produced by immune suppressor cells, CTLA-4, PD-1, MDSCs, MCP-1, and an immune checkpoint molecule, which is described below in more detail.

(18) Viral Antigens

The cancer antigen can be a viral antigen, a fragment thereof, or a variant thereof. The viral antigen can be antigen from a hepatitis B virus, a hepatitis C virus, or a human papilloma virus (HPV). The HPV can be HPV 6, HPV 11, HPV 16, or HPV 18 as discussed below.

The viral antigen can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune responses. In some embodiments, the induced or elicited cellular immune response can include induction or secretion of interferon-gamma (IFN-γ) and/or tumor necrosis factor alpha (TNF-α). In other embodiments, the induced or elicited immune response can reduce or inhibit one or more immune suppression factors that promote growth of the tumor or cancer expressing the antigen, for example, but not limited to, factors that down regulate MHC presentation, factors that up regulate antigen-specific regulatory T cells (Tregs), PD-L1, FasL, cytokines such as IL-10 and TFG-β, tumor associated macrophages, tumor associated fibroblasts, soluble factors produced by immune suppressor cells, CTLA-4, PD-1, MDSCs, MCP-1, and an immune checkpoint molecule, which is described below in more detail.

(a) Hepatitis B Virus Antigen

The viral antigen can be an antigen from Hepatitis B virus (HBV), a fragment thereof, or a variant thereof. The HBV antigen can be associated with or cause liver cancer. In some embodiments, the HBV antigen can be a heterologous nucleic acid molecule(s), such as a plasmid(s), which encodes one or more of the antigens from HBV. The HBV antigen can be full-length or immunogenic fragments of full-length proteins.

The HBV antigen can comprise consensus sequences and/or one or more modifications for improved expression. Genetic modifications, including codon optimization, RNA optimization, and the addition of a highly efficient immunoglobulin leader sequence to increase the immunogenicity of the constructs, can be included in the modified consensus sequences. The consensus HBV antigen may comprise a signal peptide such as an immunoglobulin signal peptide such as an IgE or IgG signal peptide, and in some embodiments, may comprise an HA tag. The immunogens can be designed to elicit stronger and broader cellular immune responses than corresponding codon optimized immunogens.

The HBV antigen can be a HBV core protein, a HBV surface protein, a HBV DNA polymerase, a HBV protein encoded by gene X, fragment thereof, variant thereof, or combination thereof. The HBV antigen can be a HBV genotype A core protein, a HBV genotype B core protein, a HBV genotype C core protein, a HBV genotype D core protein, a HBV genotype E core protein, a HBV genotype F core protein, a HBV genotype G core protein, a HBV genotype H core protein, a HBV genotype A surface protein, a HBV genotype B surface protein, a HBV genotype C surface protein, a HBV genotype D surface protein, a HBV genotype E surface protein, a HBV genotype F surface protein, a HBV genotype G surface protein, a HBV genotype H surface protein, fragment thereof, variant thereof, or combination thereof. The HBV antigen can be a consensus HBV core protein, or a consensus HBV surface protein.

In some embodiments, the HBV antigen can be a HBV genotype A consensus core DNA sequence construct, an IgE leader sequence linked to a consensus sequence for HBV genotype A core protein, or a HBV genotype A consensus core protein sequence.

In other embodiments, the HBV antigen can be a HBV genotype B consensus core DNA sequence construct, an IgE leader sequence linked to a consensus sequence for HBV genotype B core protein, or a HBV genotype B consensus core protein sequence.

In still other embodiments, the HBV antigen can be a HBV genotype C consensus core DNA sequence construct, an IgE leader sequence linked to a consensus sequence for HBV genotype C core protein, or a HBV genotype C consensus core protein sequence.

In some embodiments, the HBV antigen can be a HBV genotype D consensus core DNA sequence construct, an IgE leader sequence linked to a consensus sequence for HBV genotype D core protein, or a HBV genotype D consensus core protein sequence.

In other embodiments, the HBV antigen can be a HBV genotype E consensus core DNA sequence construct, an IgE leader sequence linked to a consensus sequence for HBV genotype E core protein, or a HBV genotype E consensus core protein sequence.

In some embodiments, the HBV antigen can be a HBV genotype F consensus core DNA sequence construct, an IgE leader sequence linked to a consensus sequence for HBV genotype F core protein, or a HBV genotype F consensus core protein sequence.

In other embodiments, the HBV antigen can be a HBV genotype G consensus core DNA sequence construct, an IgE leader sequence linked to a consensus sequence for HBV genotype G core protein, or a HBV genotype G consensus core protein sequence.

In some embodiments, the HBV antigen can be a HBV genotype H consensus core DNA sequence construct, an IgE leader sequence linked to a consensus sequence for HBV genotype H core protein, or a HBV genotype H consensus core protein sequence.

In still other embodiments, the HBV antigen can be a HBV genotype A consensus surface DNA sequence construct, an IgE leader sequence linked to a consensus sequence for HBV genotype A surface protein, or a HBV genotype A consensus surface protein sequence.

In some embodiments, the HBV antigen can be a HBV genotype B consensus surface DNA sequence construct, an IgE leader sequence linked to a consensus sequence for HBV genotype B surface protein, or a HBV genotype B consensus surface protein sequence.

In other embodiments, the HBV antigen can be a HBV genotype C consensus surface DNA sequence construct, an IgE leader sequence linked to a consensus sequence for HBV genotype C surface protein, or a HBV genotype C consensus surface protein sequence.

In still other embodiments, the HBV antigen can be a HBV genotype D consensus surface DNA sequence construct, an IgE leader sequence linked to a consensus sequence for HBV genotype D surface protein, or a HBV genotype D consensus surface protein sequence.

In some embodiments, the HBV antigen can be a HBV genotype E consensus surface DNA sequence construct, an IgE leader sequence linked to a consensus sequence for HBV genotype E surface protein, or a HBV genotype E consensus surface protein sequence.

In other embodiments, the HBV antigen can be a HBV genotype F consensus surface DNA sequence construct, an IgE leader sequence linked to a consensus sequence for HBV genotype F surface protein, or a HBV genotype F consensus surface protein sequence.

In still other embodiments, the HBV antigen can be a HBV genotype G consensus surface DNA sequence construct, an IgE leader sequence linked to a consensus sequence for HBV genotype G surface protein, or a HBV genotype G consensus surface protein sequence.

In other embodiments, the HBV antigen can be a HBV genotype H consensus surface DNA sequence construct, an IgE leader sequence linked to a consensus sequence for HBV genotype H surface protein, or a HBV genotype H consensus surface protein sequence.

(b) Hepatitis C Virus Antigen

The viral antigen can be an antigen from Hepatitis C virus (HCV), a fragment thereof, or a variant thereof. The HCV antigen can be associated with or cause liver cancer. In some embodiments, the HCV antigen can be a heterologous nucleic acid molecule(s), such as a plasmid(s), which encodes one or more of the antigens from HCV. The HCV antigen can be full-length or immunogenic fragments of full-length proteins.

The HCV antigen can comprise consensus sequences and/or one or more modifications for improved expression. Genetic modifications, including codon optimization, RNA optimization, and the addition of a highly efficient immunoglobulin leader sequence to increase the immunogenicity of the constructs, can be included in the modified consensus sequences. The consensus HCV antigen may comprise a signal peptide such as an immunoglobulin signal peptide such as an IgE or IgG signal peptide, and in some embodiments, may comprise an HA tag. The immunogens can be designed to elicit stronger and broader cellular immune responses than corresponding codon optimized immunogens.

The HCV antigen can be a HCV nucleocapsid protein (i.e., core protein), a HCV envelope protein (e.g., E1 and E2), a HCV non-structural protein (e.g., NS1, NS2, NS3, NS4a, NS4b, NS5a, and NS5b), a fragment thereof, a variant thereof, or a combination thereof.

(c) Human Papilloma Virus

The viral antigen can be an antigen from HPV, a fragment thereof, or a variant thereof. The HPV antigen can be from HPV types 16, 18, 31, 33, 35, 45, 52, and 58, which cause cervical cancer, rectal cancer, and/or other cancers. The HPV antigen can be from HPV types 6 and/or 11, which cause genital warts, and are known to be causes of head and neck cancer. The HPV antigen can be from HPV types 16 and/or 18, which cause cervical cancer. The HPV antigen can be from HPV types 6, 11, and/or 16, which cause RRP and anal cancer. The HPV cancer antigen can further be defined by U.S. Pat. No. 8,168,769 filed Jul. 30, 2007, U.S. Pat. No. 8,389,706 filed Jan. 21, 2010, U.S. patent application Ser. No. 13/271,576 filed Oct. 21, 2011 and U.S. Patent Appl. No. 61/777,198, filed Mar. 12, 2013, each of which are incorporated by reference in their entirety.

The HPV antigens can be the HPV E6 or E7 domains from each HPV type. For example, for HPV type 16 (HPV16), the HPV16 antigen can include the HPV16 E6 antigen, the HPV16 E7 antigen, fragments, variants, or combinations thereof. Similarly, the HPV antigen can be HPV 6 E6 and/or E7, HPV 11 E6 and/or E7, HPV 16 E6 and/or E7, HPV 18 E6 and/or E7, HPV 31 E6 and/or E7, HPV 33 E6 and/or E7, HPV 52 E6 and/or E7, or HPV 58 E6 and/or E7, fragments, variants, or combinations thereof (d) Herpes Viruses The viral antigen may be a herpes viral antigen. The herpes viral antigen can be an antigen selected from the group consisting of CMV, HSV1, HSV2, VZV, CeHV1, EBV, roseolovirus, Kaposi's sarcoma-associated herpesvirus, or MuHV, and preferably, CMV, HSV1, HSV2, CeHV1 and VZV.

A consensus protein HCMV-gB (SEQ ID NO:26), a consensus protein HCMV-gM (SEQ ID NO:28), a consensus protein HCMV-gN (SEQ ID NO:30), a consensus protein HCMV-gH (SEQ ID NO:32), a consensus protein HCMV-gL (SEQ ID NO:34), a consensus protein HCMV-gO (SEQ ID NO:36), a consensus protein HCMV-UL128 (SEQ ID NO:38), a consensus protein HCMV-UL130 (SEQ ID NO:40), a consensus protein HCMV-UL-131A (SEQ ID NO:42), a consensus protein HCMV-UL-83 (pp65) (SEQ ID NO:44).

Nucleic acid sequences including sequences encoding SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42 or SEQ ID NO: 44. Nucleic acid molecules encoding the consensus amino acid sequences were generated. Vaccines may comprise one or more nucleic acid sequences that encode one or more of the consensus versions of the immunogenic proteins selected from this group of sequences generated to optimize stability and expression in humans. Nucleic acid sequence encoding consensus protein HCMV-gB (SEQ ID NO:25), nucleic acid sequence encoding consensus protein HCMV-gM (SEQ ID NO:27), nucleic acid sequence encoding consensus protein HCMV-gN (SEQ ID NO:29), nucleic acid sequence encoding consensus protein HCMV-gH (SEQ ID NO:31), nucleic acid sequence encoding consensus protein HCMV-gL (SEQ ID NO:33), nucleic acid sequence encoding consensus protein HCMV-gO (SEQ ID NO:35), nucleic acid sequence encoding consensus protein HCMV-UL128 (SEQ ID NO:37), nucleic acid sequence encoding consensus protein HCMV-UL130 (SEQ ID NO:39), nucleic acid sequence encoding consensus protein HCMV-UL-131A (SEQ ID NO:41), nucleic acid sequence encoding consensus protein HCMV-UL-83 (pp65) (SEQ ID NO:43). The nucleic acid sequence can additionally have an encoding IgE leader linked to the 5' end.

In view of evolutionary divergence from clinical isolates and extensive genetic differences among prevalent circulating human strains consensus amino acid sequences for each of immunogenic proteins have been generated. Consensus amino acid sequences for gB, gM, gH, gL, gE, gI, gK, gC, gD, UL128, UL130, UL-131A and UL-83 (pp65) were based upon sequences from human clinical isolates. Due to the great evolutionary divergence of the gN protein, the consensus sequence was generated from only one (gN-4c) of seven serotypes that represents the most sero-prevalent (gN-4). Similarly, in the case gO, a consensus amino acid sequences was generated from one (gO-5) of eight serotypes due to that particular serotypes reported linkage with the gN-4c sero-type.

As described above, the herpes viral antigen may be a consensus herpes virus. The consensus herpes viral antigen may be provided with a signal peptide. In some embodiments, the IgE leader is linked to the N terminus. As described herein, when referring to a signal peptide linked to the N terminus of a consensus sequence, it is intended to specifically include embodiments in which the N terminal Xaa residue of the consensus sequences is replaced with a signal peptide. That is, as used herein Xaa is intended to refer to any amino acid or no amino acid. The proteins which comprise a consensus sequence set forth herein SEQ ID NOs: 26, 28, 30, 32, 34, 36, 38, 40, 42, 44 may comprise those sequences free of the N terminal Xaa.

Amino acid sequences were generated which comprised in each particular instance, the IgE leader sequence at the N terminus of the herpes virus immunogenic protein consensus sequences. In some embodiments, nucleic acid constructs are provided in which two or more herpes virus antigens are expressed as fusion proteins linked to each other by proteolytic cleavage sites. A furin proteolytic cleavage site is an example of a proteolytic cleavage site which may link herpes virus antigens in a fusion protein expressed by a construct. The viral cancer antigen of the herpes family may further be any antigen disclosed in U.S. patent application Ser. No. 13/982,457, the contents of which is incorporated by reference in its' entirety.

3. Vaccine in Combination with Immune Checkpoint Inhibitor

The vaccine can further comprise one or more inhibitors of one or more immune checkpoint molecules (i.e., an immune checkpoint inhibitor) Immune check point molecules are described below in more detail. The immune checkpoint inhibitor is any nucleic acid or protein that prevents the suppression of any component in the immune system such as MHC class presentation, T cell presentation and/or differentiation, B cell presentation and/or differentiation, any cytokine, chemokine or signaling for immune cell proliferation and/or differentiation.

Such an inhibitor can be a nucleic acid sequence, an amino acid sequence, a small molecule, or a combination thereof. The nucleic acid sequence can be DNA, RNA, cDNA, a variant thereof, a fragment thereof, or a combination thereof. The nucleic acid can also include additional sequences that encode linker or tag sequences that are linked to the immune checkpoint inhibitor by a peptide bond. The small molecule may be a low molecular weight, for example, less than 800 Daltons, organic or inorganic compound that can serve as an enzyme substrate, ligand (or analog thereof) bound by a protein or nucleic acid, or regulator of a biological process. The amino acid sequence can be protein, a peptide, a variant thereof, a fragment thereof, or a combination thereof.

In some embodiments, the immune checkpoint inhibitor can be one or more nucleic acid sequences encoding an antibody, a variant thereof, a fragment thereof, or a combination thereof. In other embodiments, the immune check point inhibitor can be an antibody, a variant thereof, a fragment thereof, or a combination thereof.

a. Immune Checkpoint Molecule

The immune check point molecule can be a nucleic acid sequence, an amino acid sequence, a small molecule, or a combination thereof. The nucleic acid sequence can be DNA, RNA, cDNA, a variant thereof, a fragment thereof, or a combination thereof. The nucleic acid can also include additional sequences that encode linker or tag sequences that are linked to the immune checkpoint inhibitor by a peptide bond. The small molecule may be a low molecular weight, for example, less than 800 Daltons, organic or inorganic compound that can serve as an enzyme substrate, ligand (or analog thereof) bound by a protein or nucleic acid, or regulator of a biological process. The amino acid sequence can be protein, a peptide, a variant thereof, a fragment thereof, or a combination thereof.

(1) PD-1 and PD-L1

The immune checkpoint molecule may programmed cell death protein 1 (PD-1), programmed cell death ligand 1 (PD-L1), a fragment thereof, a variant thereof, or a combination thereof. PD-1 is a cell surface protein encoded by the PDCD1 gene. PD-1 is a member of the immunoglobulin superfamily and is expressed on T cells and pro-B cells, and thus, contributes to the fate and/or differentiation of these cells. In particular, PD-1 is a type 1 membrane protein of the CD28/CTLA-4 family of T cell regulators and negatively regulates T cell receptor (TCR) signals, thereby negatively regulating immune responses. PD-1 can negatively regulated CD8+ T cell responses, and thus inhibit CD8-mediated cytotoxicity and enhance tumor growth.

PD-1 has two ligands, PD-L1 and PD-L2, which are members of the B7 family. PD-L1 is upregulated on macrophages and dendritic cells (DCs) in response to LPS and GM-CSF treatment and on T cells and B cells upon TCR and B cell receptor signaling. PD-L1 is expressed by many tumor cell lines, including myelomas, mastocytomas, and melanomas.

b. Anti-Immune Checkpoint Molecule Antibody

As described above, the immune checkpoint inhibitor can be an antibody. The antibody can bind or react with an antigen (i.e., the immune checkpoint molecule described above.) Accordingly, the antibody may be considered an anti-immune checkpoint molecule antibody or an immune checkpoint molecule antibody. The antibody can be encoded by a nucleic acid sequence contained in The antibody can include a heavy chain polypeptide and a light chain polypeptide. The heavy chain polypeptide can include a variable heavy chain (VH) region and/or at least one constant heavy chain (CH) region. The at least one constant heavy chain region can include a constant heavy chain region 1 (CH1), a constant heavy chain region 2 (CH2), and a constant heavy chain region 3 (CH3), and/or a hinge region.

In some embodiments, the heavy chain polypeptide can include a VH region and a CH1 region. In other embodiments, the heavy chain polypeptide can include a VH region, a CH1 region, a hinge region, a CH2 region, and a CH3 region.

The heavy chain polypeptide can include a complementarity determining region ("CDR") set. The CDR set can contain three hypervariable regions of the VH region. Proceeding from N-terminus of the heavy chain polypeptide, these CDRs are denoted "CDR1," "CDR2," and "CDR3," respectively. CDR1, CDR2, and CDR3 of the heavy chain polypeptide can contribute to binding or recognition of the antigen.

The light chain polypeptide can include a variable light chain (VL) region and/or a constant light chain (CL) region. The light chain polypeptide can include a complementarity determining region ("CDR") set. The CDR set can contain three hypervariable regions of the VL region. Proceeding from N-terminus of the light chain polypeptide, these CDRs are denoted "CDR1," "CDR2," and "CDR3," respectively. CDR1, CDR2, and CDR3 of the light chain polypeptide can contribute to binding or recognition of the antigen.

The antibody may comprise a heavy chain and a light chain complementarity determining region ("CDR") set, respectively interposed between a heavy chain and a light chain framework ("FR") set which provide support to the CDRs and define the spatial relationship of the CDRs relative to each other. The CDR set may contain three hypervariable regions of a heavy or light chain V region. Proceeding from the N-terminus of a heavy or light chain, these regions are denoted as "CDR1," "CDR2," and "CDR3," respectively. An antigen-binding site, therefore, may include six CDRs, comprising the CDR set from each of a heavy and a light chain V region.

The antibody can be an immunoglobulin (Ig). The Ig can be, for example, IgA, IgM, IgD, IgE, and IgG. The immunoglobulin can include the heavy chain polypeptide and the light chain polypeptide. The heavy chain polypeptide of the immunoglobulin can include a VH region, a CH1 region, a hinge region, a CH2 region, and a CH3 region. The light chain polypeptide of the immunoglobulin can include a VL region and CL region.

Additionally, the proteolytic enzyme papain preferentially cleaves IgG molecules to yield several fragments, two of which (the F(ab) fragments) each comprise a covalent heterodimer that includes an intact antigen-binding site. The enzyme pepsin is able to cleave IgG molecules to provide several fragments, including the F(ab')$_2$ fragment, which comprises both antigen-binding sites. Accordingly, the antibody can be the Fab or F(ab')$_2$. The Fab can include the heavy chain polypeptide and the light chain polypeptide. The heavy chain polypeptide of the Fab can include the VH region and the CH1 region. The light chain of the Fab can include the VL region and CL region.

The antibody can be a polyclonal or monoclonal antibody. The antibody can be a chimeric antibody, a single chain antibody, an affinity matured antibody, a human antibody, a humanized antibody, or a fully human antibody. The humanized antibody can be an antibody from a non-human species that binds the desired antigen having one or more complementarity determining regions (CDRs) from the non-human species and framework regions from a human immunoglobulin molecule.

(1) PD-1 Antibody

The anti-immune checkpoint molecule antibody can be an anti-PD-1 antibody (also referred to herein as "PD-1 antibody"), a variant thereof, a fragment thereof, or a combination thereof. The PD-1 antibody can be Nivolumab. The anti-PD-1 antibody can inhibit PD-1 activity, thereby inducing, eliciting, or increasing an immune response against a tumor or cancer and decreasing tumor growth.

(2) PD-L1 Antibody

The anti-immune checkpoint molecule antibody can be an anti-PD-L1 antibody (also referred to herein as "PD-L1 antibody"), a variant thereof, a fragment thereof, or a combination thereof. The anti-PD-L1 antibody can inhibit PD-L1 activity, thereby inducing, eliciting, or increasing an immune response against a tumor or cancer and decreasing tumor growth.

4. Vaccine Constructs and Plasmids

The vaccine can comprise nucleic acid constructs or plasmids that encode the above described antigens and/or antibodies. The nucleic acid constructs or plasmids can include or contain one or more heterologous nucleic acid sequences. Provided herein are genetic constructs that can comprise a nucleic acid sequence that encodes the above described antigens and/or antibodies. The genetic construct can be present in the cell as a functioning extrachromosomal molecule. The genetic construct can be a linear minichromosome including centromere, telomeres or plasmids or cosmids. The genetic constructs can include or contain one or more heterologous nucleic acid sequences.

The genetic constructs can be in the form of plasmids expressing the above described antigens and/or antibodies in any order.

The genetic construct can also be part of a genome of a recombinant viral vector, including recombinant adenovirus, recombinant adenovirus associated virus and recombinant vaccinia. The genetic construct can be part of the genetic material in attenuated live microorganisms or recombinant microbial vectors which live in cells.

The genetic constructs can comprise regulatory elements for gene expression of the coding sequences of the nucleic acid. The regulatory elements can be a promoter, an enhancer an initiation codon, a stop codon, or a polyadenylation signal.

The nucleic acid sequences can make up a genetic construct that can be a vector. The vector can be capable of expressing the above described antigens and/or antibodies in the cell of a mammal in a quantity effective to elicit an immune response in the mammal. The vector can be recombinant. The vector can comprise heterologous nucleic acid encoding the the above described antigens and/or antibodies. The vector can be a plasmid. The vector can be useful for transfecting cells with nucleic acid encoding the above described antigens and/or antibodies, which the transformed host cell is cultured and maintained under conditions wherein expression of the above described antigens and/or antibodies takes place.

Coding sequences can be optimized for stability and high levels of expression. In some instances, codons are selected to reduce secondary structure formation of the RNA such as that formed due to intramolecular bonding.

The vector can comprise heterologous nucleic acid encoding the above described antigens and/or antibodies and can further comprise an initiation codon, which can be upstream of the one or more cancer antigen coding sequence(s), and a stop codon, which can be downstream of the coding sequence(s) of the above described antigens and/or antibodies. The initiation and termination codon can be in frame with the coding sequence(s) of the above described antigens and/or antibodies. The vector can also comprise a promoter that is operably linked to the coding sequence(s) of the above described antigens and/or antibodies. The promoter operably linked to the coding sequence(s) of the above described antigens and/or antibodies can be a promoter from simian virus 40 (SV40), a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter, Epstein Barr virus (EBV) promoter, or a Rous sarcoma virus (RSV) promoter. The promoter can also be a promoter from a human gene such as human actin, human myosin, human hemoglobin, human muscle creatine, or human metalothionein. The promoter can also be a tissue specific promoter, such as a muscle or skin specific promoter, natural or synthetic. Examples of such promoters are described in US patent application publication no. US20040175727, the contents of which are incorporated herein in its entirety.

The vector can also comprise a polyadenylation signal, which can be downstream of the coding sequence(s) of the above described antigens and/or antibodies. The polyadenylation signal can be a SV40 polyadenylation signal, LTR polyadenylation signal, bovine growth hormone (bGH) polyadenylation signal, human growth hormone (hGH) polyadenylation signal, or human β-globin polyadenylation signal. The SV40 polyadenylation signal can be a polyadenylation signal from a pCEP4 vector (Invitrogen, San Diego, Calif.).

The vector can also comprise an enhancer upstream of the above described antigens and/or antibodies. The enhancer can be necessary for DNA expression. The enhancer can be human actin, human myosin, human hemoglobin, human muscle creatine or a viral enhancer such as one from CMV, HA, RSV or EBV. Polynucleotide function enhances are described in U.S. Pat. Nos. 5,593,972, 5,962,428, and WO94/016737, the contents of each are fully incorporated by reference.

The vector can also comprise a mammalian origin of replication in order to maintain the vector extrachromosomally and produce multiple copies of the vector in a cell. The vector can be pVAX1, pCEP4 or pREP4 from Invitrogen (San Diego, Calif.), which can comprise the Epstein Barr virus origin of replication and nuclear antigen EBNA-1 coding region, which can produce high copy episomal replication without integration. The vector can be pVAX1 or a pVax1 variant with changes such as the variant plasmid described herein. The variant pVax1 plasmid is a 2998 basepair variant of the backbone vector plasmid pVAX1 (Invitrogen, Carlsbad Calif.). The CMV promoter is located at bases 137-724. The T7 promoter/priming site is at bases 664-683. Multiple cloning sites are at bases 696-811. Bovine GH polyadenylation signal is at bases 829-1053. The Kanamycin resistance gene is at bases 1226-2020. The pUC origin is at bases 2320-2993.

Based upon the sequence of pVAX1 available from Invitrogen, the following mutations were found in the sequence of pVAX1 that was used as the backbone for plasmids 1-6 set forth herein:

C>G241 in CMV promoter

C>T 1942 backbone, downstream of the bovine growth hormone polyadenylation signal (bGHpolyA)

A>-2876 backbone, downstream of the Kanamycin gene

C>T 3277 in pUC origin of replication (Ori) high copy number mutation (see Nucleic Acid Research 1985)

G>C 3753 in very end of pUC Ori upstream of RNASeH site

Base pairs 2, 3 and 4 are changed from ACT to CTG in backbone, upstream of CMV promoter.

The backbone of the vector can be pAV0242. The vector can be a replication defective adenovirus type 5 (Ad5) vector.

The vector can also comprise a regulatory sequence, which can be well suited for gene expression in a mammalian or human cell into which the vector is administered. The one or more cancer antigen sequences disclosed herein can comprise a codon, which can allow more efficient transcription of the coding sequence in the host cell.

The vector can be pSE420 (Invitrogen, San Diego, Calif.), which can be used for protein production in *Escherichia coli* (*E. coli*). The vector can also be pYES2 (Invitrogen, San Diego, Calif.), which can be used for protein production in *Saccharomyces cerevisiae* strains of yeast. The vector can also be of the MAXBAC® complete baculovirus expression system (Invitrogen, San Diego, Calif.), which can be used for protein production in insect cells. The vector can also be pcDNA I or pcDNA3 (Invitrogen, San Diego, Calif.), which may be used for protein production in mammalian cells such as Chinese hamster ovary (CHO) cells. The vector can be expression vectors or systems to produce protein by routine techniques and readily available starting materials including Sambrook et al., Molecular Cloning and Laboratory Manual, Second Ed., Cold Spring Harbor (1989), which is incorporated fully by reference.

In some embodiments the vector can comprise one or more of the nucleic acid sequences of SEQ ID NOS: 1, 3, 5, 7, 9, 11, 13, 15, and/or 17.

5. Pharmaceutical Compositions of the Vaccine

The vaccine can be in the form of a pharmaceutical composition. The pharmaceutical composition can comprise the vaccine. The pharmaceutical compositions can comprise about 5 nanograms to about 10 mg of the DNA of the vaccine. In some embodiments, pharmaceutical compositions according to the present invention comprise about 25 nanogram to about 5 mg of DNA of the vaccine. In some embodiments, the pharmaceutical compositions contain about 50 nanograms to about 1 mg of DNA of the vaccine. In some embodiments, the pharmaceutical compositions contain about 0.1 to about 500 micrograms of DNA of the vaccine. In some embodiments, the pharmaceutical compositions contain about 1 to about 350 micrograms of DNA of the vaccine. In some embodiments, the pharmaceutical compositions contain about 5 to about 250 micrograms of DNA of the vaccine. In some embodiments, the pharmaceutical compositions contain about 10 to about 200 micrograms of DNA of the vaccine. In some embodiments, the pharmaceutical compositions contain about 15 to about 150 micrograms of DNA of the vaccine. In some embodiments, the pharmaceutical compositions contain about 20 to about 100 micrograms of DNA of the vaccine. In some embodiments, the pharmaceutical compositions contain about 25 to about 75 micrograms of DNA of the vaccine. In some embodiments, the pharmaceutical compositions contain about 30 to about 50 micrograms of DNA of the vaccine. In some embodiments, the pharmaceutical compositions contain about 35 to about 40 micrograms of DNA of the vaccine. In some embodiments, the pharmaceutical compositions contain about 100 to about 200 microgram DNA of the vaccine. In some embodiments, the pharmaceutical compositions comprise about 10 microgram to about 100 micrograms of DNA of the vaccine. In some embodiments, the pharmaceutical compositions comprise about 20 micrograms to about 80 micrograms of DNA of the vaccine. In some embodiments, the pharmaceutical compositions comprise about 25 micrograms to about 60 micrograms of DNA of the vaccine. In some embodiments, the pharmaceutical compositions comprise about 30 nanograms to about 50 micrograms of DNA of the vaccine. In some embodiments, the pharmaceutical compositions comprise about 35 nanograms to about 45 micrograms of DNA of the vaccine. In some preferred embodiments, the pharmaceutical compositions contain about 0.1 to about 500 micrograms of DNA of the vaccine. In some preferred embodiments, the pharmaceutical compositions contain about 1 to about 350 micrograms of DNA of the vaccine. In some preferred embodiments, the pharmaceutical compositions contain about 25 to about 250 micrograms of DNA of the vaccine. In some preferred embodiments, the pharmaceutical compositions contain about 100 to about 200 microgram DNA of the vaccine.

In some embodiments, pharmaceutical compositions according to the present invention comprise at least 10, 15, 20, 25, 30, 35, 40, 45, 50, 55, 60, 65, 70, 75, 80, 85, 90, 95 or 100 nanograms of DNA of the vaccine. In some embodiments, the pharmaceutical compositions can comprise at least 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995 or 1000 micrograms of DNA of the vaccine. In some embodiments, the pharmaceutical composition can comprise at least 1.5, 2, 2.5, 3, 3.5, 4, 4.5, 5, 5.5, 6, 6.5, 7, 7.5, 8, 8.5, 9, 9.5 or 10 mg or more of DNA of the vaccine.

In other embodiments, the pharmaceutical composition can comprise up to and including 15, 20, 25, 30, 35, 40, 45, 50, 55, 60, 65, 70, 75, 80, 85, 90, 95 or 100 nanograms of DNA of the vaccine. In some embodiments, the pharmaceutical composition can comprise up to and including 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895. 900, 905, 910, 915, 920, 925, 930, 935, 940, 945, 950, 955, 960, 965, 970, 975, 980, 985, 990, 995, or 1000 micrograms of DNA of the vaccine. In some embodiments, the pharmaceutical composition can comprise up to and including 1.5, 2, 2.5, 3, 3.5, 4, 4.5, 5, 5.5, 6, 6.5, 7, 7.5, 8, 8.5, 9, 9.5 or 10 mg of DNA of the vaccine.

The pharmaceutical composition can further comprise other agents for formulation purposes according to the mode of administration to be used. In cases where pharmaceutical compositions are injectable pharmaceutical compositions, they are sterile, pyrogen free and particulate free. An isotonic formulation is preferably used. Generally, additives for isotonicity can include sodium chloride, dextrose, mannitol, sorbitol and lactose. In some cases, isotonic solutions such as phosphate buffered saline are preferred. Stabilizers include gelatin and albumin. In some embodiments, a vasoconstriction agent is added to the formulation.

The vaccine can further comprise a pharmaceutically acceptable excipient. The pharmaceutically acceptable excipient can be functional molecules as vehicles, adjuvants, carriers, or diluents. The pharmaceutically acceptable excipient can be a transfection facilitating agent, which can include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate, and more preferably, the poly-L-glutamate is present in the vaccine at a concentration less than 6 mg/ml. The transfection facilitating agent can also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid can also be used administered in conjunction with the genetic construct. In some embodiments, the DNA vector vaccines can also include a transfection facilitating agent such as lipids, liposomes, including lecithin liposomes or other liposomes known in the art, as a DNA-liposome mixture (see for example WO9324640), calcium ions, viral proteins, polyanions, polycations, or nanoparticles, or other known transfection facilitating agents. Preferably, the transfection facilitating agent is a polyanion, polycation, including poly-L-glutamate (LGS), or lipid. Concentration of the transfection agent in the vaccine is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

The pharmaceutically acceptable excipient can be an adjuvant. The adjuvant can be other genes that are expressed in alternative plasmid or are delivered as proteins in combination with the plasmid above in the vaccine. The adjuvant can be selected from the group consisting of: α-interferon (IFN-α), β-interferon (IFN-β), γ-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15, MHC, CD80, CD86 including IL-15 having the signal sequence deleted and optionally including the signal peptide from IgE. The adjuvant can be IL-12, IL-15, IL-28, CTACK, TECK, platelet derived growth factor (PDGF), TNFα, TNFβ, GM-CSF, epidermal growth factor (EGF), IL-1, IL-2, IL-4, IL-5, IL-6, IL-10, IL-12, IL-18, or a combination thereof. In an exemplary embodiment, the adjuvant is IL-12.

Other genes which can be useful adjuvants include those encoding: MCP-1, MIP-1a, MIP-1p, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRCS, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof.

6. Combinational Vaccines for Treating Particular Cancers

Figure 15:
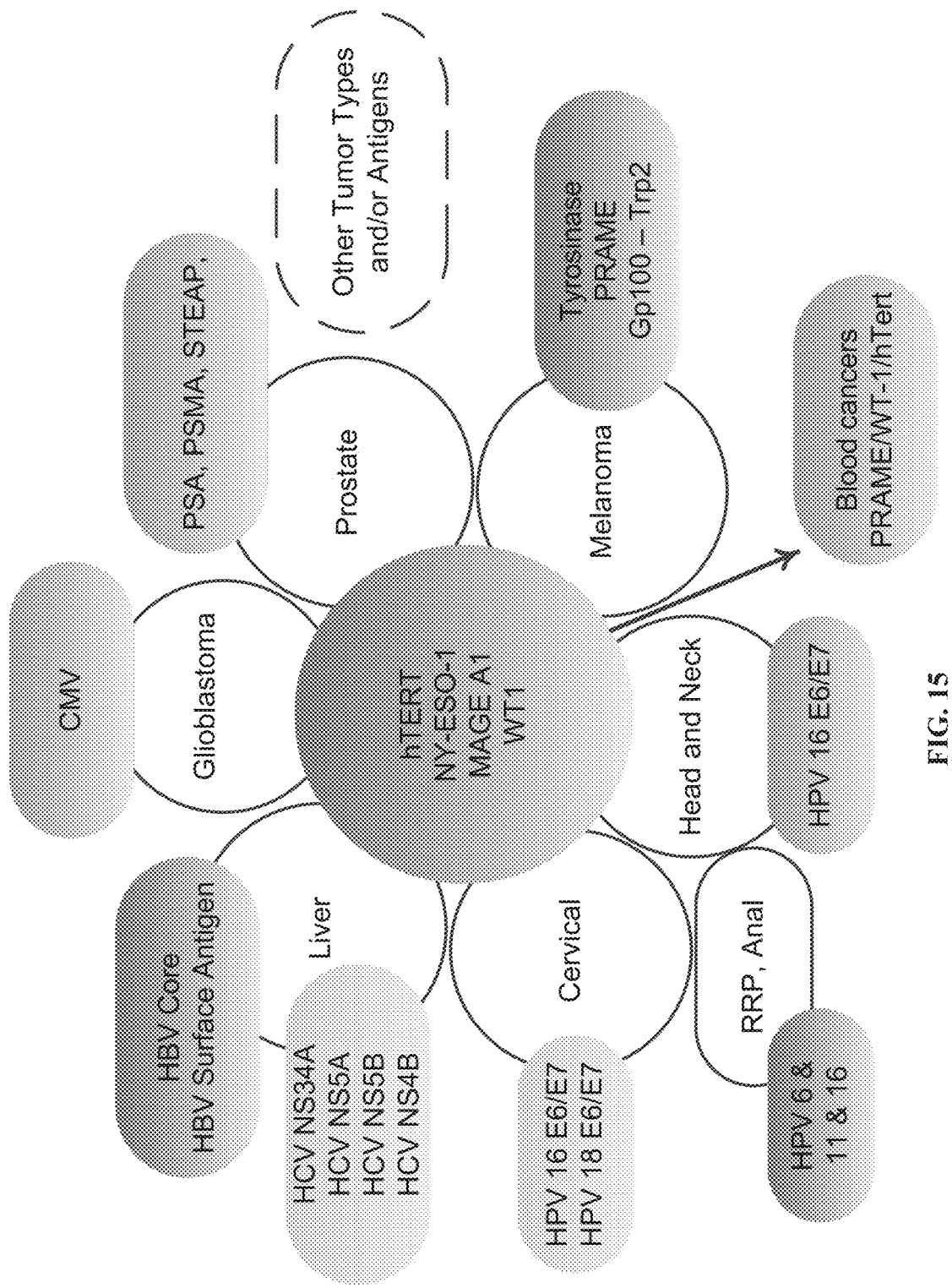
FIG. 15 shows a schematic illustrating various cancers with some of their associated cancer antigen(s).

The vaccine can be in the form of various combinations of the cancer antigens as described above to treat particular cancer or tumors. Depending upon the combination of one or more cancer antigens, various cancers or other tumor types may be targeted with the vaccine. These cancers can include melanoma, blood cancers (e.g., leukemia, lymphoma, myeloma), lung carcinomas, esophageal squamous cell carcinomas, bladder cancer, colorectal cancer, esophagus, gastric cancer, hepatocarcinoma, head and neck, brain, anal cancer, non-small cell lung carcinoma, pancreatic cancer, synovial carcinoma, prostate cancer, testicular cancer, liver cancer, cervical cancer, recurrent respiratory papillomatosis, skin cancer and stomach cancer. FIG. 15 provides examples of particular combinations of antigens that may be used to treat particular cancers.

a. Melanoma

The vaccine can combine one or more cancer antigens such as tyrosinase, PRAME, or GP100-Trp2 to treat or prevent melanoma (See FIG. 15). The vaccine can further combine one or more cancer antigen tyrosinase, PRAME, or GP100-Trp2 with any one or more cancer antigens hTERT, NY-ESO-1, MAGE-A1, or WT1 for treating or preventing melanoma. Other combinations of cancer antigens may also be applied for treating or preventing melanoma.

b. Head and Neck Cancer

The vaccine can comprise cancer antigen HPV 16 E6/E7 to treat or prevent head and neck cancer (See FIG. 15). The vaccine can further combine cancer antigen HPV 16 E6/E7 with any one or more cancer antigens hTERT, NY-ESO-1, MAGE-A1, or WT1 for treating or preventing head and neck cancer. Other combinations of cancer antigens may also be applied for treating or preventing head and neck cancer.

c. Recurrent Respiratory Papillomatosis/Anal Cancer

The vaccine can combine one or more cancer antigens such as HPV 6, HPV11, or HPV 16 to treat or prevent recurrent respiratory papilloatosis or anal cancer (See FIG. 15). The vaccine can further combine one or more cancer antigens HPV 6, HPV11 or HPV16 with one or more cancer antigens hTERT, NY-ESO-1, MAGE-A1, or WT1 for treating or preventing recurrent respiratory papilloatosis or anal cancer. Other combinations of cancer antigens may also be applied for treating or preventing recurrent respiratory papilloatosis or anal cancer.

d. Cervical Cancer

The vaccine can combine one or more cancer antigens such as HPV 16 E6/E7 or HPV 18 E6/E7 to treat or prevent cervical cancer (See FIG. 15). The vaccine can further combine one or more cancer antigens such as HPV 16 E6/E7 or HPV 18 E6/E7 with one or more cancer antigens hTERT, NY-ESO-1, MAGE-A1, or WT1 for treating or preventing cervical cancer. Other combinations of cancer antigens may also be applied for treating or preventing cervical cancer.

e. Liver Cancer

The vaccine can combine one or more cancer antigens such as HBV core antigen, HBV surface antigen, HCVNS34A, HCVNS5A, HCV NS5B, or HCVNS4B to treat or prevent liver cancer (See FIG. 15). The vaccine can further combine one or more cancer antigens HBV core antigen, HBV surface antigen, HCVNS34A, HCVNS5A, HCV NS5B, or HCVNS4B with one or more of cancer antigens hTERT, NY-ESO-1, MAGE-A1, or WT1 for treating or preventing liver cancer. Other combinations of cancer antigens may also be applied for treating or preventing liver cancer.

f. Glioblastoma

The vaccine can comprise CMV to treat or prevent glioblastoma (See FIG. 15). The vaccine can further combine CMV with one or more of cancer antigens hTERT, NY-ESO-1, MAGE-A1, or WT1 for treating or preventing glioblastoma. Other combinations of cancer antigens may also be applied for treating or preventing glioblastoma.

g. Prostate

The vaccine can combine one or more cancer antigens such as PSA, PSMA, or STEAP to treat or prevent prostate cancer (See FIG. 15). The vaccine can further combine one or more cancer antigens PSA, PSMA, or STEAP with one or more of cancer antigens hTERT, NY-ESO-1, MAGE-A1, or WT1 for treating or preventing prostate cancer. Other combinations of cancer antigens may also be applied for treating or preventing prostate cancer.

h. Blood Cancers (e.g., Leukemia, Lymphoma, Myeloma)

The vaccine can combine one or more cancer antigens such as PRAME, WT-1, hTERT to treat or prevent blood cancers such as leukemia, lymphoma and myeloma (See FIG. 51). The vaccine can further combine one or more cancer antigens PRAME, WT-1, hTERT with one or more of cancer antigens NY-ESO-1, or MAGE-A1 for treating or preventing blood cancers such as leukemia, lymphoma and myeloma. Other combinations of cancer antigens may also be applied for preventing blood cancers such as leukemia, lymphoma and myeloma cancer.

7. Method of Vaccination

Provided herein is a method for treating or prevent cancer using the pharmaceutical formulations for providing genetic constructs and proteins of the one or more cancer antigens as described above, which comprise epitopes that make them particular effective immunogens against which an immune response to the one or more cancer antigens can be induced. The method of administering the vaccine, or vaccination, can be provided to induce a therapeutic and/or prophylactic immune response. The vaccination process can generate in the mammal an immune response against one or more of the cancer antigens as disclosed herein. The vaccine can be administered to an individual to modulate the activity of the mammal's immune system and enhance the immune response. The administration of the vaccine can be the transfection of the one or more cancer antigens as disclosed herein as a nucleic acid molecule that is expressed in the cell and thus, delivered to the surface of the cell upon which the immune system recognizes and induces a cellular, humoral, or cellular and humoral response. The administration of the vaccine can be used to induce or elicit an immune response in mammals against one or more of the cancer antigens as disclosed herein by administering to the mammals the vaccine as discussed herein.

Upon administration of the vaccine to the mammal, and thereupon the vector into the cells of the mammal, the transfected cells will express and secrete one or more of the cancer antigens as disclosed herein. These secreted proteins, or synthetic antigens, will be recognized as foreign by the immune system, which will mount an immune response that can include: antibodies made against the one or more cancer antigens, and T-cell response specifically against the one or more cancer antigens. In some examples, a mammal vaccinated with the vaccines discussed herein will have a primed immune system and when challenged with the one or more cancer antigens as disclosed herein, the primed immune system will allow for rapid clearing of subsequent cancer antigens as disclosed herein, whether through the humoral, cellular, or both cellular and humoral immune responses. The vaccine can be administered to an individual to modulate the activity of the individual's immune system, thereby enhancing the immune response.

Methods of administering the DNA of a vaccine are described in U.S. Pat. Nos. 4,945,050 and 5,036,006, both of which are incorporated herein in their entirety by reference.

The vaccine can be administered to a mammal to elicit an immune response in a mammal. The mammal can be human, non-human primate, cow, pig, sheep, goat, antelope, bison, water buffalo, bovids, deer, hedgehogs, elephants, llama, alpaca, mice, rats, or chicken, and preferably human, cow, pig, or chicken.

The vaccine dose can be between 1 µg to 10 mg active component/kg body weight/time and can be 20 µg to 10 mg component/kg body weight/time. The vaccine can be administered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. The number of vaccine doses for effective treatment can be 1, 2, 3, 4, 5, 6, 7, 8, 9, 10, or more doses.

a. Method of Generating an Immune Response with the Vaccine

The vaccine can be used to generate an immune response in a mammal, including therapeutic or prophylactic immune response. The immune response can generate antibodies and/or killer T cells which are directed to the one or more cancer antigens as disclosed herein. Such antibodies and T cells can be isolated.

Some embodiments provide methods of generating immune responses against one or more of the cancer antigens as disclosed herein, which comprise administering to an individual the vaccine. Some embodiments provide methods of prophylactically vaccinating an individual against a cancer or tumor expressing one or more of the cancer antigens as described above, which comprise administering the vaccine. Some embodiments provide methods of therapeutically vaccinating an individual that has been suffering from the cancer or tumor expressing one or more of the cancer antigens, which comprise administering the vaccine. Diagnosis of the cancer or tumor expressing the one or more cancer antigens as disclosed herein prior to administration of the vaccine can be done routinely.

b. Method of Cancer Treatment with the Vaccine

The vaccine can be used to generate or elicit an immune response in a mammal that is reactive or directed to a cancer or tumor (e.g., melanoma, head and neck, cervical, liver, prostate, blood cancers, esophageal squamous, gastric) of the mammal or subject in need thereof. The elicited immune response can prevent cancer or tumor growth.

The elicited immune response can prevent and/or reduce metastasis of cancerous or tumor cells. Accordingly, the vaccine can be used in a method that treats and/or prevents cancer or tumors in the mammal or subject administered the vaccine. Depending upon the antigen used in the vaccine, the treated cancer or tumor based growth can be any type of cancer such as, but not limited to, melanoma, blood cancers (e.g., leukemia, lymphoma, myeloma), lung carcinomas, esophageal squamous cell carcinomas, bladder cancer, colorectal cancer, esophagus, gastric cancer, hepatocarcinoma, head and neck, brain, anal cancer, non-small cell lung carcinoma, pancreatic cancer, synovial carcinoma, prostate cancer, testicular cancer, liver cancer, cervical cancer, recurrent respiratory papillomatosis, skin cancer and stomach cancer.

In some embodiments, the administered vaccine can mediate clearance or prevent growth of tumor cells by inducing (1) humoral immunity via B cell responses to generate antibodies that block monocyte chemoattractant protein-1 (MCP-1) production, thereby retarding myeloid derived suppressor cells (MDSCs) and suppressing tumor growth; (2) increase cytotoxic T lymphocyte such as $CD8^+$ (CTL) to attack and kill tumor cells; (3) increase T helper cell responses; (4) and increase inflammatory responses via IFN-$\gamma$ and TFN-$\alpha$ or preferably all of the aforementioned.

In some embodiments, the immune response can generate a humoral immune response and/or an antigen-specific cytotoxic T lymphocyte (CTL) response that does not cause damage to or inflammation of various tissues or systems (e.g., brain or neurological system, etc.) in the subject administered the vaccine.

In some embodiments, the administered vaccine can increase tumor free survival, reduce tumor mass, increase tumor survival, or a combination thereof in the subject. The administered vaccine can increase tumor free survival by 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, and 60% in the subject. The administered vaccine can reduce tumor mass by 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, and 70% in the subject after immunization. The administered vaccine can prevent and block increases in monocyte chemoattractant protein 1 (MCP-1), a cytokine secreted by myeloid derived suppressor cells, in the subject. In some embodiments, the administered vaccine can prevent and block increases in MCP-1 within the cancerous or tumor tissue in the subject, thereby reducing vascularization of the cancerous or tumor tissue in the subject.

The administered vaccine can increase tumor survival by 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, and 70% in the subject. In some embodiments, the vaccine can be administered to the periphery (as described in more detail below) to establish an antigen-specific immune response targeting the cancerous or tumor cells or tissue to clear or eliminate the cancer or tumor expressing the one or more cancer antigens without damaging or causing illness or death in the subject administered the vaccine.

The administered vaccine can increase a cellular immune response in the subject by about 50-fold to about 6000-fold, about 50-fold to about 5500-fold, about 50-fold to about 5000-fold, about 50-fold to about 4500-fold, about 100-fold to about 6000-fold, about 150-fold to about 6000-fold, about 200-fold to about 6000-fold, about 250-fold to about 6000-fold, or about 300-fold to about 6000-fold. In some embodiments, the administered vaccine can increase the cellular immune response in the subject by about 50-fold, 100-fold, 150-fold, 200-fold, 250-fold, 300-fold, 350-fold, 400-fold, 450-fold, 500-fold, 550-fold, 600-fold, 650-fold, 700-fold, 750-fold, 800-fold, 850-fold, 900-fold, 950-fold, 1000-fold, 1100-fold, 1200-fold, 1300-fold, 1400-fold, 1500-fold, 1600-fold, 1700-fold, 1800-fold, 1900-fold, 2000-fold, 2100-fold, 2200-fold, 2300-fold, 2400-fold, 2500-fold, 2600-fold, 2700-fold, 2800-fold, 2900-fold, 3000-fold, 3100-fold, 3200-fold, 3300-fold, 3400-fold, 3500-fold, 3600-fold, 3700-fold, 3800-fold, 3900-fold, 4000-fold, 4100-fold, 4200-fold, 4300-fold, 4400-fold, 4500-fold, 4600-fold, 4700-fold, 4800-fold, 4900-fold, 5000-fold, 5100-fold, 5200-fold, 5300-fold, 5400-fold, 5500-fold, 5600-fold, 5700-fold, 5800-fold, 5900-fold, or 6000-fold.

The administered vaccine can increase interferon gamma (IFN-$\gamma$) levels in the subject by about 50-fold to about 6000-fold, about 50-fold to about 5500-fold, about 50-fold to about 5000-fold, about 50-fold to about 4500-fold, about 100-fold to about 6000-fold, about 150-fold to about 6000-fold, about 200-fold to about 6000-fold, about 250-fold to about 6000-fold, or about 300-fold to about 6000-fold. In some embodiments, the administered vaccine can increase IFN-$\gamma$ levels in the subject by about 50-fold, 100-fold, 150-fold, 200-fold, 250-fold, 300-fold, 350-fold, 400-fold, 450-fold, 500-fold, 550-fold, 600-fold, 650-fold, 700-fold, 750-fold, 800-fold, 850-fold, 900-fold, 950-fold, 1000-fold, 1100-fold, 1200-fold, 1300-fold, 1400-fold, 1500-fold, 1600-fold, 1700-fold, 1800-fold, 1900-fold, 2000-fold, 2100-fold, 2200-fold, 2300-fold, 2400-fold, 2500-fold, 2600-fold, 2700-fold, 2800-fold, 2900-fold, 3000-fold, 3100-fold, 3200-fold, 3300-fold, 3400-fold, 3500-fold, 3600-fold, 3700-fold, 3800-fold, 3900-fold, 4000-fold, 4100-fold, 4200-fold, 4300-fold, 4400-fold, 4500-fold, 4600-fold, 4700-fold, 4800-fold, 4900-fold, 5000-fold, 5100-fold, 5200-fold, 5300-fold, 5400-fold, 5500-fold, 5600-fold, 5700-fold, 5800-fold, 5900-fold, or 6000-fold.

The vaccine dose can be between 1 µg to 10 mg active component/kg body weight/time and can be 20 µg to 10 mg component/kg body weight/time. The vaccine can be administered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. The number of vaccine doses for effective treatment can be 1, 2, 3, 4, 5, 6, 7, 8, 9, or 10.

(1) Combinational Therapies with PD-1 and/or PD-L1 Antibodies

The present invention is also directed to a method of increasing an immune response in a mammal using the vaccine as described above. The vaccine as described above can comprise the cancer antigen and a PD1 antibody and/or PDL1 antibody as described above. The combination can be in a single formulation or can be separate and administered in sequence (either cancer antigen first and then PD1 antibody or PDL1 antibody, or PD1 antibody or PDL1 antibody first and then cancer antigen). In some embodiments, the cancer antigen can be administered to the subject about 30 seconds, 1 minute, 2 minutes, 3 minutes, 4 minutes, 5 minutes, 10 minutes, 15 minutes, 20 minutes, 25 minutes, 30 minutes, 35 minutes, 40 minutes, 45 minutes, 50 minutes, 55 minutes, 60 minutes, 0.25 hours, 0.5 hours, 0.75 hours, 1 hours, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 36 hours, 48 hours, 60 hours, 72 hours, 84 hours, 96 hours, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 1 week, 2 weeks, 3 weeks, 4 weeks, 5 weeks, 6 weeks, 7 weeks, or 8 weeks before the PD-1 antibody or PD-L1 antibody is administered to the subject. In other embodiments, the PD-1 antibody or PD-L1 antibody can be administered to the subject about 30 seconds, 1 minute, 2 minutes, 3 minutes, 4 minutes, 5 minutes, 10 minutes, 15 minutes, 20 minutes, 25 minutes, 30 minutes, 35 minutes, 40 minutes, 45 minutes, 50 minutes, 55 minutes, 60 minutes, 0.25 hours, 0.5 hours, 0.75 hours, 1 hours, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 36 hours, 48 hours, 60 hours, 72 hours, 84 hours, 96 hours, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 1 week, 2 weeks, 3 weeks, 4 weeks, 5 weeks, 6 weeks, 7 weeks, or 8 weeks before the cancer antigen is administered to the subject.

The combination of the cancer antigen and PD1 antibody or PDL1 antibody induces the immune system more efficiently than a vaccine comprising the cancer antigen alone. This more efficient immune response provides increased efficacy in the treatment and/or prevention of a particular cancer. Depending upon the antigen used in the vaccine combined with the PDL1 antibody or PD1 antibody, the treated cancer or tumor based growth can be any type of cancer such as, but not limited to, melanoma, blood cancers (e.g., leukemia, lymphoma, myeloma), lung carcinomas, esophageal squamous cell carcinomas, bladder cancer, colorectal cancer, esophagus, gastric cancer, hepatocarcinoma, head and neck, brain, anal cancer, non-small cell lung carcinoma, pancreatic cancer, synovial carcinoma, prostate cancer, testicular cancer, liver cancer, cervical cancer, recurrent respiratory papillomatosis, skin cancer and stomach cancer.

In some embodiments, the immune response can be increased by about 0.5-fold to about 15-fold, about 0.5-fold to about 10-fold, or about 0.5-fold to about 8-fold. Alternatively, the immune response in the subject administered the vaccine can be increased by at least about 0.5-fold, at least about 1.0-fold, at least about 1.5-fold, at least about 2.0-fold, at least about 2.5-fold, at least about 3.0-fold, at least about 3.5-fold, at least about 4.0-fold, at least about 4.5-fold, at least about 5.0-fold, at least about 5.5-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, or at least about 15.0-fold.

In still other alternative embodiments, the immune response in the subject administered the vaccine can be increased about 50% to about 1500%, about 50% to about 1000%, or about 50% to about 800%. In other embodiments, the immune response in the subject administered the vaccine can be increased by at least about 50%, at least about 100%, at least about 150%, at least about 200%, at least about 250%, at least about 300%, at least about 350%, at least about 400%, at least about 450%, at least about 500%, at least about 550%, at least about 600%, at least about 650%, at least about 700%, at least about 750%, at least about 800%, at least about 850%, at least about 900%, at least about 950%, at least about 1000%, at least about 1050%, at least about 1100%, at least about 1150%, at least about 1200%, at least about 1250%, at least about 1300%, at least about 1350%, at least about 1450%, or at least about 1500%.

The vaccine dose can be between 1 µg to 10 mg active component/kg body weight/time, and can be 20 µg to 10 mg component/kg body weight/time. The vaccine can be administered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. The number of vaccine doses for effective treatment can be 1, 2, 3, 4, 5, 6, 7, 8, 9, or 10.

(2) Melanoma

The vaccine can be used to generate or elicit an immune response in a mammal that is reactive or directed to melanoma in the mammal or subject in need thereof. The elicited immune response can prevent melanoma growth. The elicited immune response can reduce melanoma growth. The elicited immune response can prevent and/or reduce metastasis of cancerous or tumor cells from a melanoma. Accordingly, the vaccine can be used in a method that treats and/or prevents melanoma in the mammal or subject administered the vaccine.

In some embodiments, the administered vaccine can mediate clearance or prevent growth of melanoma cells by inducing (1) humoral immunity via B cell responses to generate antibodies that block monocyte chemoattractant protein-1 (MCP-1) production, thereby retarding myeloid derived suppressor cells (MDSCs) and suppressing melanoma growth; (2) increase cytotoxic T lymphocyte such as CD8$^+$ (CTL) to attack and kill melanoma cells; (3) increase T helper cell responses; (4) and increase inflammatory responses via IFN-γ and TFN-α or preferably all of the aforementioned.

In some embodiments, the administered vaccine can increase melanoma free survival, reduce melanoma mass, increase melanoma survival, or a combination thereof in the subject. The administered vaccine can increase melanoma free survival by 30%, 31%, 32%, 33%, 34%, 35%, 36%, 37%, 38%, 39%, 40%, 41%, 42%, 43%, 44%, and 45% in the subject. The administered vaccine can reduce melanoma mass by 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, and 60% in the subject after immunization. The administered vaccine can prevent and block increases in monocyte chemoattractant protein 1 (MCP-1), a cytokine secreted by myeloid derived suppressor cells, in the subject. In some embodiments, the administered vaccine can prevent and block increases in MCP-1 within the melanoma tissue in the subject, thereby reducing vascularization of the melanoma tissue in the subject. The administered vaccine can increase melanoma survival by 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, and 60% in the subject.

8. Routes of Administration

The vaccine or pharmaceutical composition can be administered by different routes including orally, parenterally, sublingually, transdermally, rectally, transmucosally, topically, via inhalation, via buccal administration, intrapleurally, intravenous, intraarterial, intraperitoneal, subcutaneous, intramuscular, intranasal intrathecal, and intraarticular or combinations thereof. For veterinary use, the composition can be administered as a suitably acceptable formulation in accordance with normal veterinary practice. The veterinarian can readily determine the dosing regimen and route of administration that is most appropriate for a particular animal. The vaccine can be administered by traditional syringes, needleless injection devices, "microprojectile bombardment gone guns", or other physical methods such as electroporation ("EP"), "hydrodynamic method", or ultrasound.

The vector of the vaccine can be administering to the mammal by several well known technologies including DNA injection (also referred to as DNA vaccination) with and without in vivo electroporation, liposome mediated, nanoparticle facilitated, recombinant vectors such as recombinant adenovirus, recombinant adenovirus associated virus and recombinant vaccinia. The one or more cancer antigens of the vaccine can be administered via DNA injection and along with in vivo electroporation.

a. Electroporation

The vaccine or pharmaceutical composition can be administered by electroporation. Administration of the vaccine via electroporation can be accomplished using electroporation devices that can be configured to deliver to a desired tissue of a mammal a pulse of energy effective to cause reversible pores to form in cell membranes, and preferable the pulse of energy is a constant current similar to a preset current input by a user. The electroporation device can comprise an electroporation component and an electrode assembly or handle assembly. The electroporation component can include and incorporate one or more of the various elements of the electroporation devices, including: controller, current waveform generator, impedance tester, waveform logger, input element, status reporting element, communication port, memory component, power source, and power switch. The electroporation can be accomplished using an in vivo electroporation device, for example CELLECTRA® EP system (Inovio Pharmaceuticals, Inc., Blue Bell, Pa.) or Elgen electroporator (Inovio Pharmaceuticals, Inc.) to facilitate transfection of cells by the plasmid.

Examples of electroporation devices and electroporation methods that can facilitate administration of the DNA vaccines of the present invention, include those described in U.S. Pat. No. 7,245,963 by Draghia-Akli, et al., U.S. Patent Pub. 2005/0052630 submitted by Smith, et al., the contents of which are hereby incorporated by reference in their entirety. Other electroporation devices and electroporation methods that can be used for facilitating administration of the DNA vaccines include those provided in co-pending and co-owned U.S. patent application Ser. No. 11/874,072, filed Oct. 17, 2007, which claims the benefit under 35 USC 119(e) to U.S. Provisional Application Ser. No. 60/852,149, filed Oct. 17, 2006, and 60/978,982, filed Oct. 10, 2007, all of which are hereby incorporated in their entirety.

U.S. Pat. No. 7,245,963 by Draghia-Akli, et al. describes modular electrode systems and their use for facilitating the introduction of a biomolecule into cells of a selected tissue in a body or plant. The modular electrode systems can comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The biomolecules are then administering via the hypodermic needle into the selected tissue. The programmable constant-current pulse controller is activated and constant-current electrical pulse is applied to the plurality of needle electrodes. The applied constant-current electrical pulse facilitates the introduction of the biomolecule into the cell between the plurality of electrodes. The entire content of U.S. Pat. No. 7,245,963 is hereby incorporated by reference in its' entirety.

U.S. Patent Pub. 2005/0052630 submitted by Smith, et al. describes an electroporation device which can be used to effectively facilitate the introduction of a biomolecule into cells of a selected tissue in a body or plant. The electroporation device comprises an electro-kinetic device ("EKD device") whose operation is specified by software or firmware. The EKD device produces a series of programmable constant-current pulse patterns between electrodes in an array based on user control and input of the pulse parameters, and allows the storage and acquisition of current waveform data. The electroporation device also comprises a replaceable electrode disk having an array of needle electrodes, a central injection channel for an injection needle, and a removable guide disk. The entire content of U.S. Patent Pub. 2005/0052630 is hereby fully incorporated by reference.

The electrode arrays and methods described in U.S. Pat. No. 7,245,963 and U.S. Patent Pub. 2005/0052630 can be adapted for deep penetration into not only tissues such as muscle, but also other tissues or organs. Because of the configuration of the electrode array, the injection needle (to deneurological system the biomolecule of choice) is also inserted completely into the target organ, and the injection is administered perpendicular to the target issue, in the area that is pre-delineated by the electrodes. The electrodes described in U.S. Pat. No. 7,245,963 and U.S. Patent Pub. 2005/005263 are preferably 20 mm long and 21 gauge.

Additionally, contemplated in some embodiments that incorporate electroporation devices and uses thereof, there are electroporation devices that are those described in the following patents: U.S. Pat. No. 5,273,525 issued Dec. 28, 1993, U.S. Pat. No. 6,110,161 issued Aug. 29, 2000, U.S. Pat. No. 6,261,281 issued Jul. 17, 2001, and U.S. Pat. No. 6,958,060 issued Oct. 25, 2005, and U.S. Pat. No. 6,939,862 issued Sep. 6, 2005. Furthermore, patents covering subject matter provided in U.S. Pat. No. 6,697,669 issued Feb. 24, 2004, which concerns administration of DNA using any of a variety of devices, and U.S. Pat. No. 7,328,064 issued Feb. 5, 2008, drawn to method of injecting DNA are contemplated herein. The above-patents are incorporated by reference in their entirety.

9. Method of Preparing the Vaccine

Provided herein are methods for preparing the DNA plasmids that comprise the vaccines discussed herein. The DNA plasmids, after the final subcloning step into the mammalian expression plasmid, can be used to inoculate a cell culture in a large scale fermentation tank, using known methods in the art.

The DNA plasmids for use with the EP devices of the present invention can be formulated or manufactured using a combination of known devices and techniques, but preferably they are manufactured using an optimized plasmid manufacturing technique that is described in a US published application no. 20090004716, which was filed on May 23, 2007. In some examples, the DNA plasmids used in these studies can be formulated at concentrations greater than or equal to 10 mg/mL. The manufacturing techniques also include or incorporate various devices and protocols that are commonly known to those of ordinary skill in the art, in addition to those described in U.S. Ser. No. 60/939,792, including those described in a licensed patent, U.S. Pat. No. 7,238,522, which issued on Jul. 3, 2007. The above-referenced application and patent, U.S. Ser. No. 60/939,792 and U.S. Pat. No. 7,238,522, respectively, are hereby incorporated in their entirety.

The present invention has multiple aspects, illustrated by the following non-limiting examples.

10. Examples

Example 1

Construction of pTyr

Figure 9:
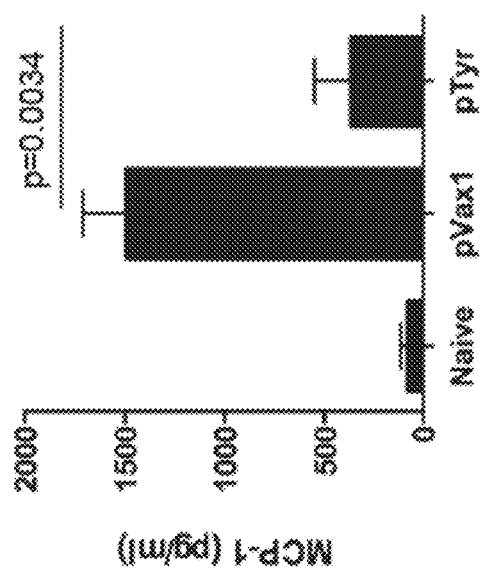
FIG. 9 shows the phylogenetic relationship of Tyr nucleotide sequences amongst the indicated organisms.
Figure 9:
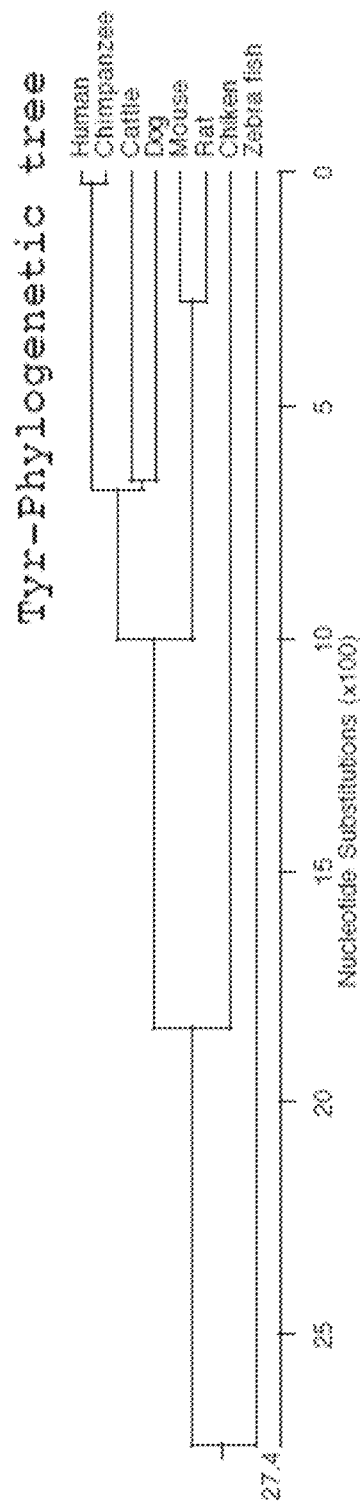

As shown in FIGS. 1A and 9, Tyrosinase (Tyr) can be found in many different organisms. Accordingly, a consensus Tyr was generated by aligning sequences corresponding to Tyr from the organisms shown in FIG. 1A, and choosing the most common amino acid and/or nucleotide for the consensus Tyr. The corresponding Tyr sequences for each organism were obtained from GenBank (NCBI). As such, the consensus Tyr reflected the conserved elements of Tyr sequences across species.

The nucleic acid sequence encoding the consensus Tyr was adapted to include the IgE leader sequence. Specifically, the IgE leader sequence was fused in frame upstream of the consensus Tyr nucleic acid sequence (FIG. 1B). The resulting sequence was then inserted into the pVax1 expression vector to create a Tyrosinase construct or plasmid (pTyr) such that a Kozak sequence preceded the nucleotide sequence encoding the IgE leader sequence and the consensus Tyr.

Insertion of the consensus Tyr nucleic acid sequence into pVax1 was confirmed by restriction enzyme analysis. As shown in FIG. 1C, the consensus Tyr nucleic acid sequence was separated from the pVax1 plasmid on a DNA agarose gel (i.e., the lane labeled BamH1/Xho1), thereby confirming that the pVax1 vector contained the consensus Tyr nucleic acid sequence.

Expression of the consensus Tyr was confirmed by transfecting HeLa cells with pTyr. Western blotting with a human anti-Tyr antibody confirmed expression of the consensus Tyr protein in HeLa cells (FIG. 1D). GPF staining further showed expression of the consensus Tyr protein in transfected HeLa cells (FIG. 1E). In both the western blotting and staining experiments,

Example 2

Vaccination with pTyr Induced a Cell Mediated Immune Response

The above described pTyr was used to vaccinate mice to evaluate whether a cellular immune response was induced by pTyr. C57/B6 mice were immunized using the immunization strategy shown in FIG. 2A. Some mice were immunized with pVax1 while other mice were immunized with pTyr. The mice immunized with pTyr were further broken into the following groups: (1) 5 μg dosage of pTyr; (2) 20 μg dosage of pTyr; (3) 30 μg dosage of pTyr; and (4) 60 μg dosage of pTyr.

Figure 2:
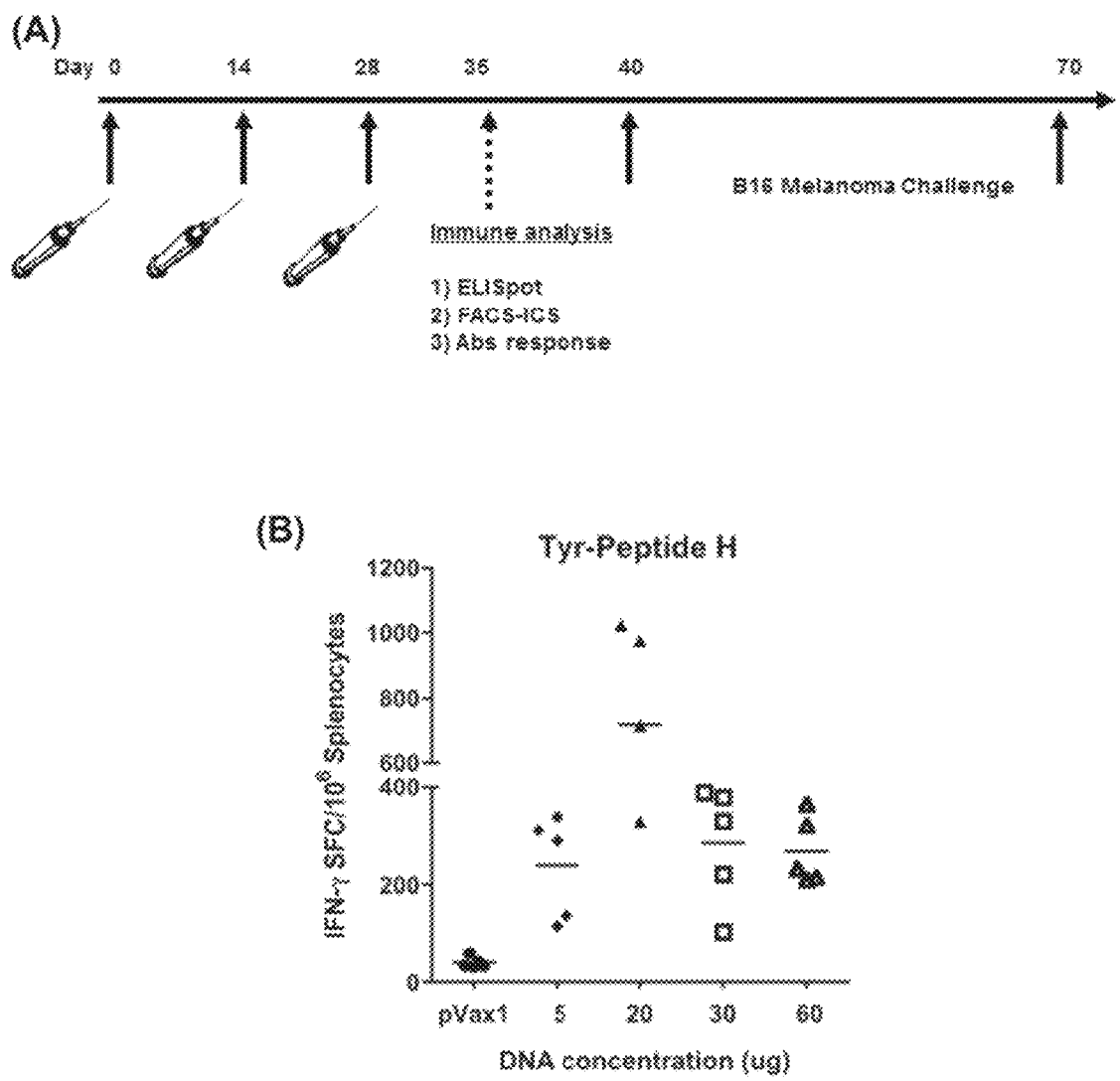
FIGS. 2A and 2B show an immunization strategy and induction of cell mediated immune responses by Tyr DNA vaccination, respectively.

At day 35 of the immunization strategy, splenocytes were isolated from the C57B/6 mice and evaluated for induction of interferon-γ (IFN-γ) by IFN-γ ELISpot analysis. As shown in FIG. 2B, the 20 μg dosage of pTyr induced the highest levels of IFN-γ.

The cellular immune response to pTyr was further evaluated in immunized Balb/c and C57B/6 mice. Mice were immunized with either pVax1 or pTyr. Splenocytes were isolated two weeks after the third immunization and stimulated with the consensus Tyr peptide. After stimulation, the number of IFN-γ secreting splenocytes was calculated as the average number of spots in the triplicate stimulant wells. This assay indicated that C57/B6 mice were suitable for pTyr vaccination (data not shown).

Example 3 pTyr Vaccination Increased Cytokines IFN-γ and TNF-α

Figure 3:
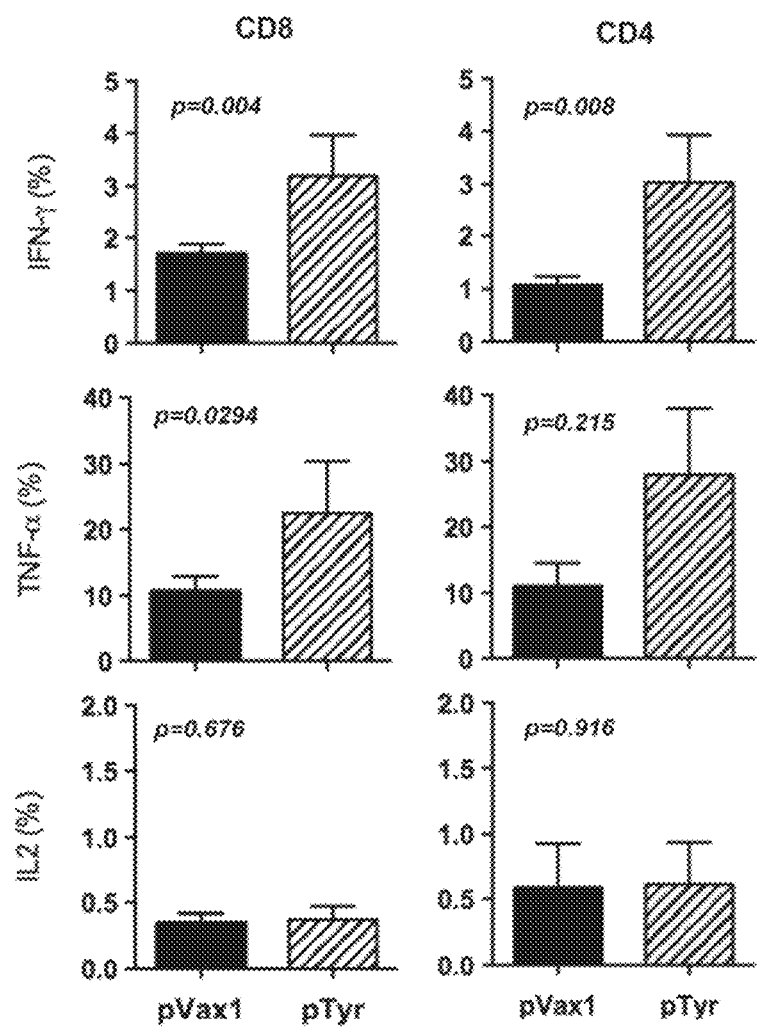
FIG. 3 shows flow fluorescence-activated cell sorting (FACS) of control and immunized mice.

Cytokine production was examined in mice immunized with pTyr and pVax1. Mice were immunized using the strategy shown in FIG. 2A. At day 35 of the immunization strategy, cells isolated from the immunized mice were stimulated overnight with Tyr peptides. After stimulation, analysis of the polyfunctional responses was measured by FACS. Specifically, the analysis examined CD8$^+$ and CD4$^+$ T cells. FACS allowed for the identification of T cells positive for the cytokines IL-2, TNF-α, and IFN-γ. Of the CD44 hi cells, a significant percentage of CD8$^+$ T cells produced IFN-γ in the mice immunized with pTyr as compared to mice immunized with pVax1 (FIG. 3).

Example 4

Tyr Specific Antibodies are Produced in Response to pTyr Vaccination

Figure 4:
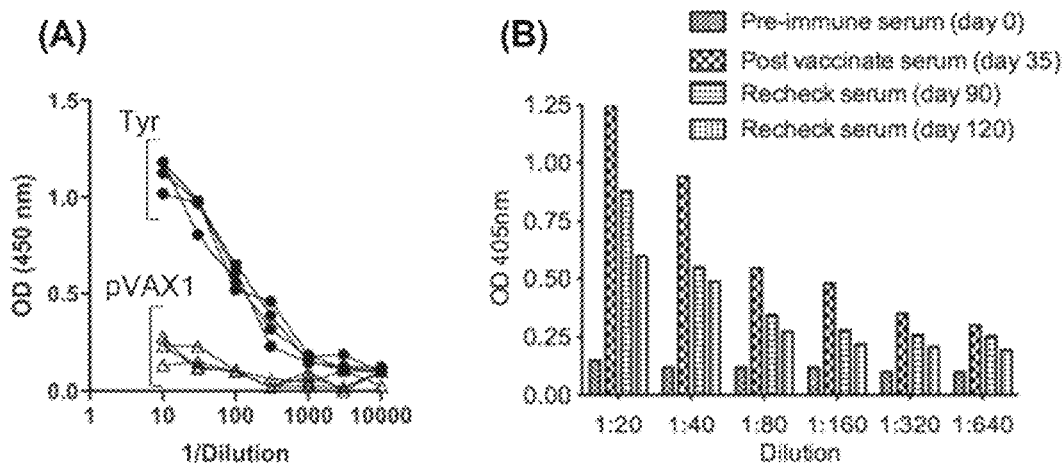
FIGS. 4A and 4B show induction of tyrosinase-specific antibodies in immunized mice.

The humoral immune response was examined in mice vaccinated with pTyr. Specifically, C57Bl/6 mice (n=4) were immunized three times at 2-week intervals with either pTyr or pVax1. Each immunization consisted of a 20 μg/intramuscular injection followed by electroporation with MID-EP. After the third immunization (i.e., day 35), serum was collected from the mice and antibody titers were measured by ELISA using total IgG-specific HRP labeled secondary antibodies. The sera were diluted as indicated in FIG. 4A. As shown in FIG. 4A, specific antibodies to Tyr were produced by the mice immunized with pTyr. Mice immunized with pTyr are represented by the filled circle in FIG. 4A while mice immunized with pVax1 are represented by the open triangle in FIG. 4A.

Additionally, the sera from the immunized mice were serially diluted at 1:20, 1:40, 1:80, 1:160, 1:320, and 1:640. Each serum dilution was added in triplicate to individual wells (50 μl/well) containing Tyr peptides. The peak increase in Tyr-specific titer, compared to the preimmune serum, was detected for all immunized groups of mice at recheck days 90 and 120. Representative results of three independent experiments at each serial dilution point are shown in FIG. 4B. These data further indicated that immunization with pTyr induced production of Tyr specific antibodies in mice immunized with pTyr.

Example 5

Mice Vaccinated with pTyr have Increased Survival to Tumor Challenge pTry was further analyzed to determine if pTyr vaccination could provide protection from tumors. Specifically, C57Bl/6 mice (10 per group) were immunized at 2-week intervals with either pTyr or pVax1. Each immunization consisted of a 20 μg/intramuscular injection followed by electroporation with MID-EP. One week after the third immunization (i.e., day 35), the immunized mice were challenged intradermally with B16 melanoma until the tumor diameter exceeded 200 mm$^2$.

Figure 5:
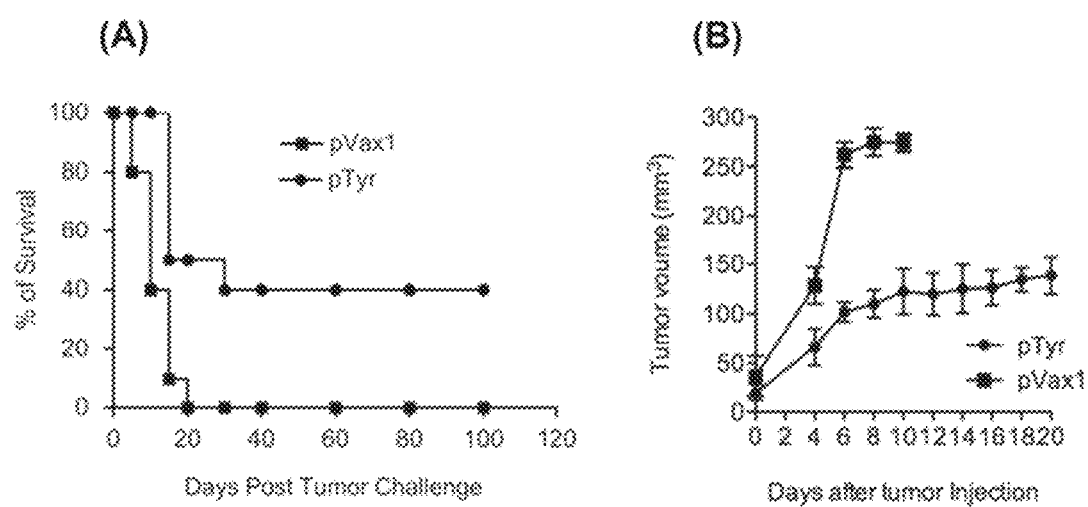
FIGS. 5A and 5B show Kaplan-Meier survival curves and tumor volume curves, respectively, after tumor challenge in control and immunized mice.

Subsequently, tumor-free survival and tumor volume was evaluated in the immunized groups of mice. As shown in FIG. 5A (a Kaplan-Meier survival curve), mice immunized with pTyr were improved in tumor-free survival (i.e., 40% at days 40 and on after tumor challenge) as compared to mice vaccinated with pVax1 (p=0.05), which were all dead by day 20 after tumor challenge. Mice immunized with pTyr also had reduced tumor volume (i.e., about 50%) as compared to mice immunized with pVax1 (FIG. 5B). For both FIGS. 5A and 5B, mice immunized with pVax1 are represented by filled squares while mice immunized with pTyr are represented by filled circles. Accordingly, these data showed that pTyr vaccination provided protection against melanoma, namely increased tumor-free survival and reduction in tumor volume.

Example 6

MDSC Population is Reduced in Tumors from Mice Vaccinated with pTyr

MDSC populations were examined in mice immunized with pTyr and non-immunized mice to examine whether vaccination with pTyr altered levels of MDSCs in tumors from the respective groups of mice. Specifically, the percentage of Gr-1+ and CD11b+ cells were examined in the immunized and non-immunized mice.

Figure 6:
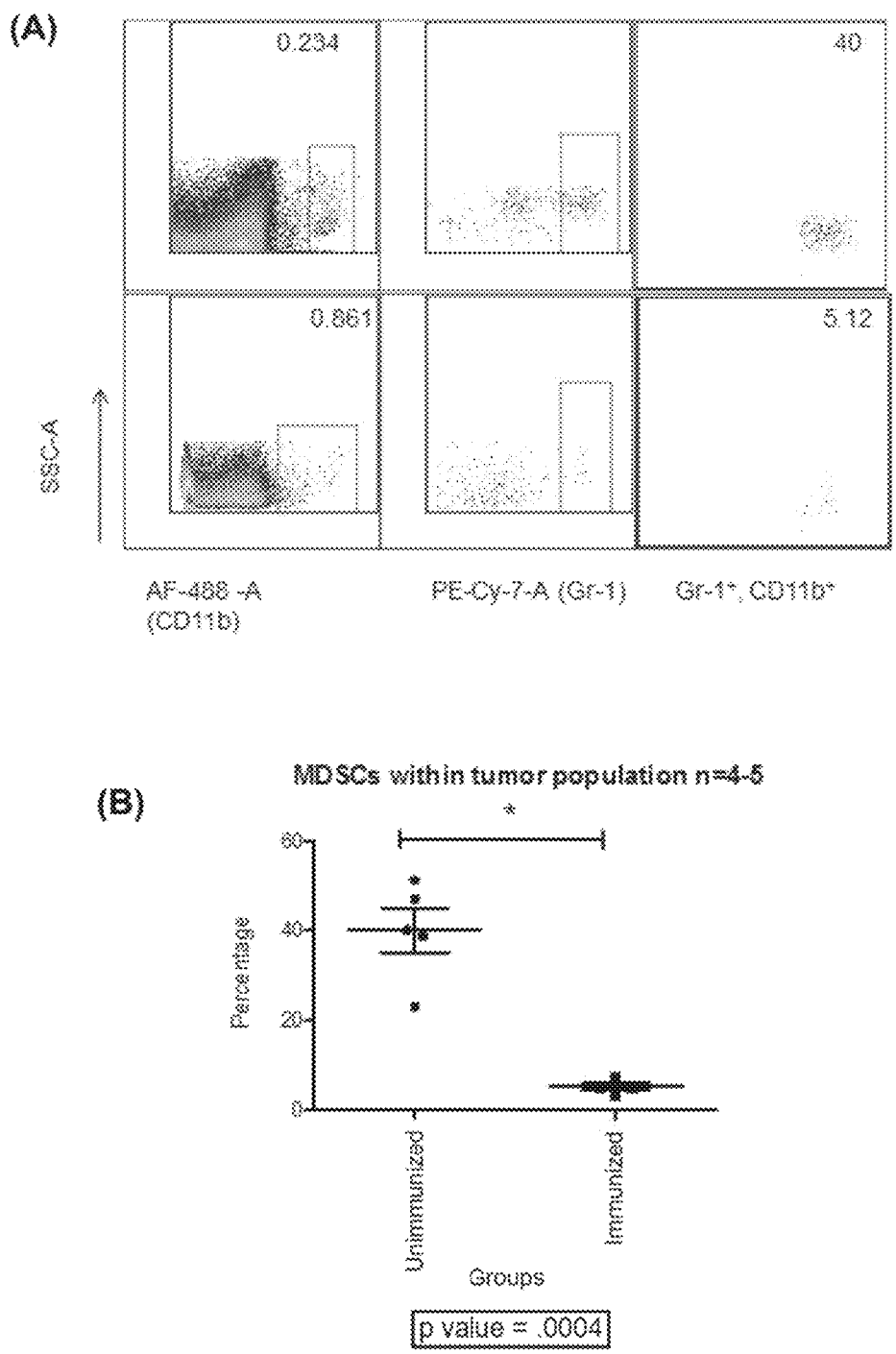
FIGS. 6A and 6B show MDSC cell populations in immunized and non-immunized mice.
Figure 7:
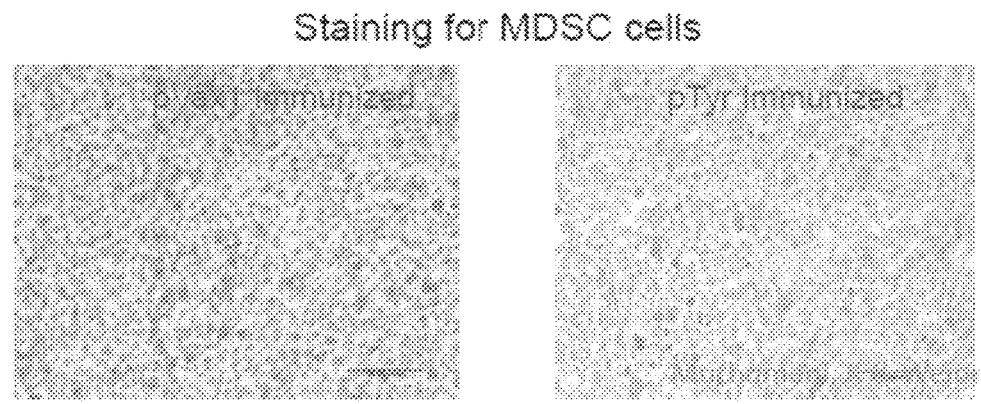
FIG. 7 shows staining for MDSCs in mice immunized with pVax1 and pTyr.

As shown in FIGS. 6 and 7, MDSC levels were significantly reduced within tumors from mice immunized with pTyr as compared to non-immunized mice (p=0.0004). The percentage of MDSC population in non-immunized mice was 40.00±4.826. The percentage of MDSC population in mice immunized with pTyr was 5.103±0.7718. Accordingly, these data showed that immunization with pTyr reduced MDSC populations within tumors of mice vaccinated with pTyr.

Example 7

MCP-1 Levels are Reduced by pTyr Vaccination

MDSCs can secrete the cytokine MCP-1, which promotes angiogenesis or vascularization by migration of endothelial cells. Given the above described effect of pTyr vaccination on MDSC levels in tumors, MCP-1 levels were examined after vaccination with pTyr.

Figure 8:
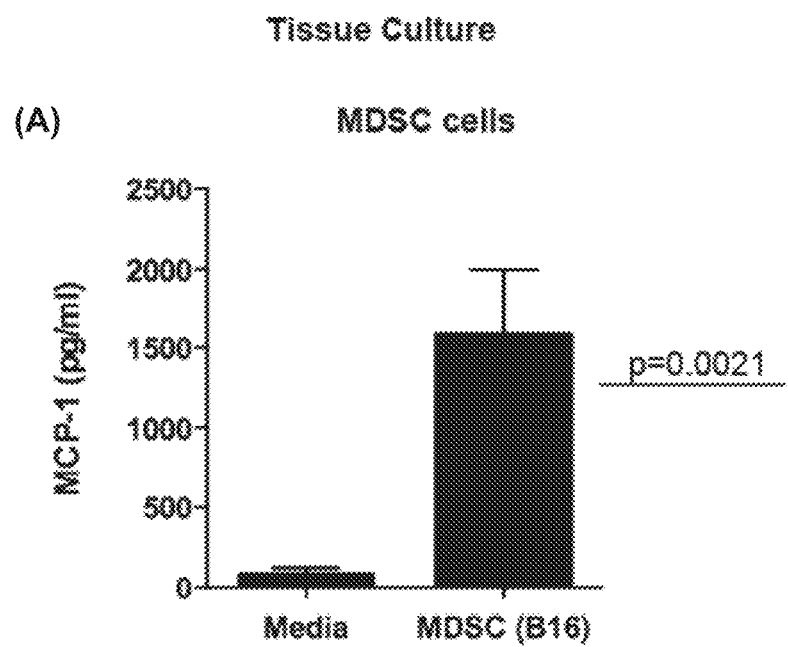
FIGS. 8A and 8b show MCP-1 secretion by MDSCs.

As shown in FIG. 8A, MDSCs within the B16 melanoma can secrete MCP-1. As such, mice immunized with pTyr and mice immunized with pVax1 were challenged with the B16 melanoma to examine whether pTyr immunization altered MCP-1 levels. Naïve mice were included as a further control. After the challenge, MDSCs were isolated directly from the tumor tissue, and MCP-1 cytokine levels were analyzed ELISA. The experiment was performed in triplicate and repeated two times.

As shown in FIG. 8B, MDSCs within the B16 melanoma or tumor tissue significantly secreted MCP-1 (see pVax1 immunized mice). Mice immunized with pTyr, however, did not have a significant increase in MCP-1 levels. Rather, MCP-1 levels in mice immunized with pTyr were about 3-fold lower than mice immunized with pVax1. Accordingly, these data showed that pTyr vaccination reduced the level of MCP-1 secretion by MDSCs within tumors of mice immunized with pTyr.

Example 8

Construction of pPRAME

Figure 10:
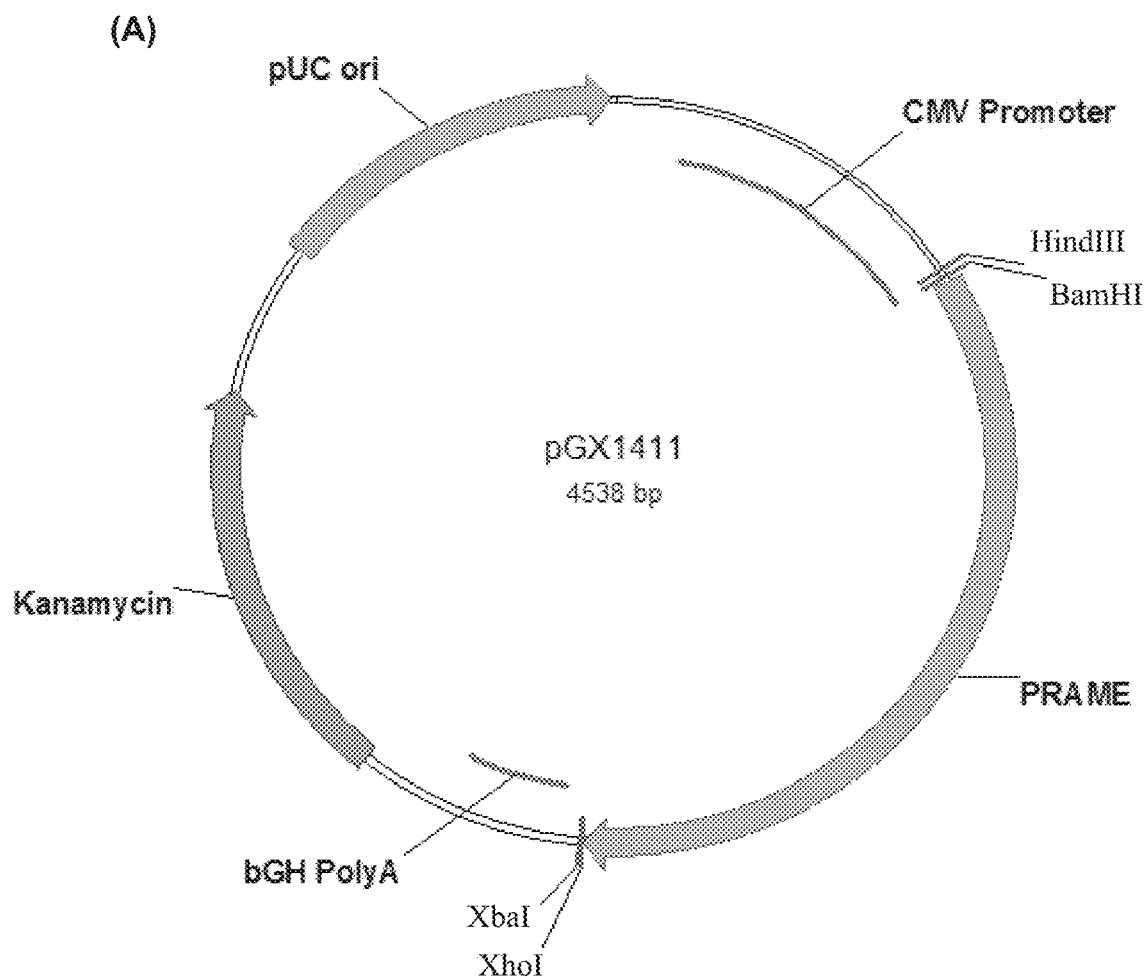
FIG. 10 shows (A) a schematic illustrating a plasmid map of pPRAME (also known herein as pGX1411); (B) staining of RD and 293T cells for nuclei with DAPI and for the consensus PRAME antigen; and (C) western blotting for the consensus PRAME antigen in lysates from non-transfected cells ("control"), cells transfected with pVAX ("pVAX"), and cells transfected with pPRAME ("PRAME-pVAX").

A consensus sequence was generated for PRAME and the nucleotide sequence encoding the consensus PRAME antigen was inserted into the BamHI and XhoI restriction enzyme sites of the expression vector or plasmid pVAX (also known as pVAX1 herein) to yield pGX1411 (also known as pPRAME herein) (see FIG. 10A).

To confirm that pPRAME resulted in expression of the consensus PRAME antigen, pVAX and pPRAME were transfected into RD cells and 293T cells. DAPI was used to stain nuclei and the consensus PRAME antigen was also fluorescently stained. This staining, along with a merge of the DAPI and consensus PRAME antigen staining, are shown in FIG. 10B. These staining demonstrated that the PRAME consensus antigen was expressed from pPRAME and no consensus PRAME antigen was detected in the cells transfected with pVAX (i.e., negative control).

Additionally, western blotting analysis of lysates from the transfected cells was used to confirm expression of the consensus PRAME antigen in transfected cells (FIG. 10C). Non-transfected cells and cells transfected with pVAX were used as negative controls (see lanes labeled "control" and "pVAX," respectively in FIG. 10C). In FIG. 10C, beta-actin detection was used as a loading control. In summary, the staining of transfected cells and western blotting of lysates from transfected cells demonstrated that the vector pPRAME provided expression of the consensus PRAME antigen within cells.

Example 9

Interferon Gamma Response to Vaccination with pPRAME

The above described pPRAME was used to vaccinate mice to evaluate whether a cellular immune response was induced by pPRAME. C57BL/6 mice were separated into groups. A first group was naïve and did not receive pPRAME. Second, third, fourth, fifth, and sixth groups of mice received 5 μg, 10 μg, 15 μg, 25 μg, and 50 μg of pPRAME, respectively.

Figure 11:
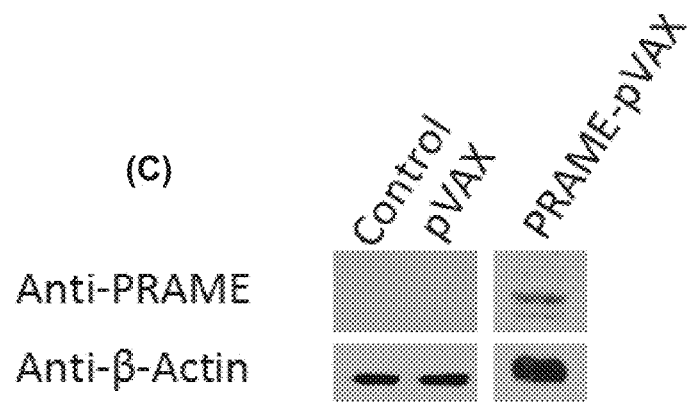
FIG. 11 shows in (A) and (B) graphs plotting mouse group vs. spot forming units (SFU)/$10^6$ splenocytes for interferon gamma (IFN-γ).
Figure 11:
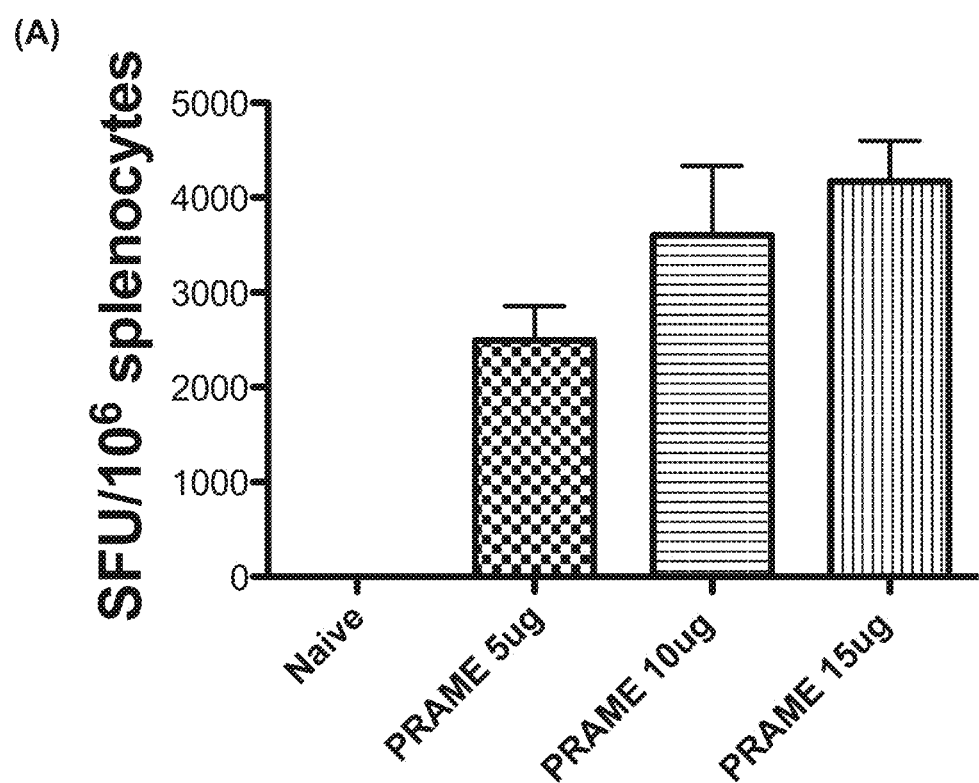

After immunization, splenocytes were isolated from the C57BL/6 mice and evaluated for induction of interferon gamma (IFN-γ) by IFN-γ ELISpot analysis. As shown in FIGS. 11A and 11B, each dosage of pPRAME induced production or secretion of IFN-γ unlike the negative control naïve mice. In particular, the IFN-γ levels were increased by about 3000-fold to about 4500-fold in vaccinated mice as compared to non-vaccinated mice. Accordingly, these data demonstrated that vaccination with pPRAME, which encodes the consensus PRAME antigen, induced a cellular immune response as evidenced by increased IFN-γ levels as compared non-vaccination.

Example 10

Construction of pNY-ESO-1

Figure 12:
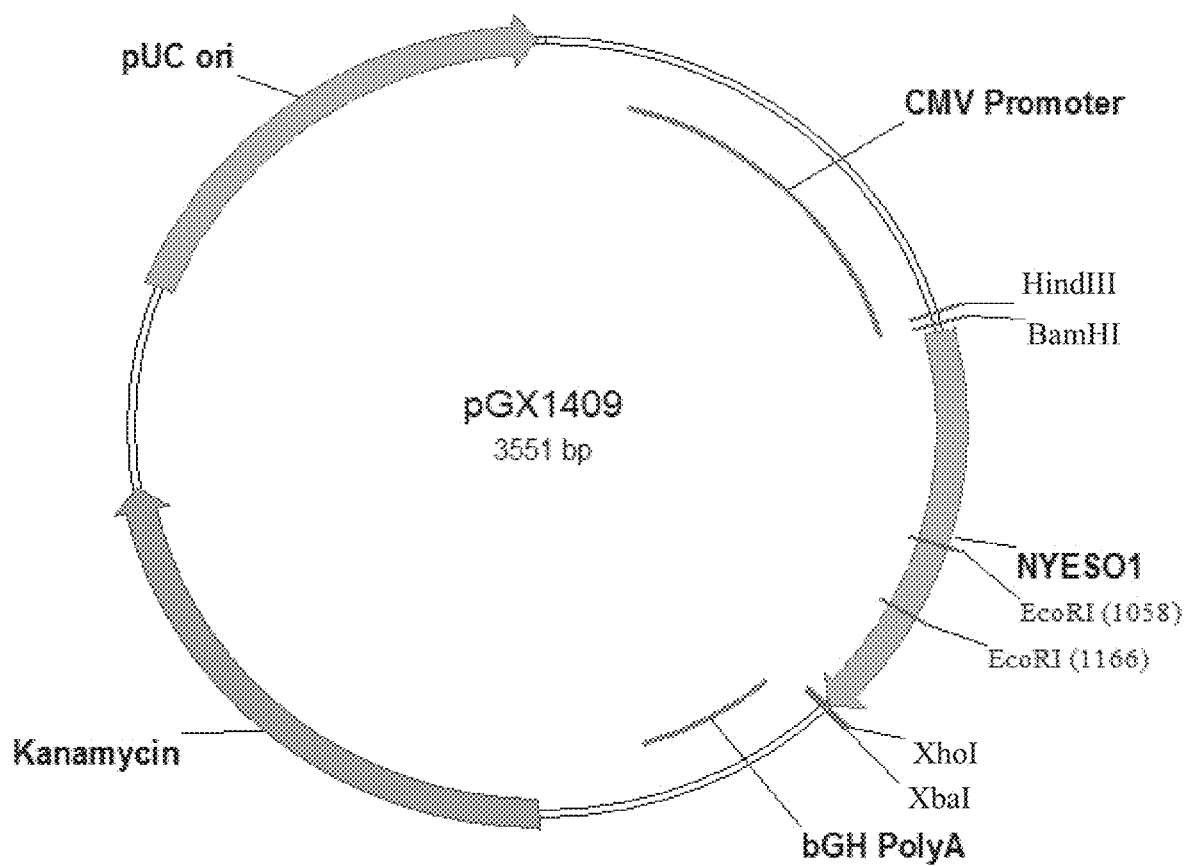
FIG. 12 shows (A) a schematic illustrating a plasmid map of pNY-ESO-1 (also known herein as pGX1409); (B) staining of cells for nuclei with DAPI and for the consensus NY-ESO-1 antigen; and (C) western blotting for the consensus NY-ESO-1 antigen in RD and 293T lysates from non-transfected cells ("control"), cells transfected with pVAX ("pVAX"), and cells transfected with pNY-ESO-1 ("pNY-ESO-1").

A consensus sequence was generated for NY-ESO-1 and the nucleotide sequence encoding the consensus NY-ESO-1 antigen was inserted into the BamHI and XhoI restriction enzyme sites of the expression vector or plasmid pVAX (also known as pVAX1 herein) to yield pGX1409 (also known as pNY-ESO-1 herein) (see FIG. 12A).

To confirm that pNY-ESO-1 resulted in expression of the consensus NY-ESO-1 antigen, pVAX and pNY-ESO-1 were transfected into cells. DAPI was used to stain nuclei and the consensus NY-ESO-1 antigen was also fluorescently stained. This staining, along with a merge of the DAPI and consensus NY-ESO-1 antigen staining, are shown in FIG. 12B. These staining demonstrated that the NY-ESO-1 consensus antigen was expressed from pNY-ESO-1 and no consensus NY-ESO-1 antigen was detected in the cells transfected with pVAX (i.e., negative control).

Additionally, western blotting analysis of lysates from 293T and RD transfected cells was used to confirm expression of the consensus NY-ESO-1 antigen in the transfected cells (FIG. 12C). Non-transfected cells and cells transfected with pVAX were used as negative controls (see lanes labeled "control" and "pVAX," respectively in FIG. 12C). In FIG. 12C, alpha-actin detection was used as a loading control. In summary, the staining of transfected cells and western blotting of lysates from the transfected cells demonstrated that the vector pNY-ESO-1 provided expression of the consensus NY-ESO-1 antigen within cells.

Example 11

Interferon Gamma Response to Vaccination with pNY-ESO-1

The above described pNY-ESO-1 was used to vaccinate mice to evaluate whether a cellular immune response was induced by pNY-ESO-1. C57BL/6 mice were separated into groups. A first group was naïve and did not receive pNY-ESO-1. Second and third groups of mice received 25 μg and 50 μg pNY-ESO-1, respectively.

Figure 13:
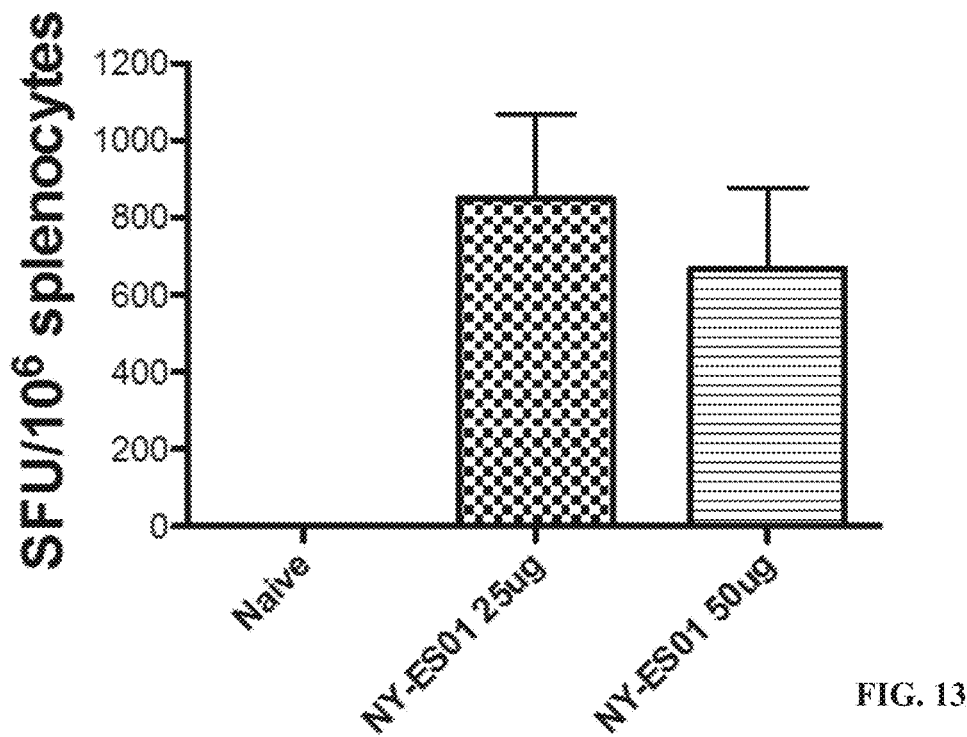
FIG. 13 shows a graph plotting mouse group vs. spot forming units (SFU)/$10^6$ splenocytes for interferon gamma (IFN-γ).

After immunization, splenocytes were isolated from the C57BL/6 mice and evaluated for induction of interferon gamma (IFN-γ) by IFN-γ ELISpot analysis. As shown in FIG. 13, each dosage of pPRAME induced production or secretion of IFN-γ unlike the negative control naïve mice. In particular, the IFN-γ levels were increased by about 700-fold to about 1100-fold in vaccinated mice as compared to non-vaccinated mice. Accordingly, these data demonstrated that vaccination with pNY-ESO-1, which encodes the consensus NY-ESO-1 antigen, induced a cellular immune response as evidenced by increased IFN-γ levels as compared non-vaccination.

Example 12

Interferon Gamma Response to Vaccination with pNY-ESO-2

A consensus sequence was generated for NY-ESO-2 and the nucleotide sequence encoding the consensus NY-ESO-2 antigen was inserted into the multiple cloning site of the expression vector or plasmid pVAX (also known as pVAX1 herein) to yield pNY-ESO-2.

This pNY-ESO-2 was used to vaccinate mice to evaluate whether a cellular immune response was induced by pNY-ESO-2. C57BL/6 mice were separated into groups. A first group was naïve and did not receive pNY-ESO-2. Second and third groups of mice received 25 μg and 50 μg of pNY-ESO-2, respectively.

Figure 14:
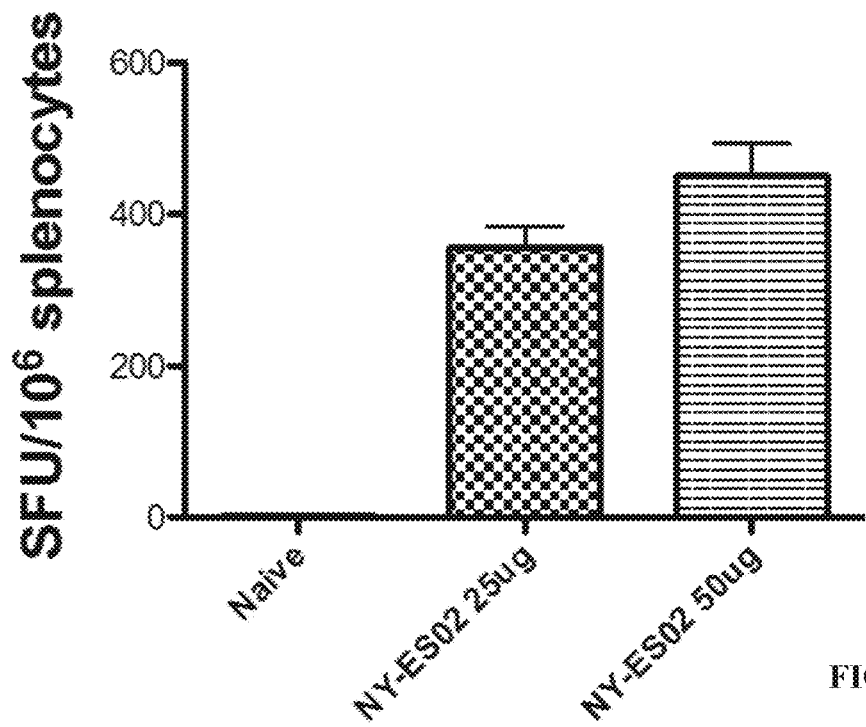
FIG. 14 shows a graph plotting mouse group vs. spot forming units (SFU)/$10^6$ splenocytes for interferon gamma (IFN-γ).

After immunization, splenocytes were isolated from the C57BL/6 mice and evaluated for induction of interferon gamma (IFN-γ) by IFN-γ ELISpot analysis. As shown in FIG. 14, each dosage of pNY-ESO-2 induced production or secretion of IFN-γ unlike the negative control naïve mice. In particular, the IFN-γ levels were increased by about 400-fold to about 500-fold in vaccinated mice as compared to non-vaccinated mice. Accordingly, these data demonstrated that vaccination with pNY-ESO-2, which encodes the consensus NY-ESO-2 antigen, induced a cellular immune response as evidenced by increased IFN-γ levels as compared non-vaccination.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:

1. A vaccine comprising two or more nucleotide sequences encoding two or more amino acid sequences; wherein the two or more nucleotide sequences encoding two or more amino acid sequences comprise:
   a) one or more nucleotide sequences encoding one or more amino acid sequences selected from the group consisting of: an amino acid sequence that is 97% identical or greater to the amino acid sequence of tyrosinase (Tyr) (SEQ ID NO:2); an amino acid sequence that is 97% identical or greater to the amino acid sequence of tyrosinase-related protein 1 (TYRP1) (SEQ ID NO: 4); an amino acid sequence that is 97% identical or greater to the amino acid sequence of tyrosinase-related protein 2 (TYRP2) (SEQ ID NO: 6); an amino acid sequence that is 97% identical or greater to the amino acid sequence of melanoma-associated antigen 4 protein (MAGEA4) (SEQ ID NO: 8); an amino acid sequence that is 95% identical or greater to the amino acid sequence of growth hormone release hormone (GHRH) (SEQ ID NO: 10); an amino acid sequence that is 95% identical or greater to the amino acid sequence of MART-1/melan-A antigen (MART-1/Melan-A) (SEQ ID NO: 12); an amino acid sequence that is 95% identical or greater to the amino acid sequence of cancer testis antigen (NY-ESO-1) (SEQ ID NO: 14); an amino acid sequence that is 95% identical or greater to the amino acid sequence of cancer testis antigen II (NY-ESO-2) (SEQ ID NO:16); an amino acid sequence that is 95% identical or greater to the amino acid sequence of PRAME (SEQ ID NO: 18); and an amino acid sequence that is 96% identical or greater to the amino acid sequence of hTERT (amino acid residues 1-1149 of SEQ ID NO:24); and
   b) one or more nucleotide sequences encoding one or more amino acid sequences selected from the group consisting of: an amino acid sequence that is 97% identical or greater to the amino acid sequence of tyrosinase (Tyr) (SEQ ID NO:2); an amino acid sequence that is 97% identical or greater to the amino acid sequence of tyrosinase-related protein 1 (TYRP1) (SEQ ID NO: 4); an amino acid sequence that is 97% identical or greater to the amino acid sequence of tyrosinase-related protein 2 (TYRP2) (SEQ ID NO: 6); an amino acid sequence that is 97% identical or greater to the amino acid sequence of melanoma-associated antigen 4 protein (MAGEA4) (SEQ ID NO: 8); an amino acid sequence that is 95% identical or greater to the amino acid sequence of growth hormone release hormone (GHRH) (SEQ ID NO: 10); an amino acid sequence that is 95% identical or greater to the amino acid sequence of MART-1/melan-A antigen (MART-1/Melan-A) (SEQ ID NO: 12); an amino acid sequence that is 95% identical or greater to the amino acid sequence of cancer testis antigen (NY-ESO-1) (SEQ ID NO: 14); an amino acid sequence that is 95% identical or greater to the amino acid sequence of cancer testis antigen II (NY-ESO-2) (SEQ ID NO:16); an amino acid sequence that is 95% identical or greater to the amino acid sequence of PRAME (SEQ ID NO: 18); an amino acid sequence that is 95% identical or greater to the amino acid sequence of ConWT1-L (SEQ ID NO:20); an amino acid sequence that is 95% identical or greater to the amino acid sequence of ConWT1-S (SEQ ID NO:22); and an amino acid sequence that is 96% identical or greater to the amino acid sequence of hTERT (amino acid residues 1-1149 of SEQ ID NO:24).

2. The vaccine of claim 1, further comprising a nucleotide sequence encoding one or more antigens selected from the group consisting of: PSA, PSMA, STEAP, PSCA, MAGE A1, gp100, a viral antigen, and combinations thereof.

3. The vaccine of claim 2, wherein the viral antigen is an antigen from Hepatitis B virus (HBV), Hepatitis C virus (HCV), or Human Papilloma Virus (HPV).

4. The vaccine of claim 3, wherein the HBV antigen is an HBV core antigen or a HBV surface antigen, or a combination thereof wherein the HCV antigen is an HCV NS34A antigen, an HCV NS5A antigen, an HCV NS5B antigen, an HCV NS4B antigen, or a combination thereof and wherein the HPV antigen is an HPV type 6 E6 antigen, an HPV type 6 E7 antigen, an HPV type 11 E6 antigen, an HPV type 11 E7 antigen, an HPV type 16 E6 antigen, an HPV type 16 E7 antigen, an HPV type 18 E6 antigen, an HPV type 18 E7 antigen, or a combination thereof.

5. The vaccine of claim 1, further comprising an immune checkpoint inhibitor selected from the group consisting of: anti-PD-1 antibody, anti-PD-L1 antibody, and a combination thereof.

6. The vaccine of claim 1, wherein the two or more nucleotide sequences are selected from the group consisting of: SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, and nucleotides 19-3467 of SEQ ID NO:23.

7. The vaccine of claim 1, wherein the nucleotide sequences are one or more plasmids.

8. The vaccine of claim 1, further comprising an adjuvant.

9. The vaccine of claim 8, wherein the adjuvant is one or more selected from the group consisting of IL-12, IL-15, IL-28, and RANTES.

10. A method of treating cancer in a subject in need thereof, the method comprising administering the vaccine of claim 1 to the subject.

11. The method of claim 10, wherein administration includes an electroporation step.

12. The method of claim 10, further comprising administering an immune checkpoint inhibitor to the subject.

13. The method of claim 12, wherein the immune checkpoint inhibitor is selected from the group consisting of: anti-PD-1 antibody, anti-PD-L1 antibody, and a combination thereof.

14. The method of claim 12, wherein the vaccine and immune checkpoint inhibitor are administered in a single formulation to the subject.

15. The method of claim 12, wherein the vaccine and immune checkpoint inhibitor are administered separately to the subject.

16. The method of claim 10, wherein the cancer is selected from the group consisting of: melanoma, head and neck cancer, prostate cancer, liver cancer, cervical cancer, recurrent respiratory papillomatosis (RRP), anal cancer, a blood cancer, and a combination thereof.

17. A composition comprising two or more nucleotide sequences; wherein the two or more nucleotide sequences comprise:
   a) one or more nucleotide sequences selected from the group consisting of: a nucleotide sequence that is 95% identical or greater to SEQ ID NO:1, a nucleotide sequence that is 97% identical or greater to SEQ ID NO:3, a nucleotide sequence that is 97% identical or greater to SEQ ID NO:5, a nucleotide sequence that is 97% identical or greater to SEQ ID NO:7, a nucleotide sequence that is 95% identical or greater to SEQ ID NO:9, a nucleotide sequence that is 95% identical or greater to SEQ ID NO:11, a nucleotide sequence that is 95% identical or greater to SEQ ID NO:13, a nucleotide sequence that is 95% identical or greater to SEQ ID NO:15, a nucleotide sequence that is 95% identical or greater to SEQ ID NO:17, a nucleotide sequence that is 96% identical or greater to nucleotides 19-3467 of SEQ ID NO:23, and a combination thereof; and
   b) one or more nucleotide sequences selected from the group consisting of: a nucleotide sequence that is 95% identical or greater to SEQ ID NO:1, a nucleotide sequence that is 97% identical or greater to SEQ ID NO:3, a nucleotide sequence that is 97% identical or greater to SEQ ID NO:5, a nucleotide sequence that is 97% identical or greater to SEQ ID NO:7, a nucleotide sequence that is 95% identical or greater to SEQ ID NO:9, a nucleotide sequence that is 95% identical or greater to SEQ ID NO:11, a nucleotide sequence that is 95% identical or greater to SEQ ID NO:13, a nucleotide sequence that is 95% identical or greater to SEQ ID NO:15, a nucleotide sequence that is 95% identical or greater to SEQ ID NO:17, a nucleotide sequence that is 95% identical or greater to SEQ ID NO:19, a nucleotide sequence that is 95% identical or greater to SEQ ID NO:21, a nucleotide sequence that is 96% identical or greater to nucleotides 19-3467 of SEQ ID NO:23, and a combination thereof.

18. The composition of claim 17, wherein the nucleotide sequences are one or more plasmids.

19. A composition comprising two or more nucleotide sequences; wherein the two or more nucleotide sequences comprise:
   a) a nucleotide sequence that is 95% identical or greater to a nucleotide sequence encoding hTERT (amino acid residues 1-1149 of SEQ ID NO:24); and
   b) one or more nucleotide sequences selected from the group consisting of: a nucleotide sequence that is 95% identical or greater to a nucleotide sequence encoding ConWT1-L (SEQ ID NO:20), a nucleotide sequence that is 95% identical or greater to a nucleotide sequence encoding ConWT1-S (SEQ ID NO:22), a nucleotide sequence that is 95% identical or greater to a nucleotide sequence encoding hTERT (amino acid residues 1-1149 of SEQ ID NO:24).

20. The composition of claim 19, wherein the two or more nucleotide sequences are selected from the group consisting of SEQ ID NO:19, SEQ ID NO:21, and nucleotides 19-3467 of SEQ ID NO:23.

* * * * *

SEQUENCE LISTING

```
<160> NUMBER OF SEQ ID NOS: 44

<210> SEQ ID NO 1
<211> LENGTH: 1608
<212> TYPE: DNA
<213> ORGANISM: Artificial Sequence
<220> FEATURE:
<223> OTHER INFORMATION: Consensus Tyrosinase

<400> SEQUENCE: 1
```

-continued

| | |
|---|---|
| atggattgga cttggatctt atttttagtt gctgctgcta ctagagttca ttctgactgg | 60 |
| acttggattc tgttcctggt cgccgccgct acccgagtgc attccgaaaa agagtgttgc | 120 |
| ccaccttggt ctggagatcg aagcccatgc ggacagctga gtgggcgggg atcatgtcag | 180 |
| aacatcctgc tgagcaatgc ccccctggga cctcagttcc ccttcaccgg cgtggacgat | 240 |
| agagagtctt ggcccagtgt cttttacaac aggacttgcc agtgtagcgg gaatttcatg | 300 |
| ggcttcaact gcggcaattg taagttcggc ttttgggggc aaactgcac cgagcggaga | 360 |
| ctgctggtga ggcgcaatat cttcgatctg tccgcccccg aaaaggacaa attctttgcc | 420 |
| tatctgaccc tggctaagca cacaattagc tccgattatg tcatccccat ggaacatac | 480 |
| ggccagatga aaacggcag cactcctatg tttaacgata tcaatatcta cgacctgttc | 540 |
| gtgtggatgc attactatgt ctccatggac gctctgctgg gcgggtctga gatcggcgg | 600 |
| gacattgatt tcgcacacga agctccagca tttctgccct ggcataggct gttcctgctg | 660 |
| cgctgggagc aggaaatcca gaagctgact ggggacgaga actttaccat tccctattgg | 720 |
| gattggcggg acgccgagaa atgcgatatc tgtactgacg aatacatggg aggccagcac | 780 |
| cccaccaacc ctaatctgct gtcacctgcc agcttctttt ctagttggca gatcgtgtgc | 840 |
| agccggctgg aggaatacaa ctcccaccag agcctgtgca atgggactcc agagggacca | 900 |
| ctgcgacgaa accctggaaa tcatgataag agccgaaccc ctcgactgcc atcaagcgcc | 960 |
| gacgtggagt tttgcctgtc cctgacacag tatgaaagcg gcagcatgga taagccgct | 1020 |
| aacttctctt ttaggaatac cctggaaggg ttcgcaagtc cactgacagg aatcgccgac | 1080 |
| gcttcacagt cctctatgca caacgctctg catatctaca tgaatggcac aatgtcacag | 1140 |
| gtgcagggga gcgcaaacga tcctatcttc ctgctgcacc atgccttcgt ggactccatt | 1200 |
| tttgagcagt ggctgagaag gcaccgccca ctgcaggagg tgtatcctga gcaaacgcc | 1260 |
| ccaatcggcc ataatcgcga atcttatatg gtccccttta tccctctgta ccgaaacgga | 1320 |
| gatttcttta ttagttcaaa ggatctgggc tacgactata gttacctgca ggacagcgat | 1380 |
| cctgactcct tccaggacta tatcaaatct tacctggagc aggcctctag aatttggagt | 1440 |
| tggctgctgg gagcagcaat ggtgggagct gtcctgaccg ctctgctggc aggactggtg | 1500 |
| tccctgctgt gccggcacaa gagaaaacag ctgcccgagg aaaagcagcc actgctgatg | 1560 |
| gaaaaagaag actaccactc actgctgtac cagacccacc tgtgataa | 1608 |

<210> SEQ ID NO 2
<211> LENGTH: 517
<212> TYPE: PRT
<213> ORGANISM: Artificial Sequence
<220> FEATURE:
<223> OTHER INFORMATION: Consensus Tyrosinase

<400> SEQUENCE: 2

Met Asp Trp Thr Trp Ile Leu Phe Leu Val Ala Ala Ala Thr Arg Val
1               5                   10                  15

His Ser Glu Lys Glu Cys Cys Pro Pro Trp Ser Gly Asp Arg Ser Pro
            20                  25                  30

Cys Gly Gln Leu Ser Gly Arg Gly Ser Cys Gln Asn Ile Leu Leu Ser
        35                  40                  45

Asn Ala Pro Leu Gly Pro Gln Phe Pro Phe Thr Gly Val Asp Asp Arg
    50                  55                  60

Glu Ser Trp Pro Ser Val Phe Tyr Asn Arg Thr Cys Gln Cys Ser Gly
65                  70                  75                  80

-continued

Asn Phe Met Gly Phe Asn Cys Gly Asn Cys Lys Phe Gly Phe Trp Gly
                85                  90                  95
Pro Asn Cys Thr Glu Arg Arg Leu Leu Val Arg Arg Asn Ile Phe Asp
            100                 105                 110
Leu Ser Ala Pro Glu Lys Asp Lys Phe Phe Ala Tyr Leu Thr Leu Ala
        115                 120                 125
Lys His Thr Ile Ser Ser Asp Tyr Val Ile Pro Ile Gly Thr Tyr Gly
    130                 135                 140
Gln Met Lys Asn Gly Ser Thr Pro Met Phe Asn Asp Ile Asn Ile Tyr
145                 150                 155                 160
Asp Leu Phe Val Trp Met His Tyr Tyr Val Ser Met Asp Ala Leu Leu
                165                 170                 175
Gly Gly Ser Glu Ile Trp Arg Asp Ile Asp Phe Ala His Glu Ala Pro
            180                 185                 190
Ala Phe Leu Pro Trp His Arg Leu Phe Leu Leu Arg Trp Glu Gln Glu
        195                 200                 205
Ile Gln Lys Leu Thr Gly Asp Glu Asn Phe Thr Ile Pro Tyr Trp Asp
    210                 215                 220
Trp Arg Asp Ala Glu Lys Cys Asp Ile Cys Thr Asp Glu Tyr Met Gly
225                 230                 235                 240
Gly Gln His Pro Thr Asn Pro Asn Leu Leu Ser Pro Ala Ser Phe Phe
                245                 250                 255
Ser Ser Trp Gln Ile Val Cys Ser Arg Leu Glu Glu Tyr Asn Ser His
            260                 265                 270
Gln Ser Leu Cys Asn Gly Thr Pro Glu Gly Pro Leu Arg Arg Asn Pro
        275                 280                 285
Gly Asn His Asp Lys Ser Arg Thr Pro Arg Leu Pro Ser Ser Ala Asp
    290                 295                 300
Val Glu Phe Cys Leu Ser Leu Thr Gln Tyr Glu Ser Gly Ser Met Asp
305                 310                 315                 320
Lys Ala Ala Asn Phe Ser Phe Arg Asn Thr Leu Glu Gly Phe Ala Ser
                325                 330                 335
Pro Leu Thr Gly Ile Ala Asp Ala Ser Gln Ser Ser Met His Asn Ala
            340                 345                 350
Leu His Ile Tyr Met Asn Gly Thr Met Ser Gln Val Gln Gly Ser Ala
        355                 360                 365
Asn Asp Pro Ile Phe Leu Leu His His Ala Phe Val Asp Ser Ile Phe
    370                 375                 380
Glu Gln Trp Leu Arg Arg His Arg Pro Leu Gln Glu Val Tyr Pro Glu
385                 390                 395                 400
Ala Asn Ala Pro Ile Gly His Asn Arg Glu Ser Tyr Met Val Pro Phe
                405                 410                 415
Ile Pro Leu Tyr Arg Asn Gly Asp Phe Phe Ile Ser Ser Lys Asp Leu
            420                 425                 430
Gly Tyr Asp Tyr Ser Tyr Leu Gln Asp Ser Asp Pro Asp Ser Phe Gln
        435                 440                 445
Asp Tyr Ile Lys Ser Tyr Leu Glu Gln Ala Ser Arg Ile Trp Ser Trp
    450                 455                 460
Leu Leu Gly Ala Ala Met Val Gly Ala Val Thr Ala Leu Leu Ala
465                 470                 475                 480
Gly Leu Val Ser Leu Leu Cys Arg His Lys Arg Lys Gln Leu Pro Glu
                485                 490                 495
Glu Lys Gln Pro Leu Leu Met Glu Lys Glu Asp Tyr His Ser Leu Leu

```
                  500             505             510
Tyr Gln Thr His Leu
        515

<210> SEQ ID NO 3
<211> LENGTH: 1668
<212> TYPE: DNA
<213> ORGANISM: Artificial Sequence
<220> FEATURE:
<223> OTHER INFORMATION: Consensus Tyrosinase-related protein 1

<400> SEQUENCE: 3
atggactgga cctggattct gttcctggtc gccgccgcaa cccgcgtgca ttcctctgcc      60
ccaaaactgc tgtctctggg atgtatcttc tttccactgc tgctgttcca gcaggcacgc     120
gcccagtttc cacgacagtg cgcaaccgtc gaggccctga ggagcgggat gtgctgtcca     180
gacctgtcac ccgtgagcgg acctggcaca gatcgctgcg gaagctcctc tgggcgggga     240
agatgtgagg ccgtgactgc tgactcacgg ccccacagcc ctcagtaccc acatgatggc     300
agggacgatc gcgaagtgtg gccctgcga ttctttaacc ggacttgcca ctgtaacggc     360
aatttctccg gcataattg cggaaccgt agacctggat ggaggggcgc cgcttgtgac     420
cagcgcgtgc tgatcgtccg gagaaacctg ctggatctgt ctaaggagga agaaccac      480 ttcgtccgag ctctggacat ggcaaagaga accacacatc ctctgtttgt gatcgccacc     540
aggcgcagcg aggaaattct ggggccagat ggaaacacac cccagttcga acatctca      600 atctacaatt atttcgtgtg gacccactac tatagcgtca agaaaacatt cctgggcgtg     660
gggcaggaga gtttcggaga gtggactttt tcacatgagg ccccgctttt ctgacatgg     720 caccggtacc atctgctgag actggaaaag gatatgcagg agatgctgca ggaacctagt     780
ttctcactgc atattggaa ctttgcaaca ggaaaaaacg tgtgcgacat ctgtactgac     840
gatctgatgg gcagcagatc caacttcgat tctacactga tttccccaaa tagcgtgttc     900
agccagtgga gggtggtctg cgactccctg gaggactacg ataccctggg cacccttgtc     960
aattctactg aagatgggcc catccgacgg aaccctgccg aaatgtggc taggccaatg    1020 gtccagcgcc tgcctgagcc acaggacgtg gcccagtgcc tggaagtcgg cctgttcgat    1080
actccccctt tttattctaa cagtacaaac tctttccgca cactgtcga gggctacagt    1140 gaccctaccg ggaaatatga tccagccgtg cggagtctgc acaacctggc tcatctgttc    1200
ctgaatggaa ctggcgggca gacccacctg tccccaaatg accctatttt tgtcctgctg    1260
catactttca ccgacgccgt gtttgatgag tggctgagaa ggtacaacgc agatatcagc    1320
acctttccac tggaaaatgc ccccattggc cacaaccggc agtataatat ggtgcctttc    1380
tggccacccg tcacaaacac tgagatgttt gtgactgctc agacaatct ggggtacacc    1440 tatgaaatcc agtggccctc cagagagttc tctgtgcctg aaatcattgc tattgcagtg    1500
gtcggcgcac tgctgctggt ggccctgatc tttgggaccg ctagctacct gattagggca    1560
cgccgatcca tggacgaggc caaccagccc tgctgacag atcagtacca gtgctatgcc    1620
gaagagtatg aaaagctgca gaaccctaac cagtccgtcg tgtgataa                 1668

<210> SEQ ID NO 4
<211> LENGTH: 554
<212> TYPE: PRT
<213> ORGANISM: Artificial Sequence
<220> FEATURE:
<223> OTHER INFORMATION: Consensus Tyrosinase-related protein 1
```

-continued

```
<400> SEQUENCE: 4

Met Asp Trp Thr Trp Ile Leu Phe Leu Val Ala Ala Thr Arg Val
1               5                   10                  15

His Ser Ser Ala Pro Lys Leu Leu Ser Leu Gly Cys Ile Phe Phe Pro
            20                  25                  30

Leu Leu Leu Phe Gln Gln Ala Arg Ala Gln Phe Pro Arg Gln Cys Ala
        35                  40                  45

Thr Val Glu Ala Leu Arg Ser Gly Met Cys Cys Pro Asp Leu Ser Pro
    50                  55                  60

Val Ser Gly Pro Gly Thr Asp Arg Cys Gly Ser Ser Gly Arg Gly
65                  70                  75                  80

Arg Cys Glu Ala Val Thr Ala Asp Ser Arg Pro His Ser Pro Gln Tyr
                85                  90                  95

Pro His Asp Gly Arg Asp Arg Glu Val Trp Pro Leu Arg Phe Phe
            100                 105                 110

Asn Arg Thr Cys His Cys Asn Gly Asn Phe Ser Gly His Asn Cys Gly
        115                 120                 125

Thr Cys Arg Pro Gly Trp Arg Gly Ala Ala Cys Asp Gln Arg Val Leu
    130                 135                 140

Ile Val Arg Arg Asn Leu Leu Asp Leu Ser Lys Glu Glu Lys Asn His
145                 150                 155                 160

Phe Val Arg Ala Leu Asp Met Ala Lys Arg Thr Thr His Pro Leu Phe
                165                 170                 175

Val Ile Ala Thr Arg Arg Ser Glu Glu Ile Leu Gly Pro Asp Gly Asn
            180                 185                 190

Thr Pro Gln Phe Glu Asn Ile Ser Ile Tyr Asn Tyr Phe Val Trp Thr
        195                 200                 205

His Tyr Tyr Ser Val Lys Lys Thr Phe Leu Gly Val Gly Gln Glu Ser
    210                 215                 220

Phe Gly Glu Val Asp Phe Ser His Glu Gly Pro Ala Phe Leu Thr Trp
225                 230                 235                 240

His Arg Tyr His Leu Leu Arg Leu Glu Lys Asp Met Gln Glu Met Leu
                245                 250                 255

Gln Glu Pro Ser Phe Ser Leu Pro Tyr Trp Asn Phe Ala Thr Gly Lys
            260                 265                 270

Asn Val Cys Asp Ile Cys Thr Asp Asp Leu Met Gly Ser Arg Ser Asn
        275                 280                 285

Phe Asp Ser Thr Leu Ile Ser Pro Asn Ser Val Phe Ser Gln Trp Arg
    290                 295                 300

Val Val Cys Asp Ser Leu Glu Asp Tyr Asp Thr Leu Gly Thr Leu Cys
305                 310                 315                 320

Asn Ser Thr Glu Asp Gly Pro Ile Arg Arg Asn Pro Ala Gly Asn Val
                325                 330                 335

Ala Arg Pro Met Val Gln Arg Leu Pro Glu Pro Gln Asp Val Ala Gln
            340                 345                 350

Cys Leu Glu Val Gly Leu Phe Asp Thr Pro Pro Phe Tyr Ser Asn Ser
        355                 360                 365

Thr Asn Ser Phe Arg Asn Thr Val Glu Gly Tyr Ser Asp Pro Thr Gly
    370                 375                 380

Lys Tyr Asp Pro Ala Val Arg Ser Leu His Asn Leu Ala His Leu Phe
385                 390                 395                 400

Leu Asn Gly Thr Gly Gly Gln Thr His Leu Ser Pro Asn Asp Pro Ile
                405                 410                 415
```

```
Phe Val Leu Leu His Thr Phe Thr Asp Ala Val Phe Asp Glu Trp Leu
            420                 425                 430

Arg Arg Tyr Asn Ala Asp Ile Ser Thr Phe Pro Leu Glu Asn Ala Pro
        435                 440                 445

Ile Gly His Asn Arg Gln Tyr Asn Met Val Pro Phe Trp Pro Pro Val
    450                 455                 460

Thr Asn Thr Glu Met Phe Val Thr Ala Pro Asp Asn Leu Gly Tyr Thr
465                 470                 475                 480

Tyr Glu Ile Gln Trp Pro Ser Arg Glu Phe Ser Val Pro Glu Ile Ile
                485                 490                 495

Ala Ile Ala Val Val Gly Ala Leu Leu Leu Val Ala Leu Ile Phe Gly
            500                 505                 510

Thr Ala Ser Tyr Leu Ile Arg Ala Arg Arg Ser Met Asp Glu Ala Asn
        515                 520                 525

Gln Pro Leu Leu Thr Asp Gln Tyr Gln Cys Tyr Ala Glu Glu Tyr Glu
    530                 535                 540

Lys Leu Gln Asn Pro Asn Gln Ser Val Val
545                 550

<210> SEQ ID NO 5
<211> LENGTH: 1614
<212> TYPE: DNA
<213> ORGANISM: Artificial Sequence
<220> FEATURE:
<223> OTHER INFORMATION: Consensus Tyrosinase-related protein 2

<400> SEQUENCE: 5
atggactgga cctggattct gttcctggtc gccgctgcta cccgcgtgca ttcatctcct      60
ctgtggtggg gatttctgct gtcttgcctg ggatgcaaga tcctgccagg agcacaggga     120
cagttccccc gggtgtgcat gaccgtcgac tctctggtga caaagagtg ctgtcctagg      180 ctgggagccg aaagcgccaa cgtgtgcggc tcccagcagg acgaggaca gtgtactgag      240 gtgcgcgcag ataccegacc atggagtgga ccctacattc tgaggaacca ggacgatcgc     300
gaactgtggc ccgaaagtt ctttcaccgg acatgcaaat gtactggaaa cttcgccggc      360
tataattgcg gggactgtaa gtttggctgg accgggccca actgcgagag aaagaaaccc     420
cctgtgatca gcagaatat tcattctctg agtcctcagg agcgggaaca gttcctgggc      480
gcactggacc tggccaagaa aagagtccac ccagattacg tgatcaccac acagcattgg     540
ctgggactgc tgggccctaa cgggacacag ccacagtttg ccaattgctc cgtctatgac     600
ttcttcgtgt ggctgcacta ctattctgtg cgggatacac tgctgggacc aggccgaccc     660
taccgagcaa tcgacttcag ccatcaggga ccagcctttg tgacttggca cagatatcat     720
ctgctgtgcc tggagcggga tctgcagaga ctgattggca cgaatccttc gctctgccc      780 tactggaact tgcaaccgg gcggaatgag tgcgacgtgt gcacagatca gctgttcgga     840
gccgctagac ctgacgatcc aactctgatc tcaagaaata gcaggtttag ctcctgggag     900
accgtctgcg actctctgga cgattacaac cacctggtga ccctgtgcaa tggaacatat     960
gaaggcctgc tgcggagaaa ccagatgggc cgcaatagta tgaagctgcc caccctgaaa    1020
gacattcgag attgtctgtc actgcagaag ttcgacaacc caccttctt tcagaattcc     1080 accttctctt ttaggaacgc cctggagggg tttgacaaag ctgatggaac actggatagt    1140
caggtcatgt cactgcacaa cctggtgcat tcattcctga cgggactaa tgccctgcct     1200 cacagcgcag ccaatgaccc aatctttgtg gtcctgcata gcttcaccga cgctatttt     1260
```

```
gatgagtgga tgaagaggtt caaccctcca gctgatgcat ggccccagga actggcacct    1320
atcggacaca accgcatgta caatatggtc cccttctttc ccctgtgac  aaatgaggaa    1380 ctgtttctga cttctgacca gctgggctac agttatgcta ttgatctgcc cgtgagcgtc    1440
gaggaaacac ccgggtggcc tactaccctg ctggtggtca tgggcactct ggtggctctg    1500
gtcgggctgt tcgtgctgct ggcatttctg cagtataggc gcctgcgcaa aggatacacc    1560
ccactgatgg aaacccacct gtcctccaag agatacaccg aagaagcatg ataa          1614
```

<210> SEQ ID NO 6
<211> LENGTH: 536
<212> TYPE: PRT
<213> ORGANISM: Artificial Sequence
<220> FEATURE:
<223> OTHER INFORMATION: Consensus Tyrosinase-related protein 2

<400> SEQUENCE: 6

```
Met Asp Trp Thr Trp Ile Leu Phe Leu Val Ala Ala Thr Arg Val
1               5                   10                  15

His Ser Ser Pro Leu Trp Trp Gly Phe Leu Leu Ser Cys Leu Gly Cys
                20                  25                  30

Lys Ile Leu Pro Gly Ala Gln Gly Gln Phe Pro Arg Val Cys Met Thr
                35                  40                  45

Val Asp Ser Leu Val Asn Lys Glu Cys Cys Pro Arg Leu Gly Ala Glu
    50                  55                  60

Ser Ala Asn Val Cys Gly Ser Gln Gln Gly Arg Gly Gln Cys Thr Glu
65                  70                  75                  80

Val Arg Ala Asp Thr Arg Pro Trp Ser Gly Pro Tyr Ile Leu Arg Asn
                    85                  90                  95

Gln Asp Asp Arg Glu Leu Trp Pro Arg Lys Phe Phe His Arg Thr Cys
                100                 105                 110

Lys Cys Thr Gly Asn Phe Ala Gly Tyr Asn Cys Gly Asp Cys Lys Phe
            115                 120                 125

Gly Trp Thr Gly Pro Asn Cys Glu Arg Lys Lys Pro Pro Val Ile Arg
        130                 135                 140

Gln Asn Ile His Ser Leu Ser Pro Gln Glu Arg Glu Gln Phe Leu Gly
145                 150                 155                 160

Ala Leu Asp Leu Ala Lys Lys Arg Val His Pro Asp Tyr Val Ile Thr
                165                 170                 175

Thr Gln His Trp Leu Gly Leu Leu Gly Pro Asn Gly Thr Gln Pro Gln
                180                 185                 190

Phe Ala Asn Cys Ser Val Tyr Asp Phe Phe Val Trp Leu His Tyr Tyr
            195                 200                 205

Ser Val Arg Asp Thr Leu Leu Gly Pro Gly Arg Pro Tyr Arg Ala Ile
        210                 215                 220

Asp Phe Ser His Gln Gly Pro Ala Phe Val Thr Trp His Arg Tyr His
225                 230                 235                 240

Leu Leu Cys Leu Glu Arg Asp Leu Gln Arg Leu Ile Gly Asn Glu Ser
                245                 250                 255

Phe Ala Leu Pro Tyr Trp Asn Phe Ala Thr Gly Arg Asn Glu Cys Asp
                260                 265                 270

Val Cys Thr Asp Gln Leu Phe Gly Ala Ala Arg Pro Asp Asp Pro Thr
            275                 280                 285

Leu Ile Ser Arg Asn Ser Arg Phe Ser Ser Trp Glu Thr Val Cys Asp
        290                 295                 300
```

Ser Leu Asp Asp Tyr Asn His Leu Val Thr Leu Cys Asn Gly Thr Tyr
305                 310                 315                 320

Glu Gly Leu Leu Arg Arg Asn Gln Met Gly Arg Asn Ser Met Lys Leu
            325                 330                 335

Pro Thr Leu Lys Asp Ile Arg Asp Cys Leu Ser Leu Gln Lys Phe Asp
        340                 345                 350

Asn Pro Pro Phe Phe Gln Asn Ser Thr Phe Ser Phe Arg Asn Ala Leu
    355                 360                 365

Glu Gly Phe Asp Lys Ala Asp Gly Thr Leu Asp Ser Gln Val Met Ser
370                 375                 380

Leu His Asn Leu Val His Ser Phe Leu Asn Gly Thr Asn Ala Leu Pro
385                 390                 395                 400

His Ser Ala Ala Asn Asp Pro Ile Phe Val Val Leu His Ser Phe Thr
                405                 410                 415

Asp Ala Ile Phe Asp Glu Trp Met Lys Arg Phe Asn Pro Pro Ala Asp
            420                 425                 430

Ala Trp Pro Gln Glu Leu Ala Pro Ile Gly His Asn Arg Met Tyr Asn
        435                 440                 445

Met Val Pro Phe Phe Pro Pro Val Thr Asn Glu Glu Leu Phe Leu Thr
    450                 455                 460

Ser Asp Gln Leu Gly Tyr Ser Tyr Ala Ile Asp Leu Pro Val Ser Val
465                 470                 475                 480

Glu Glu Thr Pro Gly Trp Pro Thr Thr Leu Leu Val Val Met Gly Thr
                485                 490                 495

Leu Val Ala Leu Val Gly Leu Phe Val Leu Leu Ala Phe Leu Gln Tyr
            500                 505                 510

Arg Arg Leu Arg Lys Gly Tyr Thr Pro Leu Met Glu Thr His Leu Ser
        515                 520                 525

Ser Lys Arg Tyr Thr Glu Glu Ala
    530                 535

<210> SEQ ID NO 7
<211> LENGTH: 1008
<212> TYPE: DNA
<213> ORGANISM: Artificial Sequence
<220> FEATURE:
<223> OTHER INFORMATION: Consensus Melanoma-associated antigen 4

<400> SEQUENCE: 7
atggattgga catgattct gttcctggtc gccgccgcaa ctagagtgca ttcatcatca      60
gagcagaagt cacagcattg taaacctgag gaaggcgtcg aggctcagga ggaagcactg     120
ggactggtgg gagctcaggc accaaccaca gaggaacagg aggccgctgt gagctcctct     180
agtccactgg tccccggcac tctggaggaa gtgcctgcag cagagagcgc cggaccccct     240
cagagtccac agggagcctc agctctgccc actaccatca gcttcacatg ctggaggcag     300
cctaacgagg gctcaagctc ccaggaggaa gaggggcctt ctactagtcc agacgcagag     360
agcctgttcc gggaagccct gtccaataag gtggatgagc tggcccactt tctgctgcgg     420
aagtacagag ctaaagaact ggtcaccaaa gcagagatgc tggaacgagt gatcaagaac     480
tataaacggt gcttccctgt gattttttgga aaggcctcag agagcctgaa atgatcttc     540 ggcattgacg tgaaggaagt cgatccagct tctaatacat acactctggt gacatgtctg     600
ggcctgagtt atgacggact gctgggcaac aatcagattt ttcccaaaac cgggctgctg     660
atcattgtgc tgggcacaat cgccatggag ggggattccg cttctgaaga ggaaatttgg     720

```
gaggaactgg gcgtgatggg agtctacgac gggcgcgagc acaccgtgta cggagaacca    780
cgaaagctgc tgacccagga ttgggtccag gagaactacc tggaatatcg gcaggtgccc    840
gggtccaatc ctgcaagata cgagtttctg tggggaccca gggcactggc cgagacatct    900
tatgtgaaag tcctggaaca tgtggtcagg gtgaacgctc gcgtgcgaat tgcctaccca    960
agcctgcgcg aagccgctct gctggaagaa gaggaaggag tgtgataa               1008
```

<210> SEQ ID NO 8
<211> LENGTH: 334
<212> TYPE: PRT
<213> ORGANISM: Artificial Sequence
<220> FEATURE:
<223> OTHER INFORMATION: Consensus Melanoma-associated antigen 4

<400> SEQUENCE: 8

```
Met Asp Trp Thr Trp Ile Leu Phe Leu Val Ala Ala Thr Arg Val
1               5                   10                  15

His Ser Ser Glu Gln Lys Ser Gln His Cys Lys Pro Glu Glu Gly
                20                  25                  30

Val Glu Ala Gln Glu Glu Ala Leu Gly Leu Val Gly Ala Gln Ala Pro
                35                  40                  45

Thr Thr Glu Glu Gln Glu Ala Ala Val Ser Ser Ser Ser Pro Leu Val
50                  55                  60

Pro Gly Thr Leu Glu Glu Val Pro Ala Ala Glu Ser Ala Gly Pro Pro
65                  70                  75                  80

Gln Ser Pro Gln Gly Ala Ser Ala Leu Pro Thr Thr Ile Ser Phe Thr
                85                  90                  95

Cys Trp Arg Gln Pro Asn Glu Gly Ser Ser Ser Gln Glu Glu Glu Gly
                100                 105                 110

Pro Ser Thr Ser Pro Asp Ala Glu Ser Leu Phe Arg Glu Ala Leu Ser
                115                 120                 125

Asn Lys Val Asp Glu Leu Ala His Phe Leu Leu Arg Lys Tyr Arg Ala
                130                 135                 140

Lys Glu Leu Val Thr Lys Ala Glu Met Leu Glu Arg Val Ile Lys Asn
145                 150                 155                 160

Tyr Lys Arg Cys Phe Pro Val Ile Phe Gly Lys Ala Ser Glu Ser Leu
                165                 170                 175

Lys Met Ile Phe Gly Ile Asp Val Lys Glu Val Asp Pro Ala Ser Asn
                180                 185                 190

Thr Tyr Thr Leu Val Thr Cys Leu Gly Leu Ser Tyr Asp Gly Leu Leu
                195                 200                 205

Gly Asn Asn Gln Ile Phe Pro Lys Thr Gly Leu Leu Ile Ile Val Leu
                210                 215                 220

Gly Thr Ile Ala Met Glu Gly Asp Ser Ala Ser Glu Glu Glu Ile Trp
225                 230                 235                 240

Glu Glu Leu Gly Val Met Gly Val Tyr Asp Gly Arg Glu His Thr Val
                245                 250                 255

Tyr Gly Glu Pro Arg Lys Leu Leu Thr Gln Asp Trp Val Gln Glu Asn
                260                 265                 270

Tyr Leu Glu Tyr Arg Gln Val Pro Gly Ser Asn Pro Ala Arg Tyr Glu
                275                 280                 285

Phe Leu Trp Gly Pro Arg Ala Leu Ala Glu Thr Ser Tyr Val Lys Val
                290                 295                 300

Leu Glu His Val Val Arg Val Asn Ala Arg Val Arg Ile Ala Tyr Pro
```

```
                    305                 310                 315                 320
Ser Leu Arg Glu Ala Ala Leu Leu Glu Glu Glu Gly Val
                325                 330

<210> SEQ ID NO 9
<211> LENGTH: 381
<212> TYPE: DNA
<213> ORGANISM: Artificial Sequence
<220> FEATURE:
<223> OTHER INFORMATION: Consensus Growth hormone releasing hormone

<400> SEQUENCE: 9
atggactgga cctggattct gttcctggtg gctgccgcaa ctcgcgtgca ttctcctctg    60
tgggtgttct tctttgtgat tctgactctg tctaacagct cccactgcag tccccctcca   120
cccctgaccc tgcgaatgcg gagatacgcc gacgctatct tcacaaattc ctatagaaag   180
gtgctgggac agctgtctgc taggaaactg ctgcaggata ttatgtcacg ccagcagggc   240
gagagcaacc aggaacgagg cgcaagggcc cgactgggcc ggcaggtcga cagcatgtgg   300
gccgagcaga agcagatgga actggaaagc atcctggtcg cactgctgca gaaacatagc   360
cgaaatagcc agggatgata a                                             381

<210> SEQ ID NO 10
<211> LENGTH: 125
<212> TYPE: PRT
<213> ORGANISM: Artificial Sequence
<220> FEATURE:
<223> OTHER INFORMATION: Consensus Growth hormone releasing hormone

<400> SEQUENCE: 10

Met Asp Trp Thr Trp Ile Leu Phe Leu Val Ala Ala Thr Arg Val
1               5                   10                  15

His Ser Pro Leu Trp Val Phe Phe Val Ile Leu Thr Leu Ser Asn
                20                  25                  30

Ser Ser His Cys Ser Pro Pro Pro Leu Thr Leu Arg Met Arg Arg
            35                  40                  45

Tyr Ala Asp Ala Ile Phe Thr Asn Ser Tyr Arg Lys Val Leu Gly Gln
50                  55                  60

Leu Ser Ala Arg Lys Leu Leu Gln Asp Ile Met Ser Arg Gln Gln Gly
65                  70                  75                  80

Glu Ser Asn Gln Glu Arg Gly Ala Arg Ala Arg Leu Gly Arg Gln Val
                85                  90                  95

Asp Ser Met Trp Ala Glu Gln Lys Gln Met Glu Leu Glu Ser Ile Leu
            100                 105                 110

Val Ala Leu Leu Gln Lys His Ser Arg Asn Ser Gln Gly
        115                 120                 125

<210> SEQ ID NO 11
<211> LENGTH: 411
<212> TYPE: DNA
<213> ORGANISM: Artificial Sequence
<220> FEATURE:
<223> OTHER INFORMATION: Consensus Melan-A

<400> SEQUENCE: 11
atggactgga catggattct gttcctggtc gctgctgcta caagggtgca ttccccacgg    60
gaggacgccc acttcatcta tggataccca aagaaaggcc acggcattc ttacaccaca   120 gctgaggaag ccgctggaat cggcattctg acagtgatcc tggggtcct gctgctgatt   180
```

-continued

| | |
|---|---|
| ggatgctggt actgtcggag aaggaacggc tatagagcac tgatggacaa gagcctgcac | 240 |
| gtgggaactc agtgcgcact gacccgccga tgtccacagg agggattcga ccatcgggat | 300 |
| agcaaggtct ccctgcagga gaaaaattgc gaacccgtgg tccctaatgc cccacccgct | 360 |
| tacgaaaaac tgtccgcaga gcagagccca ccaccttatt caccttgata a | 411 |

<210> SEQ ID NO 12
<211> LENGTH: 135
<212> TYPE: PRT
<213> ORGANISM: Artificial Sequence
<220> FEATURE:
<223> OTHER INFORMATION: Consensus Melan-A

<400> SEQUENCE: 12

Met Asp Trp Thr Trp Ile Leu Phe Leu Val Ala Ala Thr Arg Val
1               5                   10                  15

His Ser Pro Arg Glu Asp Ala His Phe Ile Tyr Gly Tyr Pro Lys Lys
            20                  25                  30

Gly His Gly His Ser Tyr Thr Thr Ala Glu Glu Ala Ala Gly Ile Gly
        35                  40                  45

Ile Leu Thr Val Ile Leu Gly Val Leu Leu Leu Ile Gly Cys Trp Tyr
    50                  55                  60

Cys Arg Arg Arg Asn Gly Tyr Arg Ala Leu Met Asp Lys Ser Leu His
65                  70                  75                  80

Val Gly Thr Gln Cys Ala Leu Thr Arg Arg Cys Pro Gln Glu Gly Phe
                85                  90                  95

Asp His Arg Asp Ser Lys Val Ser Leu Gln Glu Lys Asn Cys Glu Pro
            100                 105                 110

Val Val Pro Asn Ala Pro Pro Ala Tyr Glu Lys Leu Ser Ala Glu Gln
        115                 120                 125

Ser Pro Pro Pro Tyr Ser Pro
    130                 135

<210> SEQ ID NO 13
<211> LENGTH: 597
<212> TYPE: DNA
<213> ORGANISM: Artificial Sequence
<220> FEATURE:
<223> OTHER INFORMATION: Consensus NY-ESO-1

<400> SEQUENCE: 13

| | |
|---|---|
| atggactgga catggattct gtttctggtg gctgccgcaa ctagagtgca ttcacaggcc | 60 |
| gctggacagg gaactggagg ctcaaccgga gacgcagatg ccctggcgg gccaggggtg | 120 |
| cccgacggac ctggaggcaa cgctggggga cccggggagg ccggagctac aggcgggga | 180 |
| ggccctcagg gagccggcgc cgccagagcc agcggacccc ggggcggggc accccggggg | 240 |
| cctcacggcg gggcagcatc aggcctgaat ggatgctgtc gatgcggagc acggagacct | 300 |
| gagagcaggc tgctggaatt ctacctgact atgccttttg ccaccccaat ggaggcagaa | 360 |
| ctggcaaggc gctccctggc tcgggacgca ccccctctgc cagtgcccgg cgtcctgctg | 420 |
| aaggaattca ccgtctctgg caacatcctg accattaggc tgacagctgc agatcatcgc | 480 |
| cagctgcagc tgtctatcag ctcctgtctg cagcagctga gtctgctgat gtggattacc | 540 |
| cagtgctttc tgcccgtctt cctggctcag cctccttccg acagcgccg atgataa | 597 |

<210> SEQ ID NO 14
<211> LENGTH: 197
<212> TYPE: PRT

-continued

<213> ORGANISM: Artificial Sequence
<220> FEATURE:
<223> OTHER INFORMATION: Consensus NY-ESO-1

<400> SEQUENCE: 14

Met Asp Trp Thr Trp Ile Leu Phe Leu Val Ala Ala Thr Arg Val
1               5                   10                  15

His Ser Gln Ala Ala Gly Gln Gly Thr Gly Gly Ser Thr Gly Asp Ala
            20                  25                  30

Asp Gly Pro Gly Gly Pro Gly Val Pro Asp Gly Pro Gly Gly Asn Ala
        35                  40                  45

Gly Gly Pro Gly Glu Ala Gly Ala Thr Gly Gly Gly Pro Gln Gly
    50                  55                  60

Ala Gly Ala Ala Arg Ala Ser Gly Pro Arg Gly Gly Ala Pro Arg Gly
65              70                  75                  80

Pro His Gly Gly Ala Ala Ser Gly Leu Asn Gly Cys Cys Arg Cys Gly
            85                  90                  95

Ala Arg Arg Pro Glu Ser Arg Leu Leu Glu Phe Tyr Leu Thr Met Pro
            100                 105                 110

Phe Ala Thr Pro Met Glu Ala Glu Leu Ala Arg Arg Ser Leu Ala Arg
        115                 120                 125

Asp Ala Pro Pro Leu Pro Val Pro Gly Val Leu Leu Lys Glu Phe Thr
    130                 135                 140

Val Ser Gly Asn Ile Leu Thr Ile Arg Leu Thr Ala Ala Asp His Arg
145                 150                 155                 160

Gln Leu Gln Leu Ser Ile Ser Ser Cys Leu Gln Gln Leu Ser Leu Leu
            165                 170                 175

Met Trp Ile Thr Gln Cys Phe Leu Pro Val Phe Leu Ala Gln Pro Pro
            180                 185                 190

Ser Gly Gln Arg Arg
        195

<210> SEQ ID NO 15
<211> LENGTH: 687
<212> TYPE: DNA
<213> ORGANISM: Artificial Sequence
<220> FEATURE:
<223> OTHER INFORMATION: Consensus NY-ESO-2

<400> SEQUENCE: 15
atggactgga catggattct gtttctggtc gccgccgcaa cacgggtgca ttctcaggcc      60
gaggggcagg gaactggagg ctcaaccgga gacgcagatg gacctggcgg gccaggcatc     120
cccgacggac ctggaggcaa cgccggggga cctggggagg ccggagctac aggcgggaga     180
ggcccaaggg gcgcagggc cgctaggcc agtggacccc gcgaggcgc ccacgaggc         240
ccacacgggg gagcagcctc cgcccaggac ggcagatgcc catgtggagc tcggagaccc     300
gattctaggc tgctgcagct gcatatcact atgcccttca gctcccctat ggaggctgaa     360
ctggtgaggc gcattctgtc ccgcgacgct gcacctctgc cacgaccagg ggccgtgctg     420
aaggatttca ccgtctcagg caatctgctg tttatgagcg tccgggacca ggatagagag     480
ggagcaggac gaatgcgagt ggtcggatgg ggactgggct ctgctagtcc tgaaggccag     540
aaagcacgcg atctgcgaac ccccaagcac aaagtgagcg agcagcgccc tggcacacca     600
gggccccctc cacccgaagg cgcccaggga gacggatgta gaggagtcgc cttcaatgtc     660
atgtttagtg caccccatat tgataa                                         687

```
<210> SEQ ID NO 16
<211> LENGTH: 227
<212> TYPE: PRT
<213> ORGANISM: Artificial Sequence
<220> FEATURE:
<223> OTHER INFORMATION: Consensus NY-ESO-2

<400> SEQUENCE: 16

Met Asp Trp Thr Trp Ile Leu Phe Leu Val Ala Ala Thr Arg Val
1               5                   10                  15

His Ser Gln Ala Glu Gly Gln Gly Thr Gly Gly Ser Thr Gly Asp Ala
            20                  25                  30

Asp Gly Pro Gly Gly Pro Gly Ile Pro Asp Gly Pro Gly Gly Asn Ala
        35                  40                  45

Gly Gly Pro Gly Glu Ala Gly Ala Thr Gly Gly Arg Gly Pro Arg Gly
    50                  55                  60

Ala Gly Ala Ala Arg Ala Ser Gly Pro Arg Gly Gly Ala Pro Arg Gly
65                  70                  75                  80

Pro His Gly Gly Ala Ala Ser Ala Gln Asp Gly Arg Cys Pro Cys Gly
                85                  90                  95

Ala Arg Arg Pro Asp Ser Arg Leu Leu Gln Leu His Ile Thr Met Pro
            100                 105                 110

Phe Ser Ser Pro Met Glu Ala Glu Leu Val Arg Arg Ile Leu Ser Arg
        115                 120                 125

Asp Ala Ala Pro Leu Pro Arg Pro Gly Ala Val Leu Lys Asp Phe Thr
    130                 135                 140

Val Ser Gly Asn Leu Leu Phe Met Ser Val Arg Asp Gln Asp Arg Glu
145                 150                 155                 160

Gly Ala Gly Arg Met Arg Val Val Gly Trp Gly Leu Gly Ser Ala Ser
                165                 170                 175

Pro Glu Gly Gln Lys Ala Arg Asp Leu Arg Thr Pro Lys His Lys Val
            180                 185                 190

Ser Glu Gln Arg Pro Gly Thr Pro Gly Pro Pro Pro Glu Gly Ala
        195                 200                 205

Gln Gly Asp Gly Cys Arg Gly Val Ala Phe Asn Val Met Phe Ser Ala
    210                 215                 220

Pro His Ile
225

<210> SEQ ID NO 17
<211> LENGTH: 1584
<212> TYPE: DNA
<213> ORGANISM: Artificial Sequence
<220> FEATURE:
<223> OTHER INFORMATION: Consensus PRAME

<400> SEQUENCE: 17
atggactgga catgattct gttcctggtc gctgctgcta cacgggtgca ttcagagaga      60
cgaagactgc ggggctcaat tcagagtagg tacatcagta tgtcagtctg gacctcacca    120
cggagactgg tggaactggc cgggcagagc ctgctgaagg atgaggccct ggctattgcc    180
gctctggaac tgctgccccg agagctgttc cctcccctgt tcatggcagc cttcgacgga    240
cgccacagcc agactctgaa ggctatggtc caggcatggc cctttacctg cctgcctctg    300
ggcgtgctga tgaaggggca gcagctgcat ctggagactt tcaaagcagt gctggatggc    360
ctggacgtgc tgctggccca ggaagtgagg cctaggcgct ggaagctgga ggtcctggat    420
```

```
ctgcgcaaaa acagccacca ggacttttgg accgtgtggt ccgggaatcg ggccagtctg    480
tactcattcc cagaacccga ggctgcacag ccaatgcgga agaaaagaaa ggtggatgga    540
ctgtccaccg aagctgagca gccttttaca ccaatcgaag tgctggtcga tctgtccctg    600
aaagaaggcg catgcgacga gctgttctct tatctgatgg agaaggtcaa agacagaag    660 aacgtgctgc acctgtgctg taagaaactg aaaatctttg ctatgcccat gcaggacatc    720
aagatgattc tgaaaatggt ccagctggat tccattgaag acctggaggt cacttgtacc    780
tggaagctgc aacactggc caaattctct ccctacctgg acagatgat caatctgcga    840 cggctgctgc tgtctcacat ccatgctagc tcctctatta gtcctgagaa ggaggaagag    900
tacattgcac agtttacttc tcagttcctg agtctgcagt gcctgcaggc cctgtatgtg    960
gatagcctgt tctttctgag aggcaggctg gaccagctgc tgcgacacgt catgaacccc   1020
ctggaaacac tgagtgtgac taattgtaga ctgtcagagg gcgatgtgat gcatctgagc   1080
cagtccccta acgtgagcca gctgccgtc tgtctctga gtggcgtgat gctgacagac   1140
gtgagccctg aaccactgca ggccctgctg gagcgagcat ctgccactct gcaggacctg   1200
gattttgacg agtgtgggat catggacgat cagctgctgg tgctgctgcc ttcactgagc   1260
cactgctccc agctgaccac actgtctttc tgtgggaacc caatctccat ttctgtgctg   1320
cagaatctgc tgcaccatct gattggactg agcaacctga cccatgtgct gtaccccgtc   1380
cctctggaaa gctatgagga tgtgcacgga acactgcatc tgggcaggct ggcctatctg   1440
cacgctcgcc tgcgagaact gctgtgcgag ctgggcagac cctcaatggt gtggctgagc   1500
gccaatccat gtccccattg cggcgaccgg acattctacg accccgaacc tattctgtgc   1560
ccctgcttca tgcctaactg ataa                                          1584
```

<210> SEQ ID NO 18
<211> LENGTH: 526
<212> TYPE: PRT
<213> ORGANISM: Artificial Sequence
<220> FEATURE:
<223> OTHER INFORMATION: Consensus PRAME

<400> SEQUENCE: 18

```
Met Asp Trp Thr Trp Ile Leu Phe Leu Val Ala Ala Thr Arg Val
1               5                   10                  15

His Ser Glu Arg Arg Leu Arg Gly Ser Ile Gln Ser Arg Tyr Ile
            20                  25                  30

Ser Met Ser Val Trp Thr Ser Pro Arg Arg Leu Val Glu Leu Ala Gly
            35                  40                  45

Gln Ser Leu Leu Lys Asp Glu Ala Leu Ala Ile Ala Ala Leu Glu Leu
    50                  55                  60

Leu Pro Arg Glu Leu Phe Pro Pro Leu Phe Met Ala Ala Phe Asp Gly
65                  70                  75                  80

Arg His Ser Gln Thr Leu Lys Ala Met Val Gln Ala Trp Pro Phe Thr
                85                  90                  95

Cys Leu Pro Leu Gly Val Leu Met Lys Gly Gln Gln Leu His Leu Glu
                100                 105                 110

Thr Phe Lys Ala Val Leu Asp Gly Leu Asp Val Leu Leu Ala Gln Glu
            115                 120                 125

Val Arg Pro Arg Arg Trp Lys Leu Glu Val Leu Asp Leu Arg Lys Asn
    130                 135                 140

Ser His Gln Asp Phe Trp Thr Val Trp Ser Gly Asn Arg Ala Ser Leu
145                 150                 155                 160
```

Tyr Ser Phe Pro Glu Pro Glu Ala Ala Gln Pro Met Arg Lys Lys Arg
                165                 170                 175

Lys Val Asp Gly Leu Ser Thr Glu Ala Glu Gln Pro Phe Thr Pro Ile
            180                 185                 190

Glu Val Leu Val Asp Leu Ser Leu Lys Glu Gly Ala Cys Asp Glu Leu
        195                 200                 205

Phe Ser Tyr Leu Met Glu Lys Val Lys Arg Gln Lys Asn Val Leu His
    210                 215                 220

Leu Cys Cys Lys Lys Leu Lys Ile Phe Ala Met Pro Met Gln Asp Ile
225                 230                 235                 240

Lys Met Ile Leu Lys Met Val Gln Leu Asp Ser Ile Glu Asp Leu Glu
                245                 250                 255

Val Thr Cys Thr Trp Lys Leu Pro Thr Leu Ala Lys Phe Ser Pro Tyr
            260                 265                 270

Leu Gly Gln Met Ile Asn Leu Arg Arg Leu Leu Leu Ser His Ile His
        275                 280                 285

Ala Ser Ser Ser Ile Ser Pro Glu Lys Glu Glu Glu Tyr Ile Ala Gln
        290                 295                 300

Phe Thr Ser Gln Phe Leu Ser Leu Gln Cys Leu Gln Ala Leu Tyr Val
305                 310                 315                 320

Asp Ser Leu Phe Phe Leu Arg Gly Arg Leu Asp Gln Leu Leu Arg His
                325                 330                 335

Val Met Asn Pro Leu Glu Thr Leu Ser Val Thr Asn Cys Arg Leu Ser
            340                 345                 350

Glu Gly Asp Val Met His Leu Ser Gln Ser Pro Asn Val Ser Gln Leu
        355                 360                 365

Ser Val Leu Ser Leu Ser Gly Val Met Leu Thr Asp Val Ser Pro Glu
    370                 375                 380

Pro Leu Gln Ala Leu Leu Glu Arg Ala Ser Ala Thr Leu Gln Asp Leu
385                 390                 395                 400

Asp Phe Asp Glu Cys Gly Ile Met Asp Asp Gln Leu Leu Val Leu Leu
                405                 410                 415

Pro Ser Leu Ser His Cys Ser Gln Leu Thr Thr Leu Ser Phe Cys Gly
            420                 425                 430

Asn Pro Ile Ser Ile Ser Val Leu Gln Asn Leu Leu His His Leu Ile
        435                 440                 445

Gly Leu Ser Asn Leu Thr His Val Leu Tyr Pro Val Pro Leu Glu Ser
    450                 455                 460

Tyr Glu Asp Val His Gly Thr Leu His Leu Gly Arg Leu Ala Tyr Leu
465                 470                 475                 480

His Ala Arg Leu Arg Glu Leu Leu Cys Glu Leu Gly Arg Pro Ser Met
                485                 490                 495

Val Trp Leu Ser Ala Asn Pro Cys Pro His Cys Gly Asp Arg Thr Phe
            500                 505                 510

Tyr Asp Pro Glu Pro Ile Leu Cys Pro Cys Phe Met Pro Asn
        515                 520                 525

<210> SEQ ID NO 19
<211> LENGTH: 1332
<212> TYPE: DNA
<213> ORGANISM: Artificial Sequence
<220> FEATURE:
<223> OTHER INFORMATION: Con WT1-L with modified Zinc Fingers nucleic
      acid sequence

<400> SEQUENCE: 19

```
ggatccgcca ccatggactg gacctggatt ctgttcctgg tcgccgccgc aacacgggtg      60
catagtggga gtgatgtgag agacctgaac gccctgctgc cagcagtgcc atccctgcct     120
ggcgggggag gctgcgctct gccagtctct ggagcagctc agtgggctcc cgtgctggac     180
tttgcacccc ctgcagcccc ttacggaagt ctgggcggcc cacactcatt catcaaacag     240
gagccaagct ggggcggggc agatcctcat gaggaacagt gcctgtcagc cttcacagtc     300
cactttagcg ggcagttcac tggaaccgca ggagcttgta gatacggacc ctttggagca     360
ccacccccctt cccaggcacc ttctggacag gcacgcatgt tcccaaacgc tccctatctg     420
cctaattgtc tggaaagcca gcccgctatt aggaaccagg gctactccac agtggcattt     480
gacgggactc ctagctatgg acatacccca tcccaccatg ctgcacagtt tcctaatcac     540
tccttcaagc atgaggaccc catgggacag caggggtccc tgggagaaca gcagtactct     600
gtgccccctc ccgtgtacgg atgccacaca ccaactgaca gttgtacagg ctcacaggcc     660
ctgctgctgc gaactccata acagtgat aatctgtatc agatgacctc acagctggag     720
tgcatgacat ggaaccagat gaatctgggc agcacactga aaggccatgc cactgggtac     780
gaatctgaca ccacaccac acctatgctg tacagttgtg gagcccagta tagaatccac     840
actcatggag tcttcagagg cattcaggat gtgcggagag tcccaggagt ggcaccaact     900
atcgtgcgga gcgcctccga gaccaacgaa aagcgcccct ttatgggcgc ctaccctgga     960
ggcaataagc ggtatttcaa actgtctcac ctgcagatgg ggagtagaaa ggggaccgga    1020
gagaaacctt atcagggcga ctttaaagat ggggaaaggc gcttctctcg cagtgaccag    1080
ctgaagcgag acagcgacg aggaaccggg gtgaagccat tcagtgcaa aacatgtcag    1140
agaaagttct caaggagcga tcacctgaag acccatacaa gaactcacac cggcaagacc    1200
agcgagaaac cattttcctg ccgatggccc tcttgtcaga gaaattcgc ccgctccgac    1260
gaactggtcc gacaccacaa tatgcatcag agaaatatga caaaactgca gctggctctg    1320
tgataactcg ag                                                        1332
```

<210> SEQ ID NO 20
<211> LENGTH: 436
<212> TYPE: PRT
<213> ORGANISM: Artificial Sequence
<220> FEATURE:
<223> OTHER INFORMATION: Con WT1-L with modified Zinc Fingers protein sequence

<400> SEQUENCE: 20

```
Met Asp Trp Thr Trp Ile Leu Phe Leu Val Ala Ala Ala Thr Arg Val
1               5                   10                  15

His Ser Gly Ser Asp Val Arg Asp Leu Asn Ala Leu Leu Pro Ala Val
            20                  25                  30

Pro Ser Leu Pro Gly Gly Gly Gly Cys Ala Leu Pro Val Ser Gly Ala
        35                  40                  45

Ala Gln Trp Ala Pro Val Leu Asp Phe Ala Pro Pro Ala Pro Tyr
    50                  55                  60

Gly Ser Leu Gly Gly Pro His Ser Phe Ile Lys Gln Glu Pro Ser Trp
65                  70                  75                  80

Gly Gly Ala Asp Pro His Glu Glu Gln Cys Leu Ser Ala Phe Thr Val
            85                  90                  95

His Phe Ser Gly Gln Phe Thr Gly Thr Ala Gly Ala Cys Arg Tyr Gly
            100                 105                 110
```

Pro Phe Gly Ala Pro Pro Ser Gln Ala Pro Ser Gly Gln Ala Arg
        115                 120                 125

Met Phe Pro Asn Ala Pro Tyr Leu Pro Asn Cys Leu Glu Ser Gln Pro
    130                 135                 140

Ala Ile Arg Asn Gln Gly Tyr Ser Thr Val Ala Phe Asp Gly Thr Pro
145                 150                 155                 160

Ser Tyr Gly His Thr Pro Ser His His Ala Ala Gln Phe Pro Asn His
                165                 170                 175

Ser Phe Lys His Glu Asp Pro Met Gly Gln Gln Gly Ser Leu Gly Glu
            180                 185                 190

Gln Gln Tyr Ser Val Pro Pro Val Tyr Gly Cys His Thr Pro Thr
        195                 200                 205

Asp Ser Cys Thr Gly Ser Gln Ala Leu Leu Leu Arg Thr Pro Tyr Asn
    210                 215                 220

Ser Asp Asn Leu Tyr Gln Met Thr Ser Gln Leu Glu Cys Met Thr Trp
225                 230                 235                 240

Asn Gln Met Asn Leu Gly Ser Thr Leu Lys Gly His Ala Thr Gly Tyr
                245                 250                 255

Glu Ser Asp Asn His Thr Thr Pro Met Leu Tyr Ser Cys Gly Ala Gln
            260                 265                 270

Tyr Arg Ile His Thr His Gly Val Phe Arg Gly Ile Gln Asp Val Arg
        275                 280                 285

Arg Val Pro Gly Val Ala Pro Thr Ile Val Arg Ser Ala Ser Glu Thr
    290                 295                 300

Asn Glu Lys Arg Pro Phe Met Gly Ala Tyr Pro Gly Asn Lys Arg
305                 310                 315                 320

Tyr Phe Lys Leu Ser His Leu Gln Met Gly Ser Arg Lys Gly Thr Gly
                325                 330                 335

Glu Lys Pro Tyr Gln Gly Asp Phe Lys Asp Gly Glu Arg Arg Phe Ser
            340                 345                 350

Arg Ser Asp Gln Leu Lys Arg Gly Gln Arg Gly Thr Gly Val Lys
        355                 360                 365

Pro Phe Gln Cys Lys Thr Cys Gln Arg Lys Phe Ser Arg Ser Asp His
    370                 375                 380

Leu Lys Thr His Thr Arg Thr His Thr Gly Lys Thr Ser Glu Lys Pro
385                 390                 395                 400

Phe Ser Cys Arg Trp Pro Ser Cys Gln Lys Lys Phe Ala Arg Ser Asp
                405                 410                 415

Glu Leu Val Arg His His Asn Met His Gln Arg Asn Met Thr Lys Leu
            420                 425                 430

Gln Leu Ala Leu
        435

<210> SEQ ID NO 21
<211> LENGTH: 954
<212> TYPE: DNA
<213> ORGANISM: Artificial Sequence
<220> FEATURE:
<223> OTHER INFORMATION: Con WT1-S without Zinc fingers nucleic acid
      sequence

<400> SEQUENCE: 21
ggatccgcca ccatggactg gacctggatt ctgtttctgg tggctgctgc tacacgggtg      60
cattctggga gcgatgtgag agacctgaac gccctgctgc agctgtgcc aagtctgcct    120

```
ggcggggggag gctgcgcact gccagtgagc ggagcagctc agtgggctcc cgtcctggac    180
tttgcacccc ctgcagcacc ttacggctca ctgggcggcc acacagctt catcaagcag     240 gagccatctt ggggcggggc cgatcctcac gaggaacagt gcctgagtgc tttcacagtg    300 cattttcag gccagttcac tggaaccgca ggagcttgtc gatacggacc ctttggagcc     360 ccaccccta gccaggcacc ttccggacag gccagaatgt cccaaacgc tccctatctg      420 cctaattgtc tggaatcaca gcctgcaatt cggaaccagg gctacagcac cgtcgccttt    480
gacgggacac atcctatgg acacactccc tctcaccatg ctgcacagtt cctaatcac     540 agcttcaagc atgaggaccc catgggacag caggggagcc tgggagaaca gcagtactcc   600
gtgccacccc ctgtctatgg ctgccataca ccaactgact cttgtacagg gagtcaggcc   660
ctgctgctgc gaactccata caactctgat aatctgtatc agatgactag tcagctggag   720
tgcatgacct ggaaccagat gaatctgggg tccaccctga aggccacgc cacagggtat    780 gaatccgaca accataccac acccatgctg tactcttgtg gcgcccagta tagaatccac    840
acccatggag tgttccgcgg cattcaggat gtgcggagac tcccaggagt cgctcccacc    900
atcgtgagat ccgccagtga gaccaatgaa aagagaccct tctgataact cgag          954
```

<210> SEQ ID NO 22
<211> LENGTH: 310
<212> TYPE: PRT
<213> ORGANISM: Artificial Sequence
<220> FEATURE:
<223> OTHER INFORMATION: Con WT1-S without Zinc fingers protein sequence
<400> SEQUENCE: 22

```
Met Asp Trp Thr Trp Ile Leu Phe Leu Val Ala Ala Thr Arg Val
1               5                   10                  15

His Ser Gly Ser Asp Val Arg Asp Leu Asn Ala Leu Leu Pro Ala Val
            20                  25                  30

Pro Ser Leu Pro Gly Gly Gly Gly Cys Ala Leu Pro Val Ser Gly Ala
        35                  40                  45

Ala Gln Trp Ala Pro Val Leu Asp Phe Ala Pro Pro Ala Ala Pro Tyr
    50                  55                  60

Gly Ser Leu Gly Gly Pro His Ser Phe Ile Lys Gln Glu Pro Ser Trp
65                  70                  75                  80

Gly Gly Ala Asp Pro His Glu Glu Gln Cys Leu Ser Ala Phe Thr Val
                85                  90                  95

His Phe Ser Gly Gln Phe Thr Gly Thr Ala Gly Ala Cys Arg Tyr Gly
            100                 105                 110

Pro Phe Gly Ala Pro Pro Ser Gln Ala Pro Ser Gly Gln Ala Arg
        115                 120                 125

Met Phe Pro Asn Ala Pro Tyr Leu Pro Asn Cys Leu Glu Ser Gln Pro
    130                 135                 140

Ala Ile Arg Asn Gln Gly Tyr Ser Thr Val Ala Phe Asp Gly Thr Pro
145                 150                 155                 160

Ser Tyr Gly His Thr Pro Ser His His Ala Ala Gln Phe Pro Asn His
                165                 170                 175

Ser Phe Lys His Glu Asp Pro Met Gly Gln Gln Gly Ser Leu Gly Glu
            180                 185                 190

Gln Gln Tyr Ser Val Pro Pro Val Tyr Gly Cys His Thr Pro Thr
        195                 200                 205

Asp Ser Cys Thr Gly Ser Gln Ala Leu Leu Leu Arg Thr Pro Tyr Asn
    210                 215                 220
```

```
Ser Asp Asn Leu Tyr Gln Met Thr Ser Gln Leu Glu Cys Met Thr Trp
225                 230                 235                 240

Asn Gln Met Asn Leu Gly Ser Thr Leu Lys Gly His Ala Thr Gly Tyr
            245                 250                 255

Glu Ser Asp Asn His Thr Thr Pro Met Leu Tyr Ser Cys Gly Ala Gln
        260                 265                 270

Tyr Arg Ile His Thr His Gly Val Phe Arg Gly Ile Gln Asp Val Arg
    275                 280                 285

Arg Val Pro Gly Val Ala Pro Thr Ile Val Arg Ser Ala Ser Glu Thr
290                 295                 300

Asn Glu Lys Arg Pro Phe
305                 310

<210> SEQ ID NO 23
<211> LENGTH: 3512
<212> TYPE: DNA
<213> ORGANISM: Artificial Sequence
<220> FEATURE:
<223> OTHER INFORMATION: hTERT

<400> SEQUENCE: 23
ggtaccgaat cgccaccat ggactggacc tggatcctgt tcctggtggc cgctgccaca      60
agagtgcaca gccccagggc ccccaggtgc agagccgtgc ggagcctgct gcggagccac    120
taccgggagg tgctgcccct ggccaccttc gtgcggaggc tgggccctca ggggtggcgg    180
ctggtgcaga gaggcgaccc tgccgccttc agagccctgg tgcccagtg cctggtgtgc    240 gtgccctggg acgccagacc tccccctgcc gccctagct tccggcaggt gtcctgcctg    300
aaagaactgg tggcccgggt gctgcagcgg ctgtgcgaga ggggcgccaa gaacgtgctg    360
gccttcggct tcgccctgct ggacggcgcc agaggcggcc ctcccgaggc cttcaccacc    420
tccgtgagaa gctacctgcc caacaccgtg accgacgccc tgagaggcag cggcgcttgg    480
ggcctgctgc tgcgcagagt gggcgacgac gtgctggtgc acctgctggc cagatgcgcc    540
ctgttcgtgc tggtcgcccc cagctgcgcc taccaggtgt gcggcccacc cctgtaccag    600
ctgggagccg ccacccaggc cagaccccct cctcacgcct ccggcccag gcggagactg    660 ggctgcgagc gggcctggaa ccacagcgtg cgggaggccg gcgtgccct gggcctgcca    720 gccccctggc gccagaagaag gggcggcagc gccagcagaa gctgcccct gcccaagcgg    780 cccagacgcg gagccgcccc tgagcccgag agaaccccg tgggccaggg ctcttgggcc    840 cacccctggcc ggaccagagg ccccagcgac cggggcttct gcgtggtgtc ccccgccaga    900
cccgccgagg aagccacctc cctggaaggc gccctgagcg gcaccaggca cagccacccc    960
agcgtgggcc gccagcacca cgccggaccc ccagcacct ccaggccccc caggccctgg   1020 gacaccccctt gcccccctgt gtacgccgag accaagcact tcctgtacag cagcggcgac   1080
aaagagcagc tgcggcccag cttcctgctg tccagcctga ggccctccct gaccggcgct   1140
aggcgcctgg tggagaccat ctttctgggc agccggccct ggatgccgg caccccccagg   1200 cggctgccca ggctgcccca gcggtactgg cagatgaggc tctgttcct ggaactgctg   1260 ggcaaccacg cccagtgccc ctacggcgtg ctgctgaaaa cccactgccc cctgagagcc   1320
gccgtgaccc cagccgccgg agtgtgcgcc agagagaagc tcagggcag cgtggccgct   1380 cccgaggaag aggacaccga ccccagacgc ctggtgcagc tgctgcggca gcacagcagc   1440
ccttggcagg tgtacggctt cgtgcgggcc tgcctgaaga ggctggtgcc ccctggcctg   1500
```

| | |
|---|---|
| tggggcagca ggcacaacga gcggcggttt ctgcggaaca ccaagaagtt catcagcctg | 1560 |
| gggaagcacg ccaagctgtc cctgcaggaa ctgacctgga agatgagcgt gcggggctgc | 1620 |
| gcctggctga aagatcccc tggcgtgggc tgcgtgcctg ccgccgagca ccggctgcgg | 1680 |
| gaggaaatcc tggccaagtt cctgcactgg ctgatgagcg tgtacgtggt ggagctgctg | 1740 |
| agatccttct tctacgtgac cgagaccacc ttccagaaga actacctgtt cttctaccgg | 1800 |
| aagagcgtgt ggagcaagct gcagagcatc ggcatccggc agcacctgaa gcgggtgcag | 1860 |
| ctgagagagc tgtccgaggc cgaagtgagg cagcaccggg aggccagacc tgccctgctg | 1920 |
| accagccggc tgcggttcat ccccaagccc gacggcctgc ggcccatcgt gaacatggac | 1980 |
| tacgtggtgg gcgccaggac cttccggcgg agaagcgggc cgagcggct gacctcgagg | 2040 |
| gtgaaggccc tgttcagcgt gctgaactac gagcgggcca ggcggccagg cctgctgggc | 2100 |
| gccagcgtgc tgggcctgga cgacatccac cgggcctggc ggaccttcgt gctgagagtg | 2160 |
| cgggcccagg accccctcc cgagctgtac ttcgtgaagg tggacgtgac aggcgcctac | 2220 |
| gacaccatcc cccaggaccg gctgaccgag gtgatcgcca gcatcatcaa gccccagaac | 2280 |
| acctactgcg tgcggagata cgccgtggtg cagaaggccg cccacggcca cgtgcggaag | 2340 |
| gccttcaaga gccacgtgag caccctgacc gacctgcagc cctacatgcg gcagttcgtg | 2400 |
| gcccacctgc aggaaaccag cccctgcgg gatgccgtgg tgatcgagca gagcagcagc | 2460 |
| ctgaacgagg ccagcagcgg cctgttcgac gtgttcctga gattcatgtg ccaccacgcc | 2520 |
| gtgcggatcc ggggcaagag ctacgtgcag tgccagggca tcccacaggg cagcatcctg | 2580 |
| tccaccctgc tgtgctccct gtgctacggc gacatggaaa acaagctgtt cgccggcatc | 2640 |
| aggcgggacg gactgctgct gagactggtg gacgacttcc tgctggtgac cccccacctg | 2700 |
| acccacgcca agaccttct gcggaccctg gtgcgcggcg tgcccgagta cggctgcgtg | 2760 |
| gtgaacctga aaagaccgt ggtgaacttc cccgtggagg acgaggccct gggcggcaca | 2820 |
| gccttcgtgc agatgcctgc ccatggactg ttcccttggt gcgggctgct gctggacacc | 2880 |
| cggaccctgg aagtgcagag cgactacagc agctacgccc ggaccagcat ccgggcctcc | 2940 |
| ctgaccttca caggggcttc aaggccggc aggaacatgc ggcggaagct gtttggcgtg | 3000 |
| ctgcggctga agtgccacag cctgtttctg tacctgcagg tgaacagcct gcagaccgtg | 3060 |
| tgcaccaaca tctacaagat cctgctgctg caggcctacc ggttccacgc ctgcgtgctg | 3120 |
| cagctgccct ttcaccagca ggtgtggaag aaccctacct tcttcctgcg ggtgatcagc | 3180 |
| gacaccgcca gcctgtgcta cagcatcctg aaggccaaga cgccggcat gagcctgggc | 3240 |
| gccaagggag ccgccggacc tctgcccagc gaggccgtgc agtggctgtg ccaccaggcc | 3300 |
| tttctgctga agctgacccg gcaccgggtg acctacgtgc ccctgctggg cagcctgcgg | 3360 |
| accgcccaga cccagctgtc ccggaagctg cctggcacca ccctgacagc cctggaagcc | 3420 |
| gccgccaacc ccgccctgcc ctccgacttc aagaccatcc tggactaccc ctacgacgtg | 3480 |
| cccgactacg cctgatgagc ggccgcgagc tc | 3512 |

<210> SEQ ID NO 24
<211> LENGTH: 1158
<212> TYPE: PRT
<213> ORGANISM: Artificial Sequence
<220> FEATURE:
<223> OTHER INFORMATION: hTERT

<400> SEQUENCE: 24

Met Asp Trp Thr Trp Ile Leu Phe Leu Val Ala Ala Ala Thr Arg Val

-continued

```
  1               5               10              15
His Ser Pro Arg Ala Pro Arg Cys Arg Ala Val Arg Ser Leu Leu Arg
             20              25              30

Ser His Tyr Arg Glu Val Leu Pro Leu Ala Thr Phe Val Arg Arg Leu
             35              40              45

Gly Pro Gln Gly Trp Arg Leu Val Gln Arg Gly Asp Pro Ala Ala Phe
             50              55              60

Arg Ala Leu Val Ala Gln Cys Leu Val Cys Val Pro Trp Asp Ala Arg
65              70              75              80

Pro Pro Pro Ala Ala Pro Ser Phe Arg Gln Val Ser Cys Leu Lys Glu
             85              90              95

Leu Val Ala Arg Val Leu Gln Arg Leu Cys Glu Arg Gly Ala Lys Asn
             100             105             110

Val Leu Ala Phe Gly Phe Ala Leu Leu Asp Gly Ala Arg Gly Gly Pro
             115             120             125

Pro Glu Ala Phe Thr Thr Ser Val Arg Ser Tyr Leu Pro Asn Thr Val
             130             135             140

Thr Asp Ala Leu Arg Gly Ser Gly Ala Trp Gly Leu Leu Leu Arg Arg
145             150             155             160

Val Gly Asp Asp Val Leu Val His Leu Leu Ala Arg Cys Ala Leu Phe
             165             170             175

Val Leu Val Ala Pro Ser Cys Ala Tyr Gln Val Cys Gly Pro Pro Leu
             180             185             190

Tyr Gln Leu Gly Ala Ala Thr Gln Ala Arg Pro Pro Pro His Ala Ser
             195             200             205

Gly Pro Arg Arg Arg Leu Gly Cys Glu Arg Ala Trp Asn His Ser Val
             210             215             220

Arg Glu Ala Gly Val Pro Leu Gly Leu Pro Ala Pro Gly Ala Arg Arg
225             230             235             240

Arg Gly Gly Ser Ala Ser Arg Ser Leu Pro Leu Pro Lys Arg Pro Arg
             245             250             255

Arg Gly Ala Ala Pro Glu Pro Glu Arg Thr Pro Val Gly Gln Gly Ser
             260             265             270

Trp Ala His Pro Gly Arg Thr Arg Gly Pro Ser Asp Arg Gly Phe Cys
             275             280             285

Val Val Ser Pro Ala Arg Pro Ala Glu Glu Ala Thr Ser Leu Glu Gly
             290             295             300

Ala Leu Ser Gly Thr Arg His Ser His Pro Ser Val Gly Arg Gln His
305             310             315             320

His Ala Gly Pro Pro Ser Thr Ser Arg Pro Pro Arg Pro Trp Asp Thr
             325             330             335

Pro Cys Pro Pro Val Tyr Ala Glu Thr Lys His Phe Leu Tyr Ser Ser
             340             345             350

Gly Asp Lys Glu Gln Leu Arg Pro Ser Phe Leu Leu Ser Ser Leu Arg
             355             360             365

Pro Ser Leu Thr Gly Ala Arg Arg Leu Val Glu Thr Ile Phe Leu Gly
             370             375             380

Ser Arg Pro Trp Met Pro Gly Thr Pro Arg Arg Leu Pro Arg Leu Pro
385             390             395             400

Gln Arg Tyr Trp Gln Met Arg Pro Leu Phe Leu Glu Leu Leu Gly Asn
             405             410             415

His Ala Gln Cys Pro Tyr Gly Val Leu Leu Lys Thr His Cys Pro Leu
             420             425             430
```

```
Arg Ala Ala Val Thr Pro Ala Ala Gly Val Cys Ala Arg Glu Lys Pro
            435                 440                 445

Gln Gly Ser Val Ala Ala Pro Glu Glu Glu Asp Thr Asp Pro Arg Arg
            450                 455                 460

Leu Val Gln Leu Leu Arg Gln His Ser Ser Pro Trp Gln Val Tyr Gly
465                 470                 475                 480

Phe Val Arg Ala Cys Leu Arg Arg Leu Val Pro Pro Gly Leu Trp Gly
                485                 490                 495

Ser Arg His Asn Glu Arg Arg Phe Leu Arg Asn Thr Lys Lys Phe Ile
            500                 505                 510

Ser Leu Gly Lys His Ala Lys Leu Ser Leu Gln Glu Leu Thr Trp Lys
            515                 520                 525

Met Ser Val Arg Gly Cys Ala Trp Leu Arg Arg Ser Pro Gly Val Gly
            530                 535                 540

Cys Val Pro Ala Ala Glu His Arg Leu Arg Glu Glu Ile Leu Ala Lys
545                 550                 555                 560

Phe Leu His Trp Leu Met Ser Val Tyr Val Val Glu Leu Leu Arg Ser
                565                 570                 575

Phe Phe Tyr Val Thr Glu Thr Thr Phe Gln Lys Asn Tyr Leu Phe Phe
            580                 585                 590

Tyr Arg Lys Ser Val Trp Ser Lys Leu Gln Ser Ile Gly Ile Arg Gln
            595                 600                 605

His Leu Lys Arg Val Gln Leu Arg Glu Leu Ser Glu Ala Glu Val Arg
            610                 615                 620

Gln His Arg Glu Ala Arg Pro Ala Leu Leu Thr Ser Arg Leu Arg Phe
625                 630                 635                 640

Ile Pro Lys Pro Asp Gly Leu Arg Pro Ile Val Asn Met Asp Tyr Val
                645                 650                 655

Val Gly Ala Arg Thr Phe Arg Arg Glu Lys Arg Ala Glu Arg Leu Thr
                660                 665                 670

Ser Arg Val Lys Ala Leu Phe Ser Val Leu Asn Tyr Glu Arg Ala Arg
            675                 680                 685

Arg Pro Gly Leu Leu Gly Ala Ser Val Leu Gly Leu Asp Asp Ile His
            690                 695                 700

Arg Ala Trp Arg Thr Phe Val Leu Arg Val Arg Ala Gln Asp Pro Pro
705                 710                 715                 720

Pro Glu Leu Tyr Phe Val Lys Val Asp Val Thr Gly Ala Tyr Asp Thr
                725                 730                 735

Ile Pro Gln Asp Arg Leu Thr Glu Val Ile Ala Ser Ile Ile Lys Pro
            740                 745                 750

Gln Asn Thr Tyr Cys Val Arg Arg Tyr Ala Val Val Gln Lys Ala Ala
            755                 760                 765

His Gly His Val Arg Lys Ala Phe Lys Ser His Val Ser Thr Leu Thr
            770                 775                 780

Asp Leu Gln Pro Tyr Met Arg Gln Phe Val Ala His Leu Gln Glu Thr
785                 790                 795                 800

Ser Pro Leu Arg Asp Ala Val Val Ile Glu Gln Ser Ser Ser Leu Asn
                805                 810                 815

Glu Ala Ser Ser Gly Leu Phe Asp Val Phe Leu Arg Phe Met Cys His
                820                 825                 830

His Ala Val Arg Ile Arg Gly Lys Ser Tyr Val Gln Cys Gln Gly Ile
            835                 840                 845
```

```
Pro Gln Gly Ser Ile Leu Ser Thr Leu Leu Cys Ser Leu Cys Tyr Gly
    850                 855                 860

Asp Met Glu Asn Lys Leu Phe Ala Gly Ile Arg Arg Asp Gly Leu Leu
865                 870                 875                 880

Leu Arg Leu Val Asp Asp Phe Leu Leu Val Thr Pro His Leu Thr His
                885                 890                 895

Ala Lys Thr Phe Leu Arg Thr Leu Val Arg Gly Val Pro Glu Tyr Gly
            900                 905                 910

Cys Val Val Asn Leu Arg Lys Thr Val Val Asn Phe Pro Val Glu Asp
                915                 920                 925

Glu Ala Leu Gly Gly Thr Ala Phe Val Gln Met Pro Ala His Gly Leu
    930                 935                 940

Phe Pro Trp Cys Gly Leu Leu Asp Thr Arg Thr Leu Glu Val Gln
945                 950                 955                 960

Ser Asp Tyr Ser Ser Tyr Ala Arg Thr Ser Ile Arg Ala Ser Leu Thr
                965                 970                 975

Phe Asn Arg Gly Phe Lys Ala Gly Arg Asn Met Arg Arg Lys Leu Phe
            980                 985                 990

Gly Val Leu Arg Leu Lys Cys His Ser Leu Phe Leu Tyr Leu Gln Val
    995                 1000                1005

Asn Ser Leu Gln Thr Val Cys Thr Asn Ile Tyr Lys Ile Leu Leu
    1010                1015                1020

Leu Gln Ala Tyr Arg Phe His Ala Cys Val Leu Gln Leu Pro Phe
    1025                1030                1035

His Gln Gln Val Trp Lys Asn Pro Thr Phe Phe Leu Arg Val Ile
    1040                1045                1050

Ser Asp Thr Ala Ser Leu Cys Tyr Ser Ile Leu Lys Ala Lys Asn
    1055                1060                1065

Ala Gly Met Ser Leu Gly Ala Lys Gly Ala Gly Pro Leu Pro
    1070                1075                1080

Ser Glu Ala Val Gln Trp Leu Cys His Gln Ala Phe Leu Leu Lys
    1085                1090                1095

Leu Thr Arg His Arg Val Thr Tyr Val Pro Leu Leu Gly Ser Leu
    1100                1105                1110

Arg Thr Ala Gln Thr Gln Leu Ser Arg Lys Leu Pro Gly Thr Thr
    1115                1120                1125

Leu Thr Ala Leu Glu Ala Ala Asn Pro Ala Leu Pro Ser Asp
    1130                1135                1140

Phe Lys Thr Ile Leu Asp Tyr Pro Tyr Asp Val Pro Asp Tyr Ala
    1145                1150                1155

<210> SEQ ID NO 25
<211> LENGTH: 2724
<212> TYPE: DNA
<213> ORGANISM: Artificial Sequence
<220> FEATURE:
<223> OTHER INFORMATION: gB consensus nucleic acid sequence
<220> FEATURE:
<221> NAME/KEY: misc_feature
<222> LOCATION: (1)..(3)
<223> OTHER INFORMATION: n is a, c, g, or t

<400> SEQUENCE: 25
nnngagagca gaatctggtg cctggtcgtg tgcgtgaacc tgtgcatcgt gtgcctggga      60
gccgccgtgt ccagcagcag cacccggggc acaagcgcca cacacagcca ccacagcagc     120
cacaccacca gcgccgccca gccggagc ggaagcgtga gcagccagcg ggtgaccagc     180
```

```
agcgaggccg tgtcccaccg ggccaacgag acaatctaca acaccaccct gaagtacggc    240
gacgtcgtgg gagtgaacac caccaagtac ccctacagag tgtgcagcat ggcccagggc    300
accgacctga tcagattcga gcggaacatc gtgtgtacca gcatgaagcc catcaacgag    360
gacctggaca agggcatcat ggtggtgtac aagagaaaca tcgtggccca cccttcaaa    420 gtgcgggtgt accagaaggt gctgaccttc cggcggagct acgcctacat ccacaccacc    480
tacctgctgg cagcaacac cgagtacgtg gccctccca tgtgggagat ccaccacatc    540
aacagccaca gccagtgcta cagcagctac agccgcgtga tcgccggcac cgtgttcgtg    600
gcctaccacc gggacagcta cgagaacaag accatgcagc tgatgcccga cgactacagc    660
aacacccaca gcaccagata cgtgaccgtg aaggaccagt ggcacagccg gggaagcacc    720
tggctgtaca gagagacatg caacctgaac tgcatggtca ccatcaccac cgccagaagc    780
aagtacccct accacttctt cgccaccagc accggcgacg tggtggacat cagccccttc    840
tacaacggca ccaaccggaa cgccagctac ttcggcgaga cgccgacaa gttcttcatc    900 ttccccaact acaccatcgt gtccgacttc ggcagaccca cagcgcccc tgagacacac    960 cggctggtgg ccttcctgga cgggccgac agcgtgatca gctgggacat ccaggacgag    1020
aagaacgtga cctgccagct gaccttctgg gaggctagcg agcggaccat cagaagcgag    1080
gccgaggaca gctaccactt cagcagcgcc aagatgaccg ccaccttcct gagcaagaaa    1140
caggaagtga acatgagcga cagcgccctg gactgcgtgc gggatgaggc catcaacaag    1200
ctgcagcaga tcttcaacac cagctacaac cagacctacg agaagtatgg caacgtgtcc    1260
gtgttcgaga acaggcgg cctggtggtg ttctggcagg gcatcaagca gaagtccctg    1320
gtcgagctgg aacggctggc caacagaagc agcctgaacc tgacccaccg gaccaagcgg    1380
agcaccgacg gcaacaatac cacccacctg agcaacatgg aaagcgtcca acctggtg    1440 tacgcccagc tgcagttcac ctacgacacc ctgcggggct acatcaaccg ggccctggcc    1500
cagatcgccg aggcttggtg tgtggaccag cggcggaccc tggaagtgtt caaagagctg    1560
agcaagatca cccccagcgc catcctgagc gccatctaca acaagcctat cgccgccaga    1620
ttcatgggcg acgtgctggg cctggccagc tgcgtgacca tcaaccagac cagcgtgaag    1680
gtgctgcggg acatgaacgt gaaagaaagc cccggcagat gctactccag acccgtggtc    1740
atcttcaact cgccaacag ctcctacgtg cagtacggcc agctgggcga ggacaacgag    1800
atcctgctgg aaaccaccg gaccgaggaa tgccagctgc ccagcctgaa gatctttatc    1860
gccggcaaca gcgcctacga gtatgtggac tacctgttca gcggatgat cgacctgagc    1920 agcatcagca ccgtggacag catgatcgcc ctggacatcg accccctgga aaacaccgac    1980
ttccgggtgc tggaactgta cagccagaaa gagctgcgga gcagcaacgt gttcgacctg    2040
gaagagatca tgcgcgagtt caacagctac aagcagcgcg tgaaatacgt cgaggacaag    2100
gtggtggacc ccctgccccc ctacctgaag gccctgacg acctgatgag cggcctggga    2160
gctgctggca aggccgtggg agtggccatt ggagctgtgg cggagccgt ggccagcgtg    2220 gtggaaggcg tggccacctt tctgaagaac cccttcggcg ccttcaccat catcctggtg    2280
gctatcgccg tcgtgatcat cacctacctg atctacaccc ggcagcggcg gctgtgtacc    2340
cagcctctgc agaacctgtt ccctacctg gtgtccgccg acggcaccac cgtgacaagc    2400
ggctccacca aggacaccag cctgcaggcc cacccagct acgaggaatc cgtgtacaac    2460
agcggccgga agggcccagg ccctcctagc tctgacgcct ctacagccgc cccaccctac    2520
```

-continued

```
accaacgagc aggcctacca gatgctgctg ccctggcta gactggacgc cgagcagaga    2580
gcccagcaga acggaaccga cagcctggat ggccagaccg gcacccagga caagggccag    2640
aagcccaacc tgctggaccg gctgcggcac agaaagaacg gctaccggca cctgaaggac    2700
agcgacgaag aggaaaacgt gtga                                          2724

<210> SEQ ID NO 26
<211> LENGTH: 907
<212> TYPE: PRT
<213> ORGANISM: Artificial Sequence
<220> FEATURE:
<223> OTHER INFORMATION: gB consensus amino acid sequenc
<220> FEATURE:
<221> NAME/KEY: MISC_FEATURE
<222> LOCATION: (1)..(1)
<223> OTHER INFORMATION: Xaa can be any naturally occurring amino acid

<400> SEQUENCE: 26

Xaa Glu Ser Arg Ile Trp Cys Leu Val Val Cys Val Asn Leu Cys Ile
1               5                   10                  15

Val Cys Leu Gly Ala Ala Val Ser Ser Ser Thr Arg Gly Thr Ser
            20                  25                  30

Ala Thr His Ser His His Ser Ser His Thr Thr Ser Ala Ala His Ser
        35                  40                  45

Arg Ser Gly Ser Val Ser Ser Gln Arg Val Thr Ser Ser Glu Ala Val
    50                  55                  60

Ser His Arg Ala Asn Glu Thr Ile Tyr Asn Thr Thr Leu Lys Tyr Gly
65                  70                  75                  80

Asp Val Val Gly Val Asn Thr Thr Lys Tyr Pro Tyr Arg Val Cys Ser
                85                  90                  95

Met Ala Gln Gly Thr Asp Leu Ile Arg Phe Glu Arg Asn Ile Val Cys
            100                 105                 110

Thr Ser Met Lys Pro Ile Asn Glu Asp Leu Asp Glu Gly Ile Met Val
        115                 120                 125

Val Tyr Lys Arg Asn Ile Val Ala His Thr Phe Lys Val Arg Val Tyr
    130                 135                 140

Gln Lys Val Leu Thr Phe Arg Arg Ser Tyr Ala Tyr Ile His Thr Thr
145                 150                 155                 160

Tyr Leu Leu Gly Ser Asn Thr Glu Tyr Val Ala Pro Pro Met Trp Glu
                165                 170                 175

Ile His His Ile Asn Ser His Ser Gln Cys Tyr Ser Ser Tyr Ser Arg
            180                 185                 190

Val Ile Ala Gly Thr Val Phe Val Ala Tyr His Arg Asp Ser Tyr Glu
        195                 200                 205

Asn Lys Thr Met Gln Leu Met Pro Asp Asp Tyr Ser Asn Thr His Ser
    210                 215                 220

Thr Arg Tyr Val Thr Val Lys Asp Gln Trp His Ser Arg Gly Ser Thr
225                 230                 235                 240

Trp Leu Tyr Arg Glu Thr Cys Asn Leu Asn Cys Met Val Thr Ile Thr
                245                 250                 255

Thr Ala Arg Ser Lys Tyr Pro Tyr His Phe Phe Ala Thr Ser Thr Gly
            260                 265                 270

Asp Val Val Asp Ile Ser Pro Phe Tyr Asn Gly Thr Asn Arg Asn Ala
        275                 280                 285

Ser Tyr Phe Gly Glu Asn Ala Asp Lys Phe Phe Ile Phe Pro Asn Tyr
    290                 295                 300
```

```
Thr Ile Val Ser Asp Phe Gly Arg Pro Asn Ser Ala Leu Glu Thr His
305                 310                 315                 320

Arg Leu Val Ala Phe Leu Glu Arg Ala Asp Ser Val Ile Ser Trp Asp
                325                 330                 335

Ile Gln Asp Glu Lys Asn Val Thr Cys Gln Leu Thr Phe Trp Glu Ala
                340                 345                 350

Ser Glu Arg Thr Ile Arg Ser Glu Ala Glu Asp Ser Tyr His Phe Ser
                355                 360                 365

Ser Ala Lys Met Thr Ala Thr Phe Leu Ser Lys Lys Gln Glu Val Asn
            370                 375                 380

Met Ser Asp Ser Ala Leu Asp Cys Val Arg Asp Glu Ala Ile Asn Lys
385                 390                 395                 400

Leu Gln Gln Ile Phe Asn Thr Ser Tyr Asn Gln Thr Tyr Glu Lys Tyr
                405                 410                 415

Gly Asn Val Ser Val Phe Glu Thr Thr Gly Gly Leu Val Val Phe Trp
                420                 425                 430

Gln Gly Ile Lys Gln Lys Ser Leu Val Glu Leu Glu Arg Leu Ala Asn
            435                 440                 445

Arg Ser Ser Leu Asn Leu Thr His Arg Thr Lys Arg Ser Thr Asp Gly
450                 455                 460

Asn Asn Thr Thr His Leu Ser Asn Met Glu Ser Val His Asn Leu Val
465                 470                 475                 480

Tyr Ala Gln Leu Gln Phe Thr Tyr Asp Thr Leu Arg Gly Tyr Ile Asn
                485                 490                 495

Arg Ala Leu Ala Gln Ile Ala Glu Ala Trp Cys Val Asp Gln Arg Arg
                500                 505                 510

Thr Leu Glu Val Phe Lys Glu Leu Ser Lys Ile Asn Pro Ser Ala Ile
                515                 520                 525

Leu Ser Ala Ile Tyr Asn Lys Pro Ile Ala Ala Arg Phe Met Gly Asp
530                 535                 540

Val Leu Gly Leu Ala Ser Cys Val Thr Ile Asn Gln Thr Ser Val Lys
545                 550                 555                 560

Val Leu Arg Asp Met Asn Val Lys Glu Ser Pro Gly Arg Cys Tyr Ser
                565                 570                 575

Arg Pro Val Val Ile Phe Asn Phe Ala Asn Ser Ser Tyr Val Gln Tyr
                580                 585                 590

Gly Gln Leu Gly Glu Asp Asn Glu Ile Leu Leu Gly Asn His Arg Thr
            595                 600                 605

Glu Glu Cys Gln Leu Pro Ser Leu Lys Ile Phe Ile Ala Gly Asn Ser
610                 615                 620

Ala Tyr Glu Tyr Val Asp Tyr Leu Phe Lys Arg Met Ile Asp Leu Ser
625                 630                 635                 640

Ser Ile Ser Thr Val Asp Ser Met Ile Ala Leu Asp Ile Asp Pro Leu
                645                 650                 655

Glu Asn Thr Asp Phe Arg Val Leu Glu Leu Tyr Ser Gln Lys Glu Leu
                660                 665                 670

Arg Ser Ser Asn Val Phe Asp Leu Glu Glu Ile Met Arg Glu Phe Asn
            675                 680                 685

Ser Tyr Lys Gln Arg Val Lys Tyr Val Glu Asp Lys Val Val Asp Pro
            690                 695                 700

Leu Pro Pro Tyr Leu Lys Gly Leu Asp Asp Leu Met Ser Gly Leu Gly
705                 710                 715                 720

Ala Ala Gly Lys Ala Val Gly Val Ala Ile Gly Ala Val Gly Gly Ala
```

```
                725                 730                 735
Val Ala Ser Val Val Glu Gly Val Ala Thr Phe Leu Lys Asn Pro Phe
            740                 745                 750

Gly Ala Phe Thr Ile Ile Leu Val Ala Ile Ala Val Ile Ile Thr
            755                 760                 765

Tyr Leu Ile Tyr Thr Arg Gln Arg Arg Leu Cys Thr Gln Pro Leu Gln
        770                 775                 780

Asn Leu Phe Pro Tyr Leu Val Ser Ala Asp Gly Thr Thr Val Thr Ser
785                 790                 795                 800

Gly Ser Thr Lys Asp Thr Ser Leu Gln Ala Pro Pro Ser Tyr Glu Glu
            805                 810                 815

Ser Val Tyr Asn Ser Gly Arg Lys Gly Pro Gly Pro Ser Ser Asp
            820                 825                 830

Ala Ser Thr Ala Ala Pro Pro Tyr Thr Asn Glu Gln Ala Tyr Gln Met
            835                 840                 845

Leu Leu Ala Leu Ala Arg Leu Asp Ala Glu Gln Arg Ala Gln Gln Asn
        850                 855                 860

Gly Thr Asp Ser Leu Asp Gly Gln Thr Gly Thr Gln Asp Lys Gly Gln
865                 870                 875                 880

Lys Pro Asn Leu Leu Asp Arg Leu Arg His Arg Lys Asn Gly Tyr Arg
            885                 890                 895

His Leu Lys Asp Ser Asp Glu Glu Glu Asn Val
            900                 905

<210> SEQ ID NO 27
<211> LENGTH: 1119
<212> TYPE: DNA
<213> ORGANISM: Artificial Sequence
<220> FEATURE:
<223> OTHER INFORMATION: gM consensus nucleic acid sequence
<220> FEATURE:
<221> NAME/KEY: misc_feature
<222> LOCATION: (1)..(3)
<223> OTHER INFORMATION: n is a, c, g, or t

<400> SEQUENCE: 27
nnngcaccca gccacgtgga caaagtgaac acccggactt ggagcgccag catcgtgttc      60
atggtgctga ccttcgtgaa tgtgtccgtc cacctggtgc tgagcaactt cccccacctg     120
ggctacccct gcgtgtacta ccacgtggtg gacttcgagc ggctgaacat gagcgcctac     180
aacgtgatgc atctgcacac ccccatgctg tttctggaca gcgtgcagct cgtgtgctac     240
gccgtgttta tgcagctggt gttcctggcc gtgaccatct actacctcgt gtgctggatc     300
aagatttcta tgcggaagga caagggcatg agcctgaacc agagcacccg ggacatcagc     360
tacatgggcg acagcctgac cgccttcctg ttcatcctga gcatggacac cttccagctg     420
ttcaccctga ccatgagctt ccggctgccc agcatgatcg cctttatggc cgccgtccac     480
ttcttctgtc tgaccatctt caacgtgtcc atggtcaccc agtacagaag ctacaagcgg     540
agcctgttct tcttcagtcg gctgcacccc aagctgaagg gcaccgtcca gttccggacc     600
ctgatcgtga acctggtgga agtggccctg gcttcaaca ccaccgtggt ggctatggct     660
ctgtgctacg gcttcggcaa caacttcttc gtgcggacag ccacatggt gctggccgtg     720 ttcgtggtgt acgccattat cagcatcatc tactttctgc tgatcgaggc cgtgttcttc     780
cagtacgtga aggtgcagtt cggctaccac ctgggcgcct ttttcggcct gtgcggcctg     840
atctacccca tcgtgcagta cgacaccttc ctgagcaacg agtaccggac cggcatcagc     900
```

```
tggtccttcg gcatgctgtt cttcatctgg gccatgttca ccacctgtcg ggccgtgcgg      960
tacttcagag gcagaggcag cggctccgtg aagtaccagg ccctggccac agccagcggc     1020
gaagaagtgg ccgccctgag ccaccacgac agcctggaaa gcagacggct gagagaggaa     1080
gaggacgacg acgacgatga ggacttcgag gacgcctga                           1119
```

<210> SEQ ID NO 28
<211> LENGTH: 372
<212> TYPE: PRT
<213> ORGANISM: Artificial Sequence
<220> FEATURE:
<223> OTHER INFORMATION: gM consensus amino acid sequence
<220> FEATURE:
<221> NAME/KEY: MISC_FEATURE
<222> LOCATION: (1)..(1)
<223> OTHER INFORMATION: Xaa can be any naturally occurring amino acid

<400> SEQUENCE: 28

```
Xaa Ala Pro Ser His Val Asp Lys Val Asn Thr Arg Thr Trp Ser Ala
1               5                   10                  15

Ser Ile Val Phe Met Val Leu Thr Phe Val Asn Val Ser Val His Leu
            20                  25                  30

Val Leu Ser Asn Phe Pro His Leu Gly Tyr Pro Cys Val Tyr Tyr His
        35                  40                  45

Val Val Asp Phe Glu Arg Leu Asn Met Ser Ala Tyr Asn Val Met His
    50                  55                  60

Leu His Thr Pro Met Leu Phe Leu Asp Ser Val Gln Leu Val Cys Tyr
65                  70                  75                  80

Ala Val Phe Met Gln Leu Val Phe Leu Ala Val Thr Ile Tyr Tyr Leu
                85                  90                  95

Val Cys Trp Ile Lys Ile Ser Met Arg Lys Asp Lys Gly Met Ser Leu
            100                 105                 110

Asn Gln Ser Thr Arg Asp Ile Ser Tyr Met Gly Asp Ser Leu Thr Ala
        115                 120                 125

Phe Leu Phe Ile Leu Ser Met Asp Thr Phe Gln Leu Phe Thr Leu Thr
130                 135                 140

Met Ser Phe Arg Leu Pro Ser Met Ile Ala Phe Met Ala Ala Val His
145                 150                 155                 160

Phe Phe Cys Leu Thr Ile Phe Asn Val Ser Met Val Thr Gln Tyr Arg
                165                 170                 175

Ser Tyr Lys Arg Ser Leu Phe Phe Ser Arg Leu His Pro Lys Leu
            180                 185                 190

Lys Gly Thr Val Gln Phe Arg Thr Leu Ile Val Asn Leu Val Glu Val
        195                 200                 205

Ala Leu Gly Phe Asn Thr Thr Val Val Ala Met Ala Leu Cys Tyr Gly
    210                 215                 220

Phe Gly Asn Asn Phe Phe Val Arg Thr Gly His Met Val Leu Ala Val
225                 230                 235                 240

Phe Val Val Tyr Ala Ile Ile Ser Ile Ile Tyr Phe Leu Leu Ile Glu
                245                 250                 255

Ala Val Phe Phe Gln Tyr Val Lys Val Gln Phe Gly Tyr His Leu Gly
            260                 265                 270

Ala Phe Phe Gly Leu Cys Gly Leu Ile Tyr Pro Ile Val Gln Tyr Asp
        275                 280                 285

Thr Phe Leu Ser Asn Glu Tyr Arg Thr Gly Ile Ser Trp Ser Phe Gly
    290                 295                 300
```

| Met | Leu | Phe | Phe | Ile | Trp | Ala | Met | Phe | Thr | Thr | Cys | Arg | Ala | Val | Arg |
|---|---|---|---|---|---|---|---|---|---|---|---|---|---|---|---|
| 305 | | | | 310 | | | | 315 | | | | | | 320 | |

Tyr Phe Arg Gly Arg Gly Ser Gly Ser Val Lys Tyr Gln Ala Leu Ala
                          325                        330                        335

Thr Ala Ser Gly Glu Glu Val Ala Ala Leu Ser His His Asp Ser Leu
                          340                        345                        350

Glu Ser Arg Arg Leu Arg Glu Glu Asp Asp Asp Asp Glu Asp
                          355                        360                        365

Phe Glu Asp Ala
    370

<210> SEQ ID NO 29
<211> LENGTH: 411
<212> TYPE: DNA
<213> ORGANISM: Artificial Sequence
<220> FEATURE:
<223> OTHER INFORMATION: gN consensus nucleic acid sequence
<220> FEATURE:
<221> NAME/KEY: misc_feature
<222> LOCATION: (1)..(3)
<223> OTHER INFORMATION: n is a, c, g, or t

<400> SEQUENCE: 29

```
nnngagtgga acaccctggt gctgggtctg ctggtgctgt ctgtggccgc cagcagcaac      60
aacaccagca ctgccagcac ccccagccct agcagcagca cccacacctc caccaccgtg     120
aaggccacca ccaccgccac cacaagcacc acaacagcca ccagcaccac ctcttccacc     180
accagcacaa agcccggcag caccactcac gaccccaacg tgatgaggcc ccacgcccac     240
aacgacttct acaaggccca ctgcaccagc catatgtacg agctgagcct gagcagcttc     300
gccgcctggt ggaccatgct gaacgccctg atcctgatgg gcgccttctg catcgtgctg     360
cggcactgct gcttccagaa cttcaccgcc acaaccacca agggctactg a              411
```

<210> SEQ ID NO 30
<211> LENGTH: 136
<212> TYPE: PRT
<213> ORGANISM: Artificial Sequence
<220> FEATURE:
<223> OTHER INFORMATION: N consensus amino acid sequence
<220> FEATURE:
<221> NAME/KEY: MISC_FEATURE
<222> LOCATION: (1)..(1)
<223> OTHER INFORMATION: Xaa can be any naturally occurring amino acid

<400> SEQUENCE: 30

Xaa Glu Trp Asn Thr Leu Val Leu Gly Leu Leu Val Leu Ser Val Ala
1                      5                        10                       15

Ala Ser Ser Asn Asn Thr Ser Thr Ala Ser Thr Pro Ser Pro Ser Ser
                    20                        25                        30

Ser Thr His Thr Ser Thr Thr Val Lys Ala Thr Thr Thr Ala Thr Thr
            35                        40                        45

Ser Thr Thr Thr Ala Thr Ser Thr Thr Ser Thr Ser Thr Lys
        50                        55                        60

Pro Gly Ser Thr Thr His Asp Pro Asn Val Met Arg Pro His Ala His
65                    70                        75                       80

Asn Asp Phe Tyr Lys Ala His Cys Thr Ser His Met Tyr Glu Leu Ser
                    85                        90                        95

Leu Ser Ser Phe Ala Ala Trp Trp Thr Met Leu Asn Ala Leu Ile Leu
                    100                      105                    110

Met Gly Ala Phe Cys Ile Val Leu Arg His Cys Cys Phe Gln Asn Phe

```
            115                 120                 125
Thr Ala Thr Thr Thr Lys Gly Tyr
    130                 135

<210> SEQ ID NO 31
<211> LENGTH: 2232
<212> TYPE: DNA
<213> ORGANISM: Artificial Sequence
<220> FEATURE:
<223> OTHER INFORMATION: gH consensus nucleic acid sequence
<220> FEATURE:
<221> NAME/KEY: misc_feature
<222> LOCATION: (1)..(3)
<223> OTHER INFORMATION: n is a, c, g, or t

<400> SEQUENCE: 31
nnncgacccg gcctgcccag ctacctgacc gtgttcgccg tgtacctgct gagccatctg        60
cccagccaga gatacggcgc cgatgccgcc tctgaggccc tggatcctca cgccttccat       120
ctgctgctga acacctacgg cagacctatc cggttcctgc gcgagaacac cacccagtgc       180
acctacaaca gcagcctgcg gaacagcacc gtcgtgcgcg agaatgctat cagcttcaac       240
ttcttccaga gctacaacca gtactacgtg ttccacatgc ccggtgcct gttcgccgga        300
cctctggccg agcagttcct gaaccaggtg gacctgaccg agacactgga agataccag        360
cagcggctga atacctacgc cctggtgtcc aaggacctgg ccagctaccg gtccttcagc       420
cagcagctga aggctcagga cagcctgggc gagcagccta ccaccgtgcc ccctccaatc       480
gacctgagca tcccccacgt gtggatgccc cccagaccca cctcacggg ctggaaagag        540
agccacacca ccagcggcct gcacagaccc cacttcaacc agacctgcat tctgttcgac       600
ggccacgacc tgctgttcag caccgtgacc cctgcctgc accagggctt ctacctgatc        660
gacgagctga gatacgtgaa gatcaccctg accgaggatt tcttcgtggt caccgtgtcc       720
atcgacgacg acacccccat gctgctgatc ttcggccatc tgcctcgggt gctgttcaag       780
gcccctacc agcgggacaa cttcatcctg cggcagaccg agaagcacga gctgctggtg        840
ctggtcaaga aggaccagct gaaccggcac tcctacctga aggaccccga cttcctggac       900
gccgccctgg acttcaacta cctggacctg agcgccctgc tgagaaacag cttcacaga       960
tacgccgtgg acgtgctgaa gtccggccgg tgccagatgc tggacagacg gaccgtggaa      1020
atggccttcg cctatgccct ggccctgttt gccgccgctc ggcaggaaga ggctggcgct      1080
gaagtgtccg tgcccagagc cctggacaga caggccgctc tgctgcagat ccaggaattc      1140
atgatcacct gtctgagcca gacccccct cggaccaccc tgctgctgta ccctaccgcc       1200
gtggatctgg ccaagcgggc cctgtggacc ccaaccaga tcaccgacat cacaagcctc       1260
gtgcggctgg tgtacatcct gagcaagcag aaccagcagc acctgatccc cagtgggcc       1320
ctgagacaga tcgccgactt cgccctgaag ctgcacaaga cccacctggc tagctttctg      1380
agcgccttcg ctaggcagga actgtacctg atgggcagcc tggtgcactc catgctggtg      1440
cacaccaccg agaggcggga aatcttcatc gtggaaaccg gcctgtgcag cctggccgag      1500
ctgagccact tcacccagct gctggcccac ccccaccacg agtacctgag cgacctgtac      1560
accccctgca gctctagcgg cagacgggat cacagcctgg aacggctgac ccggctgttc      1620
cccgatgcca cagtgcctgc cactgtgcca gccgccctgt ccatcctgtc caccatgcag      1680
cccagcaccc tggaaacctt ccccgacctg ttctgcctgc cctgggcga gagcttcagc      1740
gccctgacag tgtccgagca cgtgtcctac gtggtcacca ccagtacct gatcaagggc      1800
```

-continued

```
atcagctacc ccgtgtccac caccgtcgtg ggccagagcc tgatcatcac ccagaccgac    1860
agccagacca agtgcgagct gacccggaac atgcacacca cacacagcat cactgccgcc    1920
ctgaacatca gcctggaaaa ctgcgccttc tgccagtctg ccctgctgga atacgacgat    1980
acccagggcg tgatcaacat catgtacatg cacgacagcg acgacgtgct gttcgccctg    2040 gaccccctaca acgaggtggt ggtgtccagc ccccggaccc actacctgat gctgctgaag    2100
aacggcaccg tgctggaagt gaccgacgtg gtggtggacg ccaccgacag cagactgctg    2160
atgatgagcg tgtacgccct gagcgccatc atcggcatct acctgctgta ccggatgctg    2220
aaaacctgct ga                                                        2232
```

<210> SEQ ID NO 32
<211> LENGTH: 743
<212> TYPE: PRT
<213> ORGANISM: Artificial Sequence
<220> FEATURE:
<223> OTHER INFORMATION: gH consensus amino acid sequence
<220> FEATURE:
<221> NAME/KEY: MISC_FEATURE
<222> LOCATION: (1)..(1)
<223> OTHER INFORMATION: Xaa can be any naturally occurring amino acid

<400> SEQUENCE: 32

```
Xaa Arg Pro Gly Leu Pro Ser Tyr Leu Thr Val Phe Ala Val Tyr Leu
1               5                   10                  15

Leu Ser His Leu Pro Ser Gln Arg Tyr Gly Ala Asp Ala Ala Ser Glu
            20                  25                  30

Ala Leu Asp Pro His Ala Phe His Leu Leu Leu Asn Thr Tyr Gly Arg
        35                  40                  45

Pro Ile Arg Phe Leu Arg Glu Asn Thr Thr Gln Cys Thr Tyr Asn Ser
    50                  55                  60

Ser Leu Arg Asn Ser Thr Val Val Arg Glu Asn Ala Ile Ser Phe Asn
65                  70                  75                  80

Phe Phe Gln Ser Tyr Asn Gln Tyr Tyr Val Phe His Met Pro Arg Cys
                85                  90                  95

Leu Phe Ala Gly Pro Leu Ala Glu Gln Phe Leu Asn Gln Val Asp Leu
            100                 105                 110

Thr Glu Thr Leu Glu Arg Tyr Gln Gln Arg Leu Asn Thr Tyr Ala Leu
        115                 120                 125

Val Ser Lys Asp Leu Ala Ser Tyr Arg Ser Phe Ser Gln Gln Leu Lys
    130                 135                 140

Ala Gln Asp Ser Leu Gly Glu Gln Pro Thr Thr Val Pro Pro Pro Ile
145                 150                 155                 160

Asp Leu Ser Ile Pro His Val Trp Met Pro Pro Gln Thr Thr Pro His
                165                 170                 175

Gly Trp Lys Glu Ser His Thr Thr Ser Gly Leu His Arg Pro His Phe
            180                 185                 190

Asn Gln Thr Cys Ile Leu Phe Asp Gly His Asp Leu Leu Phe Ser Thr
        195                 200                 205

Val Thr Pro Cys Leu His Gln Gly Phe Tyr Leu Ile Asp Glu Leu Arg
    210                 215                 220

Tyr Val Lys Ile Thr Leu Thr Glu Asp Phe Val Val Thr Val Ser
225                 230                 235                 240

Ile Asp Asp Asp Thr Pro Met Leu Leu Ile Phe Gly His Leu Pro Arg
                245                 250                 255

Val Leu Phe Lys Ala Pro Tyr Gln Arg Asp Asn Phe Ile Leu Arg Gln
```

-continued

```
               260                 265                 270
Thr Glu Lys His Glu Leu Leu Val Leu Val Lys Lys Asp Gln Leu Asn
        275                 280                 285
Arg His Ser Tyr Leu Lys Asp Pro Asp Phe Leu Asp Ala Ala Leu Asp
        290                 295                 300
Phe Asn Tyr Leu Asp Leu Ser Ala Leu Leu Arg Asn Ser Phe His Arg
305                 310                 315                 320
Tyr Ala Asp Val Leu Lys Ser Gly Arg Cys Gln Met Leu Asp Arg
                325                 330                 335
Arg Thr Val Glu Met Ala Phe Ala Tyr Ala Leu Ala Leu Phe Ala Ala
                340                 345                 350
Ala Arg Gln Glu Glu Ala Gly Ala Glu Val Ser Val Pro Arg Ala Leu
        355                 360                 365
Asp Arg Gln Ala Ala Leu Leu Gln Ile Gln Glu Phe Met Ile Thr Cys
        370                 375                 380
Leu Ser Gln Thr Pro Pro Arg Thr Thr Leu Leu Leu Tyr Pro Thr Ala
385                 390                 395                 400
Val Asp Leu Ala Lys Arg Ala Leu Trp Thr Pro Asn Gln Ile Thr Asp
                405                 410                 415
Ile Thr Ser Leu Val Arg Leu Val Tyr Ile Leu Ser Lys Gln Asn Gln
                420                 425                 430
Gln His Leu Ile Pro Gln Trp Ala Leu Arg Gln Ile Ala Asp Phe Ala
        435                 440                 445
Leu Lys Leu His Lys Thr His Leu Ala Ser Phe Leu Ser Ala Phe Ala
        450                 455                 460
Arg Gln Glu Leu Tyr Leu Met Gly Ser Leu Val His Ser Met Leu Val
465                 470                 475                 480
His Thr Thr Glu Arg Arg Glu Ile Phe Ile Val Glu Thr Gly Leu Cys
                485                 490                 495
Ser Leu Ala Glu Leu Ser His Phe Thr Gln Leu Leu Ala His Pro His
                500                 505                 510
His Glu Tyr Leu Ser Asp Leu Tyr Thr Pro Cys Ser Ser Ser Gly Arg
        515                 520                 525
Arg Asp His Ser Leu Glu Arg Leu Thr Arg Leu Phe Pro Asp Ala Thr
        530                 535                 540
Val Pro Ala Thr Val Pro Ala Ala Leu Ser Ile Leu Ser Thr Met Gln
545                 550                 555                 560
Pro Ser Thr Leu Glu Thr Phe Pro Asp Leu Phe Cys Leu Pro Leu Gly
                565                 570                 575
Glu Ser Phe Ser Ala Leu Thr Val Ser Glu His Val Ser Tyr Val Val
                580                 585                 590
Thr Asn Gln Tyr Leu Ile Lys Gly Ile Ser Tyr Pro Val Ser Thr Thr
        595                 600                 605
Val Val Gly Gln Ser Leu Ile Ile Thr Gln Thr Asp Ser Gln Thr Lys
        610                 615                 620
Cys Glu Leu Thr Arg Asn Met His Thr Thr His Ser Ile Thr Ala Ala
625                 630                 635                 640
Leu Asn Ile Ser Leu Glu Asn Cys Ala Phe Cys Gln Ser Ala Leu Leu
                645                 650                 655
Glu Tyr Asp Asp Thr Gln Gly Val Ile Asn Ile Met Tyr Met His Asp
                660                 665                 670
Ser Asp Asp Val Leu Phe Ala Leu Asp Pro Tyr Asn Glu Val Val Val
        675                 680                 685
```

```
Ser Ser Pro Arg Thr His Tyr Leu Met Leu Leu Lys Asn Gly Thr Val
        690                 695                 700

Leu Glu Val Thr Asp Val Val Asp Ala Thr Asp Ser Arg Leu Leu
705                 710                 715                 720

Met Met Ser Val Tyr Ala Leu Ser Ala Ile Ile Gly Ile Tyr Leu Leu
                725                 730                 735

Tyr Arg Met Leu Lys Thr Cys
            740

<210> SEQ ID NO 33
<211> LENGTH: 837
<212> TYPE: DNA
<213> ORGANISM: Artificial Sequence
<220> FEATURE:
<223> OTHER INFORMATION: gL consensus nucleic acid sequence
<220> FEATURE:
<221> NAME/KEY: misc_feature
<222> LOCATION: (1)..(3)
<223> OTHER INFORMATION: n is a, c, g, or t

<400> SEQUENCE: 33
nnntgcaggc ggcccgactg cggcttcagc ttcagccctg gccccgtgat cctgctgtgg      60
tgctgcctgc tgctgcccat cgtgtcctct gccgccgtgt ctgtggcccc tacagccgcc     120
gagaaggtgc cagccgagtg ccctgagctg accagacggt gtctgctggg cgaggtgttc     180
cagggcgata agtacgagag ctggctgcgg cccctggtca acgtgaccgg cagagatggc     240
cccctgagcc agctgatccg gtacagaccc gtgacccctg aggccgccaa cagcgtgctg     300
ctggacgaag cctttctgga cacactggcc ctgctgtaca acaaccccga ccagctgcgg     360
gccctgctga cactgctgag cagcgatacc gcccccagat ggatgaccgt gatgcggggc     420
tacagcgagt gcggcgacgg atctcccgcc gtgtacacct gtgtggacga cctgtgccgg     480
ggctacgacc tgaccagact gagctacggc cggtccatct tcacagagca cgtgctgggc     540
ttcgagctgg tgcccccag cctgttcaat gtggtggtgg ccatccggaa cgaggccacc     600
cggaccaaca gagcagtgcg gctgcctgtg tccaccgctg ctgctccaga gggcatcacc     660
ctgttctacg gcctgtacaa cgccgtgaaa gagttctgcc tgagacacca gctggacccc     720
cccctgctgc ggcacctgga caagtactac gccggcctgc ctcccgagct gaagcagacc     780
agagtgaacc tgcccgccca cagcagatac ggccctcagg ccgtggacgc cagatga      837

<210> SEQ ID NO 34
<211> LENGTH: 278
<212> TYPE: PRT
<213> ORGANISM: Artificial Sequence
<220> FEATURE:
<223> OTHER INFORMATION: gL consensus amino acid sequence
<220> FEATURE:
<221> NAME/KEY: MISC_FEATURE
<222> LOCATION: (1)..(1)
<223> OTHER INFORMATION: Xaa can be any naturally occurring amino acid

<400> SEQUENCE: 34

Xaa Cys Arg Arg Pro Asp Cys Gly Phe Ser Phe Ser Pro Gly Pro Val
1               5                   10                  15

Ile Leu Leu Trp Cys Cys Leu Leu Leu Pro Ile Val Ser Ser Ala Ala
            20                  25                  30

Val Ser Val Ala Pro Thr Ala Ala Glu Lys Val Pro Ala Glu Cys Pro
        35                  40                  45

Glu Leu Thr Arg Arg Cys Leu Leu Gly Glu Val Phe Gln Gly Asp Lys
```

```
                50                   55                  60
Tyr Glu Ser Trp Leu Arg Pro Leu Val Asn Val Thr Gly Arg Asp Gly
 65                  70                  75                  80

Pro Leu Ser Gln Leu Ile Arg Tyr Arg Pro Val Thr Pro Glu Ala Ala
                 85                  90                  95

Asn Ser Val Leu Leu Asp Glu Ala Phe Leu Asp Thr Leu Ala Leu Leu
            100                 105                 110

Tyr Asn Asn Pro Asp Gln Leu Arg Ala Leu Leu Thr Leu Leu Ser Ser
            115                 120                 125

Asp Thr Ala Pro Arg Trp Met Thr Val Met Arg Gly Tyr Ser Glu Cys
            130                 135                 140

Gly Asp Gly Ser Pro Ala Val Tyr Thr Cys Val Asp Asp Leu Cys Arg
145                 150                 155                 160

Gly Tyr Asp Leu Thr Arg Leu Ser Tyr Gly Arg Ser Ile Phe Thr Glu
                165                 170                 175

His Val Leu Gly Phe Glu Leu Val Pro Pro Ser Leu Phe Asn Val Val
            180                 185                 190

Val Ala Ile Arg Asn Glu Ala Thr Arg Thr Asn Arg Ala Val Arg Leu
            195                 200                 205

Pro Val Ser Thr Ala Ala Pro Glu Gly Ile Thr Leu Phe Tyr Gly
            210                 215                 220

Leu Tyr Asn Ala Val Lys Glu Phe Cys Leu Arg His Gln Leu Asp Pro
225                 230                 235                 240

Pro Leu Leu Arg His Leu Asp Lys Tyr Tyr Ala Gly Leu Pro Pro Glu
                245                 250                 255

Leu Lys Gln Thr Arg Val Asn Leu Pro Ala His Ser Arg Tyr Gly Pro
            260                 265                 270

Gln Ala Val Asp Ala Arg
            275
```

<210> SEQ ID NO 35
<211> LENGTH: 1419
<212> TYPE: DNA
<213> ORGANISM: Artificial Sequence
<220> FEATURE:
<223> OTHER INFORMATION: gO consensus nucleic acid sequence
<220> FEATURE:
<221> NAME/KEY: misc_feature
<222> LOCATION: (1)..(3)
<223> OTHER INFORMATION: n is a, c, g, or t

<400> SEQUENCE: 35

```
nnnggcaaga aagaaatgat catggtcaag ggcatcccca agatcatgct gctgatcagc    60
atcaccttc tgctgctgag cctgatcaac tgcaacgtgc tggtcaacag caagggcaca   120
cggcggagct ggccctacac cgtgctgagc taccggggca agagatcct gaagaagcag   180
aaagaggaca tcctgaagcg gctgatgagc accagcagcg acggctaccg gttcctgatg   240
tacccccagcc agcagaaatt ccacgccatc gtgatcagca tggacaagtt ccccccaggac   300
tacatcctgg ccggacccat ccggaacgac agcatcaccc acatgtggtt cgacttctac   360
agcacccagc tgcggaagcc cgccaaatac gtgtacagcg agtacaacca caccgcccac   420
aagatcaccc tgcggcctcc ccttgcggc accgtgccca gcatgaactg cctgagcgag   480
atgctgaacg tgtccaagcg gaacgacacc ggcgagaagg gctgcggcaa cttcaccacc   540
ttcaacccca tgttcttcaa cgtgcccggg tggaacacca gctgtacat cggcagcaac   600
aaagtgaacg tggacagcca gaccatctac tttctggggcc tgaccgccct gctgctgcgc   660
```

-continued

```
tacgcccaga gaaactgcac ccggtccttc tacctggtca acgccatgag ccggaacctg    720
ttccgggtgc ccaagtacat caacggcacc aagctgaaga acaccatgcg gaagctgaag    780
cggaagcagg ccctggtcaa agagcagccc cagaagaaga acaagaagtc ccagagcacc    840
accaccccct acctgagcta caccaccagc accgccttca acgtgaccac caacgtgacc    900
tacagcgcca cagccgccgt gaccagagtg ccacctcca ccaccggcta ccggcccgac    960
agcaacttca tgaagtccat catggccacc cagctgaggg acctggccac ctgggtgtac   1020
accaccctgc ggtacagaaa cgagcccttc tgcaagcccg accggaacag aaccgccgtg   1080
tccgagttca tgaagaatac ccacgtgctg atccgcaacg agacaccta ccatcatctac   1140 ggcaccctgg acatgagcag cctgtactac aacgagacaa tgagcgtcga gaacgagaca   1200
gccagcgaca caacgaaac cacccccacc agccccagca cccggttcca gcggaccttc   1260
atcgaccccc tgtgggacta cctggacagc ctgctgttcc tggacaagat ccggaacttc   1320
agcctgcagc tgcccgccta cggcaacctg acccccctg aacacagaag ggccgccaac   1380
ctgagcaccc tgaacagcct gtggtggtgg ctgcagtga                          1419
```

```
<210> SEQ ID NO 36
<211> LENGTH: 472
<212> TYPE: PRT
<213> ORGANISM: Artificial Sequence
<220> FEATURE:
<223> OTHER INFORMATION: gO consensus amino acid sequence
<220> FEATURE:
<221> NAME/KEY: MISC_FEATURE
<222> LOCATION: (1)..(1)
<223> OTHER INFORMATION: Xaa can be any naturally occurring amino acid

<400> SEQUENCE: 36

Xaa Gly Lys Lys Glu Met Ile Met Val Lys Gly Ile Pro Lys Ile Met
1               5                   10                  15

Leu Leu Ile Ser Ile Thr Phe Leu Leu Ser Leu Ile Asn Cys Asn
            20                  25                  30

Val Leu Val Asn Ser Lys Gly Thr Arg Arg Ser Trp Pro Tyr Thr Val
        35                  40                  45

Leu Ser Tyr Arg Gly Lys Glu Ile Leu Lys Lys Gln Lys Glu Asp Ile
    50                  55                  60

Leu Lys Arg Leu Met Ser Thr Ser Ser Asp Gly Tyr Arg Phe Leu Met
65                  70                  75                  80

Tyr Pro Ser Gln Gln Lys Phe His Ala Ile Val Ile Ser Met Asp Lys
                85                  90                  95

Phe Pro Gln Asp Tyr Ile Leu Ala Gly Pro Ile Arg Asn Asp Ser Ile
            100                 105                 110

Thr His Met Trp Phe Asp Phe Tyr Ser Thr Gln Leu Arg Lys Pro Ala
        115                 120                 125

Lys Tyr Val Tyr Ser Glu Tyr Asn His Thr Ala His Lys Ile Thr Leu
    130                 135                 140

Arg Pro Pro Cys Gly Thr Val Pro Ser Met Asn Cys Leu Ser Glu
145                 150                 155                 160

Met Leu Asn Val Ser Lys Arg Asn Asp Thr Gly Glu Lys Gly Cys Gly
                165                 170                 175

Asn Phe Thr Thr Phe Asn Pro Met Phe Phe Asn Val Pro Arg Trp Asn
            180                 185                 190

Thr Lys Leu Tyr Ile Gly Ser Asn Lys Val Asn Val Asp Ser Gln Thr
        195                 200                 205
```

Ile Tyr Phe Leu Gly Leu Thr Ala Leu Leu Arg Tyr Ala Gln Arg
    210                 215                 220

Asn Cys Thr Arg Ser Phe Tyr Leu Val Asn Ala Met Ser Arg Asn Leu
225                 230                 235                 240

Phe Arg Val Pro Lys Tyr Ile Asn Gly Thr Lys Leu Lys Asn Thr Met
                245                 250                 255

Arg Lys Leu Lys Arg Lys Gln Ala Leu Val Lys Glu Gln Pro Gln Lys
                260                 265                 270

Lys Asn Lys Lys Ser Gln Ser Thr Thr Thr Pro Tyr Leu Ser Tyr Thr
                275                 280                 285

Thr Ser Thr Ala Phe Asn Val Thr Thr Asn Val Thr Tyr Ser Ala Thr
    290                 295                 300

Ala Ala Val Thr Arg Val Ala Thr Ser Thr Thr Gly Tyr Arg Pro Asp
305                 310                 315                 320

Ser Asn Phe Met Lys Ser Ile Met Ala Thr Gln Leu Arg Asp Leu Ala
                325                 330                 335

Thr Trp Val Tyr Thr Thr Leu Arg Tyr Arg Asn Glu Pro Phe Cys Lys
                340                 345                 350

Pro Asp Arg Asn Arg Thr Ala Val Ser Glu Phe Met Lys Asn Thr His
                355                 360                 365

Val Leu Ile Arg Asn Glu Thr Pro Tyr Thr Ile Tyr Gly Thr Leu Asp
    370                 375                 380

Met Ser Ser Leu Tyr Tyr Asn Glu Thr Met Ser Val Glu Asn Glu Thr
385                 390                 395                 400

Ala Ser Asp Asn Asn Glu Thr Thr Pro Thr Ser Pro Ser Thr Arg Phe
                405                 410                 415

Gln Arg Thr Phe Ile Asp Pro Leu Trp Asp Tyr Leu Asp Ser Leu Leu
                420                 425                 430

Phe Leu Asp Lys Ile Arg Asn Phe Ser Leu Gln Leu Pro Ala Tyr Gly
    435                 440                 445

Asn Leu Thr Pro Pro Glu His Arg Arg Ala Ala Asn Leu Ser Thr Leu
450                 455                 460

Asn Ser Leu Trp Trp Trp Leu Gln
465                 470

<210> SEQ ID NO 37
<211> LENGTH: 516
<212> TYPE: DNA
<213> ORGANISM: Artificial Sequence
<220> FEATURE:
<223> OTHER INFORMATION: UL128 consensus nucleic acid sequence
<220> FEATURE:
<221> NAME/KEY: misc_feature
<222> LOCATION: (1)..(3)
<223> OTHER INFORMATION: n is a, c, g, or t

<400> SEQUENCE: 37
nnnagcccca aggatctgac cccttcctg accgccctgt ggctgctcct gggccacagc      60
agagtgccta gagtgcgggc cgaggaatgc tgcgagttca tcaacgtgaa ccaccccccc     120
gagcggtgct acgacttcaa gatgtgcaac cggttcaccg tggctctgag atgccccgac     180
ggcgaagtgt gctacagccc cgagaaaacc gccgagatcc ggggcatcgt gaccaccatg     240
acccacagcc tgaccagaca ggtggtgcat aacaagctga ccagttgcaa ctacaacccc     300
ctgtacctgg aagccgacgg ccggatcaga tgcggcaaag tgaacgacaa ggcccagtac     360
ctgctgggcg ctgcaggcag tgtgccctac agatggatca acctggaata cgacaagatc     420

```
acccggatcg tgggcctgga ccagtacctg gaaagcgtga agaagcacaa gcggctggac    480
gtgtgccggg ccaagatggg ctacatgctg cagtga                              516

<210> SEQ ID NO 38
<211> LENGTH: 171
<212> TYPE: PRT
<213> ORGANISM: Artificial Sequence
<220> FEATURE:
<223> OTHER INFORMATION: UL128 consensus amino acid sequence
<220> FEATURE:
<221> NAME/KEY: MISC_FEATURE
<222> LOCATION: (1)..(1)
<223> OTHER INFORMATION: Xaa can be any naturally occurring amino acid

<400> SEQUENCE: 38
```

Xaa Ser Pro Lys Asp Leu Thr Pro Phe Leu Thr Ala Leu Trp Leu Leu
1               5                   10                  15

Leu Gly His Ser Arg Val Pro Arg Val Arg Ala Glu Glu Cys Cys Glu
            20                  25                  30

Phe Ile Asn Val Asn His Pro Pro Glu Arg Cys Tyr Asp Phe Lys Met
        35                  40                  45

Cys Asn Arg Phe Thr Val Ala Leu Arg Cys Pro Asp Gly Glu Val Cys
    50                  55                  60

Tyr Ser Pro Glu Lys Thr Ala Glu Ile Arg Gly Ile Val Thr Thr Met
65                  70                  75                  80

Thr His Ser Leu Thr Arg Gln Val Val His Asn Lys Leu Thr Ser Cys
                85                  90                  95

Asn Tyr Asn Pro Leu Tyr Leu Glu Ala Asp Gly Arg Ile Arg Cys Gly
            100                 105                 110

Lys Val Asn Asp Lys Ala Gln Tyr Leu Leu Gly Ala Ala Gly Ser Val
        115                 120                 125

Pro Tyr Arg Trp Ile Asn Leu Glu Tyr Asp Lys Ile Thr Arg Ile Val
    130                 135                 140

Gly Leu Asp Gln Tyr Leu Glu Ser Val Lys Lys His Lys Arg Leu Asp
145                 150                 155                 160

Val Cys Arg Ala Lys Met Gly Tyr Met Leu Gln
                165                 170

```
<210> SEQ ID NO 39
<211> LENGTH: 646
<212> TYPE: DNA
<213> ORGANISM: Artificial Sequence
<220> FEATURE:
<223> OTHER INFORMATION: UL130 consensus amino acid sequence
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (1)..(3)
<223> OTHER INFORMATION: n is a, c, g, or t

<400> SEQUENCE: 39
nnngctgcgg ctgctgctgc ggcaccactt ccactgcctg ctgctgtgtg ccgtgtgggc    60
caccccttgt ctggccagcc cttggagcac cctgaccgcc aaccagaacc ctagcccccc    120
ctggtccaag ctgacctaca gcaagcccca cgacgccgct accttctact gcccattcct    180
gtaccccagc cctcccagaa gccccctgca gttcagcggg ttccagcggg tgtccaccgg    240
ccctgagtgc cggaacgaga cactgtacct gctgtacaac cgcgagggcc agaccctggt    300
```

```
ggaacggtct agcacctggg tcaagaaagt gatctggtat ctgagcggcc ggaaccagac    360
catcctgcag cggatgcctc ggaccgccag caagcctagc gacggcaacg tgcagatcag    420
cgtggaagat gccaaaatct tcggcgccca catggtgccc aagcagacca agctgctgag    480
attcgtggtc aacgacggca ccagatacca gatgtgcgtg atgaagctgg aaagctgggc    540
ccacgtgttc cgggactaca gcgtgtcatt ccaggtccga ctgaccttca ccgaggccaa    600
caaccagacc tacaccttct gcacccaccc caacctgatc gtctga                  646
```

```
<210> SEQ ID NO 40
<211> LENGTH: 214
<212> TYPE: PRT
<213> ORGANISM: Artificial Sequence
<220> FEATURE:
<223> OTHER INFORMATION: UL130 consensus amino acid sequence
<220> FEATURE:
<221> NAME/KEY: MISC_FEATURE
<222> LOCATION: (1)..(1)
<223> OTHER INFORMATION: Xaa can be any naturally occurring amino acid
<220> FEATURE:
<221> NAME/KEY: MISC_FEATURE
<222> LOCATION: (1)..(1)
<223> OTHER INFORMATION: Xaa can be any naturally occurring amino acid

<400> SEQUENCE: 40
```

Xaa Leu Arg Leu Leu Arg His His Phe His Cys Leu Leu Leu Cys
 1               5                  10                  15

Ala Val Trp Ala Thr Pro Cys Leu Ala Ser Pro Trp Ser Thr Leu Thr
                20                  25                  30

Ala Asn Gln Asn Pro Ser Pro Pro Trp Ser Lys Leu Thr Tyr Ser Lys
            35                  40                  45

Pro His Asp Ala Ala Thr Phe Tyr Cys Pro Phe Leu Tyr Pro Ser Pro
        50                  55                  60

Pro Arg Ser Pro Leu Gln Phe Ser Gly Phe Gln Arg Val Ser Thr Gly
65                  70                  75                  80

Pro Glu Cys Arg Asn Glu Thr Leu Tyr Leu Leu Tyr Asn Arg Glu Gly
                85                  90                  95

Gln Thr Leu Val Glu Arg Ser Ser Thr Trp Val Lys Lys Val Ile Trp
            100                 105                 110

Tyr Leu Ser Gly Arg Asn Gln Thr Ile Leu Gln Arg Met Pro Arg Thr
        115                 120                 125

Ala Ser Lys Pro Ser Asp Gly Asn Val Gln Ile Ser Val Glu Asp Ala
    130                 135                 140

Lys Ile Phe Gly Ala His Met Val Pro Lys Gln Thr Lys Leu Leu Arg
145                 150                 155                 160

Phe Val Val Asn Asp Gly Thr Arg Tyr Gln Met Cys Val Met Lys Leu
                165                 170                 175

Glu Ser Trp Ala His Val Phe Arg Asp Tyr Ser Val Ser Phe Gln Val
            180                 185                 190

Arg Leu Thr Phe Thr Glu Ala Asn Asn Gln Thr Tyr Thr Phe Cys Thr
        195                 200                 205

His Pro Asn Leu Ile Val
    210

```
<210> SEQ ID NO 41
<211> LENGTH: 390
<212> TYPE: DNA
<213> ORGANISM: Artificial Sequence
<220> FEATURE:
```

<223> OTHER INFORMATION: UL131a consensus nucleic acid sequence
<220> FEATURE:
<221> NAME/KEY: misc_feature
<222> LOCATION: (1)..(3)
<223> OTHER INFORMATION: n is a, c, g, or t

<400> SEQUENCE: 41

```
nnnagactgt gcagagtgtg gctgagcgtg tgcctgtgcg ccgtggtgct gggccagtgc      60
cagagagaga cagccgagaa gaacgactac taccgggtgc cccactactg ggacgcctgc     120
tctagagccc tgcccgacca gacccggtac aaatacgtgg aacagctggt ggacctgacc     180
ctgaactacc actacgacgc cagccacggc ctggacaact tcgacgtgct gaagcggatc     240
aacgtgaccg aggtgtccct gctgatcagc gacttccggc ggcagaacag aagaggcggc     300
accaacaagc ggactacctt caacgccgct ggcagcctgg cccctcacgc cagatccctg     360
gaattcagcg tgcggctgtt cgccaactga                                      390
```

<210> SEQ ID NO 42
<211> LENGTH: 129
<212> TYPE: PRT
<213> ORGANISM: Artificial Sequence
<220> FEATURE:
<223> OTHER INFORMATION: UL131a consensus amino acid sequence
<220> FEATURE:
<221> NAME/KEY: MISC_FEATURE
<222> LOCATION: (1)..(1)
<223> OTHER INFORMATION: Xaa can be any naturally occurring amino acid

<400> SEQUENCE: 42

Xaa Arg Leu Cys Arg Val Trp Leu Ser Val Cys Leu Cys Ala Val Val
1               5                   10                  15

Leu Gly Gln Cys Gln Arg Glu Thr Ala Glu Lys Asn Asp Tyr Tyr Arg
            20                  25                  30

Val Pro His Tyr Trp Asp Ala Cys Ser Arg Ala Leu Pro Asp Gln Thr
        35                  40                  45

Arg Tyr Lys Tyr Val Glu Gln Leu Val Asp Leu Thr Leu Asn Tyr His
    50                  55                  60

Tyr Asp Ala Ser His Gly Leu Asp Asn Phe Asp Val Leu Lys Arg Ile
65                  70                  75                  80

Asn Val Thr Glu Val Ser Leu Leu Ile Ser Asp Phe Arg Arg Gln Asn
                85                  90                  95

Arg Arg Gly Gly Thr Asn Lys Arg Thr Thr Phe Asn Ala Ala Gly Ser
            100                 105                 110

Leu Ala Pro His Ala Arg Ser Leu Glu Phe Ser Val Arg Leu Phe Ala
        115                 120                 125

Asn

<210> SEQ ID NO 43
<211> LENGTH: 1687
<212> TYPE: DNA
<213> ORGANISM: Artificial Sequence
<220> FEATURE:
<223> OTHER INFORMATION: UL83 consensus nucleic acid sequence
<220> FEATURE:
<221> NAME/KEY: misc_feature
<222> LOCATION: (1)..(3)
<223> OTHER INFORMATION: n is a, c, g, or t

<400> SEQUENCE: 43

```
nnntgagagt cgcgggcgga gatgccctga aatgatcagc gtgctgggcc caatttccgg      60
gcatgtgctg aaggccgtct tctcccgcgg agacaccccc gtgctgcctc acgagacaag    120
```

```
actgctgcag actggcatcc atgtgagggt ctcccagcca tctctgattc tggtgtctca    180
gtacacccca gatagtacac cctgccacag aggggacaac cagctgcagg tgcagcatac    240
ctacttcacc ggatcagagg tcgaaaatgt gagcgtcaac gtgcacaatc ccacaggcag    300
gagtatctgt ccttcacagg agccaatgag catctacgtg tacgccctgc cctgaaaat    360
gctgaacatc cctagcatta atgtgcacca ttacccctcc gccgctgaac gaaagcaccg    420
gcatctgcct gtggcagatg ccgtcatcca tgcttcaggc aaacagatgt ggcaggcacg    480
actgaccgtg agcggactgg catggacacg acagcagaac cagtggaagg agccagacgt    540
gtactatact agcgccttcg tgttccccac caaagacgtg gccctgcgac acgtggtctg    600
cgcacatgag ctggtgtgct ctatggaaaa tactcgggcc accaagatgc aggtcattgg    660
cgatcagtac gtcaaagtgt atctggagtc cttttgtgaa gacgtgccct ctgggaagct    720
gttcatgcac gtgaccctgg gaagcgatgt cgaggaagac ctgactatga cccggaaccc    780
acagcccttt atgagacctc acgagaggaa cggcttcact gtgctgtgcc caaagaatat    840
gatcattaag cccgggaaaa tctctcatat tatgctggat gtggcctta caagtcacga    900
gcatttcgga ctgctgtgcc ccaaaagcat ccctgggctg tcaattagcg gaaacctgct    960
gatgaatggc cagcagatct ttctggaagt gcaggccatt cgagagaccg tcgaactgcg   1020
acagtacgac ccagtggcag ccctgttctt tttcgatatc gacctgctgc tgcagagagg   1080
ccctcagtat agtgagcacc caacattcac ttcacagtac aggattcagg ggaagctgga   1140
gtatcggcac acttgggata gacatgacga aggagctgca cagggcgacg atgacgtgtg   1200
gacctccggc tctgatagtg acgaggaact ggtgaccaca gagcgaaaaa ctccccgggt   1260
gaccggagga ggagctatgg caggagcatc aaccagcgcc ggacgaaaga gaaaaagcgc   1320
cagcagcgcc acagcatgca ctgcaggcgt gatgacaagg gggcgcctga aggcagaatc   1380
cacagtcgcc cctgaggaag atactgacga ggattctgac aacgaaatcc acaatccagc   1440
cgtgttcacc tggccacctt ggcaggcagg aattctggct cgcaatctgg tccctatggt   1500
ggccactgtc cagggacaga acctgaagta ccaggagttt ttctgggatg ctaatgacat   1560
ctatcggatt ttcgcagagc tggaaggcgt gtggcagcca gcagctcagc caaaaaggcg   1620
ccgacacaga caggacgcac tgcctggacc atgtatcgcc tccaccccaa agaaacatag   1680
gggctga                                                              1687
```

<210> SEQ ID NO 44
<211> LENGTH: 561
<212> TYPE: PRT
<213> ORGANISM: Artificial Sequence
<220> FEATURE:
<223> OTHER INFORMATION: UL83 consensus amino acid sequence
<220> FEATURE:
<221> NAME/KEY: MISC_FEATURE
<222> LOCATION: (1)..(1)
<223> OTHER INFORMATION: Xaa can be any naturally occurring amino acid

<400> SEQUENCE: 44

Xaa Glu Ser Arg Gly Arg Arg Cys Pro Glu Met Ile Ser Val Leu Gly
1               5                   10                  15

Pro Ile Ser Gly His Val Leu Lys Ala Val Phe Ser Arg Gly Asp Thr
            20                  25                  30

Pro Val Leu Pro His Glu Thr Arg Leu Leu Gln Thr Gly Ile His Val
        35                  40                  45

Arg Val Ser Gln Pro Ser Leu Ile Leu Val Ser Gln Tyr Thr Pro Asp

```
            50                  55                  60
Ser Thr Pro Cys His Arg Gly Asp Asn Gln Leu Gln Val Gln His Thr
 65                  70                  75                  80

Tyr Phe Thr Gly Ser Glu Val Glu Asn Val Ser Val Asn Val His Asn
                 85                  90                  95

Pro Thr Gly Arg Ser Ile Cys Pro Ser Gln Glu Pro Met Ser Ile Tyr
                100                 105                 110

Val Tyr Ala Leu Pro Leu Lys Met Leu Asn Ile Pro Ser Ile Asn Val
                115                 120                 125

His His Tyr Pro Ser Ala Ala Glu Arg Lys His Arg His Leu Pro Val
            130                 135                 140

Ala Asp Ala Val Ile His Ala Ser Gly Lys Gln Met Trp Gln Ala Arg
145                 150                 155                 160

Leu Thr Val Ser Gly Leu Ala Trp Thr Arg Gln Gln Asn Gln Trp Lys
                165                 170                 175

Glu Pro Asp Val Tyr Tyr Thr Ser Ala Phe Val Phe Pro Thr Lys Asp
                180                 185                 190

Val Ala Leu Arg His Val Val Cys Ala His Glu Leu Val Cys Ser Met
                195                 200                 205

Glu Asn Thr Arg Ala Thr Lys Met Gln Val Ile Gly Asp Gln Tyr Val
                210                 215                 220

Lys Val Tyr Leu Glu Ser Phe Cys Glu Asp Val Pro Ser Gly Lys Leu
225                 230                 235                 240

Phe Met His Val Thr Leu Gly Ser Asp Val Glu Glu Asp Leu Thr Met
                245                 250                 255

Thr Arg Asn Pro Gln Pro Phe Met Arg Pro His Glu Arg Asn Gly Phe
                260                 265                 270

Thr Val Leu Cys Pro Lys Asn Met Ile Ile Lys Pro Gly Lys Ile Ser
                275                 280                 285

His Ile Met Leu Asp Val Ala Phe Thr Ser His Glu His Phe Gly Leu
                290                 295                 300

Leu Cys Pro Lys Ser Ile Pro Gly Leu Ser Ile Ser Gly Asn Leu Leu
305                 310                 315                 320

Met Asn Gly Gln Gln Ile Phe Leu Glu Val Gln Ala Ile Arg Glu Thr
                325                 330                 335

Val Glu Leu Arg Gln Tyr Asp Pro Val Ala Ala Leu Phe Phe Phe Asp
                340                 345                 350

Ile Asp Leu Leu Leu Gln Arg Gly Pro Gln Tyr Ser Glu His Pro Thr
                355                 360                 365

Phe Thr Ser Gln Tyr Arg Ile Gln Gly Lys Leu Glu Tyr Arg His Thr
                370                 375                 380

Trp Asp Arg His Asp Glu Gly Ala Ala Gln Gly Asp Asp Val Trp
385                 390                 395                 400

Thr Ser Gly Ser Asp Ser Asp Glu Glu Leu Val Thr Thr Glu Arg Lys
                405                 410                 415

Thr Pro Arg Val Thr Gly Gly Ala Met Ala Gly Ala Ser Thr Ser
                420                 425                 430

Ala Gly Arg Lys Arg Lys Ser Ala Ser Ser Ala Thr Ala Cys Thr Ala
                435                 440                 445

Gly Val Met Thr Arg Gly Arg Leu Lys Ala Glu Ser Thr Val Ala Pro
                450                 455                 460

Glu Glu Asp Thr Asp Glu Asp Ser Asp Asn Glu Ile His Asn Pro Ala
465                 470                 475                 480
```

```
Val Phe Thr Trp Pro Pro Trp Gln Ala Gly Ile Leu Ala Arg Asn Leu
            485                 490                 495

Val Pro Met Val Ala Thr Val Gln Gly Gln Asn Leu Lys Tyr Gln Glu
            500                 505                 510

Phe Phe Trp Asp Ala Asn Asp Ile Tyr Arg Ile Phe Ala Glu Leu Glu
            515                 520                 525

Gly Val Trp Gln Pro Ala Ala Gln Pro Lys Arg Arg Arg His Arg Gln
            530                 535                 540

Asp Ala Leu Pro Gly Pro Cys Ile Ala Ser Thr Pro Lys Lys His Arg
545                 550                 555                 560

Gly
```